United States Patent [19]

Matumoto et al.

[11] Patent Number: 5,149,834
[45] Date of Patent: Sep. 22, 1992

[54] 4-HYDROXYTETRAHYDROPYRAN-2-ONE DERIVATIVES

[75] Inventors: Masakatsu Matumoto, Sagamihara; Nobuko Watanabe, Kamakura; Eiko Mori, Kodaira; Jun Kusunoki, Tokyo, all of Japan

[73] Assignee: Fujirebio Inc., Tokyo, Japan

[21] Appl. No.: 665,666

[22] Filed: Mar. 7, 1991

[30] Foreign Application Priority Data

| Mar. 7, 1990 | [JP] | Japan | 2-53489 |
| Jun. 1, 1990 | [JP] | Japan | 2-141492 |
| Jun. 1, 1990 | [JP] | Japan | 2-141493 |
| Jul. 4, 1990 | [JP] | Japan | 2-175392 |

[51] Int. Cl.$^5$ .................. C07D 309/30; C07D 409/14; C07D 405/14
[52] U.S. Cl. ..................... 549/292; 549/60; 548/336; 546/269
[58] Field of Search ............ 549/292, 60; 548/336; 546/269

[56] References Cited

U.S. PATENT DOCUMENTS

| 4,375,475 | 3/1983 | Willard et al. | 549/292 |
| 4,772,626 | 9/1988 | Smith et al. | 549/292 |

FOREIGN PATENT DOCUMENTS 3722809 1/1989 Fed. Rep. of Germany .

OTHER PUBLICATIONS

Bulletin of the Chemical Society of Japan, vol. 60, No. 6, Jun. 1987, K. Mukai et al., "Kinetic Studies of Antioxidant Activity of . . . ", pp. 2163-2167.
ACTA Chemica Scandinavia, vol. 22, No. 10, 1968, J. Lars et al., "Synthesis of Methyl Substituted 6-Hydroxychromans, . . . ", pp. 3160-3170.
Patent Abstracts of Japan, vol. 12, No. 186, May 31, 1988, JP-A-62-292777, Daikin Ind. Ltd., "Fluorine-Containing Coumarones".
Chemical Abstracts, vol. 53, No. 7, 1959, C. Cardani et al., "Some Products from Flavoglaucin", pp. 6217-6220.
World Intellectual Property Organization, 90/00053 (Merck), Jan. 11, 1990, Mark Duggan et al., "5-Oxa, 5-Thia, 5-Aza HMG-CoA . . . ", pp. 1-78.
The Journal of Organic Chemistry, vol. 54, No. 3, Feb. 3, 1989, K. Mukai et al., "Synthesis and Stopped-Flow Investigation . . . ", pp. 557-560.

*Primary Examiner*—C. Warren Ivy
*Assistant Examiner*—Amelia A. Owens
*Attorney, Agent, or Firm*—Oblon, Spivak, McClelland, Maier & Neustadt

[57] ABSTRACT 4-hydroxytetrahydropyran-2-one derivatives with general formula (I) are useful as cholesterol reducing agents as well as lipid reducing agents, serving as inhibitors of HMG-CoA reductase, and capable of inhibiting the biosynthesis of peroxidized lipids, and therefore effective for curing arteriosclerosis:

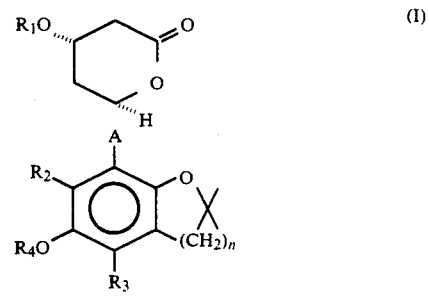

wherein $R_1$ represent hydrogen or a 2-tetrahydropyranyl group; $R_2$ and $R_3$ each represent hydrogen or an alkyl group having 1 to 6 carbon atoms; $R_4$ represents hydrogen, an alkyl group having 1 to 6 carbon atoms, an alkenyl group having 2 to 6 carbon atoms, an aryl group, an aralkyl group, an acyl group, an aroyl group or a substituted sulfonyl group; A represents —$CH_2CH_2$—, or —$CH=CH$—; and n is an integer of 1 or 2, and intermediates for synthesizing the 4-hydroxytetrahydropyran-2-one derivatives are disclosed.

28 Claims, No Drawings

4-HYDROXYTETRAHYDROPYRAN-2-ONE DERIVATIVES

BACKGROUND OF THE INVENTION

1. Field of the Invention

The present invention relates to 4-hydroxytetrahydropyran-2-one derivatives, which are useful as cholesterol reducing agents as well as lipid reducing agents, more particularly which serve as inhibitors of hydroxymethylglutaryl Co-enzyme A reductase (hereinafter referred to as HMG-CoA reductase) and also has a capability of inhibiting the biosynthesis of peroxidized lipids, which is effective for curing arteriosclerosis.

The present invention also relates to intermediates for synthesizing the above 4-hydroxytetrahydropyran-2-one derivatives.

2. Discussion of Background

It is conventionally known that high-level blood cholesterol and blood lipid are significant factors relating to the development of arteriosclerosis. Therefore it is an effective treatment for arteriosclerosis to reduce the level of blood cholesterol by hindering the biosynthesis of cholesterol. Japanese Laid-Open Patent Application 50-155690 discloses ML-236B as an inhibitor which hinders the biosynthesis of cholesterol by the competitive inhibition of the effect of HMG-CoA reductase, which serves as a rate-determining enzyme for the formation of cholesterol, thereby reducing the level of the blood cholesterol in individual vital bodies.

ML-236B is a compound having a 6-substituted 4-hydroxytetrahydropyran-2-one skeleton. Following the proposal of the ML-236B, various compounds with a 4-hydroxytetrahydropyran-2-one skeleton, having a lipid-reducing effect, have been proposed, for instance, as in T. J. Lee, Trends in Pharmacol. Scie., 8(1), 4420 (1987), and Drugs of the Future 12, (5), (1987).

Furthermore, it is considered that the inhibition of the formation of peroxidized lipids will also be effective for curing arteriosclerosis, and that vitamin E and probucol has such an inhibition function.

However, none of them are sufficiently satisfactory for substantial reduction of the blood cholesterol level and the blood lipid level.

SUMMARY OF THE INVENTION

It is therefore a first object of the present invention to provide 4-hydroxytetrahydropyran-2-one derivatives which are capable of inhibiting HMG-CoA reductase, thereby significantly lowering the blood cholesterol level in vital bodies, and which are also capable of inhibiting the biosynthesis of peroxidized lipids like vitamin E.

A second object of the present invention is to provide intermediates for synthesizing the above 4-hydroxytetrahydropyran-2-one derivatives.

The first object of the present invention can be achieved by 4-hydroxytetrahydropyran-2-one derivatives with the following general formula (I):

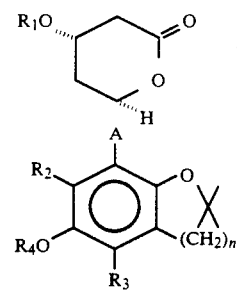

wherein $R_1$ represents hydrogen or a 2-tetrahydropyranyl group; $R_2$ and $R_3$ each represent hydrogen or an alkyl group having 1 to 6 carbon atoms; $R_4$ represents hydrogen, an alkyl group having 1 to 6 carbon atoms, an alkenyl group having 2 to 6 carbon atoms, an aryl group, an aralkyl group, an acyl group, an aroyl group or a substituted sulfonyl group; A represents —$CH_2CH_2$—, or —$CH=CH$—; and n is an integer of 1 or 2.

The second object of the present invention is achieved by the following three intermediates, which are novel and particularly useful for the synthesis of the 4-hydroxytetrahydropyran-2-one derivatives:

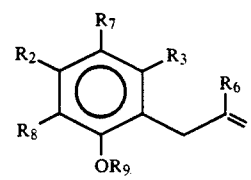

wherein $R_2$ and $R_3$ each represent hydrogen or an alkyl group having 1 to 6 carbon atoms; $R_6$ represents hydrogen or a methyl group; $R_7$ represents hydrogen, a hydroxyl group, or an acyloxy group; and $R_8$ and $R_9$ each represent hydrogen, a 2-methyl-2-propenyl group, or a 2-propenyl group.

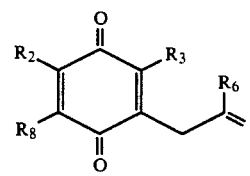

wherein $R_2$, $R_3$, $R_6$ and $R_8$ are respectively the same as defined in the above formula (II).

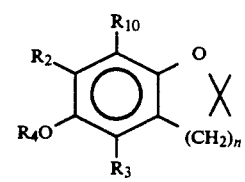

wherein $R_2$ and $R_3$ each represent hydrogen or an alkyl group having 1 to 6 carbon atoms; $R_4$ represents hydrogen, an alkyl group having 1 to 6 carbon atoms, an alkenyl group having 2 to 6 carbon atoms, an aryl group, an aralkyl group, an acyl group, an aroyl group or a substituted sulfonyl group; $R_{10}$ represents hydrogen, a halogen, a formyl group,

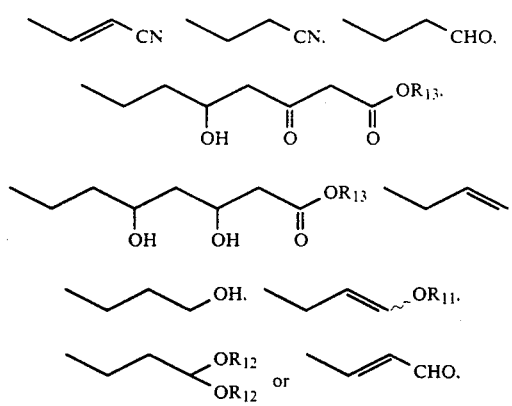

in which $R_{11}$ and $R_{13}$ each represent an alkyl group having 1 to 6 carbon atoms; $R_{12}$ represents an alkyl group having 1 to 6 carbon atoms, and the two $R_{12}$s may be combined to form —$CH_2CH_2$— or —$CH_2CH_2CH_2$—; and n is an integer of 1 or 2.

DETAILED DESCRIPTION OF THE PREFERRED EMBODIMENTS

A 4-hydroxytetrahydropyran-2-one derivative of the previously mentioned formula (I), in which A is —$CH_2CH_2$—, and n is 1, can be synthesized in accordance with the following reaction scheme:

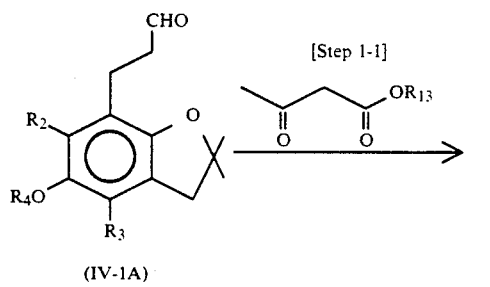

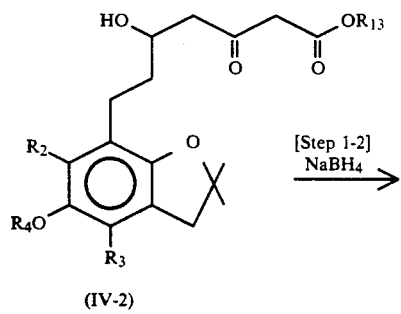

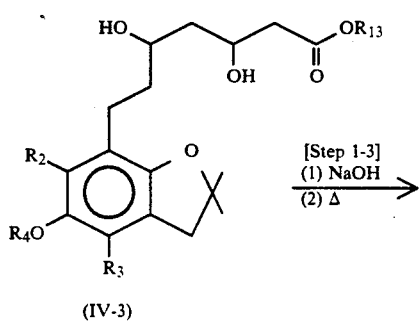

In the above formulas, $R_2$, $R_3$ and $R_4$ are respectively the same as those defined in formula (I), and $R_{13}$ is an alkyl group having 1 to 6 carbon atoms.

Step 1-1

In this step, the aldehyde of formula (IV-1A) and acetoacetic ester are allowed to react to produce a keto alcohol of formula (IV-2).

In the aldehyde of the formula (IV-1A) for use in this step, $R_2$ and $R_3$ represent hydrogen, an alkyl group having 1 to 6 carbon atoms, preferably having 1 to 4 carbon atoms, which may be a straight chain alkyl group, a branched chain alkyl group, or a cyclic alkyl group; and $R_4$ represents hydrogen, an alkyl group having 1 to 6 carbon atoms, which may be a straight chain alkyl group, a branched chain alkyl group, or a cyclic alkyl group, an alkenyl group having 2 to 6 carbon atoms, which may be a straight chain alkenyl group or a branched chain alkenyl group, an aryl group, an aralkyl group, an acyl group, an aroyl group, or a substituted sulfonyl group.

Specific examples of the alkyl group represented by $R_2$ or $R_4$ include methyl group, ethyl group, n-propyl group, 2-propyl group, cyclopropyl group, n-butyl group, sec-butyl group, tert-butyl group, cyclobutyl group, n-pentyl group, 2-pentyl group, neopentyl group, cyclopentyl group, hexyl group, and cyclohexyl group.

Specific examples of the alkenyl group represented by $R_4$ include allyl group, methallyl group, prenyl group, and 4-methyl-3-penten-1-yl group.

Specific examples of the aryl group represented by $R_4$ include phenyl group, pyridyl group, naphthyl group, thienyl group, furyl group, and imidazolyl group.

Specific examples of the aralkyl group represented by $R_4$ include benzyl group, pyridylmethyl group, naphthylmethyl group, thiophenylmethyl group, furylmethyl group, imidazolylmethyl group, or these aromatic nuclei with substituents.

Specific examples of the acyl group represented by $R_4$ include acetyl group, propionyl group, butyryl group, valeryl group, and hexanoyl group.

Specific examples of the aroyl group represented by $R_4$ include benzoyl group, toluoyl group, naphthoyl group, pyridinecarbonyl group, and furoyl group.

Specific examples of the substituted sulfonyl group represented by $R_4$ include methanesulfonyl group, benzenesulfonyl group, and toluenesulfonyl group.

Examples of the acetoacetic ester for use in this step include esters with $R_{13}$ which is an alkyl group having 1 to 6 carbon atoms. Specific examples of the acetoacetic ester are methyl acetoacetate, ethyl acetoacetate, propyl acetoacetate, and butyl acetoacetate.

In this step, the amount of the acetoacetic ester to be employed is at least an equivalent amount to one mole of the aldehyde represented by formula (IV-1A), preferably in the 1 to 2 mole range.

In carrying out this step, a dianion of the acetoacetic ester can be employed, which is derived by use of a strong base such as sodium hydride and/or butyl lithium. It is preferable that Step 1-1 be carried out in an inert atmosphere by use of an inert gas such as nitrogen gas or argon gas.

The reaction in Step 1-1 is usually carried out in an appropriate inert solvent, for example, in an ether such as diethyl ether, tetrahydrofuran, dioxane, or dimethoxyethane, which may be used alone or in combination, at temperatures of $-78°$ C. to room temperature.

The preparation of the aldehyde of formula (IV-1A) for use in this step will be described in detail later.

Step 1-2

In this step, the keto alcohol represented by formula (IV-2) is reduced to produce a 3,5-dihydroxyheptanoic acid ester represented by formula (IV-3). For the reduction in this step, a variety of reductants for reducing carbonyl group can be used. A representative example of the reductant is sodium borohydride.

This step is carried out by use of a reductant in an amount of 1 to 6 equivalents, preferably 2 to 4 equivalents, to one mole of the keto alcohol.

The reaction in this step is usually carried out in an inert solvent at temperatures of $-78°$ C. to room temperature. Examples of the inert solvent include water; alcohols such as methanol, ethanol, and butanol; ethers such as tetrahydrofuran and dioxane; halogenated hydrocarbons such as dichloromethane, and dichloroethane; and aromatic hydrocarbons such as benzene and toluene. These solvents can be used alone or in combination.

In order to allow the reduction in this step to proceed more selectively with steric factors taken into consideration, a conventional method as described in Tetrahedron, 40, 2233 (1983) can be utilized.

Step 1-3

In this step, the ester represented by formula (IV-3) is hydrolyzed by use of a base to produce a hydroxyheptanoic acid derivative. In this hydroxyheptanoic acid derivative, a ring closure is then caused to take place with application of heat thereto, so that a lactone represented by formula (I-1) is produced.

Examples of the base for use in the hydrolysis in the above reaction include hydroxides of alkali metals and alkaline earth metals such as sodium hydroxide, potassium hydroxide, and barium hydroxide.

In this step, the base is employed in an amount of 0.5 to 3 equivalents, preferably in an amount of 0.8 to 1.2 equivalents, to 1 one mole of the ester of formula (IV-3).

The reaction in this step is usually carried out in water, or a mixed solvent of water and a water-miscible solvent or solvents at temperatures of 0° to 80° C.

From the hydroxyheptanoic acid derivative obtained by the hydrolysis, the lactone of formula (I-1) can be obtained without isolating the hydroxyheptanoic acid derivative. The reaction is carried out in an inert solvent, for example, in an aromatic hydrocarbon solvent such as toluene or xylene, under a neutral or nearly neutral condition, at temperatures of 40° to 150° C.

This step can also be carried out without isolating the ester of formula (IV-3) produced in Step 1-2.

The compounds of general formula (I) can be obtained through Steps 1-1 to 1-3. However, the compound in which $R_4$ is an acyl group, an aroyl group or a substituted sulfonyl group can be obtained by direct esterification of the compound of formula (I) in which $R_1$ and $R_4$ are both hydrogen.

Step 1-4

In this step, the lactone derivative of formula (I-1) in which $R_4$ is a benzyl group is converted by catalytic reduction to a lactone derivative of formula (I-2) in which $R_4$ in formula (I-1) is to converted to hydrogen.

The catalytic reduction in this step is carried out in a hydrogen atmosphere by use of a catalyst such as palladium-carbon catalyst, Lindlar catalyst, and platinum group catalyst.

The reaction is usually carried out in an inert solvent. Examples of the inert solvent include alcohols such as methanol and ethanol; aromatic hydrocarbons such as benzene and toluene; ethyl acetate; and tetrahydrofuran which may be used alone or in combination.

When the compound of formula (I) in which $R_1$ is hydrogen, and $R_4$ is an acyl group, an aroyl group or a substituted sulfonyl group can be prepared from the compound of formula (I) in which $R_1$ is hydrogen and $R_4$ is a benzyl group as follows:

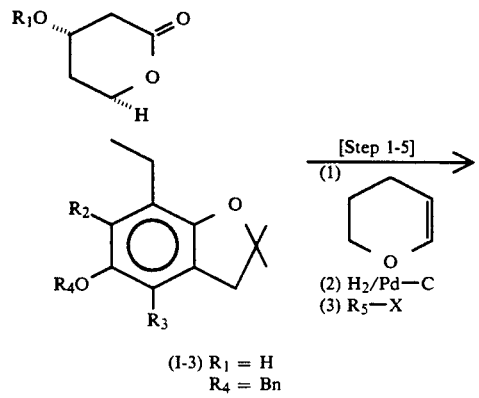

-continued

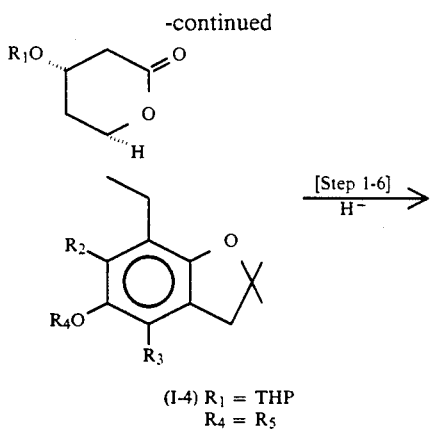

(I-4) R₁ = THP
R₄ = R₅

[Step 1-6]
H⁻→

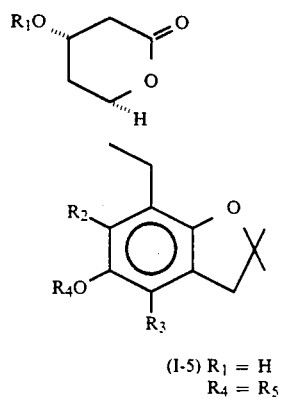

(I-5) R₁ = H
R₄ = R₅ wherein $R_2$ and $R_3$ are the same as those defined previously, Bn represents a benzyl group, THP represents a tetrahydropyranyl group, $R_5$ represents an acyl group, an aroyl group or a substituted sulfonyl group, and X represents a halogen, an acyloxy group or an aroyloxy group.

Step 1-5

In this step, a lactone derivative of formula (I-4) is produced from the lactone derivative of formula (I-3) in which $R_4$ is a benzyl group.

In this step, the hydroxyl group of the lactone ring of the lactone derivative (I-3) is protected by use of dihydropyran. The reaction can be carried out in an inert solvent, for example, in halogenated hydrocarbons such as dichloromethane and dichloroethane; and ethers such as tetrahydrofuran and dioxane. In this reaction, it is preferable to employ an acid catalyst such as p-toluenesulfonic acid, pyridine p-toluenesulfonate, and hydrochloric acid. Further the reaction is usually carried out at 0° C. to 100° C., preferably at room temperature to 80° C.

In the next reaction, the benzyl group of the dihydrobenzofuran ring is released. This reaction is allowed to proceed in accordance with the previously mentioned Step 1-4.

The produced hydroxyl group is allowed to react with an acid halide or acid anhydride of formula $R_5$-X by a conventional method, whereby the lactone derivative of formula (I-4) is produced.

Examples of the acid halide employed in this step include acetyl chloride, propionic acid chloride, straight chain or branched chain butanoic acid chloride, pivalic acid chloride, benzoyl chloride, naphthalenecarboxylic acid chloride, nicotinic acid chloride, isonicotinic acid chloride, thiophenecarboxylic acid chloride, furancarboxylic acid chloride, toluenesulfonylchloride, and methanesulfonyl chloride and their corresponding acid anhydride.

The amount of such an acid halide or acid anhydride is usually 0.5 to 2 moles to one mole of the lactone derivative of formula (I-3).

This reaction can be carried out without solvent or in an inert solvent, for example, in a halogenated hydrocarbon such as dichloromethane, dichloroethane, or chloroform, or in an aromatic hydrocarbon such as benzene or toluene.

It is preferable that a base such as triethylamine or pyridine be added to the reaction mixture in carrying out this reaction. The reaction is usually carried out at temperatures of 0° to 80° C.

Step 1-6

In this step, the lactone derivative of formula (I-5) is produced from the compound of formula (I-4) while deprotecting the hydroxyl group using an acid.

Examples of the acid employed in this reaction include mineral acids such as sulfuric acid, hydrochloric acid; organic acids such as p-toluenesulfonic acid, camphorsulfonic acid; and citric acid; and salts such as pyridine p-toluenesulfonate, and pyridinium chloride. In this reaction, a catalytic amount of such an acid is enough. The reaction is usually carried out in a solvent, for example, water, acetone, alcohol such as methanol, ethanol and propanol, or a mixed solvent of these solvents. The reaction is usually carried out in the range from room temperature to 80° C.

The 4-hydroxytetrahydropyran-2-one derivatives of formula (I) have the effect of inhibiting the biosynthesis of cholesterol, which effect is based on the inhibition effect thereof against the HMG-CoA reductase, so that the 4-hydroxytetrahydropyran-2-one derivatives are effective drugs for treatment of arteriosclerosis.

These derivatives can be administered not only by oral administration, but by intravernous administration, subcutanous administration, and intramuscular administration. Therefore, these derivatives can be used in various administration forms, such as tablets, capsules, liquid, and suppository.

The 3,5-dihydroheptanoic acid derivatives, which are derived by opening the lactone ring of the 4-hydroxytetrahydropyran-2-one derivatives, can be biosynthesized within vital bodies after the administration of the 4-hydroxytetrahydropyran-2-one derivatives of formula (I), and the same inhibition function against HMG-Co A reductase as in the case of the 4-hydroxytetrahydropyran-2-one derivatives. Therefore, the ring-opened 3,5-dihydro-heptanoic acid derivatives and alkali metal salts thereof also have the inhibitin function against the HMG-Co A reductase.

Of the 4-hydroxytetrahydropyran-2-one derivatives of formula (I), the derivatives as shown below in which n=1, A is —CH₂CH₂—, $R_1$ is hydrogen, $R_2$ is 2-propyl group, or t-butyl group, $R_3$ is hydrogen or methyl group, or $R_4$ is benzyl group, or

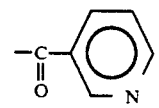

are particularly useful for the objects of the present invention:

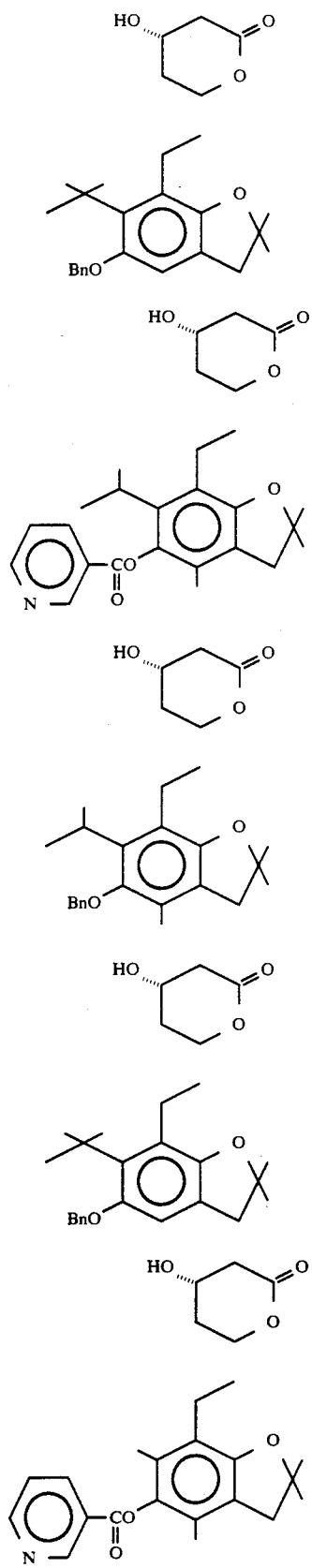

Of the 4-hydroxytetrahydropyran-2-one derivatives of formula (I), (1) the derivatives in which A is —CH$_2$CH$_2$— and n is 2, and (2) the derivatives in which A is —CH=CH—, and n is 1 or 2, can be prepared from the following aldehyde compounds (IV-1B), (IV-1C) and (IV-1D) in accordance with the preparation method for the 4-hydroxytetrahydropyran-2-one derivatives in which A is —CH$_2$CH$_2$— and n is 1:

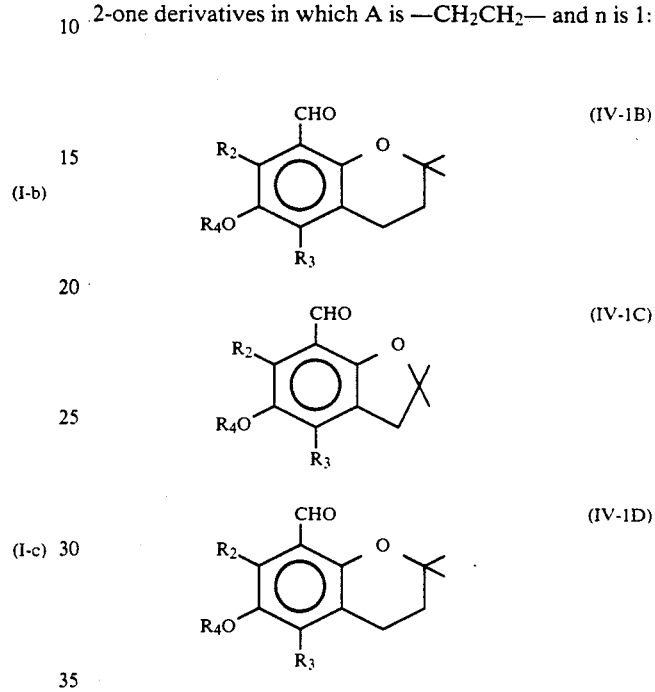

wherein R$_2$, R$_3$ and R$_4$ are respectively the same as defined previously.

The aldehyde compound represented by general formula (IV-1A) can be synthesized from a phenol compound, for example, in accordance with the following reaction scheme:

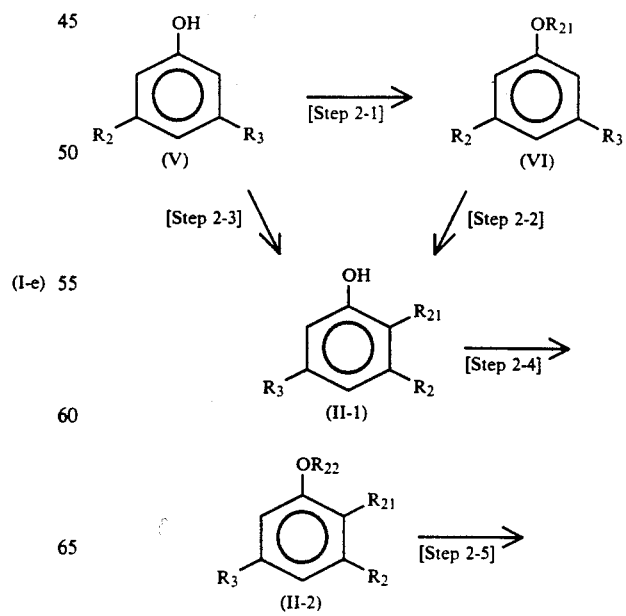

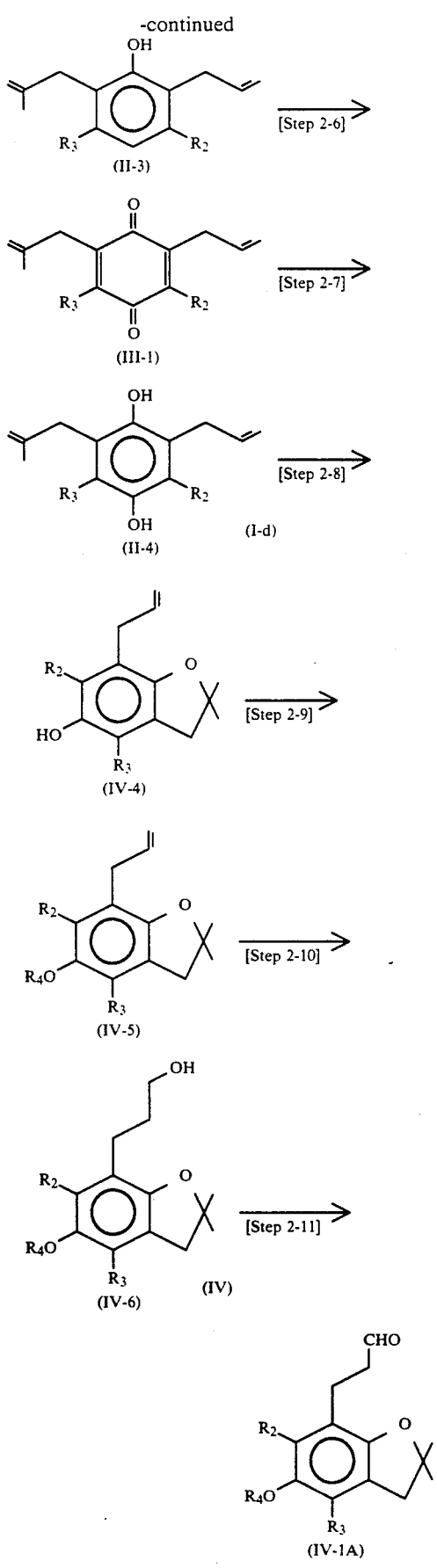

In the above formulas, $R_2$, $R_3$. and $R_4$ are respectively the same as defined in formula (I), $R_{21}$ and $R_{22}$ are 2-methyl-2-propeny group or 2-propenyl group.

Step 2-1

In this step, an ether compound of formula (VI) is prepared from a phenol compound of formula (V) and a halogenated compound represented by $R_{21}$-X.

The phenol compound of formula (V) and the halogenated compound represented by $R_{21}$-X, for example, 3-chloro-1-propene, 3-bromo-2-methyl-1-propene, or the like, are allowed to react in the presence of a base, whereby the ether compound of formula (VI) can be prepared.

In the phenol compound of formula (V), $R_2$ and $R_3$ each represent hydrogen, a straight chain, branched or cyclic alkyl group having 1 to 6 carbon atoms, which may be the same or different. Specific examples of the alkyl group represented by $R_2$ or $R_3$ include methyl group, ethyl group, propyl group, isopropyl group, butyl group, isobutyl group, s-butyl group, t-butyl group, and pentyl group.

Specific examples of the phenol compound of formula (V) include 3-methylphenol, 3-ethylphenol, 3-propylphenol, 3-(2-propyl)phenol, 3-(t-butyl)phenol, 3,5-dimethylphenol, 3-(t-butyl)-5-methyl-phenol, 3-methyl-5-(2-propyl)phenol, 3,5-di-(2-propyl)-phenol, and 3-(t-butyl)-5-(2-propyl)phenol.

In this step, the halogenated compound represented by $R_{21}$-X is used at least in an equimolar amount to the phenol compound of formula (V), preferably in an amount of 1 mole to 2 moles per one mole of the phenol compound of formula (V).

It is preferable that this step be carried out in the presence of a base, such as sodium carbonate, potassium carbonate, sodium hydroxide, potassium hydroxide, or sodium hydride.

Furthermore, it is preferable that this step be carried out in an inert solvent, for example, ketones such as acetone and methyl ethyl ketone; ethers such as diethyl ether, tetrahydrofuran (THF), dioxane, 1,2-dimethoxyethane (DME); or dimethylformamide (DMF). These inert solvents may be used alone or in combination.

The reaction in this step usually proceeds at temperatures ranging from 30° C. to 150° C., but it is preferable that the reaction be carried out at 60° C. to 100° C. in order to attain a high yield.

The phenol compounds for use in this step are commercially available.

Step 2-2

In this step, a phenol compound of formula (II-1) is prepared by application of heat to the ether compound of formula (VI) prepared in Step 2-1.

The reaction in this step proceeds without solvent, but when a solvent is employed, solvents having high boiling points, such as N,N-dimethylaniline, N,N-diethylaniline, N-methyl-2-pyrrolidone, tetralin, and decalin, can be employed.

The reaction in this step usually proceeds at temperatures ranging from 100° C. to 300° C., but it is preferable that the reaction be carried out at 150° C. to 250° C. in order to attain a high yield.

Specific examples of the phenol compound of formula (II-1) prepared in this step are as follows:
3,5-dimethyl-2-(2-methyl-2-propenyl)phenol,
3,5-dimethyl-2-(2-propenyl)phenol,
3-methyl-2-(2-methyl-2-propenyl)-5-(2-propyl)phenol, 3-methyl-2-(2-propenyl)-5-(2-propyl)phenol,
5-methyl-2-(2-methyl-2-propenyl)-3-(2-propyl)phenol,
5-methyl-2-(2-propenyl)-3-(2-propyl)phenol,
5-(t-butyl)-2-(2-methyl-2-propenyl)phenol,
5-(t-butyl)-2-(2-propenyl)phenol,
2-(2-methyl-2-propenyl)-5-(2-propyl)phenol,
2-(2-propenyl)-5-(2-propyl)phenol,
2-(2-methyl-2-propenyl)-3-(2-propyl)phenol, and
2-(2-propenyl)-3-(2-propyl)phenol.

Step 2-3

In this step, the phenol compound of formula (II-1) is prepared by allowing the phenol compound of formula (V) to react with a halogenated compound of formula $R_{21}X$ in the presence of a base to produce the phenol compound of formula (II-1). As the halogenated compound of formula $R_{21}X$, the same halogenated compound as employed in Step 2-1 can be employed.

As the base for use in this step, for example, lithium hydroxide, butyl lithium, and lithium carbonate can be employed. It is preferable that the amount of the base to be employed be in the range of 1 to 1.5 moles to one mole of the phenol compound of formula (V).

Furthermore, it is preferable that the reaction in this step be carried out in an atmosphere of an inert gas by use of an inert solvent such as benzene, toluene or xylene. The reaction is usually carried out at temperatures of 80° C. to 150° C.

Step 2-4

In this step, an ether compound of formula (II-2) is prepared by allowing the phenol compound of formula (II-1) to react with a halogenated compound of formula $R_{22}X$ in the presence of a base.

As the halogenated compound of formula $R_{22}X$, when $R_{21}$ of the phenol compound of formula (II-1) is 2-propenyl group, the halogenated compound of formula $R_{22}X$ is 3-halogeno-2-methyl-1-propene, while when $R_{21}$ of the phenol compound of formula (II-1) is 2-methyl-2-propenyl group, the halogenated compound of formula $R_{22}X$ is 3-halogeno-1-propene.

Furthermore, as the halogenated compound of formula $R_{22}X$ for use in this step, the same halogenated compounds as employed in Step 1 can be employed.

The reaction in this step can be carried out under the same conditions as in Step 1, including the use of the base and solvent.

Specific examples of the ether compound of formula (II-2) produced in this step are as follows:
3,5-dimethyl-2-(2-methyl-2-propenyl)-1-(2-propenyloxy)benzene,
3,5-dimethyl-1-(2-methyl-2-propenyloxy)-2-(2-propenyl)benzene,
5-(t-butyl)-2-(2-methyl-2-propenyl)-1-(2-propenyloxy)benzene,
5-(t-butyl)-1-(2-methyl-2-propenyloxy)-2-(2-propenyl)benzene,
2-(2-methyl-2-propenyl)-1-(2-propenyloxy)-5-(2-propyl)benzene, and
2-(2-methyl-2-propenyl)-1-(2-propenyloxy)-3-(2-propyl)benzene.

Step 2-5

In this step, a phenol compound of formula (II-3) is produced by application of heat to the ether compound of formula (II-1). The reaction in this step can be carried out under the same conditions, using the same solvents, as in Step 2-2.

Specific examples of the phenol compound of formula (II-3) produced in this step are as follows:
3,5-dimethyl-6-(2-methyl-2-propenyl)-2-(2-propenyl)phenol,
3-(t-butyl)-6-(2-methyl-2-propenyl)-2-(2-propenyl)phenol,
6-(2-methyl-2-propenyl)-2-(2-propenyl)-3-(2-propyl)phenol,
2-(2-methyl-2-propenyl)-6-(2-propenyl)-3-(2-propyl)phenol.

Step 2-6

In this step, a quinone compound of formula (III-1) is produced by oxidizing the phenol compound of formula (II-3) in the presence of a catalyst. The reaction in this step can be carried out in an atmosphere of oxygen. As the catalyst for this reaction, for example, salcomine, cupric chloride and cupric bromide can be employed.

It is preferable that the reaction be carried out in a solvent. Specific examples of the solvent for use in this reaction include alcohols such as methanol, ethanol and propanol, and polar solvents such as dimethylformamide.

The reaction in this step usually proceeds at temperatures ranging from 0° C. to 100° C., but it is preferable that the reaction be carried out at or near room temperature in order to attain a high yield.

Specific examples of the quinone compound of formula (III-1) are as follows:
2,6-dimethyl-5-(2-methyl-2-propenyl)-3-(2-propenyl)-p-benzoquinone,
2-(t-butyl)-5-(2-methyl-2-propenyl)-3-(2-propenyl)-p-benzoquinone,
5-(2-methyl-2-propenyl)-3-(2-propenyl)-2-(2-propyl)-p-benzoquinone, and
3-(2-methyl-2-propenyl)-5-(2-propenyl)-2-(2-propyl)-p-benzoquinone.

Step 2-7

In this step, a hydroquinone compound of formula (II-4) is produced by reducing the quinone compound of formula (III-1).

As a reductant for use in this step, for example, sodium borohydride can be employed. The reductant can be employed at least in an equivalent amount to the quinone compound of formula (III-1).

The reaction in this step can be carried out in a solvent. Examples of the solvent are alcohols such as methanol, ethanol and propanol, and halogenated hydrocarbons such as dichloromethane, chloroform, and 1,2-dichloroethane. These solvents can be used alone or in combination.

The reaction can be carried out at temperatures of $-10°$ C. to 50° C.

Specific examples of the hydroquinone of formula (II-4) produced in this step are as follows:
2,6-dimethyl-5-(2-methyl-2-propenyl)-3-(2-propenyl)hydroquinone,
2-(t-butyl)-5-(2-methyl-2-propenyl)-3-(2-propenyl)hydroquinone, 5-(2-methyl-2-propenyl)-3-(2-propenyl)-2-(2-propyl)hydroquinone, and
3-(2-methyl-2-propenyl)-5-(2-propenyl)-2-(2-propyl)hydroquinone.

Step 2-8

In this step, a cyclization reaction of the hydroquinone compound of formula (II-4) is conducted in the presence of an acid to produce a benzofuran derivative of formula (IV-4).

Preferable examples of the acid for use in this reaction include boron trifluoride etherate, p-toluenesulfonic acid, and hydrochloric acid. A catalytic amount of such an acid is sufficient for the hydroquinone compound of formula (II-4) in this reaction.

It is preferable that the reaction be carried out in an atmosphere of an inert gas in an inert solvent. Examples of the inert solvent for this reaction are halogenated hydrocarbons such as methylene chloride, chloroform, and 1,2-dichloroethane; esters such as ethyl acetate; and organic aromatic hydrocarbons such as benzene, toluene and xylene.

The reaction can be carried out at temperatures of −5° C. to 150° C.

Specific examples of the benzofuran derivative of formula (IV-4) are as follows:
2,3-dihydro-5-hydroxy-7-(2-propenyl)-2,2,4,6-tetramethylbenzo[b]furan,
2,3-dihydro-2,2-dimethyl-4,6-di(2-propyl)-5-hydroxy-7-(2-propenyl)benzo[b]furan,
6-(t-butyl)-2,3-dihydro-5-hydroxy-7-(2-propenyl)-2,2,4-trimethylbenzo[b]furan,
6-(t-butyl)-2,3-dihydro-2,2-dimethyl-5-hydroxy-7-(2-propenyl)benzo[b]furan,
4-(t-butyl)-2,3-dihydro-5-hydroxy-7-(2-propenyl)-2,2,6-trimethylbenzo[b]furan,
2,3-dihydro-5-hydroxy-7-(2-propenyl)-6-(2-propyl)benzo[b]furan, and
2,3-dihydro-2,2-dimethyl-5-hydroxy-7-(2-propenyl)-6-(2-propyl)benzo[b]furan.

Step 2-9

In this step, a benzofuran derivative of formula (IV-5) is produced by allowing the benzofuran derivative of formula (IV-4) to react with a halogenated compound of $R_4X$, such as benzyl bromide.

It is preferable that the reaction in this step be carried out in the presence of a base. Examples of the base include inorganic bases such as potassium carbonate, sodium carbonate, potassium hydroxide, and sodium hydroxide, and organic bases such as triethylamine, and pyridine.

Such a base is employed at least in an equivalent amount to the ring-formed starting material of formula (IV-4), preferably in an amount of 1 to 3 equivalents to the starting material in order to attain a high yield.

It is preferable that the reaction be carried out in an inert solvent. Specific examples of the inert solvent include amides such as dimethylformamide (DMF); aromatic hydrocarbons such as benzene, toluene and xylene; ethers such as diethyl ether, tetrahydrofuran, diethoxyethane, and dioxane; and ketones such as acetone and methyl ethyl ketone. These solvents can be used alone or in combination.

The reaction is carried out at temperatures of 0° C. to 100° C.

Furthermore, when benzofuran derivatives of formula (IV-5) in which $R_4$ is an acyl group, or an aroyl group are produced, acid anhydrides including the corresponding the acyl group or aroyl group can be employed.

Specific examples of the benzofuran derivative of formula (IV-5) are as follows:
3-acetoxy-2,3-dihydro-2,2-dimethyl-4,6-di(2-propyl)-7-(2-propenyl)benzo[b]furan,
5-benzyloxy-2,3-dihydro-2,2-dimethyl-4,6-di(2-propyl)-7-(2-propenyl)-benzo[b]furan,
5-acetoxy-6-(t-butyl)-2,3-dihydro-7-(2-propenyl)-2,2,4-trimethylbenzo[b]furan,
5-benzyloxy-6-(t-butyl)-2,3-dihydro-7-(2-propenyl)-2,2,4-trimethylbenzo[b]furan,
5-benzyloxy-6-(t-butyl)-2,3-dihydro-2,2-dimethyl-7-(2-propenyl)benzo[b]furan,
5-acetoxy-2,3-dihydro-4-(t-butyl)-7-(2-propenyl)-2,2,6-trimethylbenzo[b]furan, and
5-benzyloxy-4-(t-butyl)-2,3-dihydro-7-(2-propenyl)-2,3,6-trimethylbenzo[b]furan.

Step 2-10

In this step, an alcohol derivative of formula (IV-6) is produced by subjecting the benzofuran derivative of formula (IV-5) to hydroboration by use of a boran derivative to produce a boron compound, followed by the oxidation of the boron compound.

Examples of the boran derivative for use in this step include diboran and dialkylborans, and 9-borabicyclo[3.3.1]nonane, which is referred to as 9-BBN. Of these boran derivatives, 9-BBN is preferable for use in this reaction. It is preferable that the boran derivative be employed in an amount of 1 to 2 equivalents to the benzofuran derivative of formula (IV-5) in order to attain a high yield of the alcohol derivative of formula (IV-6).

It is preferable that the reaction be carried out in an atmosphere of an inert gas in an inert solvent. Examples of the inert solvent include ethers such as ethyl ether, tetrahydrofuran (THF), and dioxane. The reaction proceeds at temperatures of 0° C. to 100° C.

The oxidation of the boron compound produced can be performed by use of a conventionally employed alkaline hydrogen peroxide.

Specific examples of the alcohol derivative of formula (IV-6) are as follows:
3-[5-benzyloxy-2,3-dihydro-2,2,4,6-tetramethylbenzo[b]furan-7-yl]propanol,
3-[5-benzyloxy-2,3-dihydro-2,2-dimethyl-4,6-di-(2-propyl)benzo[b]furan-7-yl]propanol,
3-[5-benzyloxy-6-(t-butyl)-2,3-dihydro-2,2,4-trimethylbenzo[b]furan-7-yl]propanol,
3-[5-benzyloxy-4-(t-butyl)-2,3-dihydro-2,2,6-trimethylbenzo[b]furan-7-yl]propanol, and
3-[5-benzyloxy-2,3-dihydro-2,2-dimethyl-6-(2-propyl)benzo[b]furan-7-yl]propanol.

Step 2-11

In this step, the aldehyde derivative of formula (IV-1A) is produced by oxidizing the alcohol derivative of formula (IV-6).

As an oxidizing agent for this reaction, any oxidizing agents which oxidize a hydroxyl group to an aldehyde group can be employed. Specific examples of such an oxidizing agent are chrome compounds such as pyridinium chlorochromate, sulfur trioxide pyridine complex, and N-chlorosuccinimide.

It is preferable that the reaction be carried out in an atmosphere of an inert gas in a solvent. Examples of the solvent are ethers such as ethyl ether and THF, and inert solvents such as DMF and DMSO. The reaction can be carried out at temperatures of 0° C. to 100° C.

Specific examples of the aldehyde derivatives of formula (IV-1A) are as follows:
3-[5-benzyloxy-2,3-dihydro-2,2,4,6-tetramethylbenzo[b]furan-7-yl]propanal, 3-[5-benzyloxy-2,3-dihydro-2,2-dimethyl-4,6-di(2-propyl)benzo[b]furan-7-yl]propanal, 3-[5-benzyloxy-6-(t-butyl)-2,3-dihydro-2,2,4-trimethylbenzo[b]furan-7-yl]propanal, 3-[5-benzyloxy-6-(t-butyl)-2,3-dihydro-2,2-dimethylbenzo[b]furan-7-yl]propanal, 3-[5-benzyloxy-4-(t-butyl)-2,3-dihydro-2,2,6-trimethylbenzo[b]furan-7-yl]propanal, and 3-[5-benzyloxy-2,3-dihydro-2,2-dimethyl-6-(2-propyl)-benzo[b]furan-7-yl]propanal.

The aldehyde derivative of formula (IV-1A) can also be prepared by Step 2-13 through Step 2-20 as shown in the following reaction scheme:

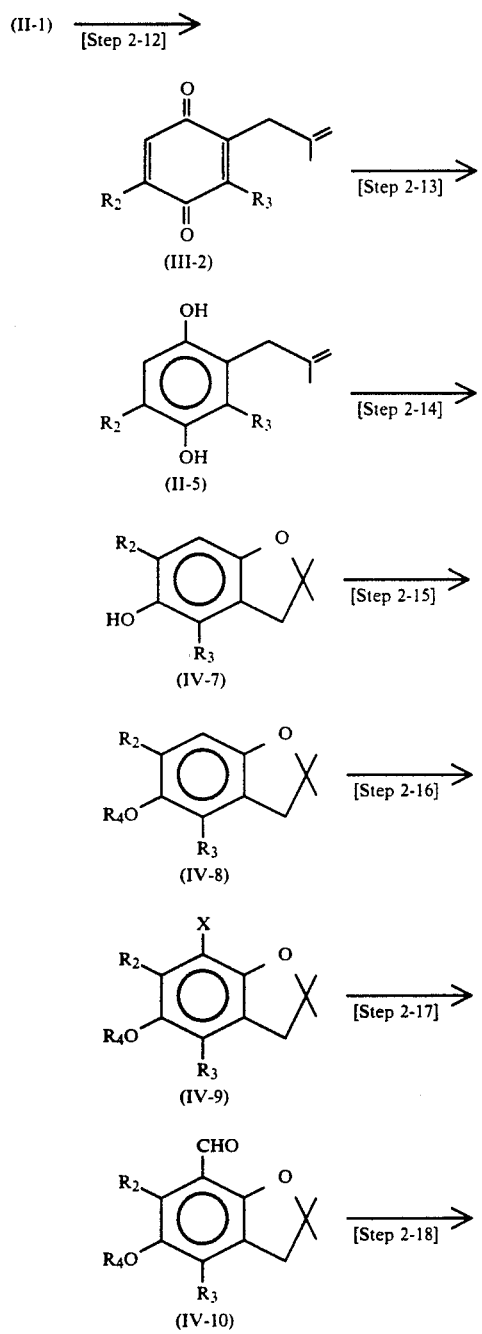

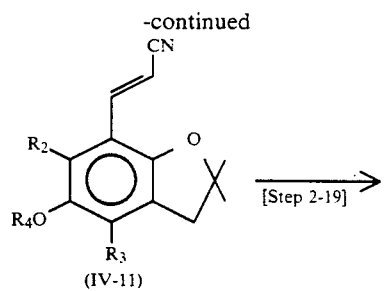

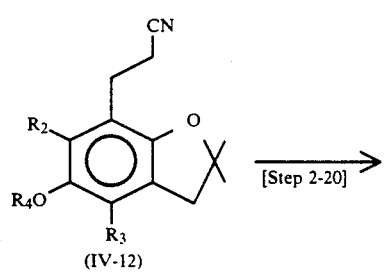

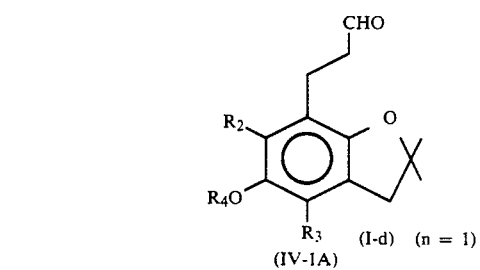

Step 2-12

In this step, a quinone compound of formula (III-2) is prepared by oxidizing the phenol compound of formula (II-1) which is mentioned previously.

The catalysts, solvents and reaction conditions for the reaction in this step are respectively the same as in the previously described Step 2-6.

Specific examples of the quinone compound of formula (III-2) produced in this step are as follows:

3-methyl-2-(2-methyl-2-propenyl)-5-(2-propyl)-p-benzoquinone, and 5-methyl-2-(2-methyl-2-propenyl)-3-(2-propyl)-p-benzoquinone.

Step 2-13

In this step, the hydroquinone compound of formula (II-5) is produced by reducing the quinone compound of formula (III-2) which is mentioned previously.

The reducing agents, solvents and reaction conditions for the reaction in this step are respectively the same as in the previously mentioned Step 2-7.

Specific examples of the hydroquinone compound of formula (II-5) produced in this step are 3-methyl-2-(2-methyl-2-propenyl)-5-(2-propyl)hydroquinone, and 5-methyl-2-(2-methyl-2-propenyl)-3-(2-propyl)hydroquinone.

Step 2-14

In this step, the benzofuran derivative of formula (IV-7) is produced by reducing the hydroquinone derivative of formula (II-5) in the presence of an acid.

The catalysts, solvents and reaction conditions for the reaction in this step are respectively the same as in the previously mentioned Step 2-8.

Specific examples of the benzofuran derivative of formula (IV-7) produced in this step are 2,3-dihydro-5-hydroxy-6-(2-propyl)-2,2,4-trimethylbenzo[b]furan, and 2,3-dihydro-5-hydroxy-6-(2-propyl)-2,2,6-trimethylbenzo[b]furan.

Step 2-15

In this step, a benzofuran derivative of formula (IV-8) is produced by the reaction of the hydroxyl group of the phenol compound of formula (IV-7) and the halogenated compound of $R_4X$. The halogenated compound of $R_4X$, solvents and reaction conditions are respectively the same as in Step 2-9, provided that the case where substituents which are unstable under the reaction conditions in Step 2-16 and the succeeding steps, such as an acyloxy group, aroyl group, and hydrogen, are involved, is eliminated.

Specific examples of the benzofuran derivative of formula (IV-8) produced in this step are 5-benzyloxy-2,3-dihydro-6-(2-propyl)-2,2,4-trimethylbenzo[b]furan, and 5-benzyloxy-2,3-dihydro-4-(2-propyl)-2,2,6-trimethylbenzo[b]furan.

Step 2-16

In this step, the halogenated compound of formula (IV-9) is produced by allowing the benzofuran derivative of formula (IV-8) to react with a halogenation agent. X in the formula (IV-9) represents a halogen, such as chlorine, bromine and iodine.

Examples of the halogenation agent are chlorine, bromine, N-bromosuccinimide, N-chlorosuccinimde, and pyridinium bromide perbromide.

It is preferable that such a halogenation agent be employed in an amount of 0.5 to 1.5 equivalents to the benzofuran derivative of formula (IV-9). Furthermore, it is preferable that the reaction be carried out in a solvent in an atmosphere of an inert gas. Specific examples of the solvent include halogenated hydrocarbons such as chloroform, carbon tetrachloride; ethers such as ethyl ether, THF, and dioxane; and water. These solvents can be used alone or in combination. The reaction can be carried out at temperatures of 0° C. to 50° C.

A example of the halogenated compound of formula (IV-9) produced in this step is 5-benzyloxy-7-bromo-2,3-dihydro-6-(2-propyl)-2,2,4-trimethylbenzo[b]furan.

Step 2-17

In this step, a benzaldehyde derivative of formula (IV-10) is produced by preparing a Grignard reagent by allowing the halogenated compound of formula (IV-9) to react with magnesium, and subjecting the halogenated compound of formula (IV-9) to formylation.

X in the formula (IV-9) represents, for example, chlorine, bromine and iodine.

It is preferable that magnesium be employed in an amount of 1 to 2 equivalents to the halogenated compound of formula (IV-9). Furthermore, it is preferable that the reaction be carried out in an atmosphere of an inert gas, in a solvent free from water. Examples of the solvent include ethers such as ether, THF and dioxane. The reaction can be carried out at temperatures of 0° C. to 80° C.

A specific example of the benzaldehyde derivative of formula (IV-10) is 5-benzyloxy-2,3-dihydro-7-formyl-6-(2-propyl)-2,2,4-trimethylbenzo[b]furan.

Step 2-18

In this step, a cyano derivative of formula (IV-11) is produced by allowing the benzaldehyde derivative of formula (IV-10) to react with a phosphonate derivative.

A specific example of the phosphonate derivative for use in the reaction in this step is diethylcyanomethyl phosphonate.

The phosphonate derivative is employed in an amount of at least one equivalent, preferably 1.0 to 2.5 equivalents, to the benzaldehyde derivative of formula (IV-10).

It is preferable that the reaction in this step be carried out in the presence of an alkali, such as sodium hydride, potassium hydride, sodium carbonate, and potassium carbonate. Furthermore, it is preferable that such an alkali be employed in an amount of 0.8 to 2.5 equivalents to the aldehyde derivative of formula (IV-10). The reaction is carried out, preferably in an atmosphere of an inert gas, in a solvent, for example, ethers such as diethyl ether, THF, dioxane and dimethoxyethane, esters such as ethyl acetate, and mixed solvents of these solvents and water. The reaction can be carried out at temperatures of 0° C. to 80° C.

A specific example of the cyano derivative of formula (IV-11) produced in this step is 3-[5-benzyloxy-2,3-dihydro-6-(2-propyl)-2,2,4-trimethylbenzo[b]furan-7-yl]-2-propanenitrile.

Step 2-19

In this step, a cyanoethyl derivative of formula (IV-12) is produced by reducing the cyano derivative of formula (IV-11).

This can be carried out by allowing the cyano derivative of formula (IV-11) to react with magnesium in an alcohol solvent. It is preferable that the magnesium be employed in an amount of 1 to 5 equivalents to the cyano derivative of formula (IV-11). It is preferable that the reaction be carried out in an atmosphere of an inert gas. The reaction can be carried out in an alcohol serving as a hydrogen-donating agent and as a solvent. To this solvent, ethers such as diethyl ether, THF, dioxane can be added.

Alternatively the reaction can also be carried out by hydrogenation in the presence of a palladium carbon catalyst.

A specific example of the cyanoethyl derivative of formula (IV-12) produced in this step is 3-[5-benzyloxy-2,3-dihydro-6-(2-propyl)-2,2,4-trimethylbenzo[b]furan-7-yl]propanonitrile.

Step 2-20

In this step, the aldehyde derivative of formula (IV-1A) is produced by reducing the cyanoethyl derivative of formula (IV-12).

As a reducing agent for use in this step, for example, diisobutyl aluminum hydride can be employed. It is preferable that such a reducing agent be employed in an amount of 0.8 to 1.2 equivalents to the caynoethyl derivative of formula (IV-12).

It is preferable that the reaction be carried out in an atmosphere of an inert gas, in a solvent free from water. Examples of the solvent include aromatic hydrocarbons such as benzene and toluene, and ethers such as THF, and dioxane. The reaction can be effectively carried out at temperatures of −78° C. to room temperature.

The aldehyde derivative of formula (IV-A) obtained above can be used for producing the 4-hydroxytetrahydropyran-2-one derivative of formula (I) through the previously described Step 1-1 and the succeeding steps.

The aldehyde derivative of formula (IV-1A) can also be produced by the following reaction scheme including Steps 2-21 through Step 24:

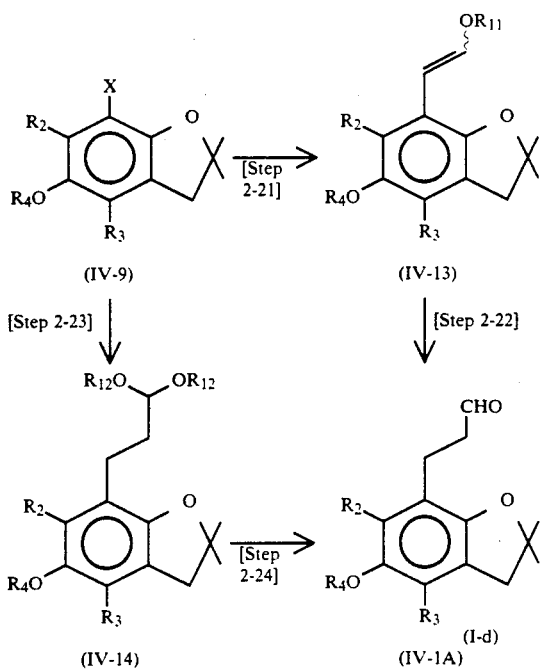

wherein X, $R_2$, $R_3$, $R_4$, $R_6$ and $R_7$ are respectively the same as defined previously.

Step 2-21

In this step, a benzofuran derivative of formula (IV-B) is produced by preparing a Grignard reagent by allowing the halogenated compound of formula (IV-9) synthesized in Step 2-16 to react with magnesium, and allowing the Grignard reagent to react with acrolein acetal in the presence of a catalyst.

As the halogenated compound of formula (IV-9), the same halogenated compound as employed in Step 2-17 can be employed, and the amount of the magnesium, the solvent employed, and the reaction conditions are also the same as in Step 2-17.

As a catalyst the reaction of the Grignard reagent with acrolein acetal, transition metal catalysts, for example, palladium catalysts such as tetrakistriphenyl-phosphine palladium, and tristriphenylphosphine palladium chloride; and nickel catalysts such as nickel dppp complex.

It is preferable that such a catalyst be employed in an amount of 0.1 to 5 wt. % of the amount of the substrate materials in this reaction.

Step 2-22

In this step, the aldehyde derivative of formula (IV-1A) is produced from the benzofuran derivative of formula (IV-B) in the presence of an acid.

Specific examples of the acid for use in the reaction in this step include inorganic acids such as sulfuric acid and hydrochloric acid; and organic acids such as p-toluene sulfonic acid, and pyridine p-toluene sulfonate.

A catalytic amount of such an acid is sufficient for this reaction.

The reaction can be carried out either with or without a solvent. If a solvent is employed, ethers such as ether, THF, and dioxane, and mixed solvents of the ethers and water can be employed. The reaction can be carried out at temperatures of 0° C. to 100° C.

Step 2-23

In this step, an acetal derivative of formula (IV-14) is produced by preparing a Grignard reagent from the halogenated compound of formula (IV-9) in the same manner as in Step 2-21, and then allowing the Grignard reagent to react with acrolein acetal and then with an alcohol compound with a formula of $R_{12}OH$ in the presence of an acid catalyst.

As the alcohol of formula $R_{12}OH$ for use in this step, for instance, monohydric alcohols such as methanol, ethanol and propanol can be employed. Furthermore, dihydric alcohols, for instance, glycols such as ethylene glycol, and propylene glycol, can also be employed. In this case, cyclic acetal derivatives can be produced.

As the acid catalyst, the same acids as employed in Step 2-22 can be employed.

Step 2-24

In this step, the aldehyde derivative of formula (IV-1A) is produced from the acetal derivative of formula (IV-IV) in the presence of an acid.

The acids and solvents employed in this reaction, and the reaction conditions are respectively the same as in Step 2-22.

The aldehyde compound of the previously mentioned formula (IV-1B) can be prepared in accordance with the previously mentioned Steps 2-10 and 2-11 by producing the chroman derivative of formula (IV-15) from the previously mentioned phenol compound of formula (II-1) as shown below:

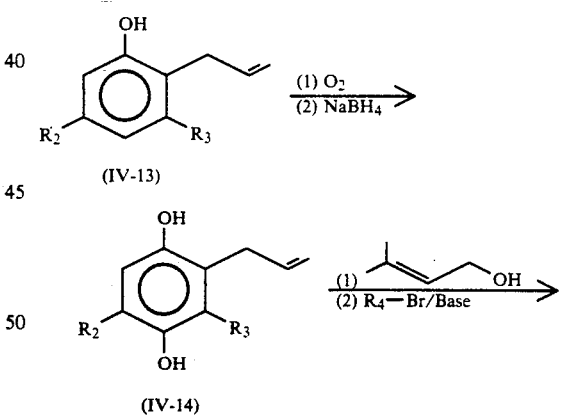

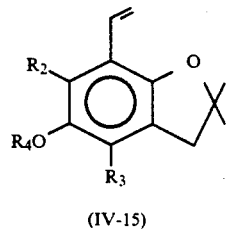

wherein $R_2$, $R_3$ and $R_4$ are respectively the same as defined previously.

The aldehyde compound of the previously mentioned formula (IV-1C) can be prepared from a cyano derivative of formula (IV-11) in accordance with the following reaction scheme:

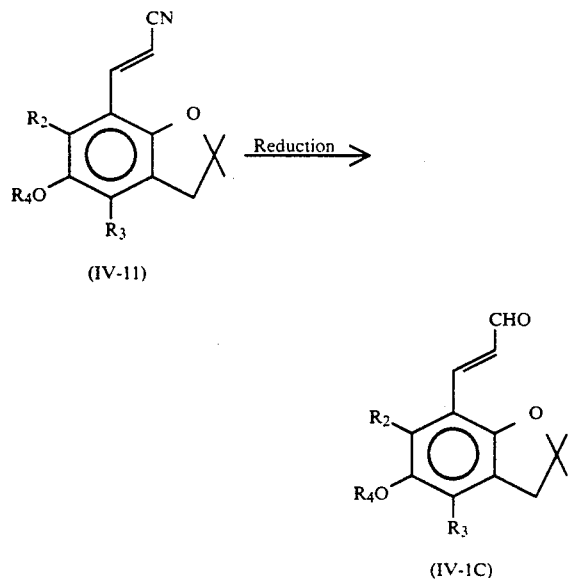

wherein $R_2$, $R_3$ and $R_4$ are respectively the same as defined previously.

The aldehyde compound of the previously mentioned formula (IV-1D) can be prepared from an aldehyde derivative of formula (IV-16) in accordance with the following reaction scheme:

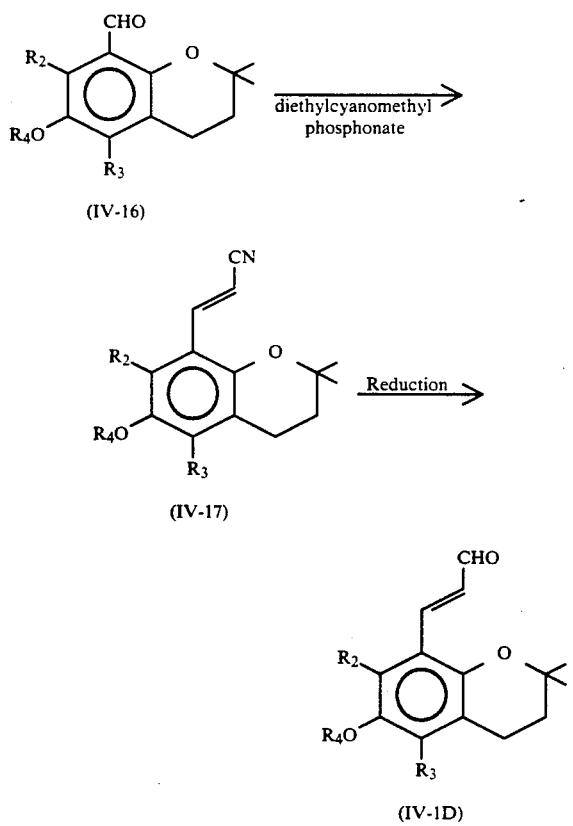

wherein $R_2$, $R_3$ and $R_4$ are respectively the same as defined previously.

EXAMPLE 1

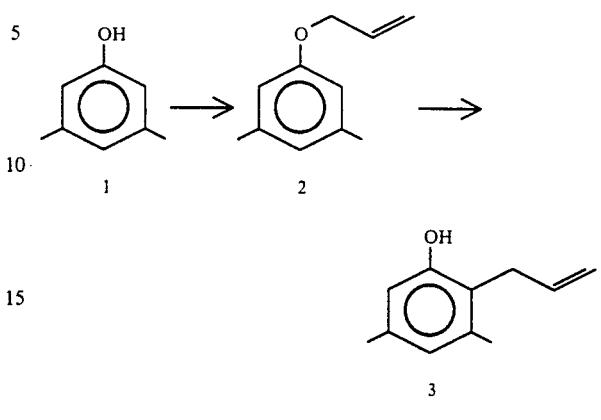

46.73 g (383 mmol) of 3,5-dimethylphenol (Compound No. 1) was dissolved in 100 ml of methyl ethyl ketone. To this solution, 55.6 g (460 mmol) of allyl bromide and 79.3 g (575 mmol) of anhydrous potassium carbonate were added. The thus obtained mixture was refluxed overnight under an argon atmosphere. The reaction mixture was then extracted with hexane. The extract was washed with a saturated aqueous solution of sodium chloride, dried over anhydrous magnesium sulfate, and concentrated, whereby 65.0 g of a crude 3,5-dimethyl-1-(2-propenyloxy)benzene (Compound No. 2) was obtained as a colorless oil.

$^1$H NMR (CDCl$_3$, 300 MHz) δ2.28(s, 6H), 4.50(ddd, J=5.4, 1.5 and 1.5 Hz, 2H), 5.27(ddd, J=10.5, 1.5 and 1.5 Hz, 1H), 5.40(ddd, J=17.4, 1.5 and 1.5 Hz, 1H), 6.05(ddt, J=17.4, 10.5 and 5.4 Hz, 1H), 6.55(s, 2H), 6.60(s, 1H) ppm.

IR (liquid film) 3088, 3026, 1617, 1597 cm$^{-1}$.

65.0 g of a crude Compound No. 2 was dissolved in 200 ml of N,N-dimethylaniline. The mixture was then stirred under an argon atmosphere at 200° C. for 2 days. After the completion of the reaction, the reaction mixture was added to 1N hydrochloric acid. A reaction product was extracted with ethyl acetate. The extraction layer was then subjected to a reverse extraction by use of a 1N aqueous solution of sodium hydroxide. The aqueous layer was then made acidic by a 6N hydrochloric acid aqueous solution and was extracted with hexane. The extract layer was washed with a saturated aqueous solution of sodium hydrogencarbonate and then with a saturated aqueous solution of sodium chloride, dried over anhydrous magnesium sulfate, and condensed, whereby 3,5-dimethyl-2-(2-propenyl)phenol (Compound No. 3) was obtained in a yield of 43.0 g (66.0%).

Compound No. 3 is as yellow needles, with a melting point of 46.0°–47.5° C. when recrystallized from ethyl acetate.

$^1$H NMR (CDCl$_3$, 300 MHz) δ2.24(s, 6H), 3.38(d, J=6.0 Hz, 2H), 4.77(s, 1H), 5.02(d with fine coupling, J=17.1 Hz, 1H), 5.05(d with fine coupling, J=10.2 Hz, 1H), 5.95(ddt, J=17.1, 10.2 and 4.2 Hz, 1H), 6.50(s, 1H), 6.60(s, 1H) ppm.

IR (KBr) 3348, 2984, 2932, 1736, 1625 cm$^{-1}$.

EXAMPLE 2

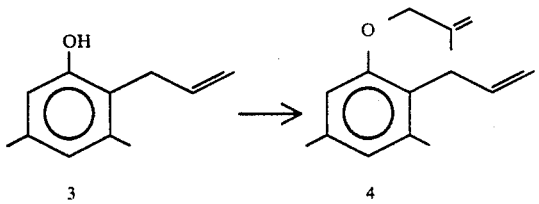

22.56 g (139.2 mmol) of Compound No. 3 synthesized in Example 1 was dissolved in 75 ml of a mixed solvent consisting of 25 ml of N,N-dimethylformamide (hereinafter referred to as DMF) and 75 ml of ethylene glycol dimethyl ether (hereinafter referred to as DME). To this solution, 57.6 g (417.6 mmol) of anhydrous potassium carbonate and 15.13 g (167.1 mmol) of methallyl chloride were added. The thus obtained mixture was refluxed by use of an oil bath at 105° C. for 10 hours. After the completion of the reaction, the reaction mixture was added to water, and a reaction product was extracted with hexane. The extract layer was washed with a saturated aqueous solution of sodium chloride, dried over anhydrous magnesium sulfate and concentrated, whereby a crude 3,5-dimethyl-1-(2-methyl-2-propenyloxy)-2-(2-propenyl)benzene (Compound No. 4) was obtained in a yield of 25.28 g (84.0%) as a light yellow oil.

The thus obtained Compound No. 4 was subjected to the next reaction without purification.

$^1$H NMR (CDCl$_3$, 300 MHz) δ1.82(s, 3H), 2.25(s, 3H), 2.28(s, 3H), 3.42(d, J=6.6 Hz, 2H), 4.39(s, 2H), 4.90~4.98(m, 3H), 5.10(s, 1H), 5.84~5.96 (m, 1H), 6.54(s, 1H), 6.61(s, 1H) ppm.

IR (liquid film) 2928, 1652 cm$^{-1}$.

EXAMPLE 3

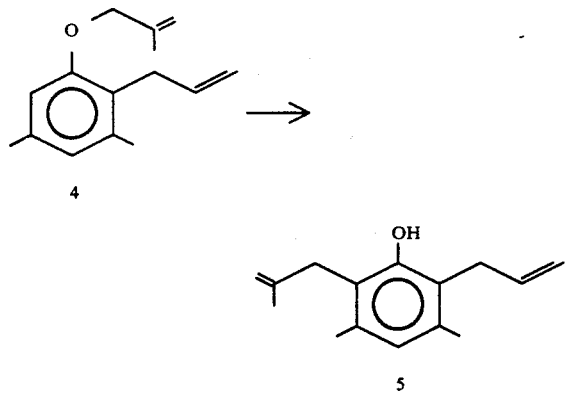

1.465 g of Compound No. 4 synthesized in Example 2 was dissolved in 5 ml of N,N-diethylaniline. This solution was refluxed by use of an oil bath at 210° for 5 hours. After the completion of the reaction, the reaction mixture was poured into 1N hydrochloric acid and extracted with ethyl acetate. The extract layer was washed with water, and then with a saturated aqueous solution of sodium chloride, dried over anhydrous magnesium sulfate, and concentrated.

The concentrated product was chromatographed on silica gel and eluted with a mixed solvent of ethyl acetate and hexane (1:10), whereby 3,5-dimethyl-6-(2-methyl-2-propenyl)-2-(2-propenyl)phenol (Compound No. 5) was obtained as a light yellow oil in a yield of 1.02 g (69.7%).

$^1$H NMR (CDCl$_3$, 300 MHz) δ1.77(s, 3H), 2.22(s, 3H), 2.24(s, 3H), 3.35(s, 2H), 3.39(d with fine coupling, J=4.5 Hz, 2H), 4.66(s, 1H), 4.84(s, 1H), 4.98(d with fine coupling, J=17.1 Hz, 1H), 5.03(d with fine coupling, J=10.2 Hz, 1H), 5.12(s, 1H), 5.95(ddt, J=17.1, 10.2 and 4.5 Hz, 1H), 6.30(s, 1H) ppm.

IR (liquid, film) 3550, 2984, 2932, 1639 cm$^{-1}$.

EXAMPLE 4

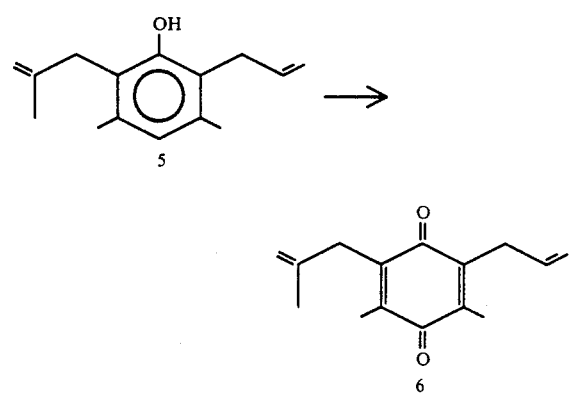

432 mg (2.00 mmol) of Compound No. 5 synthesized in Example 4 and 65 mg (0.2 mmol) of salcomine were added to 10 ml of ethanol. The mixture was stirred in an atmosphere of oxygen at room temperature for 3 days. After the completion of the reaction, the reaction mixture was concentrated. To this concentrated reaction mixture, a mixed solvent of hexane and ethyl acetate was added. The mixture was then filtered through a celite filter. The filtrate was concentrated, chromatographed on silica gel and eluted with a mixed solvent of ethyl acetate and hexane (1:10), whereby 3,5-dimethyl-2-(2-methyl-2-propenyl)-6-(2-propenyl)-p-benzoquinone (Compound No. 6) was obtained as a yellow oil in a yield of 326 mg (70.9%).

$^1$H NMR (CDCl$_3$, 300 MHz) δ1.76(s, 3H), 2.02(s, 3H), 2.05(s, 3H), 3.21(s, 2H), 3.26(d, J=5.4 Hz, 2H), 4.53(s, 1H), 4.76(s with fine coupling, 1H), 5.03(d with fine coupling, J=17.7 Hz, 1H), 5.03(d with fine coupling, J=9.9 Hz, 1H), 5.76(ddt, J=17.7, 9.9 and 5.4 Hz, 1H) ppm.

IR (liquid, film) 2984, 2932, 1648 cm$^{-1}$.

EXAMPLE 5

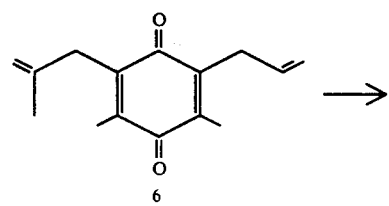

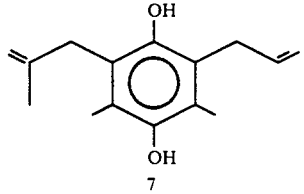

310 mg of Compound No. 6 synthesized in Example 4 was dissolved in 2 ml of dichloromethane. To this solution, 56 mg (1.48 mmol) of sodium borohydride was added. To this mixture, several drops of methanol were added until the color of the mixture turned from red to white yellow. The reaction mixture was then cooled to 0° C. and stirred for 130 minutes. To this mixture, 22 mg (0.58 mmol) of sodium borohydride was added, and then several drops of methanol were further added. The reaction mixture was stirred for 2 hours. The reaction mixture was then added to a saturated aqueous solution of ammonium chloride and extracted with ethyl acetate. The extract layer was washed with water and then with a saturated aqueous solution of sodium chloride, dried over anhydrous magnesium sulfate, concentrated, chromatographed on silica gel, eluted with a mixed solvent of ethyl acetate and hexane (1:6), whereby 3,5-dimethyl-2-(2-methyl-2-propenyl)-6-(2-propenyl)hydroquinone (Compound No. 7) was obtained in a yield of 240 mg (76.6%).

Compound No. 7 is in the form of colorless crystals, with a melting point of 97.0°-99.0° C. when recrystallized from a mixed solvent of diethyl ether and hexane.

$^1$H NMR (CDCl$_3$, 300 MHz) δ1.79(s, 3H), 2.17(s, 3H), 2.18(s, 3H), 3.37(s, 2H), 3.43(d, J=5.7 Hz, 1H), 4.28(s, 1H), 4.61(s with fine coupling, 1H), 4.68(s, 1H), 4.83(s with fine coupling, 1H), 4.95(d with fine coupling, J=17.1 Hz, 1H), 5.03(d with fine coupling, J=10.5 Hz, 1H), 5.95(ddt, J=17.1, 10.5 and 5.7 Hz, 1H) ppm.

IR (KBr) 3478, 1641 cm$^{-1}$.

Mass (m/z, %) 232 (M+, 100), 176(29), 161(12), 91(16), 43(36), 41(24).

EXAMPLE 6

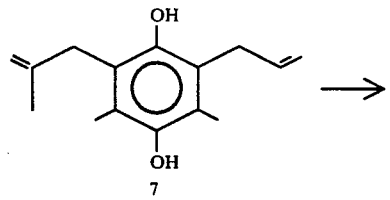

165 mg (0.711 mmol) of Compound No. 7 synthesized in Example 5 was dissolved in 2 ml of dichloromethane. To this solution, 121 mg (0.853 mmol) of boron trifluoride etherate was added and the mixture was stirred in a stream of argon for 25 minutes. The reaction mixture was then added to a saturated aqueous solution of sodium hydrogencarbonate, and extracted with ethyl acetate. The extract layer was washed with water and then with a saturated aqueous solution of sodium chloride, dried over anhydrous magnesium sulfate, and concentrated. The concentrated product was chromatographed on silica gel, and eluted with a mixed solvent of ethyl acetate and hexane (1:6), whereby 2,3-dihydro-5-hydroxy-7-(2-propenyl)-2,2,4,6-tetramethylbenzo[b]furan (Compound No. 8) was obtained in a yield of 152 mg (92.1%).

Compound No. 8 is in the form of colorless columns, with a melting point of 93.0°-94.8° C. when recrystallized from a mixed solvent of diethyl ether and hexane.

$^1$H NMR (CDCl$_3$, 300 MHz) δ1.43(s, 6H), 2.11(s, 3H), 2.13(s, 3H), 2.91(s, 2H), 3.31(d, with fine coupling, J=6.0 Hz, 2H), 4.13(s, 1H), 4.94(d with fine coupling, J=17.1 Hz, 1H), 4.95(d with fine coupling, J=10.3 Hz, 1H), 5.88(ddt, J=17.1, 10.3 and 6.0 Hz, 1H) ppm.

IR (KBr) 3530, 2978, 1640 cm$^{-1}$.

Mass (m/z, %) 232 (M+, 100), 176(21), 161(7), 91(10), 43(28), 41(16).

EXAMPLE 7

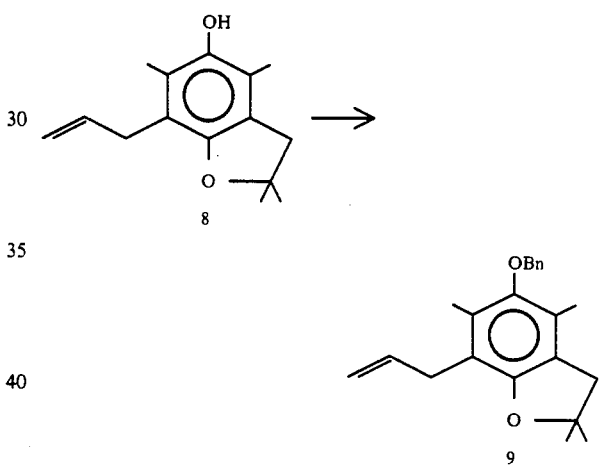

182 mg (0.784 mmol) of Compound No. 8 synthesized in Example 6 was dissolved in a mixed solvent consisting of 0.5 ml of DMF and 1.5 ml of DME. To this solution, 161 mg (0.94 mmol) of benzyl bromide and 325 mg (2.35 mmol) of anhydrous potassium carbonate were added. The mixture was refluxed in an atmosphere of argon for 2 hours and 30 minutes.

After the completion of the reaction, the reaction mixture was cooled to room temperature and poured into water. The mixture was extracted with hexane. The extract layer was washed with water and then with a saturated aqueous solution of sodium chloride, dried over anhydrous magnesium sulfate, concentrated, chromatographed on silica gel, and eluted with a mixed solvent of ethyl acetate and hexane (1:9), whereby 5-benzyloxy-3,3-dihydro-7-(2-propenyl)-2,2,4,6-tetramethylbenzo[b]furan (Compound No. 9) was obtained in a yield of 228 mg (90.5%).

Compound No. 9 is in the form of colorless crystals, with a melting point of 35.5°-36.2° C. when recrystallized from ethanol and water.

$^1$H NMR (CDCl$_3$, 300 MHz) δ1.45(s, 6H), 2.16(s, 3H), 2.20(s, 3H), 2.91(s, 2H), 3.31(d, J=6.9 Hz, 1H), 4.71(s, 2H), 4.95(d with fine coupling, J=16.2 Hz, 1H), 4.96(d with fine coupling, J=10.2 Hz, 1H), 5.90(ddt, J=16.2, 10.2 and 6.9 Hz, 1H), 7.30~7.54(m, 5H) ppm.
IR (KBr) 2980, 1642 cm$^{-1}$.
Mass (m/z, %) 322 (M$^+$, 6), 231(100), 175(5), 91(21).

EXAMPLE 8

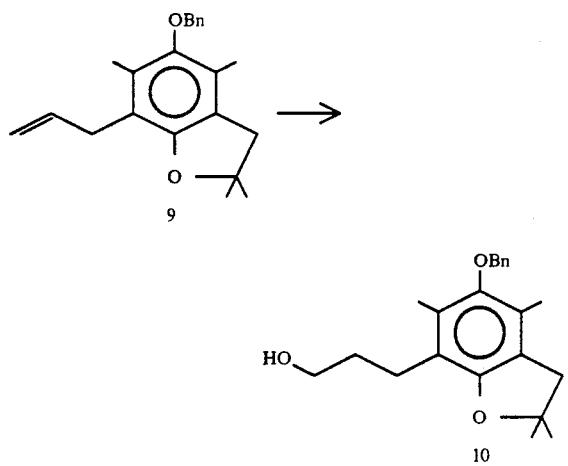
9

10

35 ml of anhydrous tetrahydrofuran (hereinafter referred to as THF) was placed in a flask filled with argon gas. In this flask, 4.65 g (19.1 mmol) of 9-borabicyclo[3.3.1]nonane (hereinafter referred to as 9-BBN dimer) was further placed at room temperature. To this mixture, 9.68 g (30.1 mmol) of Compound No. 9 synthesized in Example 7, which was dissolved in 5 ml of anhydrous THF was added. The reaction mixture was stirred in a stream of argon at room temperature for 1 hour. 3.64 ml (60.1 mmol) of ethanol was added to this reaction mixture. The reaction mixture was stirred for 20 minutes. With addition of 30.1 ml (60.2 mmol) of a 2N aqueous solution of sodium hydroxide, the reaction mixture was cooled to 0° C. To this reaction mixture, 13.6 ml (120.2 mmol) of a 30% aqueous solution of hydrogen peroxide was gradually added. After the elevation of the temperature of the reaction mixture to room temperature, the reaction mixture was refluxed for 1 hour.

The reaction mixture was then cooled to room temperature and extracted with ethyl acetate. The extract layer was subsequently washed with an aqueous solution of sodium thiosulfate, water, and a saturated aqueous solution of sodium chloride, dried over anhydrous magnesium sulfate, and concentrated. The concentrated product was chromatographed on silica gel and eluted with a mixed solvent of ethyl acetate and hexane (1:3), whereby 3-[5-benzyloxy-2,3-dihydro-2,3,4,6-tetramethylbenzo[b]furan-7-yl]propanol (Compound No. 10) was obtained in a yield of 9.19 g (89.9%).

Compound No. 10 is as colorless needles, with a melting point of 42.5°-43.5° C. when recrystallized from hexane.

$^1$H NMR (CDCl$_3$, 300 MHz) δ1.49(s, 6H), 1.70~1.80(m, 2H), 2.16(s, 3H), 2.22(s, 3H), 2.70(t, J=6.3 Hz, 2H), 2.94(s, 2H), 3.51(t, J=5.4 Hz, 1H), 4.72(s, 2H), 7.30~7.55(m, 5H) ppm.
IR (KBr) 3468, 2944 cm$^{-1}$.
Mass (m/z, %) 340 (M$^+$, 7), 249(100), 205(19), 91(32).

EXAMPLE 9

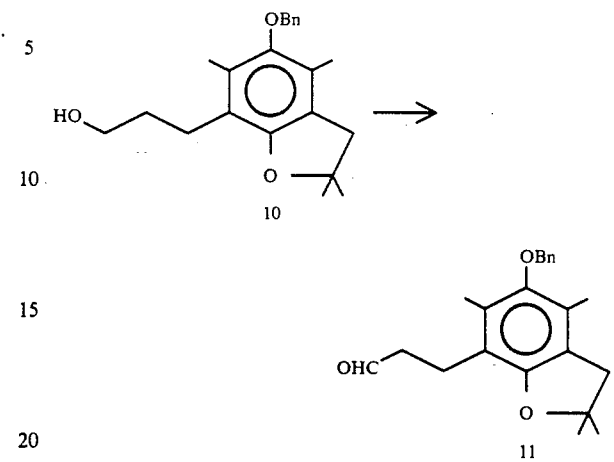
10

11

4.0 ml (55.6 mmol) of dimethylsulfide was added to 100 ml of toluene in a stream of argon at 0° C. To this mixture, 5.33 g (39.9 mmol) of N-chlorosuccinimide was added. The reaction mixture was stirred for 30 minutes.

The reaction mixture was cooled to −25° C. To this reaction mixture, there was added 7.0 g (21.5 mmol) of Compound No. 10 synthesized in Example 10. The mixture was then stirred at −20° to −35° C. for 2 hours.

4.04 g (39.9 mmol) of triethylamine was added dropwise to the above reaction mixture and the temperature of the reaction mixture was raised to room temperature.

The reaction mixture was washed with water, 1N hydrochloric acid, a saturated aqueous solution of sodium thiosulfate, an aqueous solution of sodium hydrogencarbonate, and a saturated aqueous solution of sodium chloride, dried over anhydrous magnesium sulfate, and concentrated.

The concentrated product was chromatographed on silica gel and eluted with a mixed solvent of ethyl acetate and hexane (2:9), and recrystallized from hexane, whereby 3-[5-benzyloxy-2,3-dihydro-2,2,4,6-tetramethyl-benzo[b]furan-7-yl]propanal (Compound No. 11) was obtained in a yield of 6.19 g (88.9%).

The thus obtained Compound No. 11 was in the form of colorless crystals, with a melting point of 100.0°-101.5° C.

$^1$H NMR (CDCl$_3$, 300 MHz) δ1.45(s, 6H), 2.16(s, 3H), 2.22(s, 3H), 2.63(t with fine coupling, J=7.8 Hz, 2H), 2.89(t, J=7.8 Hz, 2H), 2.90(s, 2H), 4.71(s, 2H), 7.30~7.55(m, 5H), 9.82(s with fine coupling, 1H) ppm.
IR (KBr) 2904, 2864, 2740, 1718 cm$^{-1}$.
Mass (m/z, %) 338 (M$^+$, 6), 247(100), 205(21), 203(29), 91(37), 41(9).

EXAMPLE 10

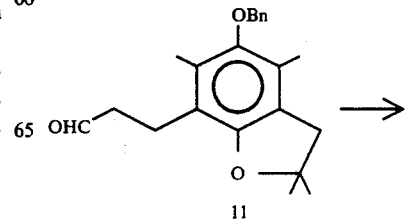
11

-continued

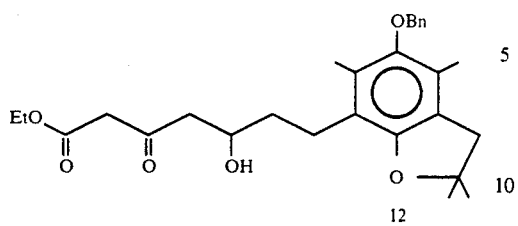

550 mg (13.8 mmol) of a 60% sodium hydride was suspended in 100 ml of anhydrous THF in a stream of argon at 0° C. To this suspension, 1.75 ml (13.8 mmol) of ethyl acetoacetate was added. The mixture was then stirred for 30 minutes, followed by the addition of 8.81 ml (13.8 mmol) of a 15% hexane solution of butyl lithium thereto. The reaction mixture was stirred for 1 hour.

The reaction mixture was then cooled to −78° C. With addition of 10 ml of an anhydrous THF solution containing 3.10 g (9.17 mmol) of Compound No. 11 synthesized in Example 9, the mixture was stirred for 30 minutes.

After the completion of the reaction, water was added to the reaction mixture. After the elevation of the temperature of the mixture to room temperature, the mixture was extracted with ethyl acetate. The extract layer was washed with a saturated aqueous solution of ammonium chloride, water and a saturated aqueous solution of sodium chloride, dried over anhydrous magnesium sulfate, and concentrated.

The concentrated product was chromatographed on silica gel and eluted with a mixed solvent of ethyl acetate and hexane (1:2), whereby ethyl 7-[5-benzyloxy-2,3-dihydro-2,2,4,6-tetramethylbenzo[b]furan-7-yl]-5-hydroxy-3-oxoheptanoate (Compound No. 12) was obtained as a yellow oil in a yield of 3.03 g (70.6%).

$^1$H NMR (CDCl$_3$, 300 MHz) δ1.26(t, J=7.2 Hz, 3H), 1.47(s, 3H), 1.48(s, 3H), 1.54∼1.75(m, 2H), 2.16(s, 3H), 2.21(s, 3H), 2.52∼2.81(m, 4H), 2.93(s, 2H), 3.50(s, 2H), 3.64(d, J=3.3 Hz, 1H), 3.85∼3.98(m, 1H), 4.17(q, J=7.2 Hz, 2H), 4.72(s, 2H), 7.31∼7.57(m, 5H) ppm.

IR (film) 3528, 2980, 2940, 1748, 1716 cm$^{-1}$.

Mass (m/z, %) 468 (M$^+$, 4), 377(61), 331(14), 247(66), 205(52), 203(100), 91(85), 43(82), 31(72).

EXAMPLE 11

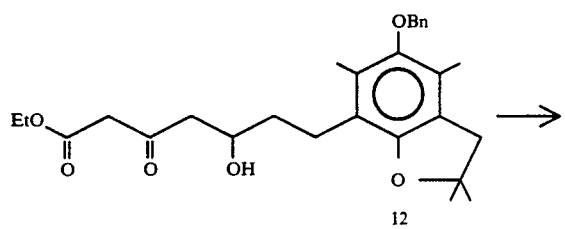

-continued

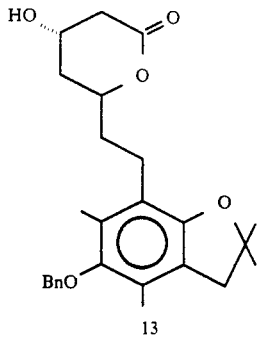

16.5 ml (16.5 mmol) of triethylborane (1.0M THF solution) was added to 80 mg (0.78 mmol) of pivalic acid in a stream of argon at room temperature. The mixture was stirred for 1 hour to obtain a solution. To this solution was added dropwise 50 ml of an anhydrous THF solution of 6.22 g (13.3 mmol) of Compound No. 12 synthesized in Example 10. One hour later, the reaction mixture was cooled to −78° C., and 18 ml of methanol and 430 mg (11.4 mmol) of sodium borohydride were successively added thereto. To this reaction mixture, 28 ml of a 30% aqueous solution of hydrogen peroxide was added. After the elevation of the reaction mixture to room temperature, the reaction mixture was stirred for 1 hour.

The reaction mixture was made acidic with addition of 1N hydrochloric acid and extracted with ethyl acetate. The extract layer was washed with water, a saturated aqueous solution of sodium thiosulfate, and a saturated aqueous solution of sodium chloride, dried over anhydrous magnesium sulfate, and concentrated.

The concentrated product was dissolved in 50 ml of toluene. The solution was refluxed for 4 hours. After the completion of the reaction, the solvent was distilled away, and the residue was chromatographed on silica gel, and eluted with a mixed solvent of ethyl acetate and hexane (2:1), whereby trans-(±)-6-(5-benzyloxy-2,3-dihydro-2,2,4,6-tetramethylbenzo[b]furan-7-ethyl-4-hydroxytetrahydropyran-2-one (Compound No. 13) was obtained in a yield of 4.74 g (84.12%).

Compound No. 13 is as colorless columns, with a melting point of 121.0°-122.0° C. when recrystallized from a mixed solvent of ethyl acetate and hexane.

$^1$H NMR (CDCl$_3$, 300 MHz) δ1.45(s, 3H), 1.46(s, 3H), 1.75∼2.04(m, 4H), 2.16(s, 3H), 2.24(s, 3H), 2.45∼2.82(m, 4H), 2.90(s, 2H), 4.35∼4.45(m, 1H), 4.66∼4.77(m, 1H), 4.71(s, 2H), 7.32∼7.53(m, 5H) ppm.

IR (KBr) 3520, 2974, 2934, 1734, 1594 cm$^{-1}$.

Mass (m/z, %) 424 (M$^+$, 6), 333(71), 315(11), 229(11), 205(27), 203(100), 61(91).

EXAMPLE 12

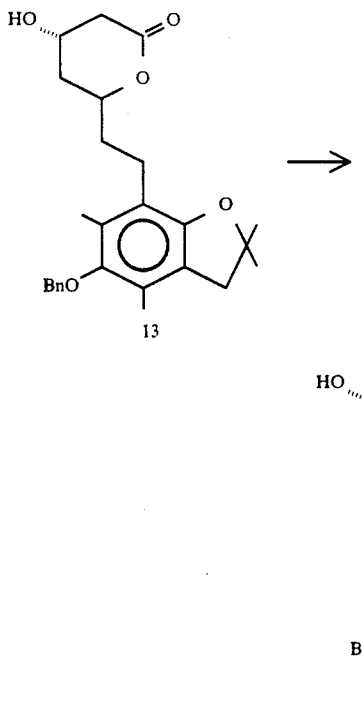

50 mg of Compound No. 13 synthesized in Example 11 was dissolved in 1 ml of methanol. To this solution was added 10 mg of a 10% Pd/C, and the mixture was stirred in an atmosphere of hydrogen at room temperature for 2 hours.

The reaction mixture was diluted with ethyl acetate and dichloromethane and filtered through a celite filter. The filtrate was concentrated. The concentrated product was chromatographed on silica gel and eluted with a mixed solvent of ethyl acetate and hexane (1:1) and then with ethyl acetate, whereby trans-(±)-6-(2,3-dihydro-5-hydroxy-2,2,4,6-tetramethylbenzo[b]furan-7-yl)ethyl-4-hydroxytetrahydropyran-2-one (Compound No. 14) was obtained in a yield of 33 mg (83.7%).

Compound No. 14 is as colorless columns, with a melting point of 131.0°–133.0° C. when recrystallized from ethyl acetate and hexane.

$^1$H NMR (CDCl$_3$, 300 MHz) δ1.42(s, 3H), 1.44(s, 3H), 1.70~1.96(m, 4H), 1.97~2.06(m, 1H), 2.10(s, 3H), 2.18(s, 3H), 2.61(ddd, J=17.4, 3.9 and 1.5 Hz, 1H), 2.76(dd, J=17.4 and 4.8 Hz, 1H), 2.65~2.81(m, 2H), 2.90(s, 2H), 4.18(s, 1H), 4.35~4.43(m, 1H), 4.64~4.75(m, 1H) ppm.

IR (KBr) 3546, 2972, 2930, 1684 cm$^{-1}$.

Mass (m/z, %) 334 (M+, 100), 205(60), 204(44), 189(26), 43(45).

EXAMPLE 13

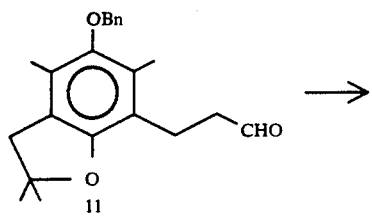

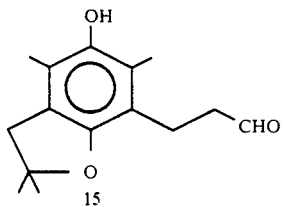

2.27 g (6.72 mmol) of Compound No. 11 synthesized in Example 9 was dissolved in 7.5 ml of ethyl acetate. To this solution, 227 mg of a 10% Pd/C was added. The mixture was placed in an atmosphere of hydrogen, and 2.5 ml of methanol was added thereto. The reaction mixture was stirred at room temperature for 20 minutes, and 100 mg of the 10% Pd/C was further added thereto. The reaction mixture was stirred for 2 days.

The reaction mixture was then diluted with ethyl acetate and filtered through a celite filter. The filtrate was concentrated and crystallized from hexane, whereby 3-[2,3-dihydro-5-hydroxy-2,2,4,6-tetramethylbenzo[b]furan-7-yl]propanal (Compound No. 15) was obtained as colorless crystals with a melting point of 100.8°–102.5° C. in a yield of 1.475 g (88.5%).

$^1$H NMR (CDCl$_3$, 300 MHz) δ1.43(s, 6H), 2.10(s, 3H), 2.16(s, 3H), 2.61(td with fine coupling, J=7.7 and 1.8 Hz, 2H), 2.89(t, J=7.7 Hz, 2H), 2.90(s, 2H), 4.15(s, 2H), 9.80(t, J=1.8 Hz, 1H) ppm.

IR (KBr) 3380, 2976, 1703 cm$^{-1}$.

Mass (m/z, %) 248 (M+, 90), 205(93), 189(55), 91(49), 77(39), 55(26), 43(100), 39(82), 29(86).

EXAMPLE 14

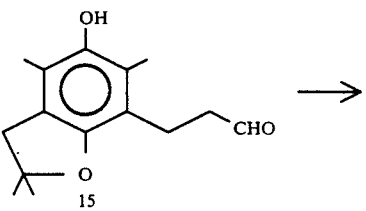

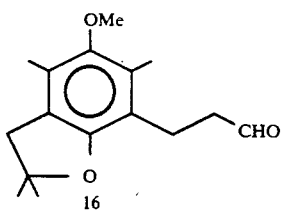

1.00 g (4.03 mmol) of Compound No. 15 synthesized in Example 13 was dissolved in a mixed solvent of 1 ml of DMF and 3 ml of DME. To this solution, 3.63 ml (4.23 mmol) of methyl iodide and 1.67 g (12.1 mmol) of anhydrous potassium carbonate were added. This mixture was refluxed in an atmosphere of argon for 4 hours.

After the completion of the reaction, with the temperature of the reaction mixture lowered to room temperature, the reaction mixture was extracted with ethyl acetate. The extract layer was washed with a saturated aqueous solution of sodium chloride, dried over anhydrous magnesium sulfate, and condensed. The condensed product was chromatographed on silica gel and eluted with a mixed solvent of ethyl acetate and hexane (1:10), and then with ethyl acetate, whereby 3-[2,3-dihydro-5-methoxy-2,2,4,6-tetramethylbenzo[b]furan-7-yl]propanal (Compound No. 16) was obtained in a yield of 601 mg (56.9%).

Compound No. 16 is in the form of colorless columns, with a melting point of 52.0°-54.0° C. when recrystallized from a mixed solvent of ethyl acetate and hexane.

$^1$H NMR (CDCl$_3$, 300 MHz) δ1.44(s, 6H), 2.13(s, 3H), 2.20(s, 3H), 2.62(td, J=7.8 and 1.8 Hz, 2H), 2.87(t, J=7.8 Hz, 2H), 2.89(s, 2H), 3.64(s, 3H), 9.81(t, J=1.8 Hz, 1H) ppm.

IR (KBr) 2978, 2950, 2818, 1723 cm$^{-1}$.

Mass (m/z, %) 262 (M$^+$, 100), 247(33), 219(27), 203(44), 191(10), 91(17), 53(16), 43(22), 41(28), 39(20), 29(20).

EXAMPLE 15

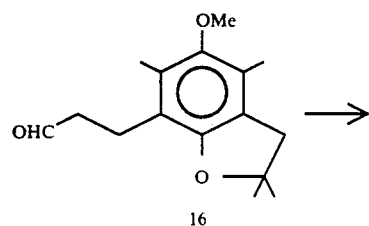

16

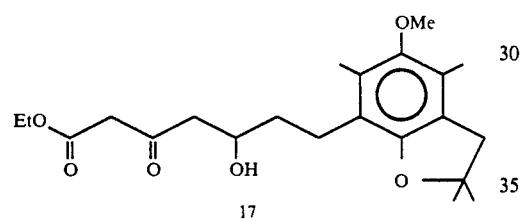

17

152 mg (3.82 mmol) of a 60% sodium hydride was suspended in 70 ml of anhydrous THF at 0° C. in a stream of argon. To this suspension, 484 mg (3.8 mmol) of ethyl acetoacetate was added. The mixture was stirred for 35 minutes, followed by the addition of 2.43 ml (3.80 mmol) of a 15% hexane solution of butyl lithium thereto. The mixture was further stirred for 35 minutes.

The reaction mixture was cooled to −78° C. and 3 ml of an anhydrous THF solution of 600 mg (2.29 mmol) of Compound No. 16 synthesized in Example 14 was added thereto. The reaction mixture was stirred for 2 hours.

A saturated aqueous solution of ammonium chloride was added to this reaction mixture and the temperature thereof was raised to room temperature. The reaction mixture was extracted with ethyl acetate. The extract layer was washed with a saturated aqueous solution of ammonium chloride, water, and a saturated aqueous solution of sodium chloride, dried over anhydrous magnesium sulfate, and concentrated. The concentrated product was chromatographed on silica gel, and eluted with a mixed solvent of ethyl acetate and hexane (1:2), whereby ethyl 7-[2,3-dihydro-5-methoxy-2,3,4,6-tetramethylbenzo[b]furan-7-yl]-5-hydroxy-3-oxoheptanoate (Compound No. 17) was obtained as a light yellow oil in a yield of 469 mg (52.5%).

$^1$H NMR (CDCl$_3$, 300 MHz) δ1.26(t, J=7.2 Hz, 3H), 1.46(s, 3H), 1.47(s, 3H), 2.13(s, 3H), 2.19(s, 3H), 2.52~2.80(m, 4H), 2.92(s, 2H), 3.49(s, 2H), 3.60~3.65(m, 1H), 3.64(s, 3H), 3.85~3.95 (m, 1H), 4.17(q, J=7.2 Hz, 2H) ppm.

IR (liquid, film) 3528, 2980, 2940, 1750, 1718 cm$^{-1}$.

Mass (m/z, %) 392 (M$^+$, 51), 346(17), 262(25), 219(64), 203(53), 189(9), 115(13), 91(17), 53(13), 43(100), 41(25), 31(25), 29(84)

EXAMPLE 16

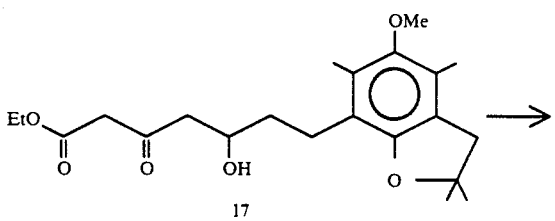

17

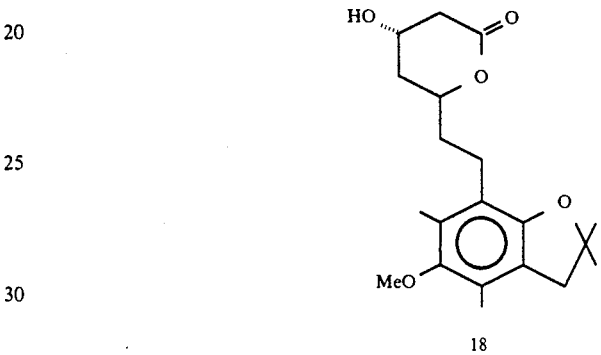

18

1.26 ml (1.26 mmol) of triethylborane (1.0M THF solution) was added to 6 mg (0.063 mmol) of pivalic acid (0.063 mmol) at room temperature in a stream of argon. The mixture was stirred for 1 hour. To this mixture, 3 ml of an anhydrous THF solution of 449 mg (1.145 mmol) of Compound No. 19 synthesized in Example 15 was added dropwise. One hour later, the reaction mixture was cooled to −78° C. To this reaction mixture, 1.79 ml of methanol and 48 mg (1.26 mmol) of sodium borohydride were successively added. 55 minutes later, to this reaction mixture, 4.66 ml of a 5N aqueous solution of sodium hydroxide and 4.66 ml of a 30% aqueous solution of hydrogen peroxide were added. With the temperature of the reaction mixture raised to room temperature, the reaction mixture was stirred overnight.

The reaction mixture was then made acidic with addition of 1N hydrochloric acid and extracted with ethyl acetate. The extract layer was washed with water, a saturated aqueous solution of sodium thiosulfate, and a saturated aqueous solution of sodium chloride, dried over anhydrous magnesium sulfate, and concentrated.

The concentrated product was dissolved in 3 ml of toluene and the solution was refluxed for 5 hours. After the completion of the reaction, the solvent was distilled away from the reaction mixture. The reaction mixture was chromatographed on silica gel, and eluted with a mixed solvent of ethyl acetate and hexane (2:1), whereby trans-(±)-6-(2,3-dihydro-5-methoxy-2,2,4,6-tetramethylbenzo[b]furan-7-yl)ethyl-4-hydroxytetrahydropyran-2-one (Compound No. 18) was obtained in a yield of 260 mg (62.7%).

Compound No. 18 is in the form of colorless columns when recrystallized from a mixed solvent of diethyl ether and hexane and has a melting point of 112.0°-113.5° C.

$^1$H NMR (CDCl$_3$, 300 MHz) δ1.43(s, 3H), 1.44(s, 3H), 1.72~2.08(m, 5H), 2.13(s, 3H), 2.21(s, 3H), 2.61(ddd, J=17.4, 3.9 and 1.5 Hz, 1H), 2.76(dd, J=17.4 and 5.1 Hz, 1H), 2.60~2.80(m, 2H), 2.89(s, 2H), 3.64(s, 3H), 4.35~4.44(m, 1H), 4.65~4.78(m, 1H) ppm.

IR (KBr) 3502, 2978, 2940, 1708, 1704 cm$^{-1}$.

Mass (m/z, %) 348 (M$^+$, 100), 219(30), 203(58).

EXAMPLE 17

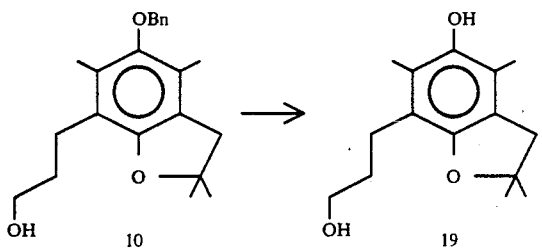

To 30 ml of a mixed solvent of methanol and ethyl acetate (1:1), 6.618 g (19.5 mmol) of Compound No. 10 synthesized in Example 8 and 310 mg of a 10% Pd/C were added. This reaction mixture was stirred at room temperature in an atmosphere of hydrogen under 1 atmospheric pressure for 21 hours. After the completion of the reaction, ethyl acetate was added to the reaction mixture. The reaction mixture was then filtered through a celite filter. The filtrate was condensed and crystallized from a mixed solvent of ethyl acetate and hexane, whereby 3-[2,3-dihydro-5-hydroxy-2,2,4,6-tetramethyl-benzo[b]furan-7-yl]propanol (Compound No. 19) was obtained in a yield of 2.866 g (58.9%). The mother liquor was concentrated and placed on a silica gel column and eluted with a mixed solvent of ethyl acetate and hexane (1:2), whereby Compound No. 19 was further obtained in a yield of 1.568 g (32.2%).

Compound No. 19 is in the form of colorless crystals, when recrystallized from a mixed solvent of diethyl ether and hexane and has a melting point of 122.0°-123.0° C.

$^1$H NMR (CDCl$_3$, 300 MHz) δ1.47(s, 6H), 1.67~1.79(m, 2H), 2.11(s, 3H), 2.16(s, 3H), 2.67~2.75(m, 2H), 2.95(s, 2H), 2.98(t, J=7.0 Hz, 1H), 3.44~3.53(m, 2H), 4.23(s, 1H) ppm.

IR (KBr) 3460, 3336, 2976, 2944 cm$^{-1}$.

Mass (m/z, %) 250 (M$^+$, 60), 205(61), 189(24), 91(27), 53(27), 43(78), 41(57), 31(100).

EXAMPLE 18

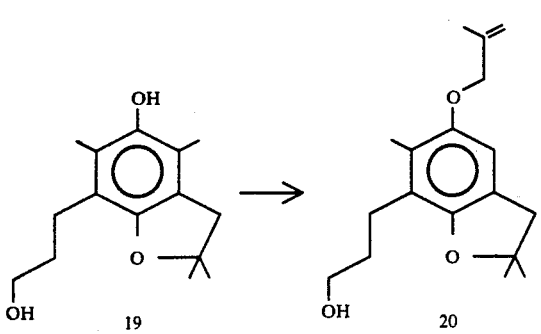

To a mixed solvent consisting of 2 ml of DMF and 3 ml of DME, 500 mg (2.00 mmol) of Compound No. 19 synthesized in Example 17, 500 mg (3.62 mmol) of potassium carbonate, and 0.40 ml (4.05 mmol) of methallyl chloride were added. The reaction mixture was refluxed in an atmosphere of argon for 3 hours. After the completion of the reaction, the reaction mixture was poured into 1N hydrochloric acid. The reaction mixture was then extracted with ethyl acetate. The extract layer was washed with a saturated aqueous solution of sodium chloride two times, dried over magnesium sulfate, and concentrated. The concentrated product was placed on a silica gel column and eluted with a mixed solvent of hexane and ethyl acetate (4:1), whereby 3-[2,3-dihydro-5-(2-methyl-2-propenyloxy)-2,2,4,6-tetramethylbenzo[b]furan-7-yl]propanol (Compound No. 20) was obtained in a yield of 603 mg (99.2%).

Compound No. 18 is in the form of colorless needles, with a melting point of 59.0°-59.5° C. when recrystallized from hexane.

$^1$H NMR (CDCl$_3$, 300 MHz) δ1.48(s, 6H), 1.69~1.79(m, 2H), 1.88(s, 3H), 2.13(s, 3H), 2.19(s, 3H), 2.64~2.73(m, 2H), 2.84~2.96(m, 1H), 2.92(s, 2H), 3.44~3.54(m, 2H), 4.08(s, 2H), 4.97(s With fine coupling, 1H), 5.17(s With fine coupling, 1H) ppm.

IR (KBr) 3488, 2980, 2936, 2868, 1802, 1660 cm$^{-1}$.

Mass (m/z, %) 304 (M$^+$, 7), 249(70), 205(28), 55(100), 29(75).

EXAMPLE 19

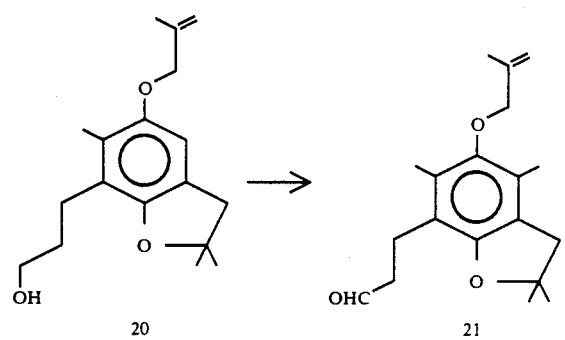

To a mixed solvent consisting of 25 ml of dimethyl sulfoxide and 15 ml of dried THF, 2.25 g (7.40 mmol) of Compound No. 20 synthesized in Example 18, 4.5 ml (32.3 mmol) of triethylamine and 3.5 g (22.0 mmol) of sulfur trioxide pyridine complex were successively added, and the mixture was stirred in an atmosphere of argon at room temperature for 5 hours.

The reaction mixture was poured into 1N hydrochloric acid and extracted with hexane. The extract layer was washed with a saturated aqueous solution of sodium chloride three times, dried over anhydrous magnesium sulfate, and concentrated. The concentrated product was placed on a silica gel column and eluted with a mixed solvent of hexane and ethyl acetate (10:1), whereby 3-[2,3-dihydro-5-(2-methyl-2-propenyloxy)-2,2,4,6-tetra-methylbenzo[b]furan-7-yl]propanal (Compound No. 21) was obtained in a yield of 1.80 g (80.5%).

Compound No. 21 is as colorless columns, with a melting point of 55.5°-56.0° C. when recrystallized from hexane.

$^1$H NMR (CDCl$_3$, 300 MHz) δ1.44(s, 6H), 1.88(s, 3H), 2.12(s, 3H), 2.19(s, 3H), 2.61(td, J=7.8 and 1.8 Hz, 2H), 2.87(t, J=7.8 Hz, 2H), 2.88(s, 2H), 4.06(s, 2H), 4.97(broad s, 1H), 5.17(broad s, 1H), 9.81(t, J=1.8 Hz, 1H) ppm.

IR (KBr) 2984, 2924, 2864, 2816, 2716, 1724, 1662 cm$^{-1}$.

Mass (m/z, %) 302 (M$^+$, 9), 247(100), 205(47), 203(61), 91(24), 55(100), 41(59), 39(57), 29(94), 27(94).

EXAMPLE 20

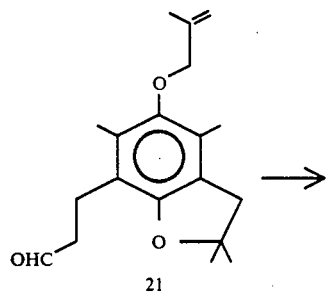

21

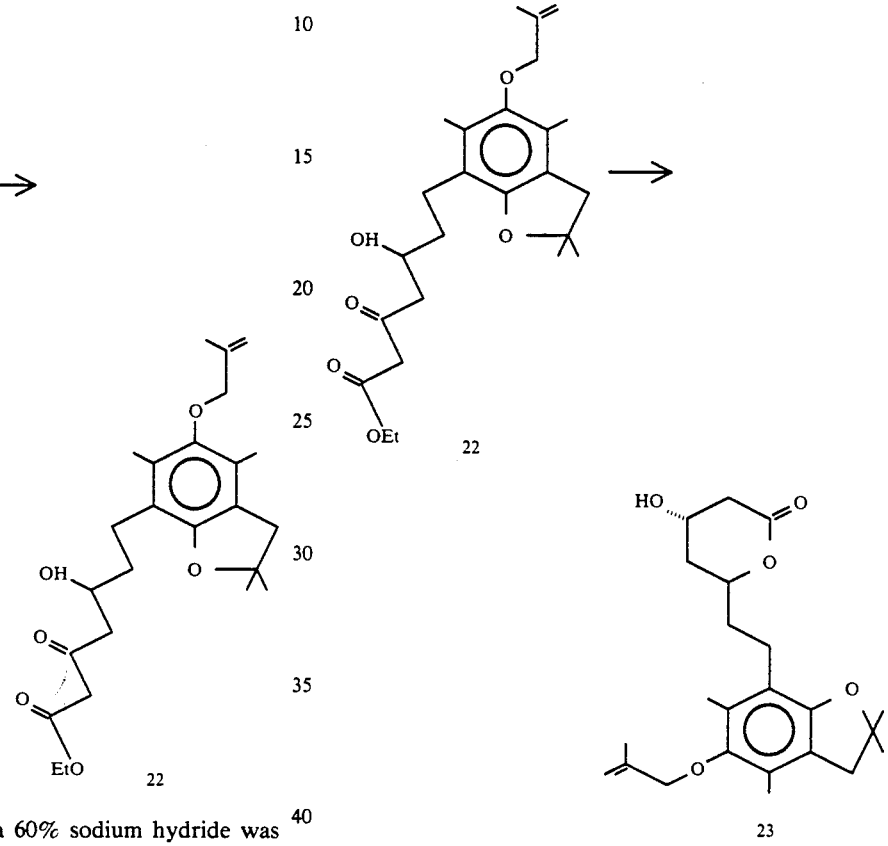

258 mg (6.45 mmol) of a 60% sodium hydride was suspended in 10 ml of dried THF. To this dispersion, 0.83 ml (6.51 mmol) of ethyl acetoacetate was added in a stream of argon at 0° C. To this solution, 4.1 ml (6.41 mmol) of a 15% hexane solution of butyl lithium was added. The mixture was stirred for 25 minutes, and then cooled to −78° C. To this mixture, 1.423 g (4.71 mmol) of Compound No. 21 synthesized in Example 20, which was dissolved in 10 ml of dried THF, was added. The mixture was stirred for 1 hour and 20 minutes. After the completion of the reaction, the reaction mixture was poured into 1N hydrochloric acid. The mixture was then extracted with ethyl acetate. The extract layer was washed with a saturated aqueous solution of sodium chloride three times, dried over anhydrous magnesium sulfate, and concentrated. The concentrated product was placed on a silica gel column and eluted with a mixed solvent of hexane and ethyl acetate (4:1), whereby ethyl 7-[2,3-dihydro-5-(2-methyl-2-propenyloxy)-2,2,4,6-tetramethylbenzo[b]furan-7-yl]-5-hydroxy-3-oxoheptanoate (Compound No. 22) was obtained in a yield of 1.605 g (78.8%).

Compound No. 22 is in the form of colorless columns, with a melting point of 53.5°–55.0° C. when recrystallized from ethyl acetate and hexane.

$^1$H NMR (CDCl$_3$, 300 MHz) δ1.26(t, J=7.1 Hz, 3H), 1.46(s, 3H), 1.47(s, 3H), 1.50~1.75(m, 2H), 1.89(s, 3H), 2.12(s, 3H), 2.18(s, 3H), 2.50~2.81(m, 4H), 2.92(s, 2H), 3.49(s, 2H), 3.64(d with fine coupling, J=3.6 Hz, 1H), 3.84~3.96(m, 1H), 4.08(s, 2H), 4.17(q, J=7.1 Hz, 2H), 4.97(broad s, 1H), 5.17(broad s, 1H) ppm.

IR (KBr) 3572, 2984, 2932, 1744, 1704, 1660 cm$^{-1}$.

Mass (m/z, %) 432 (M$^+$, 2), 377(18), 247(35), 205(28), 203(54), 55(59), 43(85), 29(100), 27(45).

EXAMPLE 21

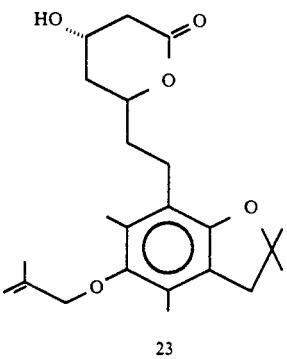

23

22 mg (0.22 mmol) of pivalic acid was added to 5 ml (5.00 mmol) of triethylborane (1M THF solution) in an atmosphere of argon at room temperature, and the mixture was stirred for 1 hour, whereby a solution was obtained. To this solution was added 1.435 g (3.32 mmol) of Compound No. 22 synthesized in Example 20, which was dissolved in 15 ml of dried THF. The mixture was stirred for 1 hour and 20 minutes, and then cooled to −78° C. To this mixture, 5 ml of methanol, and then 140 mg (3.70 mmol) of sodium borohydride were added. The mixture was stirred for 20 minutes. To this mixture, 5 ml of a 5N aqueous solution of sodium hydroxide and 9.0 g (79.4 mmol) of a 30% aqueous solution of hydrogen peroxide were added, and then ice-cooled. To this mixture, 5.5 ml of a 5N aqueous solution of sodium hydroxide was further added, and the mixture was stirred for 1 hour.

The reaction mixture was then poured into 1N hydrochloric acid. The mixture was extracted with ethyl acetate. The extract layer was successively washed with 1N hydrochloric acid, an aqueous solution of sodium thiosulfate, and a saturated aqueous solution of sodium chloride, dried over anhydrous magnesium sulfate, and concentrated. The concentrated product was dissolved in 15 ml of dried toluene. The mixture was refluxed for 6 hours. The thus obtained reaction mixture was placed on a silica gel column and eluted with a mixed solvent of hexane and ethyl acetate (2:1) and then with another mixed solvent of hexane and ethyl acetate (1:1), whereby trans-(±)-6-(2,3-dihydro-5-(2-methyl-2-propenyloxy)-2,2,4,6-tetramethylbenzo[b]furan-7-yl)ethyl-4-hydroxytetrahydropyran-2-one (Compound No. 23) was obtained in a yield of 1.043 g (81.3%).

Compound No. 23 is in the form of colorless columns, with a melting point of 78.0°–79.5° C. when recrystallized from diethyl ether and hexane. $^1$H NMR (CDCl$_3$, 300 MHz) δ1.43(s, 3H), 1.44(s, 3H), 1.73~2.08 (m, 4H), 1.88(s, 3H), 2.12(s, 3H), 2.20(s, 3H), 2.61(ddd, J=17.5, 4.0 and 1.5 Hz, 1H), 2.60~2.81(m, 2H), 2.76(dd, J=17.5 and 5.0 Hz, 1H), 2.88(s, 2H), 4.07(s, 2H), 4.35~4.44(m, 1H), 4.64~4.74(m, 1H), 4.97(broad s, 1H), 5.17(broad s, 1H) ppm.

IR (KBr) 3464, 2984, 2932, 1698, 1660 cm$^{-1}$.

Mass (m/z, %) 388 (M$^+$, 5), 333(36), 205(27), 203(100), 55(53), 43(45).

EXAMPLE 22

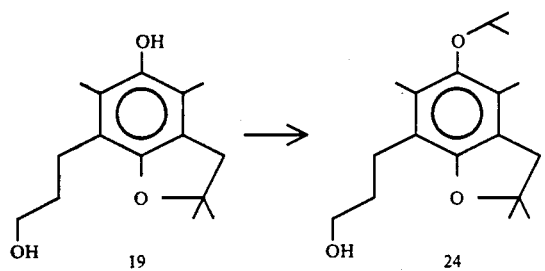

To a mixed solvent consisting of 3 ml of DMF and 6 ml of DME, there were added 1.104 g (4.42 mmol) of Compound No. 19 synthesized in Example 17, 1.50 g (10.9 mmol) of potassium carbonate and 0.83 ml (10.9 mmol) of isopropyl bromide. This reaction mixture was refluxed under an argon atmosphere for 10 hours and 30 minutes. To this reaction mixture, 0.4 ml (4.26 mmol) of isopropyl bromide was added and the refluxing was continued for another 3 hours.

The reaction mixture was poured into 1N hydrochloric acid. The mixture was then extracted with ethyl acetate. The extract layer was washed with a saturated aqueous solution of sodium chloride two times, dried over anhydrous magnesium sulfate, and concentrated. The concentrated product was placed on a silica gel column and eluted with a mixed solvent of hexane and ethyl acetate (5:1), whereby 3-[2,3-dihydro-5-(2-propyloxy)-2,2,4,6-tetramethylbenzo[b]furan-7-yl]propanol (Compound No. 24) was obtained in a yield of 1.039 g (80.6%).

Compound No. 24 is in the form of colorless needles, with a melting point of 29.0°–32.9° C. when recrystallized from hexane.

$^1$H NMR (CDCl$_3$, 300 MHz) δ1.26(d, J=6.1 Hz, 6H), 1.47(s, 6H), 1.67~1.79(m, 2H), 2.10(s, 3H), 2.17(s, 3H), 2.64~2.72(m, 2H), 2.92(s, 2H), 2.99(t, J=7.0 Hz, 1H), 3.44~3.53(m, 2H), 4.00(hept, J=6.1 Hz, 1H) ppm.

IR (KBr) 3480, 2980, 2936 cm$^{-1}$.

Mass (m/z, %) 292 (M$^+$, 74), 250(100), 249(53), 205(59), 43(82), 41(64).

EXAMPLE 23

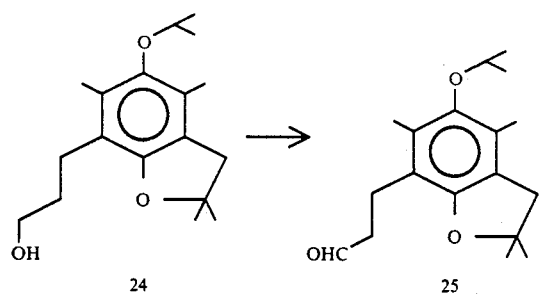

To a mixed solvent consisting of 12.5 ml of dimethyl sulfoxide and 7.5 ml of dried THF, there were successively added 1.00 g (3.42 mmol) of Compound No. 24 synthesized in Example 22, 2.0 ml (14.3 mmol) of triethylamine, and 1.70 g (10.7 mmol) of sulfur trioxide pyridine complex, and the mixture was stirred for 20 minutes.

The reaction mixture was poured into 1N hydrochloric acid. The mixture was then extracted with hexane. The extract layer was washed with a saturated aqueous solution of sodium chloride two times, dried over anhydrous magnesium sulfate, and concentrated. The concentrated product was placed on a silica gel column and eluted with a mixed solvent of hexane and ethyl acetate (10:1), whereby 3-[2,3-dihydro-5-(2-propyloxy)-2,2,4,6-tetramethylbenzo[b]furan-7-yl]propanal (Compound No. 25) was obtained as a colorless oil in a yield of 789 mg (79.4%).

$^1$H NMR (CDCl$_3$, 300 MHz) δ1.26(d, J=6.2 Hz, 6H), 1.44(s, 6H), 2.10(s, 3H), 2.17(s, 3H), 2.61(td with fine coupling, J=7.7 Hz and 1.9 Hz, 2H), 2.87(t, J=7.7 Hz, 2H), 2.88(s, 2H), 3.98(hept, J=6.2 Hz, 1H), 9.80(t, J=1.9 Hz, 1H) ppm.

IR (liquid film) 2980, 2936, 2728, 1728 cm$^{-1}$.

Mass (m/z, %) 290 (M$^+$, 100), 248(65), 247(53), 205(52), 203(27).

EXAMPLE 24

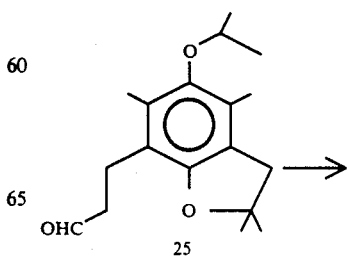

EXAMPLE 25

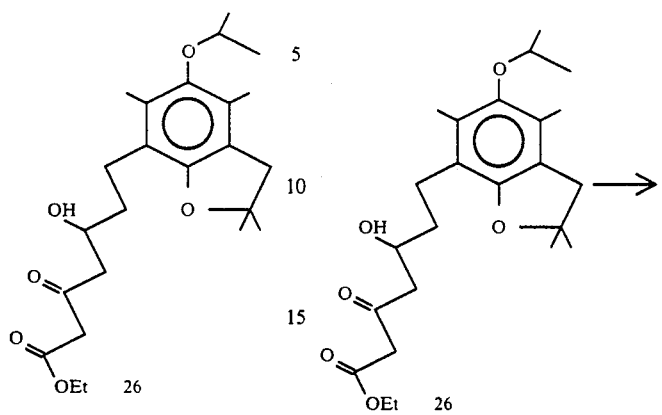

137 mg (3.43 mmol) of a 60% sodium hydride was suspended in 6 ml of dried THF. To this dispersion, 0.43 ml (3.37 mmol) of ethyl acetoacetate was added in a stream of argon at 0° C. The mixture was stirred for 15 minutes to to obtain a solution. To this solution, 2.2 ml (3.44 mmol) of a 15% hexane solution of butyl lithium was added. The mixture was stirred for 25 minutes, and then cooled to −78° C. To this mixture, 691 mg (2.38 mmol) of Compound No. 25 synthesized in Example 23, which was dissolved in 5 ml of dried THF, was added. The mixture was stirred for 30 minutes. After the completion of the reaction, the reaction mixture was poured into 1N hydrochloric acid. The mixture was then extracted with ethyl acetate. The extract layer was washed with a saturated aqueous solution of sodium chloride three times, dried over anhydrous magnesium sulfate, and concentrated. The concentrated product was placed on a silica gel column and eluted with a mixed solvent of hexane and ethyl acetate (5:1), whereby ethyl 7-[2,3-dihydro-5-(2-propyloxy)-2,2,4,6-tetramethylbenzo[b]furan-7-yl]-5-hydroxy-3-oxo-6-heptanoate (Compound No. 26) was obtained as a colorless oil in a yield of 792 mg (79.1%).

$^1$H NMR (CDCl$_3$, 300 MHz) δ1.26(t, J=7.1 Hz, 3H), 1.27(d, J=6.2 Hz, 3H), 1.27(d, J=6.2 Hz, 3H), 1.46(s, 3H), 1.47(s, 3H), 1.50∼1.75(m, 2H), 2.10(s, 3H), 2.16(s, 3H), 2.50∼2.81(m, 4H), 2.91(s, 2H), 3.49(s, 2H), 3.67(d with fine coupling, J=3.7 Hz, 1H), 3.85∼3.96(m, 1H), 3.99(hept, J=6.2 Hz, 1H), 4.17(q, J=7.1 Hz, 2H) ppm.

IR (liquid film) 3528, 2980, 2936, 1748, 1720, 1652 cm$^{-1}$.

Mass (m/z, %) 420 (M$^+$, 8), 378(10), 248(18), 205(42), 203(26), 43(100), 41(51), 29(80), 27(56).

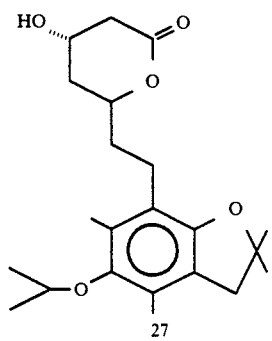

22 mg (0.22 mmol) of pivalic acid was added to 2.7 ml (2.7 mmol) of triethylborane (1M THF solution) in an atmosphere of argon at room temperature, and the mixture was stirred for 1 hour and 25 minutes, whereby a solution was obtained. To this solution was added 900 mg (2.14 mmol) of Compound No. 26 synthesized in Example 24, which was dissolved in 10 ml of dried THF. The mixture was stirred for 1 hour and 10 minutes, and then cooled to −78° C. To this mixture, 3 ml of methanol, and then 87 mg (2.30 mmol) of sodium borohydride were added. The mixture was stirred for 40 minutes. To this mixture, 3 ml of a 5N aqueous solution of sodium hydroxide and 5.0 g (44.1 mmol) of a 30% aqueous solution of hydrogen peroxide were added, and then ice-cooled. To this mixture, 3 ml of a 5N aqueous solution of sodium hydroxide was further added, and the mixture was stirred for 1 hour.

The reaction mixture was then poured into 1N hydrochloric acid. The mixture was extracted with ethyl acetate. The extract layer was successively washed with 1N hydrochloric acid, an aqueous solution of sodium thiosulfate, and a saturated aqueous solution of sodium chloride, dried over anhydrous magnesium sulfate, and concentrated.

The concentrated product was dissolved in 10 ml of dried toluene. The mixture was refluxed for 3 hours and 30 minutes. The thus obtained reaction mixture was placed on a silica gel column and eluted with a mixed solvent of hexane and ethyl acetate (3:1) and then with another mixed solvent of hexane and ethyl acetate (3:2), whereby trans-(±)-6-(2,3-dihydro-5-(2-propyloxy)-2,2,4,6-tetramethylbenzo[b]furan-7-yl)ethyl-4-hydroxytetrahydropyran-2-one (Compound No. 27) was obtained as a colorless viscous material in a yield of 625 mg (78.0%).

¹H NMR (CDCl₃, 300 MHz) δ1.26(d, J=6.1 Hz, 6H), 1.43(s, 3H), 1.44(s, 3H), 1.75~2.15(m, 4H), 2.09(s, 3H), 2.18(s, 3H), 2.60(dd with fine coupling, J=17.5 and 4.0 Hz, 1H), 2.59~2.79(m, 2H), 2.75(dd, J=17.5 and 5.1 Hz, 1H), 2.87(s, 2H). 3.98(hept, J=6.1 Hz, 1H), 4.32~4.42(m, 1H), 4.62~4.75(m, 1H) ppm.

IR (KBr) 3464, 2980, 2936, 1716, 1705 cm⁻¹.

Mass (m/z, %) 376 (M⁺, 13), 334(46), 205(34), 203(41), 43(100), 41(73), 27(44).

EXAMPLE 26

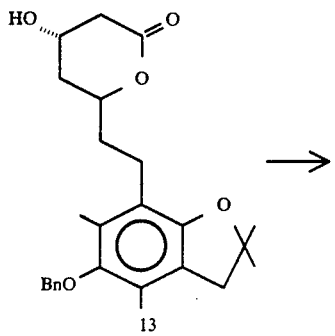

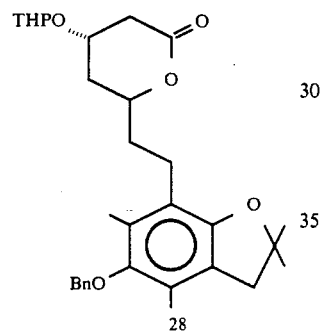

166 mg (0.379 mmol) of Compound No. 13 synthesized in Example 11 was dissolved in 2 ml of 1,2-dichloroethane. To this solution, 0.038 ml (0.454 mmol) of dihydropyran and 10 mg (0.04 mmol) of pyridine p-toluenesulfonate were added. The mixture was stirred in a stream of argon at room temperature overnight. To this reaction mixture, 0.038 ml (0.454 mmol) of dihydropyran and 10 mg (0.04 mmol) of pyridine p-toluenesulfonate were added, and the mixture was stirred for 6 hours.

The reaction mixture was extracted with ethyl acetate. The extract layer was successively washed with a saturated solution of sodium hydrogencarbonate, water, and a saturated aqueous solution of sodium chloride, dried over anhydrous magnesium sulfate, and concentrated.

The concentrated product was subjected to silica gel column chromatography and eluted with a mixed solvent of hexane and ethyl acetate (1:1), whereby trans-(±)-6-(5-benzyloxy-2,3-dihydro-2,2,4,6-tetramethylbenzo[b]furan-7-yl)ethyl-4-(2-tetrahydropyranyloxy)-pyran-2-one (Compound No. 28) was obtained as a colorless oil in a yield of 189 mg (94.4%).

¹H NMR (CDCl₃, 300 MHz) δ1.45(s, 6H), 1.46~1.60(m, 4H), 1.60~1.98(m, 5H), 2.05~2.14(m, 1H), 2.16(s, 3H), 2.24(s, 3H), 2.62~2.80(m, 4H), 2.90(s, 2H), 3.44~3.57(m, 1H), 3.76~3.88(m, 1H), 4.20~4.35(m, 1H), 4.55~4.75(m, 2H). 4.71(s, 2H), 7.30~7.52(m, 5H) ppm IR (liquid film) 2940, 2876, 1744, 1598 cm⁻¹

Mass (m/z, %) 508 (M⁺, 3), 417(36), 315(13), 205(22), 203(47), 91(33), 85(100).

EXAMPLE 27

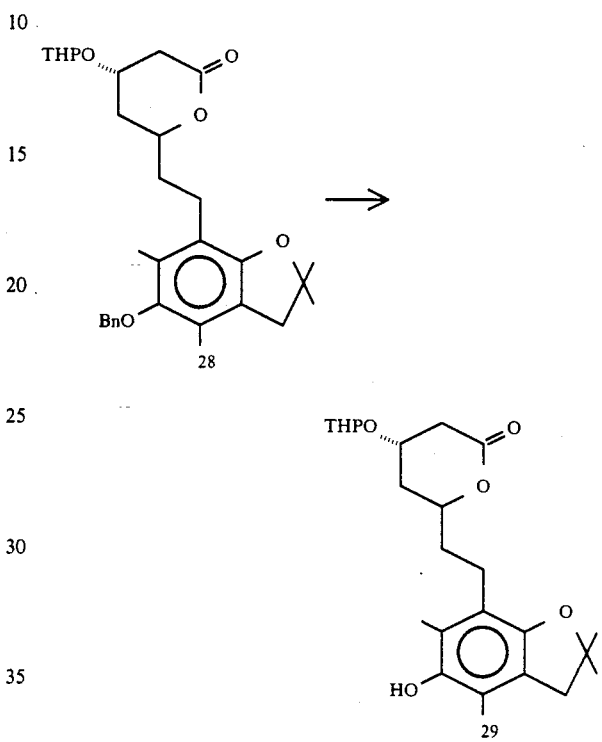

123 mg (0.242 mmol) of Compound No. 28 synthesized in Example 26 was dissolved in 3 ml of methanol. To this solution was added 35 mg of a 10% Pd/C, and the mixture was stirred in an atmosphere of hydrogen at room temperature for 2 hours.

After the completion of the reaction, the reaction mixture was diluted with ethyl acetate and methylene chloride and filtered through a Sellaite filter. The filtrate was concentrated. The concentrated filtrate was chromatographed on silica gel and eluted with a mixed solvent of hexane and ethyl acetate (1:1), whereby trans-(±)-6-(2,3-dihydro-5-hydroxy-2,2,4,6-tetramethylbenzo[b]furan-7-yl)ethyl-4-(2-tetrahydropyranyloxy)pyran-2-one (Compound No. 29) was obtained as an amorphous solid material in a yield of 93 mg (91.9%).

¹H NMR (CDCl₃, 300 MHz) δ1.43(s, 6H), 1.45~1.61(m, 4H), 1.60~2.00(m, 5H), 2.03~2.09(m, 1H), 2.10(s, 3H), 2.17(s, 3H), 2.60~2.85(m, 4H), 2.90(s, 2H), 3.45~3.60(m, 1H), 3.77~3.90 (m, 1H), 4.18(d, J=2.4 Hz, 1H), 4.20~4.30(m, 1H), 4.55~4.77(m, 2H) ppm.

IR (KBr) 3488, 2944, 2874, 1725 cm⁻¹.

Mass (m/z, %) 418 (M⁺, 71), 334(47), 205(76), 204(39), 189(15), 85(100), 41(51).

EXAMPLE 28

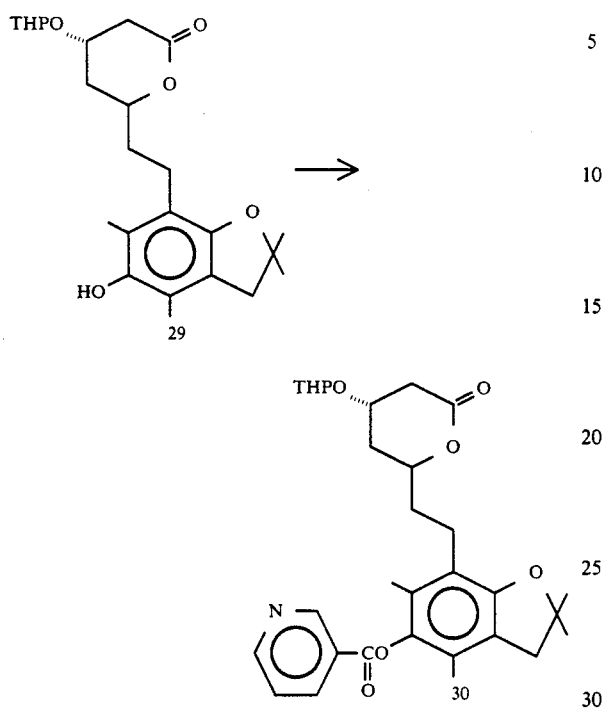

1.276 g (3.03 mmol) of Compound No. 29 synthesized in Example 27 was dissolved in 20 ml of 1,2-dichloroethane. This solution was ice-cooled and 1.16 ml (8.32 mmol) of triethylamine was added in a stream of argon. To this mixture, 712 mg (3.99 mmol) of nicotinoyl chloride hydrochloride was added, and the mixture was stirred for 15 minutes.

With the temperature of the reaction mixture raised to room temperature, the reaction mixture was extracted with ethyl acetate. The extract layer was successively washed with diluted hydrochloric acid, water, a saturated solution of sodium hydrogencarbonate, and a saturated aqueous solution of sodium chloride, dried over anhydrous magnesium sulfate, and concentrated.

The concentrated product was chlormatographed on silica and eluted with a mixed solvent of hexane and ethyl acetate (2:1), whereby trans-(±)-6-(2,3-dihydro-5-(pyridine-3-carboxy)-2,2,4,6-tetramethylbenzo[b]furan-7-yl)ethyl-4-(2-tetrahydropyranyloxy)tetrahydropyran-2-one (Compound No. 30) was obtained in a yield of 1.64 mg (100%).

Compound No. 30 is in the form of colorless columns, with a melting point of 149.0°–150.5° C. when recrystallized from diethyl ether.

$^1$H NMR (CDCl$_3$, 300 MHz) δ1.47(s, 6H), 1.45~1.60(m, 2H), 1.60~1.95(m, 6H), 2.01(s, 3H), 2.09(s, 3H), 1.95~2.18(m, 2H), 2.64~2.88(m, 4H), 2.95(s, 2H), 3.44~3.58(m, 1H), 3.75~3.88(m, 1H), 4.22~4.31(m, 1H), 4.57~4.80(m, 2H), 7.51(dd, J=4.6 and 7.8 Hz, 1H), 8.50(d with fine coupling, J=7.8 Hz, 1H), 8.88(d with fine coupling, J=4.6 Hz, 1H), 9.43(s with fine coupling, 1H) ppm.

IR (KBr) 2974, 2948, 2876, 1744, 1592 cm$^{-1}$.

Mass (m/z, %) 523 (M$^+$, 20), 310(13), 205(13), 203(33), 106(48), 85(100), 78(27), 41(43).

EXAMPLE 29

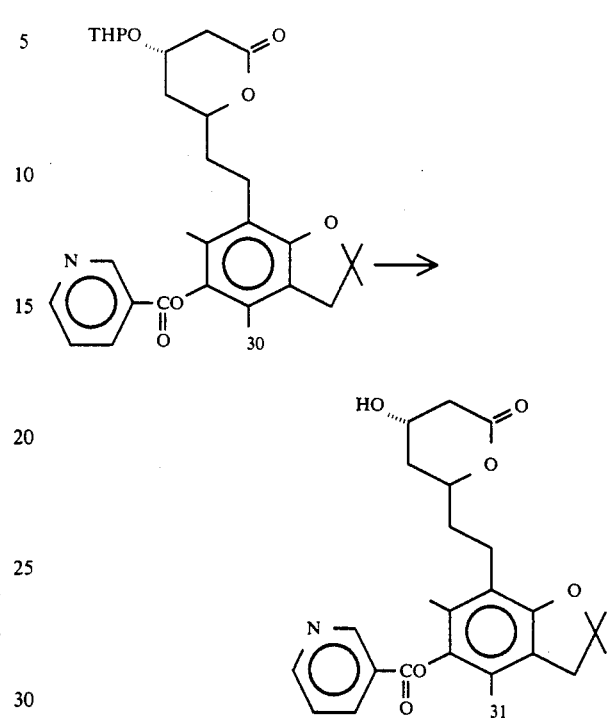

14 mg (0.0268 mmol) of Compound No. 30 synthesized in Example 28 was dissolved in 1.3 ml of ethyl acetate. To this solution, a catalytic amount of 12N hydrochloric acid was added. The thus obtained mixture was stirred in a stream of argon at room temperature for 1 day.

The reaction mixture was diluted with ethyl acetate, and successively washed with a saturated solution of sodium hydrogencarbonate, water and a saturated aqueous solution of sodium chloride, dried over anhydrous magnesium sulfate, and concentrated.

The concentrated product was chromatographed on silica gel and eluted with ethyl acetate, whereby trans-(±)-6-[2,3-dihydro-5-(pyridine-3-carboxy)-2,2,4,6-tetramethylbenzo[b]furan-7-yl]ethyl-4-hydroxytetrahydropyran-2-one (Compound No. 31) was obtained in a yield of 11 mg (93.5%).

Compound No. 31 is in the form of colorless crystals with a melting point of 182.5°–184.0° C. when recrystallized from diethyl ether and hexane.

$^1$H NMR (CDCl$_3$, 300 MHz) δ1.47(s, 6H), 1.70~2.00(m, 4H), 2.01(s, 3H), 2.09(s, 3H), 2.10~2.21(m, 1H), 2.61(ddd, J=17.7, 3.9 and 1.5 Hz, 1H), 2.76(dd, J=17.7 and 5.0 Hz, 1H), 2.65~2.88(m, 2H), 2.95(s, 2H), 4.32~4.41(m, 1H), 4.65~4.77(m, 1H), 7.49(dd, J=8.1 and 4.8 Hz, 1H), 8.48(ddd, J=8.1, 1.8 and 1.5 Hz, 1H), 8.87(dd, J=4.8 and 1.8 Hz, 1H), 9.43(d, J=1.5 Hz, 1H) ppm.

IR (KBr) 3550, 2970, 2936, 1737, 1593 cm$^{-1}$.

Mass (m/z, %) 439 (M$^+$, 78), 421(13), 333(20), 310(12), 205(26), 203(100), 191(15), 106(78), 78(44)

EXAMPLE 30

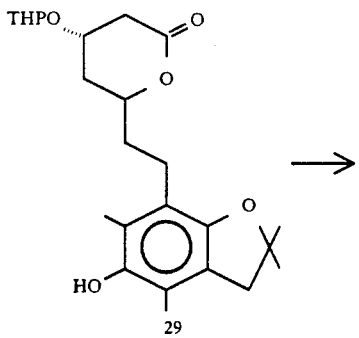

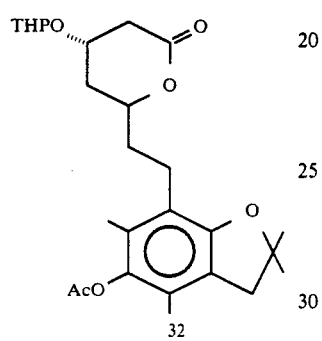

59 mg of Compound No. 29 synthesized in Example 27 was dissolved in 0.5 ml of pyridine. To this solution, 0.5 ml (5.30 mmol) of acetic anhydride was added. The mixture was stirred in a stream of argon at room temperature overnight.

The reaction mixture was extracted with ethyl acetate. The extract layer was successively washed with diluted hydrochloric acid, water, a saturated solution of sodium hydrogencarbonate, and a saturated aqueous solution of sodium chloride, dried over anhydrous magnesium sulfate, and concentrated.

The concentrated product was chromatographed on silica gel and eluted with a mixed solvent of ethyl acetate and hexane (1:1), whereby trans-($\pm$)-6-[5-acetoxy-2,3-dihydro-2,2,4,6-tetramethylbenzo[b]furan-7-yl]-ethyl-4-(2-tetrahydropyranyloxy)tetrahydropyran-2-one (Compound No. 32) was obtained in a yield of 62 mg (95.5%).

Compound No. 32 is in the form of colorless crystals with a melting point of 116.0°–117.5° C. when recrystallized from diethyl ether.

$^1$H NMR (CDCl$_3$, 300 MHz) $\delta$1.44(s, 6H), 1.48~1.62(m, 4H), 1.64~1.98(m, 5H), 1.95~2.10(m, 1H), 1.97(s, 3H), 2.04(s, 3H), 2.32(s, 2H), 2.62~2.87(m, 4H), 2.91(s, 2H), 3.45~3.58(m, 1H), 3.78~3.90(m, 1H), 4.22~4.32(m, 1H), 4.55~4.77(m, 2H) ppm.

IR (KBr) 2942, 2862, 1762, 1741, 1597 cm$^{-1}$.

EXAMPLE 31

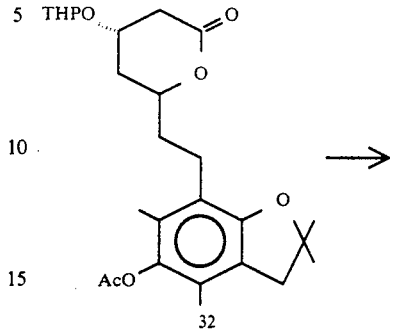

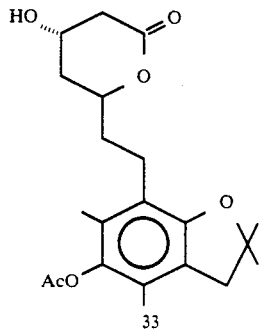

824 mg (1.79 mmol) of Compound No. 32 synthesized in Example 32 was dissolved in 10 ml of diethyl ether. To this solution, 0.3 ml of a 60% perchloric acid was added, and the mixture was stirred for 15 minutes, in an atmosphere of argon at 0° C.

After the completion of the reaction, the reaction mixture was poured into a saturated aqueous solution of sodium chloride. The mixture was extracted with ethyl acetate. The extract layer was successively washed with a saturated aqueous solution of sodium chloride, dried over anhydrous magnesium sulfate, and concentrated.

The concentrated product was chromatographed on silica gel and eluted with a mixed solvent of dichloromethane and ethyl acetate (3:1), whereby trans-($\pm$)-6-(5-acetoxy-2,3-dihydro-2,2,4,6-tetramethylbenzo[b]furan-7-yl)ethyl-4-hydroxytetrahydropyran-2-one (Compound No. 33) was obtained in a yield of 305 mg (45.3%).

Compound No. 33 is in the form of colorless crystals with a melting point of 126.5°–128.0° C. when recrystallized from diethyl ether and hexane.

$^1$H NMR (CDCl$_3$, 300 MHz) $\delta$1.44(s, 6H), 1.65~1.98(m, 4H), 1.97(s, 3H), 2.05(s, 3H), 2.32(s, 3H), 2.60(ddd, J=17.7, 3.9 and 1.5 Hz, 1H), 2.75(dd, J=17.7 and 5.1 Hz, 1H), 2.65~2.80(m, 2H), 2.91(s, 2H), 4.30~4.40(m, 1H), 4.60~4.72(m, 1H) ppm.

IR (KBr) 3542, 2980, 2938, 1733, 1594 cm$^{-1}$.

Mass (m/z, %) 376 (M$^+$, 11), 334(100), 205(23), 204(18), 43(36).

EXAMPLE 32

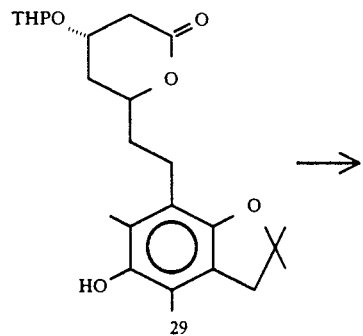

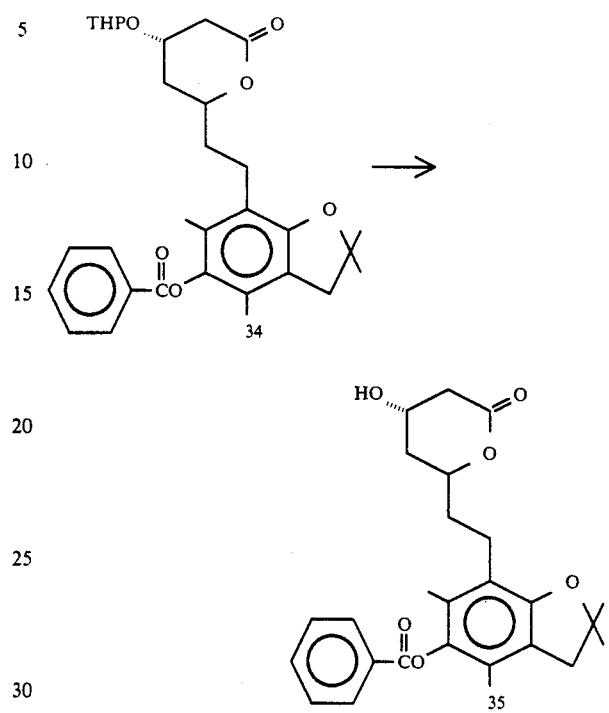

203 mg (0.49 mmol) of Compound No. 29 synthesized in Example 27 was dissolved in 2 ml of 1,2-dichloroethane. To this solution, 0.20 ml (1.43 mmol) of triethylamine and 0.10 ml (1.43 mmol) of benzoyl chloride were added, and the mixture was stirred for 1 hour and 30 minutes, in an atmosphere of argon at room temperature.

After the completion of the reaction, a saturated aqueous solution of sodium hydrogencarbonate and dichloromethane were added to the reaction mixture.

The thus obtained reaction mixture was placed in a separatory funnel and an organic layer was separated out. The organic layer was washed with a saturated aqueous solution of sodium chloride, dried over anhydrous magnesium sulfate, and concentrated.

The concentrated product was placed on a silica gel column and eluted with dichloromethane, whereby trans-($\pm$)-6-(2,3-dihydro-5-benzoyloxy-2,2,4,6-tetramethylbenzo[b]furan-7-yl)ethyl-4-(2-tetrahydropyranyloxy)-tetrahydropyran-2-one (Compound No. 34) was obtained in a yield of 241 mg (95.0%).

Compound No. 34 is in the form of colorless columns, with a melting point of 139.0°-140.5° C. when recrystallized from diethyl ether and hexane.

$^1$H NMR (CDCl$_3$, 300 MHz) $\delta$1.47(s, 6H), 1.40~2.20(m, 10H), 2.01(s, 3H), 2.09(s, 3H), 2.61~2.86(m, 4H), 2.94(s, 2H), 3.44~3.57(m, 1H), 3.75~3.89(m, 1H), 4.20~4.32(m, 1H), 4.56~4.78(m, 2H), 7.53(t, J=7.6 Hz, 2H), 7.65(t with fine coupling, J=7.6 Hz, 1H), 8.24(d with fine coupling, J=7.6 Hz, 2H) ppm.

IR (KBr) 2976, 2950, 2874, 1743, 1735, 1601 cm$^{-1}$.

EXAMPLE 33

141 mg (0.27 mmol) of Compound No. 34 synthesized in Example 32 was dissolved in 2 ml of ethyl acetate. To this solution, one drop of conc. hydrochloric acid was added, and the mixture was stirred at room temperature for 7 hours. In the course of the stirring process, 2 ml of ethyl acetate was added to the reaction mixture 3 hours and 20 minutes after the initiation of the reaction.

After the completion of the reaction, the reaction mixture was poured into an aqueous solution of sodium hydrogencarbonate. The mixture was extracted with ethyl acetate. The extract layer was washed with a saturated aqueous solution of sodium chloride, dried over anhydrous magnesium sulfate, and concentrated.

The concentrated product was placed on a silica gel column and eluted with a mixed solvent of dichloromethane and ethyl acetate (10:1), whereby trans-($\pm$)-6-(5-benzoyloxy-2,3-dihydro-2,2,4,6-tetramethylbenzo[b]furan-7-yl)ethyl-4-hydroxytetrahydropyran-2-one (Compound No. 35) was obtained in a yield of 77 mg (65.1%).

Compound No. 35 is as colorless columns, with a melting point of 188.0°-190.0° C. when recrystallized from diethyl ether and hexane.

$^1$H NMR (CDCl$_3$, 300 MHz) $\delta$1.47(s, 6H), 1.40~2.20(m, 4H), 2.01(s, 3H), 2.08(s, 3H), 2.60(dd with fine coupling, J=17.4 and 3.6 Hz, 1H), 2.65~2.87(m, 3H), 2.94(s, 2H), 4.29~4.40(m, 1H), 4.63~4.76(m, 1H), 7.52(t, J=7.5 Hz, 2H), 7.65(t, J=7.5 Hz, 1H), 8.23(d with fine coupling, J=7.5 Hz, 2H) ppm.

IR (KBr) 3536, 2976, 2936, 1744, 1717, 1599 cm$^{-1}$.
Mass (m/z, %) 438 (M$^+$, 23), 203(22), 105(100).

EXAMPLE 34

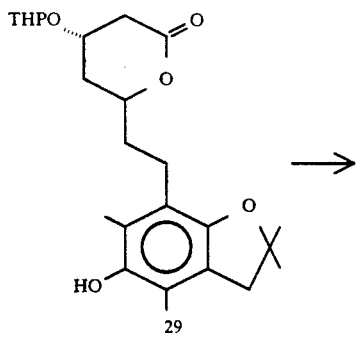

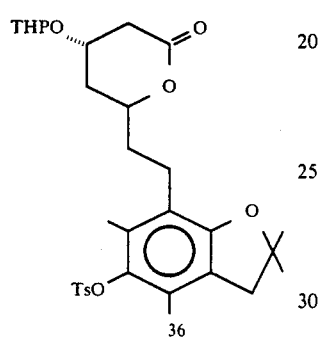

173 mg (0.42 mmol) of Compound No. 29 synthesized in Example 27 was dissolved in 2 ml of 1,2-dichloroethane. To this solution, 0.18 ml (1.29 mmol) of triethylamine and 126 mg (0.66 mmol) of p-toluenesulfonyl chloride were added and the mixture was stirred in a stream of argon at room temperature for 45 minutes. After the completion of the reaction, the reaction mixture was poured into diluted hydrochloric acid.

The mixture was extracted with ethyl acetate. The extract layer was washed with a saturated aqueous solution of sodium chloride, dried over anhydrous magnesium sulfate, and concentrated.

The concentrated product was placed on a silica gel column and eluted with dichloromethane and then with a mixed solvent of dichloromethane and ethyl acetate (4:1), whereby trans-($\pm$)-6-[2,3-dihydro-2,2,4,6-tetramethyl-5-(p-toluenesulfonyloxy)benzo[b]furan-7-yl]ethyl-4-(2-tetrahydropyranyloxy)tetrahydropyran-2-one (Compound No. 36) was obtained as an amorphous solid in a yield of 228 mg (90.2%).

$^1$H NMR (CDCl$_3$, 300 MHz) $\delta$1.45(s, 6H), 1.40~2.20(m, 10H), 1.90(s, 3H), 2.06(s, 3H), 2.48(s, 3H), 2.54~2.86(m, 4H), 2.89(s, 2H), 3.43~3.57(m, 1H), 3.76~3.88(m, 1H), 4.20~4.30(m, 1H), 4.48~4.74(m, 2H), 7.36(d, J=8.1 Hz, 2H), 7.83(d, J=8.1 Hz, 2H) ppm.

IR (KBr) 2944, 2876, 1743, 1598, 1371, 1178 cm$^{-1}$.

EXAMPLE 35

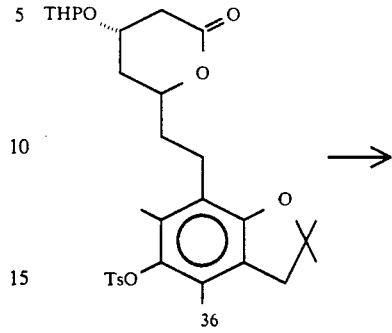

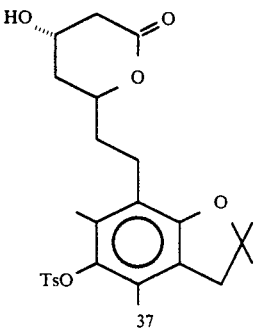

202 mg (0.35 mmol) of Compound No. 36 synthesized in Example 34 was dissolved in 2 ml of ethyl acetate. To this solution, one drop of conc. hydrochloric acid was added, and the mixture was stirred at room temperature for 7 hours. In the course of the stirring step, 2 ml of ethyl acetate was added to the reaction mixture 3 hours after the initiation of the reaction.

After the completion of the reaction, the reaction mixture was poured into an aqueous solution of sodium hydrogencarbonate. The mixture was extracted with ethyl acetate. The extract layer was washed with a saturated aqueous solution of sodium chloride, dried over anhydrous magnesium sulfate, and concentrated.

The concentrated product was placed on a silica gel column and eluted with a mixed solvent of dichloromethane and ethyl acetate (10:1), whereby trans-($\pm$)-6-[2,3-dihydro-2,2,4,6-tetramethyl-5-(p-toluenesulfonyloxy)benzo[b]furan-7-yl]ethyl-4-hydroxytetrahydropyran-2-one (Compound No. 37) was obtained as a colorless, amorphous solid in a yield of 103 mg (59.6%).

$^1$H NMR (CDCl$_3$, 300 MHz) $\delta$1.44(s, 6H), 1.40~2.20(m, 4H), 1.91(s, 3H), 2.04(s, 3H), 2.48(s, 3H), 2.53~2.80(m, 4H), 2.88(s, 2H), 4.31~4.42(m, 1H), 4.58~4.70(m, 1H), 7.36(d, J=8.1 Hz, 2H), 7.83(d, J=8.1 Hz, 2H) ppm.

IR (KBr) 3482, 2978, 2932, 1736, 1717, 1599, 1370, 1178 cm$^{-1}$.

Mass (m/z, %) 488 (M$^+$, 3), 333(61), 315(32), 205(27), 203(100), 91(30).

EXAMPLE 36

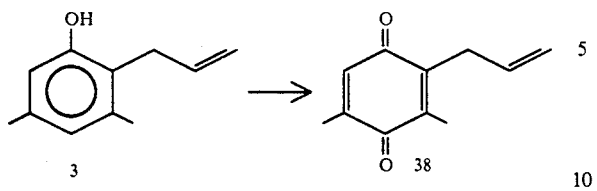

8.02 g (49.5 mmol) of Compound No. 3 synthesized in Example 1 was dissolved in 250 ml of ethanol. To this solution, 1.61 g (4.95 mmol) of salcomine was added. The mixture was stirred in an atmosphere of oxygen at room temperature for 5 days. After the completion of the reaction, the solvent was distilled away from the reaction mixture. The reaction mixture was diluted with ethyl acetate, and then filtered through a celite filter. The filtrate was concentrated, chromatographed on silica gel and eluted with a mixed solvent of ethyl acetate and hexane (1:6), whereby 2,6-dimethyl-3-(2-propenyl)-p-benzoquinone (Compound No. 38) was obtained as a yellow oil in a yield of 5.478 g (62.9%).

$^1$H NMR (CDCl$_3$, 300 MHz) δ2.05(s, 6H), 3.24(d, J=6.3 Hz, 2H), 5.04(d with fine coupling, J=17.4 Hz, 1H), 5.04(d with fine coupling, J=9.6 Hz, 1H), 5.76(ddt, J=17.4, 9.6 and 6.3 Hz, 1H), 6.57(s with fine coupling, 1H) ppm.

IR (liquid film) 2930, 1652, 1618 cm$^{-1}$.

EXAMPLE 37

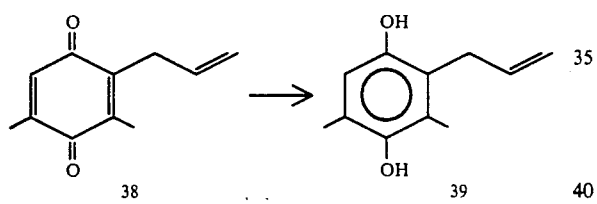

226 mg of Compound No. 38 synthesized in Example 36 was dissolved in 2 ml of dichloromethane. To this solution, 53.3 mg (1.41 mmol) of sodium borohydride was added in a stream of argon. To this mixture, methanol was gradually added dropwise until the color of the mixture turned from red to white. 90 minutes later, to this mixture, a saturated aqueous solution of ammonium chloride was added. With the temperature of the reaction mixture raised to room temperature, the reaction mixture was extracted with ethyl acetate. The extract layer was washed with a saturated aqueous solution of ammonium chloride, water and a saturated aqueous solution of sodium chloride, dried over anhydrous magnesium sulfate, and concentrated, whereby 2,6-dimethyl-3-(2-propenyl)hydroquinone (Compound No. 39) was obtained in a yield of 217 mg (95.2%).

Compound No. 39 is in the form of colorless crystals, with a melting point of 113.6°–115.5° C. when recrystallized from ethyl acetate and hexane.

$^1$H NMR (CDCl$_3$, 300 MHz) δ2.18(s, 3H), 2.20(s, 3H), 3.41(ddd, J=5.7, 1.8 and 1.5 Hz, 2H), 4.25(s, 1H), 4.39(s, 1H), 4.99(ddd, J=17.1, 1.8 and 1.5 Hz, 1H), 5.06(ddd, J=10.2, 1.8 and 1.5 Hz, 1H), 5.95(ddt, J=17.1, 10.2 and 5.7 Hz, 1H), 6.50(s, 1H) ppm.

IR (KBr) 3276, 1641 cm$^{-1}$.

Mass (m/z, %) 178 (M$^+$, 100), 163(29), 151(13), 135(22), 91(13), 77(13).

EXAMPLE 38

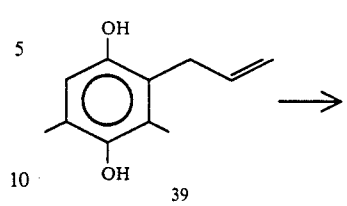

6.00 g (33.7 mmol) of Compound No. 39 synthesized in Example 37 was dissolved in 150 ml of 1,2-dichloroethane. To this solution, 5.98 ml (48.54 mmol) of boron trifluoride etherate was added in a stream of argon at 0° C. To this mixture, 4.11 ml (40.46 mmol) of 3-methyl-2-butene-1-ol, which was dissolved in 100 ml of 1,2-dichloroethane, was added dropwise over a period of 1 hour, with the temperature of the reaction mixture maintained at 0° C.

To this reaction mixture, a saturated aqueous solution of sodium hydrogencarbonate was added, and the mixture was stirred for a while and the temperature thereof was elevated to room temperature. The reaction mixture was then extracted with dichloromethane. The extract layer was washed with a saturated aqueous solution of sodium hydrogencarbonate, and a saturated aqueous solution of sodium chloride, dried over anhydrous magnesium sulfate, and concentrated, whereby a crude 6-hydroxy-8-(2-propenyl)-2,2,5,7-tetramethylchroman (Compound No. 40) was obtained as a yellow oil in a yield of 9.75 g.

$^1$H NMR (CDCl$_3$, 300 MHz) δ1.27(s, 6H), 1.79(t, J=6.9 Hz, 2H), 2.11(s, 3H), 2.17(s, 3H), 2.62(t, J=6.9 Hz, 2H), 3.38(ddd, J=6.3, 1.5 and 1.5 Hz, 2H), 4.18(s, 1H), 4.92(ddd, J=10.2, 1.5 and 1.5 Hz, 1H), 4.96(ddd, J=17.1, 1.5 and 1.5 Hz, 1H), 5.86(ddt, J=17.1, 10.2 and 6.3 Hz, 1H) ppm.

IR (liquid film) 3498, 2982, 2936, 1640 cm$^{-1}$.

Mass (m/z, %) 246 (M$^+$, 100), 191(51), 175(45), 147(10), 91(16).

EXAMPLE 39

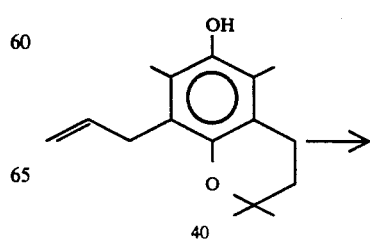

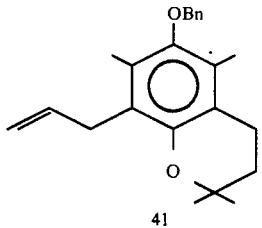

5.24 g of a crude Compound No. 40 synthesized in Example 38 was dissolved in 20 ml of methyl ethyl ketone. To this solution, 2.52 ml (21.2 mmol) of benzyl bromide and 9.33 g (67.6 mmol) of anhydrous potassium carbonate were added. The mixture was refluxed in an atmosphere of argon for 6 hours.

After the completion of the reaction, the reaction mixture was cooled to room temperature and poured into water. The mixture was extracted with ethyl acetate. The extract layer was washed with water and then with a saturated aqueous solution of sodium chloride, dried over anhydrous magnesium sulfate, concentrated, chromatographed on silica gel, and eluted with hexane and a mixed solvent of hexane and ethyl acetate (6:1), whereby 6-benzyloxy-8-(2-propenyl)-2,2,5,7-tetramethylchroman (Compound No. 41) was obtained in a yield of 4.43 g (74.5%). 606 mg (13.9%) of Compound No. 40 was recovered.

Compound No. 41 is as colorless needles, with a melting point of 46.8°–48.0° C. when recrystallized from ethanol and water.

$^1$H NMR (CDCl$_3$, 300 MHz) δ1.29(s, 6H), 1.81(t, J=6.8 Hz, 2H), 2.18(s, 3H), 2.24(s, 3H), 2.61(t, J=6.8 Hz, 2H), 3.38(d, J=6.2 Hz, 2H), 4.70(s, 2H), 4.93(d with fine coupling, J=10.1 Hz, 1H), 4.96(d with fine coupling, J=17.1 Hz, 1H), 5.89(ddt, J=17.1, 10.1 and 6.2 Hz, 1H), 7.30~7.54(m, 5H) ppm.

IR (KBr) 2982, 2946, 1637 cm$^{-1}$.

Mass (m/z, %) 336 (M$^+$, 8), 245(100), 204(9), 189(9), 91(33).

EXAMPLE 40

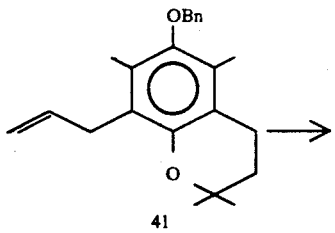

2 ml of a THF solution of 75 mg of Compound No. 41 synthesized in Example 39 was added to 10 ml of a THF solution of 409 mg (1.68 mmol) of 9-BBN dimer in a stream of argon at room temperature, and the mixture was stirred for 20 minutes.

To this reaction mixture, 1.34 ml of ethanol, 2.23 ml (4.46 mmol) of a 2N aqueous solution of sodium hydroxide, and then 0.591 ml (5.69 mmol) of a 30 aqueous solution of hydrogen peroxide were successively added with the utmost care. The reaction mixture was stirred for 10 minutes, and then refluxed for 1 hour.

The reaction mixture was extracted with ethyl acetate. The extract layer was subsequently washed with an aqueous solution of sodium thiosulfate, water, and a saturated aqueous solution of sodium chloride, dried over anhydrous magnesium sulfate, and concentrated. The concentrated product was chromatographed on silica gel and eluted with a mixed solvent of ethyl acetate and hexane (1:6), whereby a crude 3-[6-benzyloxy-2,3,5,7-tetramethylchroman-8-yl]propanol (Compound No. 42) was obtained as a yellow oil in a yield of 706 mg.

$^1$H NMR (CDCl$_3$, 300 MHz) δ1.34(s, 6H), 1.76(t, J=6.9 Hz, 2H), 1.83(t, J=6.8 Hz, 2H), 2.18(s, 3H), 2.25(s, 3H), 2.63(t, J=6.9 Hz, 2H), 2.60~2.75(m, 1H), 2.76(t, J=6.9 Hz, 2H), 3.46~3.56(m, 2H), 4.71(s, 2H), 7.30~7.53(m, 5H) ppm.

IR (liquid film) 3456, 2934 cm$^{-1}$.

Mass (m/z, %) 354 (M$^+$, 8), 263(100), 245(11), 219(6), 163(6), 108(10), 91(54).

EXAMPLE 41

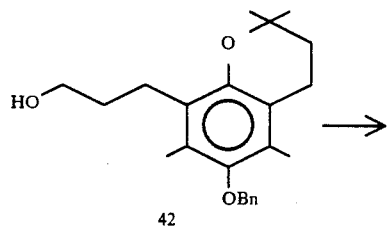

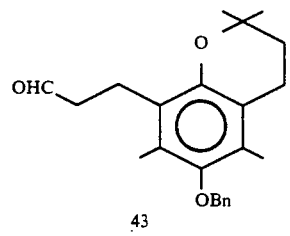

2.448 g (6.9 mmol) of Compound No. 42 synthesized in Example 40 was dissolved in 25 ml of dimethylsulfoxide. To this solution, 5.0 ml (35.9 mmol) of triethylamine, 15 ml of THF, and 3.5 g (22.0 mmol) of sulfur trioxide pyridine complex were successively added, and the mixture was stirred in an atmosphere of argon at room temperature for 30 minutes.

The reaction mixture was poured into 1N hydrochloric acid. The mixture was then extracted with ethyl acetate. The extract layer was washed with a saturated aqueous solution of sodium chloride, dried over anhydrous magnesium sulfate, and concentrated. The concentrated product was placed on a silica gel column and eluted with a mixed solvent of hexane and ethyl acetate (9:1), whereby 3-[6-benzyloxy-2,2,5,7-tetramethylchroman-8-yl]propanal (Compound No. 43) was obtained as a light yellow oil in a yield of 1.723 g (70.8%).

$^1$H NMR (CDCl$_3$, 300 MHz) δ1.30(s, 6H), 1.80(t, J=7.0 Hz, 2H), 2.18(s, 3H), 2.24(s, 3H), 2.58(td, J=7.2 and 1.8 Hz, 2H), 2.61(t, J=7.0 Hz, 2H), 2.94(t, J=7.2

Hz, 2H), 4.70(s, 2H), 7.31~7.55(m, 5H), 9.82(t, J=1.8 Hz, 1H) ppm.

IR (liquid film) 2980, 1728 cm$^{-1}$.

Mass (m/z, %) 352 (M$^+$, 8), 261(100), 217(16), 163(5), 91(51).

EXAMPLE 42

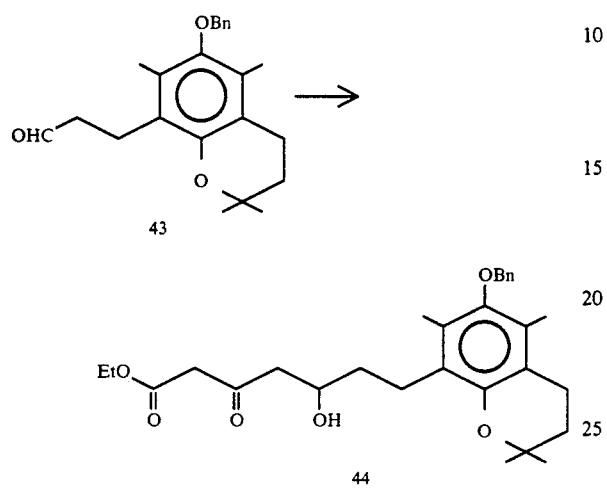

530 mg (13.3 mmol) of a 60% sodium hydride was suspended in 40 ml of anhydrous THF in a stream of argon at 0° C. To this suspension, 1.69 ml (13.3 mmol) of ethyl acetoacetate was added. The mixture was then stirred for 30 minutes, followed by the addition of 8.48 ml (13.3 mmol) of a 15% hexane solution of butyl lithium thereto. The reaction mixture was stirred for 30 minutes.

The reaction mixture was then cooled to $-78°$ C. With addition of 10 ml of an anhydrous THF solution containing 3.11 g (8.83 mmol) of Compound No. 43 synthesized in Example 41, the mixture was stirred for 20 minutes.

After the completion of the reaction, an aqueous solution of ammonium chloride was added to the reaction mixture. After the elevation of the temperature of the mixture to room temperature, the mixture was extracted with ethyl acetate. The extract layer was washed with a saturated aqueous solution of ammonium chloride, water and a saturated aqueous solution of sodium chloride, dried over anhydrous magnesium sulfate, and concentrated.

The concentrated product was chromatographed on silica gel and eluted with a mixed solvent of ethyl acetate and hexane (1:3), whereby ethyl 7-[6-benzyloxy-2,2,5,7-tetramethylchroman-8-yl]-5-hydroxy-3-oxoheptanoate (Compound No. 44) was obtained as a yellow oil in a yield of 2.98 g (70.0%).

$^1$H NMR (CDCl$_3$, 300 MHz) δ1.27(t, J=7.2 Hz, 3H), 1.30(s, 3H), 1.36(s, 3H), 1.55~1.70(m, 2H), 1.83(t, J=7.1 Hz, 2H), 2.18(s, 3H), 2.24(s, 3H), 2.55~2.95(m, 6H), 3.45(d, J=2.4 Hz, 1H), 3.50(s, 2H), 3.90~4.00(m, 1H), 4.18(q, J=7.2 Hz, 2H), 4.71(s, 2H), 7.30~7.52(m, 5H) ppm.

IR (liquid film) 3524, 2982, 2936, 1744, 1717 cm$^{-1}$.

Mass (m/z, %) 482 (M$^+$, 3), 391(33), 345(16), 261(84), 217(30), 205(12), 130(13), 105(10), 91(74), 43(100).

EXAMPLE 43

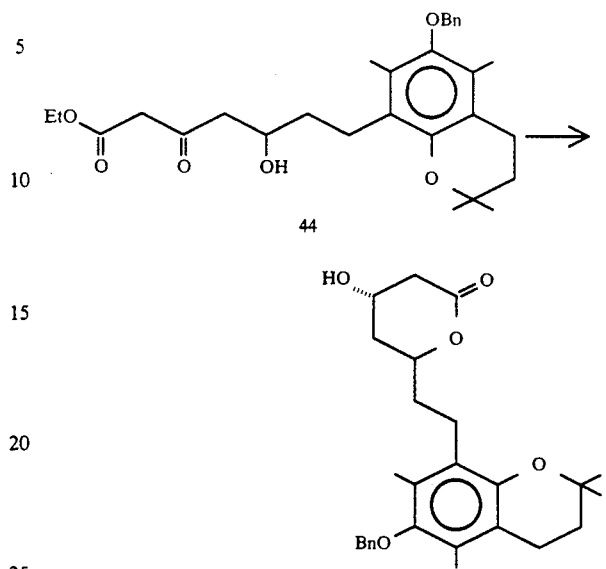

6.82 ml (6.82 mmol) of triethylborane (1.0M hexane solution) was added to 35 mg (0.341 mmol) of pivalic acid in a stream of argon at room temperature. The mixture was stirred for 1 hour to obtain a solution. To this solution was added 15 ml of an anhydrous THF solution of 2.9 g (6.04 mmol) of Compound No. 44 synthesized in Example 42.

The reaction mixture was stirred for 1 hour and 20 minutes and then cooled to $-78°$ C., and 5.58 ml of methanol and 234 mg (6.20 mmol) of sodium borohydride were successively added thereto. 20 minutes later, to this reaction mixture, 24.8 ml of a 5N aqueous solution of sodium hydroxide and 24.8 ml of a 30% aqueous solution of hydrogen peroxide were successively added. After the elevation of the reaction mixture to 0° C., and then to room temperature, the reaction mixture was stirred for 2 hours.

The reaction mixture was made acidic with addition of 1N hydrochloric acid and extracted with ethyl acetate. The extract layer was washed with a saturated aqueous solution of sodium thiosulfate, and a saturated aqueous solution of sodium chloride, dried over anhydrous magnesium sulfate, and concentrated.

The concentrated product was dissolved in 20 ml of toluene. The solution was refluxed for 3 hours. After the completion of the reaction, the solvent was distilled away, and the residue was chromatographed on silica gel, and eluted with a mixed solvent of ethyl acetate and hexane (1:1), whereby trans-($\pm$)-6-[(6-benzyloxy-2,2,5,7-tetramethyl)chroman-8-yl]-4-hydroxytetrahydropyran-2-one (Compound No. 45) was obtained as a colorless amorphous solid in a yield of 1.75 g (66.3%).

$^1$H NMR (CDCl$_3$, 300 MHz) δ1.30(s, 3H), 1.31(s, 3H), 1.80(t, J=6.9 Hz, 2H), 1.52~1.94(m, 4H), 1.96~2.06(m, 1H), 2.18(s, 3H), 2.26(s, 3H), 2.61(t, J=6.9 Hz, 2H), 2.60~2.67(m, 1H), 2.70~2.82(m, 3H), 4.37~4.45(m, 1H), 4.70(s, 2H), 4.70~4.79 (m, 1H), 7.31~7.55(m, 5H) ppm.

IR (KBr) 3466, 2978, 2938, 1717, 1707 cm$^{-1}$.

Mass (m/z, %) 438 (M$^+$, 6), 347(100), 329(19), 217(18), 91(56).

EXAMPLE 44

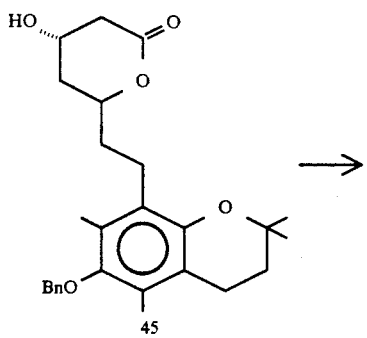

↓

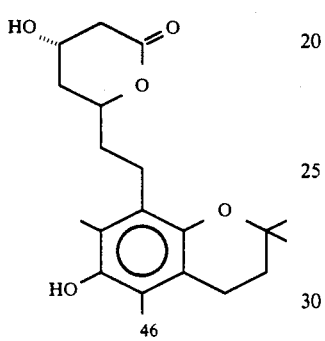

592 mg (1.32 mmol) of Compound No. 45 synthesized in Example 43 was dissolved in 5 ml of methanol. To this solution was added 59 mg of a 10% Pd/C, and the mixture was stirred in an atmosphere of hydrogen at room temperature for 5 hours. To this reaction mixture, 30 mg of the 10% Pd/C was further added and the reaction mixture was stirred at room temperature for 3 days.

The reaction mixture was diluted with ethyl acetate and filtered through a celite filter. The filtrate was concentrated. The concentrated product was chromatographed on silica gel and eluted with a mixed solvent of ethyl acetate and hexane (2:1), whereby trans-(±)-6-[(6-hydroxy-2,2,5,7-tetramethyl)chroman-8-yl]ethyl-4-hydroxytetrahydropyran-2-one (Compound No. 46) was obtained in a yield of 309 mg (65.5%).

Compound No. 46 is in the form of colorless crystals, with a melting point of 136.6°–137.0° C. when recrystallized from ethyl acetate and hexane.

$^1$H NMR (CDCl$_3$, 300 MHz) δ1.28(s, 3H), 1.28(s, 3H), 1.70~1.95(m, 4H), 1.78(t, J=6.9 Hz, 2H), 1.96~2.08(m, 1H), 2.12(s, 3H), 2.20(s, 3H), 2.62(t, J=6.9 Hz, 2H), 2.59~2.69(m, 1H), 2.70~2.84(m, 3H), 4.22(s, 1H), 4.37~4.46(m, 1H), 4.67~4.80 (m, 1H) ppm.

IR (KBr) 3380, 2980, 2930, 1708 cm$^{-1}$.

Mass (m/z, %) 348 (M$^+$, 100), 330(10), 293(25), 219(15), 203(19), 163(41).

EXAMPLE 45

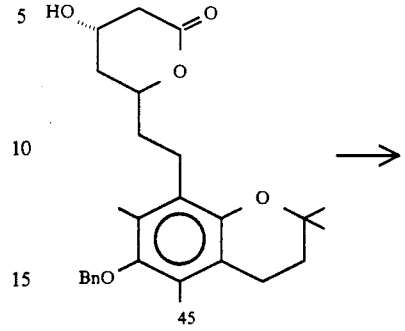

↓

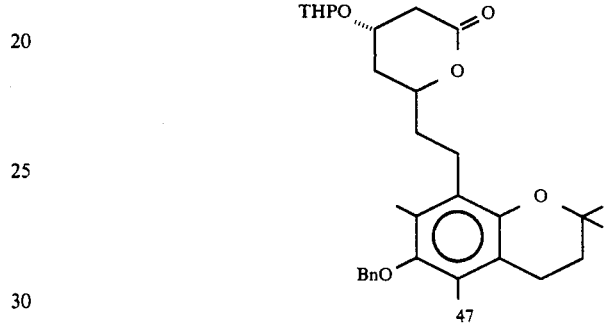

101 mg (0.231 mmol) of Compound No. 45 synthesized in Example 43 was dissolved in 2 ml of 1,2-dichlorethane. To this solution, 80 μl (0.877 mmol) of dihydropyran and 10 mg (0.040 mmol) of pyridine p-toluenesulfonate were added. The mixture was stirred in a stream of argon at room temperature for 3 hours.

After the completion of the reaction, the reaction mixture was poured into a saturated aqueous solution of sodium hydrogencarbonate. The mixture was then extracted with ethyl acetate. The extract layer was successively washed with water, and a saturated solution of sodium chloride, dried over anhydrous magnesium sulfate, and concentrated.

The concentrated product was chromatographed on silica gel and eluted with a mixed solvent of hexane and ethyl acetate (1:1), whereby trans-(±)-6-[(6-benzyloxy-2,2,5,7-tetramethylchroman-8-yl]ethyl-4-(2-tetrahydropyranyloxy)tetrahydropyran-2-one (Compound No. 47) was obtained in a yield of 122 mg (100%).

Compound No. 47 is in the form of colorless crystals, with a melting point of 95.0°–95.5° C. when recrystallized from diethyl ether and hexane.

$^1$H NMR (CDCl$_3$, 300 MHz) δ1.31(s, 6H), 1.48~1.59(m, 4H), 1.65~1.96(m, 5H), 1.81(t, J=6.9 Hz, 2H), 2.05~2.15(m, 1H), 2.18(s, 3H), 2.26(s, 3H), 2.61(t, J=6.9 Hz, 2H), 2.65~2.70(m, 1H), 2.70~2.80(m, 3H), 3.45~3.57(m, 1H), 3.79~3.88(m, 1H), 4.22~4.34(m, 1H), 4.58~4.80(m, 2H), 4.70(s, 2H), 7.30~7.53(m, 5H) ppm.

IR (KBr) 2944, 2856, 1724, 1606 cm$^{-1}$.

EXAMPLE 46

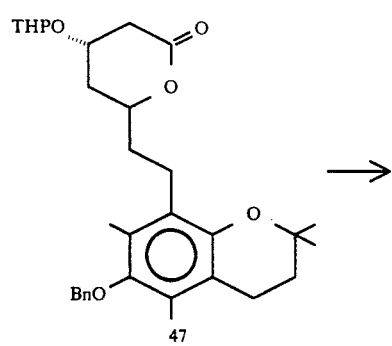

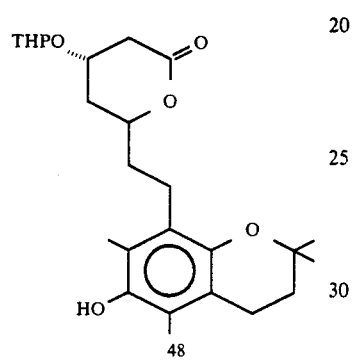

209 mg (0.400 mmol) of Compound No. 47 synthesized in Example 45 was dissolved in 3 ml of methanol. To this solution was added 40 mg of a 10% Pd/C, and the mixture was stirred in an atmosphere of hydrogen at room temperature for 2 hours and 30 minutes.

The reaction mixture was diluted with ethyl acetate and dichloromethane and filtered through a celite filter. The filtrate was concentrated and chromatographed on silica gel and eluted with a mixed solvent of ethyl acetate and hexane (1:1) and then with ethyl acetate, whereby trans-($\pm$)-6-[(6-hydroxy-2,2,5,7-tetramethyl)-chroman-8-yl]ethyl-4-(2-tetrahydropyranyloxy)tetrahydropyran-2-one (Compound No. 48) was obtained as a colorless amorphous solid in a yield of 161 mg (93.1%).

$^1$H NMR (CDCl$_3$, 300 MHz) $\delta$1.28(s, 6H), 1.45~1.66(m, 4H), 1.66~1.90(m, 5H), 1.78(t, J=6.9 Hz, 2H), 2.02~2.19(m, 1H), 2.11(s, 3H), 2.20(s, 3H), 2.62(t, J=6.9 Hz, 2H), 2.64~2.69(m, 1H), 2.71~2.82(m, 3H), 3.45~3.57(m, 1H), 3.76~3.87(m, 1H), 4.20~4.33(m, 2H), 4.57~4.80(m, 2H) ppm.

IR (KBr) 3477, 2944, 2876, 1738 cm$^{-1}$.

EXAMPLE 47

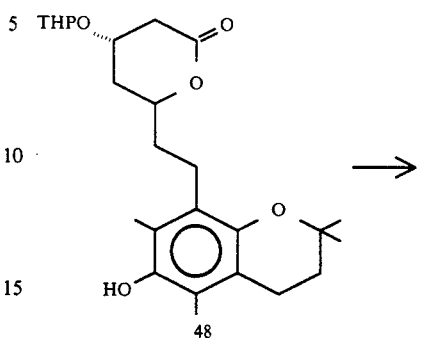

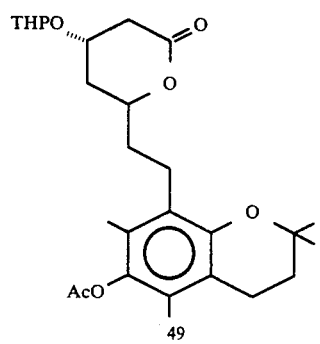

1.15 g (2.67 mmol) of Compound No. 48 synthesized in Example 46 was dissolved in 12 ml of 1,2-dichloroethane. To this solution, 1.2 ml (14.8 mmol) of pyridine and 0.6 ml (6.36 mmol) of acetic anhydride were added. The mixture was stirred in a stream of argon at room temperature for 17 hours.

The reaction mixture was poured into diluted hydrochloric acid and the mixture was then extracted with ethyl acetate. The extract layer was successively washed with a saturated solution of sodium hydrogencarbonate, and a saturated aqueous solution of sodium chloride, dried over anhydrous magnesium sulfate, and concentrated.

The concentrated product was chromatographed on silica gel and eluted with a mixed solvent of hexane and ethyl acetate (2:1), whereby trans-($\pm$)-6-[(6-acetoxy-2,2,5,7-tetramethyl)chroman-8-yl]ethyl-4-(2-tetrahydropyranyloxy)tetrahydropyran-2-one (Compound No. 49) was obtained in a yield of 1.20 g (94.7%).

Compound No. 49 is in the form of colorless crystals, with a melting point of 117.5°–119.5° C. when recrystallized from diethyl ether and hexane.

$^1$H NMR (CDCl$_3$, 300 MHz) $\delta$1.30(s, 6H), 1.46~1.62(m, 4H), 1.64~1.94(m, 5H), 1.79(t, J=6.9 Hz, 2H), 1.96~2.17(m, 1H), 1.98(s, 3H), 2.06(s, 3H), 2.33(s, 3H), 2.61(t, J=6.9 Hz, 2H), 2.65~2.70(m, 1H), 2.71~2.87(m, 3H), 3.45~3.57(m, 1H), 3.78~3.88(m, 1H), 4.21~4.33(m, 1H), 4.56~4.79(m, 2H) ppm.

IR (KBr) 2960, 2852, 2746, 1757, 1747 cm$^{-1}$.

EXAMPLE 48

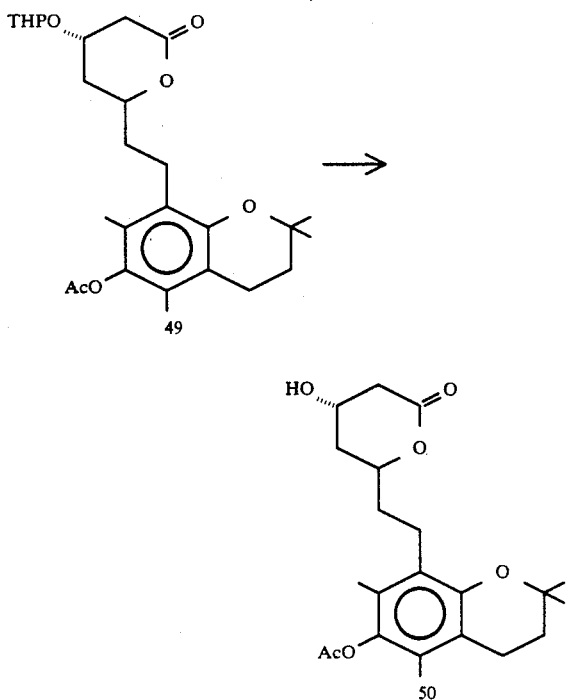

40 mg (0.0844 mmol) of Compound No. 49 synthesized in Example 47 was dissolved in 1 ml of ethyl acetate. To this solution, a catalytic amount of 12N hydrochloric acid was added. The thus obtained mixture was stirred in a stream of argon at room temperature for 7 hours.

The reaction mixture was poured into a saturated aqueous solution of sodium hydrogencarbonate and was extracted with ethyl acetate. The extract layer was successively washed with water, a saturated solution of sodium chloride, dried over anhydrous magnesium sulfate, and concentrated.

The concentrated product was chromatographed on silica gel and eluted with a mixed solvent of ethyl acetate and hexane (2:1), and then with ethyl acetate, whereby trans-($\pm$)-6-[(6-acetoxy-2,2,5,7-tetramethyl)-chroman-8-yl]ethyl-4-hydroxytetrahydropyran-2-one (Compound No. 50) was obtained in a yield of 23 mg (69.9%).

Compound No. 50 is in the form of colorless columns, with a melting point of 143.0°-143.5° C. when recrystallized from ethyl ether and hexane.

$^1$H NMR (CDCl$_3$, 300 MHz) δ1.30(s, 6H), 1.79(t, J=6.9 Hz, 2H), 1.65~1.90(m, 3H), 1.98(s, 3H), 2.06(s, 3H), 1.90~2.10(m, 2H), 2.33(s, 3H), 2.54~2.65(m, 1H), 2.61(t, J=6.9 Hz, 2H), 2.70~2.85(m, 3H), 4.30~4.40(m, 1H), 4.65~4.76(m, 1H) ppm.

IR (KBr) 3492, 2978, 2938, 1753, 1710 cm$^{-1}$.

Mass (m/z, %) 390 (M$^+$, 12), 348(100), 330(23), 163(17), 43(50).

EXAMPLE 49

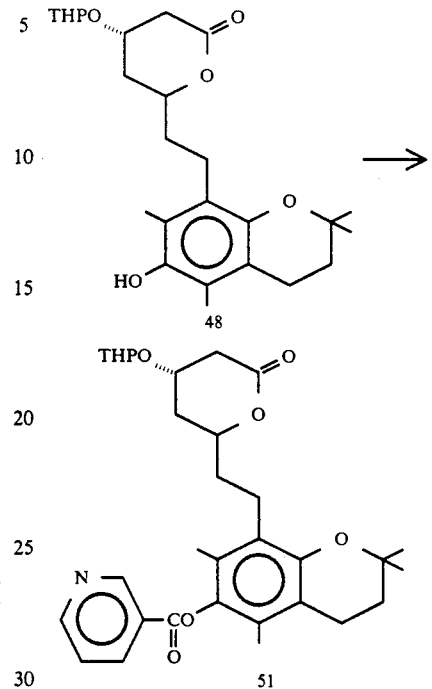

511 mg (1.18 mmol) of Compound No. 48 synthesized in Example 46 was dissolved in 5 ml of 1,2-dichloroethane in a stream of argon at room temperature. To this solution, 295 mg (1.66 mmol) of nicotinoyl chloride hydrochloride and 694 μl (4.98 mmol) were added, and the mixture was stirred at room temperature for 3 hours.

The reaction mixture was poured into a saturated aqueous solution of ammonium chloride and extracted with ethyl acetate. The extract layer was successively washed with water, and a saturated aqueous solution of sodium chloride, dried over anhydrous magnesium sulfate, and concentrated.

The concentrated product was chromatographed on silica gel and eluted with a mixed solvent of ethyl acetate and hexane (2:1), whereby trans-($\pm$)-6-[(6-pyridine-3-carboxy)-2,2,5,7-tetramethyl]chroman-8-yl)ethyl-4-(2-tetrahydropyranyloxy)tetrahydropyran-2-one (Compound No. 51) was obtained in a yield of 577 mg (91.1%).

Compound No. 51 is in the form of colorless crystals, with a melting point of 75.0°-77.0° C. when recrystallized from diethyl ether.

$^1$H NMR (CDCl$_3$, 300 MHz) δ1.31(s, 3H), 1.34(s, 3H), 1.46~1.62(m, 4H), 1.65~1.95(m, 5H), 1.82(t, J=6.9 Hz, 2H), 1.96~2.19(m, 1H), 2.02(s, 3H), 2.10(s, 3H), 2.60~2.70(m, 3H), 2.70~2.88(m, 3H), 3.45~3.58(m, 1H), 3.77~3.90(m, 1H), 4.23~4.35(m, 1H), 4.60~4.80(m, 2H), 7.49(dd with fine coupling, J=8.1 and 4.8 Hz, 1H), 8.48(ddd, J=8.1, 1.8 and 1.8 Hz, 1H), 8.87(dd, J=4.8 and 1.8 Hz, 1H), 9.44(d with fine coupling, J=1.8 Hz, 1H) ppm.

IR (KBr) 2952, 2878, 1735, 1728, 1633, 1592 cm$^{-1}$.

EXAMPLE 50

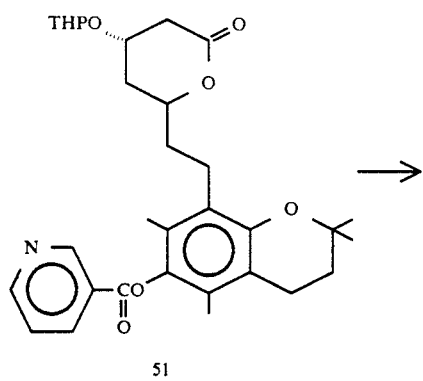

26 mg (0.050 mmol) of Compound No. 51 synthesized in Example 49 was dissolved in 1 ml of ethyl acetate. To this solution, a catalytic amount of 12N hydrochloric acid was added. The thus obtained mixture was stirred in a stream of argon at room temperature overnight.

The reaction mixture was extracted with ethyl acetate. The extract layer was successively washed with a saturated solution of sodium hydrogencarbonate, and a saturated aqueous solution of sodium chloride, dried over anhydrous magnesium sulfate, and concentrated.

The concentrated product was chromatographed on silica gel and eluted with ethyl acetate, whereby trans-(±)-6-[[6-pyridine-3-carboxy)-2,2,5,7-tetramethyl]-chroman-8-yl]ethyl-4-hydroxytetrahydropyran-2-one (Compound No. 52) was obtained in a yield of 17 mg (77.5%).

Compound No. 52 is in the form of colorless crystals, with a melting point of 124.0°-125.0° C. when recrystallized from ethyl ether and hexane.

$^1$H NMR (CDCl$_3$, 300 MHz) δ1.32(broad s, 6H), 1.82(t, J=6.9 Hz, 2H), 1.73~2.10(m, 5H), 2.02(s, 3H), 2.10(s, 3H), 2.64(t, J=6.9 Hz, 2H), 2.55~2.70(m, 1H), 2.70~2.90(m, 3H), 4.34~4.44(m, 1H), 4.76~4.89(m, 1H), 7.49(dd, J=7.8 and 4.8 Hz, 1H), 8.48(ddd, J=7.8, 1.8 and 1.8 Hz, 1H), 8.87(dd, J=4.8 and 1.8 Hz, 1H), 9.44(d, J=1.8 Hz, 1H) ppm.

IR (KBr) 3472, 2980, 2936, 1736, 1596 cm$^{-1}$.

Mass (m/z, %) 453 (M$^+$, 69), 435(16), 347(29), 217(19), 106(100), 78(48).

EXAMPLE 51

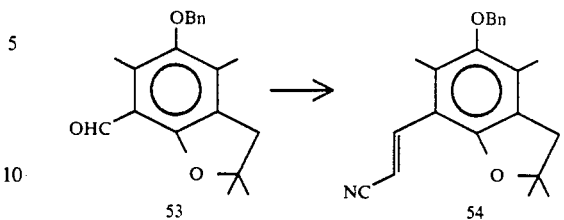

25.20 g (81.5 mmol) of 5-benzyloxy-2,3-dihydro-7-formyl-2,2,4,6-tetramethylbenzo[b]furan (Compound No. 53) and 15.0 ml (92.7 mmol) of diethylcyanomethylphosphonate were dissolved in 7 ml of ethyl acetate. To this solution, 30 ml of water, 612 mg (1.80 mmol) of tetrabutylammonium hydrogensulfate and 45.0 g (0.326 mol) of potassium carbonate were added. The thus obtained mixture was refluxed in a stream of argon for 2 hours and 30 minutes.

After the completion of the reaction, the reaction mixture was poured into water and extracted with ethyl acetate. The extract layer was successively washed with 1N hydrochloric acid, and with a saturated solution of sodium chloride two times, dried over anhydrous magnesium sulfate, and concentrated.

The concentrated product was crystallized from a mixed solvent of hexane and ethyl acetate, and filtered off, whereby 3-[5-benzyloxy-2,3-dihydro-2,2,4,6-tetramethylbenzo[b]furan-7-yl]-2-propenenonitrile (Compound No. 54) was obtained in a yield of 21.254 g (78.2%).

The mother liquor was condensed and placed on a silica gel column and eluted with a mixed solvent of hexane and dichloromethane (1:2), and with a mixed solvent of hexane and dichloromethane (1:1), whereby Compound No. 54 was further obtained in a yield of 3.467 g (12.8%).

Compound No. 54 is in the form of colorless crystals, with a melting point of 118.0°-119.5° C. when recrystallized from hexane and ethyl acetate.

$^1$H NMR (CDCl$_3$, 300 MHz) δ1.51(s, 6H), 2.19(s, 3H), 2.32(s, 3H), 2.91(s, 2H), 4.70(s, 2H), 6.45(d, J=16.5 Hz, 1H), 7.32~7.50(m, 5H), 7.49(d, J=16.5 Hz, 1H) ppm.

IR (KBr) 2940, 2884, 2220, 1606, 1586 cm$^{-1}$.

Mass (m/z, %) 333 (M$^+$, 8), 242(100), 91(34).

EXAMPLE 52

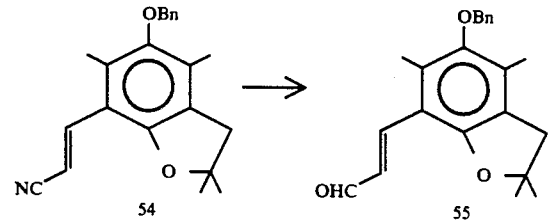

3.00 g (9.01 mmol) of Compound No. 54 synthesized in Example 51 was dissolved in 30 ml of dried toluene. To this solution, 5.5 ml (9.67 mmol) of diisobutyl aluminum hydride (25 g/100 ml hexane solution) was added in a stream of argon at −78° C., and the mixture was stirred for 30 minutes.

After the completion of the reaction, the reaction mixture was poured into 1N hydrochloric acid and successively extracted with ethyl acetate and dichloromethane. The extract layer was washed with a saturated solution of sodium chloride two times, dried over anhydrous magnesium sulfate, and concentrated.

The concentrated product was placed on a silica gel column and eluted with a mixed solvent of hexane and dichloromethane (1:1), and then with a mixed solvent of hexane and dichloromethane (2:3), whereby 3-[5-benzyloxy-2,3-dihydro-2,2,4,6-tetramethylbenzo[b]furan-7-yl]-2-propen-1-al (Compound No. 55) was obtained in a yield of 2.983 g (98.5%).

Compound No. 55 is in the form of colorless columns, with a melting point of 108.0°-109.0° C. when recrystallized from ethyl acetate.

$^1$H NMR (CDCl$_3$, 300 MHz) δ1.51(s, 6H), 2.20(s, 3H), 2.40(s, 3H), 2.92(s, 2H), 4.72(s, 2H), 7.19(dd, J=15.8 and 8.0 Hz, 1H), 7.32~7.52(m, 5H), 7.60(d, J=15.8 Hz, 1H), 9.66(d, J=8.0 Hz, 1H) ppm.

IR (KBr) 2984, 2884, 2860, 1684, 1618, 1604, 1584 cm$^{-1}$.

Mass (m/z, %) 336 (M$^+$, 9), 245(100), 91(33).

EXAMPLE 53

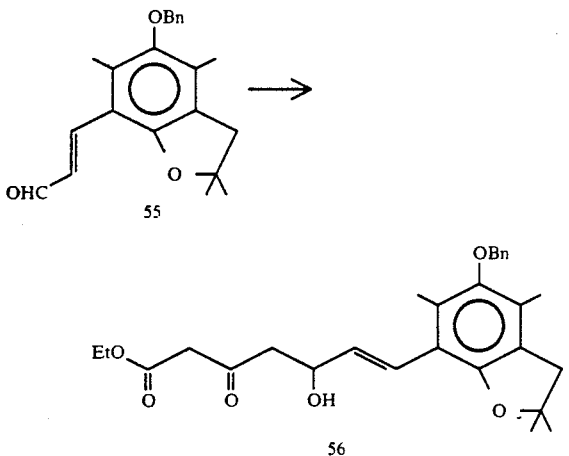

450 mg (11.3 mmol) of a 60% sodium hydride was suspended in 10 ml of dried THF in a stream of argon at 0° C. To this suspension, 1.45 ml (11.4 mmol) of ethyl acetoacetate was added. The mixture was then stirred for 30 minutes, followed by the addition of 7.2 ml (11.3 mmol) of a 15% hexane solution of butyl lithium thereto. The reaction mixture was stirred for 30 minutes.

The above reaction mixture was added to 2.867 g (8.58 mmol) of Compound No. 55 synthesized in Example 52 which was dissolved in 20 ml of dried THF in a stream of argon at −78° C. The mixture was stirred for 50 minutes.

After the completion of the reaction, the reaction mixture was poured into a saturated aqueous solution of ammonium chloride and extracted with ethyl acetate. The extract layer was washed with a saturated aqueous solution of sodium chloride three times, dried over anhydrous magnesium sulfate, and concentrated.

The concentrated product was placed on a silica gel column and eluted with a mixed solvent of hexane and ethyl acetate (4:1), whereby ethyl 7-[5-benzyloxy-2,3-dihydro-2,2,4,6-tetramethylbenzo[b]furan-7-yl]-5-hydroxy-3-oxo-6-heptanoate (Compound No. 56) was obtained in a yield of 3.206 g (80.5%). Compound No. 56 is in the form of colorless crystals, with a melting point of 96.0°-96.5° C. when recrystallized from hexane and ethyl acetate.

$^1$H NMR (CDCl$_3$, 300 MHz) δ1.28(t, J=7.2 Hz, 3H), 1.48(s, 6H), 2.16(s, 3H), 2.29(s, 3H), 2.69(d, J=3.7 Hz, 1H), 2.80~2.94(m, 2H), 2.89(s, 2H), 3.53(s, 2H), 4.21(q, J=7.2 Hz, 2H), 4.69(s, 2H), 4.70~4.84(m, 1H), 6.56(dd, J=15.9 and 6.1 Hz, 1H), 6.68(d, J=15.9 Hz, 1H), 7.30~7.52(m, 5H) ppm IR (KBr) 3528, 2988, 1748, 1718, 1648 cm$^{-1}$.

Mass (m/z, %) 466 (M$^+$, trace), 245(100), 91(51), 43(57), 31(26).

EXAMPLE 54

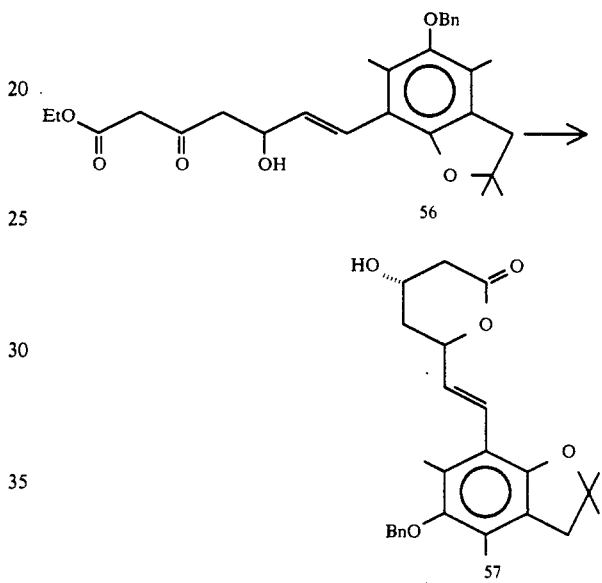

2.0 ml (2.00 mmol) of triethylborane (1.0M THF solution) was added to 12 mg (0.12 mmol) of pivalic acid in a stream of argon at room temperature. The mixture was stirred for 1 hour and 40 minutes to obtain a solution. To this solution was added 710 mg (1.53 mmol) of Compound No. 56 synthesized in Example 53, which was dissolved in 6 ml of a dried THF, and the mixture was stirred for 1 hour and 20 minutes.

The reaction mixture was cooled to −78° C., and 2 ml of methanol and 60 mg (1.59 mmol) of sodium borohydride were successively added thereto. This reaction mixture was stirred for 30 minutes. To this reaction mixture, 2 ml of a 5N aqueous solution of sodium hydroxide and 3.5 g (30.9 mmol) of a 30% aqueous solution of hydrogen peroxide were added, and the reaction mixture was ice-cooled. With further addition of 2 ml of a 5N aqueous solution of sodium hydroxide, the reaction mixture was stirred for 1 hour.

The reaction mixture was poured into 1N hydrochloric acid and the mixture was extracted with ethyl acetate. The extract layer was washed with 1N hydrochloric acid, an aqueous solution of sodium thiosulfate, and a saturated aqueous solution of sodium chloride, dried over anhydrous magnesium sulfate, and concentrated.

The concentrated product was dissolved in 15 ml of toluene. The solution was refluxed for 5 hours. After the completion of the reaction, the reaction mixture was concentrated, and placed on a silica gel column, and eluted with a mixed solvent of hexane and ethyl acetate (2:1), whereby trans-(±)-6-[5-benzyloxy-2,3-dihydro-2,2,4,6-tetramethylbenzo[b]furan-7-yl]ethenyl-4-hydroxytetrahydropyran-2-one (Compound No. 57) was obtained in a yield of 379 mg (58.9%).

Compound No. 57 is in the form of colorless crystals, with a melting point of 144.0°–145.5° C. when recrystallized from hexane and ethyl acetate.

$^1$H NMR (CDCl$_3$, 300 MHz) δ1.49(s, 3H), 1.49(s, 3H), 1.96~2.20(m, 2H), 2.17(s, 3H), 2.30(s, 3H), 2.66(ddd, 17.7, 4.1 and 1.6 Hz, 1H), 2.83(dd, J=17.7 and 5.1 Hz, 1H), 2.89(s, 2H), 4.40~4.50(m, 1H), 4.69(s, 2H), 5.28~5.39(m, 1H), 6.61(dd, J=16.0 and 6.3 Hz, 1H), 6.72(dd, J=16.0 and 0.7 Hz, 1H), 7.30~7.53(m, 5H) ppm.

IR (KBr) 3504, 2980, 2932, 2872, 1704, 1654 cm$^{-1}$.

Mass (m/z, %) 422 (M$^+$, 6), 331(58), 269(88), 243(100), 225(27), 91(87), 65(21), 44(25), 43(36).

EXAMPLE 55

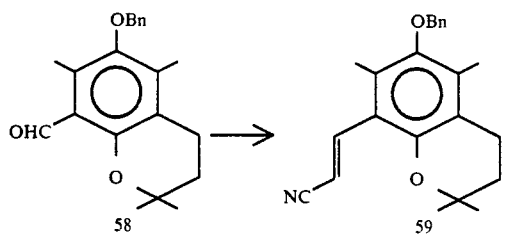

417 mg (10.4 mmol) of a 60% sodium hydride was suspended in 15 ml of dried THF. To this suspension, 1.78 ml (11.0 mmol) of diethylcyanomethylphosphonate was added in a stream of argon at 0° C., and the mixture was stirred for 20 minutes. To this solution, 2.541 g (7.84 mmol) of 6-benzyloxy-8-formyl-2,2,5,7-tetramethylchroman (Compound No. 58), which was dissolved in 10 ml of THF, was added, and the mixture was stirred for 30 minutes.

After the completion of the reaction, the reaction mixture was poured into 1N hydrochloric acid, and was then extracted with ethyl acetate. The extract layer was washed with a saturated aqueous solution of sodium chloride three times, dried over anhydrous magnesium sulfate, and concentrated.

The concentrated product was crystallized from a mixed solvent of hexane and ethyl acetate, and filtered off, whereby 3-[6-benzyloxy-2,2,5,7-tetramethylchroman-8-yl]-2-propenonitrile (Compound No. 59) was obtained in a yield of 1.350 g (49.6%). The mother liquor was condensed and placed on a silica gel column and eluted with a mixed solvent of hexane and ethyl acetate (10:1), whereby Compound No. 59 was obtained in a yield of 960 mg (35.3%).

Compound No. 59 is as colorless columns, with a melting point of 107.5°–108.0° C. when recrystallized from hexane and ethyl acetate.

$^1$H NMR (CDCl$_3$, 300 MHz) δ1.36(s, 6H), 1.85(t, J=6.9 Hz, 2H), 2.21(s, 3H), 2.34(s, 3H), 2.64(t, J=6.9 Hz, 2H), 4.68(s, 2H), 6.38(d, J=16.7 Hz, 1H), 7.32~7.52(m, 5H), 7.53(d, J=16.7 Hz, 1H) ppm.

IR (KBr) 2984, 2940, 2880, 2212, 1608, 1586 cm$^{-1}$.

Mass (m/z, %) 347 (M$^+$, 10), 256(100), 91(48).

EXAMPLE 56

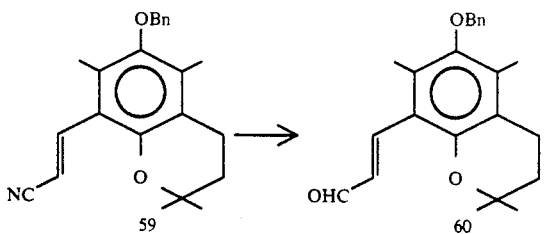

1.885 g (5.43 mmol) of Compound No. 59 synthesized in Example 55 was dissolved in 20 ml of dried toluene. To this solution, 3.3 ml (5.80 mmol) of diisobutyl aluminum hydride (25 g/100 ml hexane solution) was added in a stream of argon at −78° C., and the mixture was stirred for 30 minutes.

After the completion of the reaction, the reaction mixture was poured into 1N hydrochloric acid and successively extracted with ethyl acetate and dichloromethane. The extract layer was washed with a saturated solution of sodium chloride two times, dried over anhydrous magnesium sulfate, and concentrated.

The concentrated product was placed on a silica gel column and eluted with a mixed solvent of hexane and dichloromethane (5:1), whereby 3-[6-benzyloxy-2,2,5,7-tetramethylchroman-8-yl]-2-propen-1-al (Compound No. 60) was obtained in a yield of 1.727 g (90.8%).

Compound No. 60 is in the form of colorless columns, with a melting point of 89.0°–99.5° C. when recrystallized from hexane and ethyl acetate.

$^1$H NMR (CDCl$_3$, 300 MHz) δ1.37(s, 6H), 1.86(t, J=6.9 Hz, 2H), 2.23(s, 3H), 2.40(s, 3H), 2.65(t, J=6.9 Hz, 2H), 4.71(s, 2H), 7.02(dd, J=16.0 and 7.9 Hz, 1H), 7.32~7.52(m, 5H), 7.69(d, J=16.0 Hz, 1H), 9.65(d, J=7.9 Hz, 1H) ppm.

IR (KBr) 2984, 2936, 1678, 1616, 1582 cm$^{-1}$.

Mass (m/z, %) 350 (M$^+$, 11), 259(100), 91(51).

EXAMPLE 57

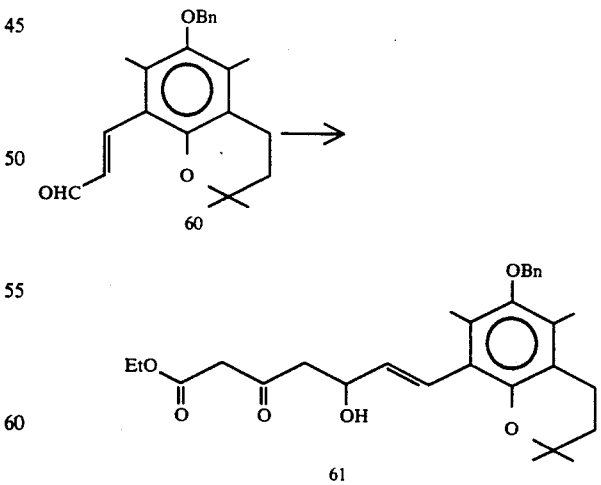

229 mg (5.72 mmol) of a 60% sodium hydride was suspended in 12.5 ml of dried THF. To this suspension, 0.73 ml (5.73 mmol) of ethyl acetoacetate was added in a steam of argon at 0° C. The mixture was then stirred for 10 minutes. 3.65 ml (5.73 mmol) of a 15% hexane solution of butyl lithium was added to the mixture. The reaction mixture was then stirred for 15 minutes.

The reaction mixture was then cooled to −78° C. With addition of 1.506 g (4.30 mmol) of Compound No. 60 synthesized in Example 56, which was dissolved in 10 ml of a dried THF, the mixture was stirred for 1 hour.

After the completion of the reaction, the reaction mixture was poured into a saturated aqueous solution of ammonium chloride, and then extracted with ethyl acetate. The extract layer was washed with a saturated aqueous solution of sodium chloride three times, dried over anhydrous magnesium sulfate, and concentrated.

The concentrated product was placed on a silica gel column and eluted with a mixed solvent of hexane and ethyl acetate (4:1) and then with a mixed solvent of hexane and ethyl acetate (3:1), whereby ethyl 7-[6-benzyloxy-2,2,5,7-tetramethylchroman-8-yl]-5-hydroxy-3-oxo-6-heptenoate (Compound No. 61) was obtained in a yield of 1.607 g (77.8%).

Compound No. 61 is in the form of colorless crystals, with a melting point of 83.0°–83.5° C. when recrystallized from hexane and ethyl acetate.

$^1$H NMR (CDCl$_3$, 300 MHz) δ1.28(t, J=7.2 Hz, 3H), 1.32(s, 6H), 1.81(t, J=6.8 Hz, 2H), 2.18(s, 3H), 2.30(s, 3H), 2.55~2.68(m, 3H), 2.83~2.93(m, 2H), 3.53(s, 2H), 4.21(q, J=7.2 Hz, 2H), 4.69(s, 2H), 4.70~4.85(m, 1H), 6.25(dd, J=16.0 and 6.6 Hz, 1H), 6.66(d, J=16.0 Hz, 1H), 7.30~7.54(m, 5H) ppm.

IR (KBr) 3556, 2984, 2936, 1730, 1718 cm$^{-1}$.

Mass (m/z, %) 480 (M$^+$, trace), 259(100), 91(65), 43(62), 31(39).

EXAMPLE 58

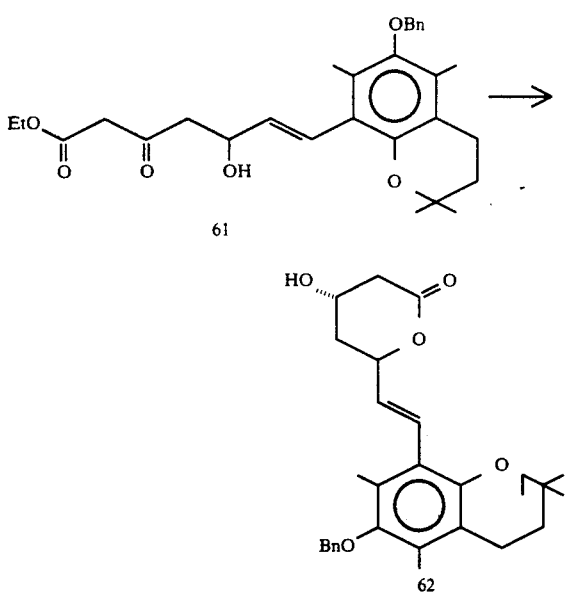

20 mg (0.20 mmol) of pivalic acid was added to 4.9 ml (4.90 mmol) of triethylborane (1M THF solution) in an atmosphere of argon at room temperature, and the mixture was stirred for 1 hour and 10 minutes, whereby a solution was obtained. To this solution was added 2.502 g (3.13 mmol) of Compound No. 61 synthesized in Example 57, which was dissolved in 15 ml of dried THF. The mixture was stirred for 1 hour and 10 minutes, and then cooled to −78° C. To this mixture, 5 ml of methanol, and then 135 mg (3.57 mmol) of sodium borohydride were added. The mixture was stirred for 30 minutes. To this mixture, 5 ml of a 5N aqueous solution of sodium hydroxide and 8.5 g (75.0 mmol) of a 30% aqueous solution of hydrogen peroxide were added, and then ice-cooled. To this mixture, 5 ml of a 5N aqueous solution of sodium hydroxide was further added, and the mixture was stirred for 30 minutes.

The reaction mixture was then poured into 1N hydrochloric acid. The mixture was extracted with ethyl acetate. The extract layer was successively washed with 1N hydrochloric acid, an aqueous solution of sodium thiosulfate, and a saturated aqueous solution of sodium chloride, dried over anhydrous magnesium sulfate, and concentrated.

The concentrated product was dissolved in 12.5 ml of dried toluene. The mixture was refluxed for 3 hours and 30 minutes. The thus obtained reaction mixture was placed on a silica gel column and eluted with a mixed solvent of hexane and ethyl acetate (2:1), whereby trans-(±)-6-[(6-benzyloxy-2,2,5,7-tetramethyl)chroman-8-yl]ethenyl-4-hydroxytetrahydropyran-2-one (Compound No. 62) was obtained in a yield of 544 mg (39.9%).

Compound No. 62 is in the form of colorless crystals, with a melting point of 122.0°–124.5° C. when recrystallized from hexane and ethyl acetate.

$^1$H NMR (CDCl$_3$, 300 MHz) δ1.32(s, 6H), 1.82(t, J=6.8 Hz, 2H), 1.87(d, J=3.3 Hz, 1H), 1.94~2.20(m, 2H), 2.19(s, 3H), 2.30(s, 3H), 2.62(t, J=6.8 Hz, 2H), 2.56~2.72(m, 1H), 2.84(dd, J=17.7 and 5.1 Hz, 1H), 4.40~4.50(m, 1H), 4.70(s, 2H), 5.27~5.40(m, 1H), 6.25(dd, J=16.0 and 6.7 Hz, 1H), 6.70(d, J=16.0 Hz, 1H), 7.30~7.54(m, 5H) ppm.

IR (KBr) 3476, 2980, 2936, 1714, 1594 cm$^{-1}$

Mass (m/z, %) 436 (M$^+$, 5), 374(21), 345(47), 283(82), 257(52), 91(100), 65(20), 44(46).

EXAMPLE 59

70.6 g (471 mmol) of 3-methyl-5-(2-propyl)phenol (Compound No. 63) was dissolved in a mixed solvent consisting of 30 ml of DMF and 90 ml of 1,2-dimethoxyethane. To this solution, 59.3 ml (600 mmol) of methallyl chloride and 166 g (1.2 mol) of potassium carbonate were added. The thus obtained mixture was heated, with stirring, in an atmosphere of argon for 5 hours. After the completion of the reaction, the reaction mixture was poured into water, and extracted with hexane. The extract layer was washed successively with a mixed solvent of an aqueous solution of potassium hydroxide and methanol, water, a saturated aqueous solution of ammonium chloride, and a saturated aqueous solution of sodium chloride, dried over anhydrous magnesium sulfate and concentrated, whereby a crude 3-methyl-1-(2-methyl-2-propenyloxy)-5-(2-propyl)benzene (Compound No. 64) was obtained as a light yellow oil in a yield of 88.8 g.

$^1$H NMR (300 MHz, CDCl$_3$) δ1.22 (d, J=6.9 Hz, 6H), 1.83 (s, 3H), 2.31 (s, 3H), 2.83 (hept, J=6.9 Hz, 1H), 4.40 (s, 2H), 4.97 (broad s, 1H), 5.09 (broad s, 1H), 6.56 (broad s, 1H), 6.62 (broad s, 1H), 6.64 (broad s, 1H) ppm.

IR (liquid film) 2966, 1610, 1596 cm$^{-1}$.

Mass (m/s, %) 204 (M$^+$, 5), 189 (5), 161 (5), 91 (5), 55 (100).

EXAMPLE 60

88.0 g (431 mmol) of the crude Compound No. 64 synthesized in Example 59 was dissolved in 200 ml of N,N-diethylaniline. This solution was heated in an atmosphere of argon at 200°-210° for 11 hours. Most of the N,N-diethylaniline was distilled away from the reaction mixture under reduced pressure. The thus obtained reaction mixture was poured into 1N hydrochloric acid and extracted with hexane.

The extract layer was washed with water, and then with a saturated aqueous solution of sodium chloride, dried over anhydrous magnesium sulfate, and concentrated.

The concentrated product was placed on a silica gel column and eluted with a mixed solvent of ethyl acetate, diethyl ether and hexane (1:2:12), whereby a mixture of 3-methyl-2-(2-methyl-2-propenyl)-5-(2-propyl)-phenol (Compound No. 65) and 5-methyl-2-(2-methyl-2-propenyl)-3-(2-propyl)phenol (Compound No. 66) with a mixing ratio of 3:2 was obtained as a yellow oil in a yield of 74.3 g.

$^1$H NMR (300 MHz, CDCl$_3$) δ1.18 (d, J=6.9 Hz, 2.4H), 1.21 (d, J=7.0 Hz, 3.6H), 1.79 (s, 1.8H), 1.81 (s, 1.2H), 2.25 (s, 1.8H), 2.28 (s, 1.2H), 2.79 (hept, J=7.0 Hz, 0.6H), 3.05 (hept, J=6.9 Hz, 0.4H), 3.34 (s, 1.2H), 3.37 (s, 0.8H), 4.58 (broad s, 0.14H), 4.65 (broad s, 0.6H), 4.83 (broad s, 1H), 4.87 (s, 0.4H), 4.93 (s, 0.6H), 6.52 (s, 0.4H), 6.57 (s, 0.6H), 6.64 (s, 0.6H), 6.70 (s, 0.4H) ppm.

EXAMPLE 61

69.6 g of a mixture of Compound No. 65 and Compound No. 66 with a mixing ratio of 3:2 synthesized in Example 60 was dissolved in 150 ml of DMF. To this solution, 13.1 g (40.3 mmol) of salcomine was added, and the mixture was stirred in an atmosphere of oxygen at 0° C. for 3 hours, and at room temperature for 3 days.

To this reaction mixture, water and hexane were added, and the mixture was filtered through a celite filter. A hexane layer was washed with a saturated aqueous solution of sodium chloride, dried over anhydrous magnesium sulfate, and concentrated. The concentrated product was placed on a silica gel column and eluted with a mixed solvent of ethyl acetate and hexane (1:10), whereby a mixture of 3-methyl-2-(2-methyl-2-propenyl)-5-(2-propyl)-p-benzoquinone (Compound No. 67) and 5-methyl-2-(2-methyl-2-propenyl)-3-(2-propyl)-p-benzoquinone (Compound No. 68) with a mixing ratio of 2:1 was obtained as a red oil in a yield of 32.4 g.

$^1$H NMR (300 MHz, CDCl$_3$) δ1.12 (d, J=6.9 Hz, 4H), 1.25 (d, J=7.0 Hz, 2H), 1.76 (s, 2H), 1.78 (s, 1H), 2.02 (s, 3H), 2.95 (hept, J=7.0 Hz, 0.3H), 3.07 (hept, J=6.9 Hz, 0.7H), 3.19 (s, 2H), 4.50 (s, with fine coupling, 0.3H), 4.53 (s with fine coupling, 0.7H), 4.77 (s with fine coupling, 1H), 6.50 (s with fine coupling, 0.7H), 6.55 (s with fine coupling, 0.3H) ppm.

EXAMPLE 62

31.9 g of the mixture of Compound No. 67 and Compound No. 68 with a mixing ratio of 2:1 synthesized in Example 61 was dissolved in a mixed solvent of 100 ml of dichloromethane and 30 ml of methanol. To this solution, 1.80 g (47.6 mmol) of sodium borohydride was added in a stream of argon at 0° C.

To this mixture, several drops of acetone were added, and the mixture was then poured into 1N hydrochloric acid and extracted with ethyl acetate. The extract layer was washed with water and then with a saturated aqueous solution of sodium chloride, dried over anhydrous magnesium sulfate, concentrated.

The concentrated product was placed on a silica gel column and eluted with a mixed solvent of ethyl acetate and hexane (1:4), whereby a mixture of 3-methyl-2-(2-methyl-2-propenyl)-5-(2-propyl)hydroquinone (Compound No. 69) and 5-methyl-2-(2-methyl-2-propenyl)-3-(2-propyl)hydroquinone (Compound No. 70) with a mixing ratio of 8:1 was obtained in a yield of 7.85 g.

Then 22.4 g of a mixture of Compound No. 69 and Compound No. 70 (7:3) was obtained, which was further placed on a silica gel column and eluted with a mixed solvent of ethyl acetate, hexane and diethyl ether (2:8:1), whereby 9.13 g of Compound No. 69 and 4.32 g of Compound No. 70 were isolated.

Compound No. 69 is in the form of colorless crystals, with a melting point of 97.5°-98.5° C. when recrystallized from cyclohexane.

$^1$H NMR (300 MHz, CDCl$_3$) δ1.34 (d, J=7.1 Hz, 6H), 1.82 (s, 3H), 2.18 (s, 3H), 3.10~3.24 (m, 1H), 3.36 (s, 2H), 4.25 (s, 1H), 4.42 (s, 1H), 4.53 (broad s, 1H), 4.82 (broad s, 1H), 6.51 (s, 1H) ppm.

IR (KBr) 3324, 2968 cm$^{-1}$.

Mass (m/z, %) 220 (M$^+$, 13), 205 (7), 177 (5), 163 (6), 91 (2).

Compound No. 70 is as colorless columns, with a melting point of 61.0°-62.0° C. when recrystallized from diethyl ether and hexane.

$^1$H NMR (300 MHz, CDCl$_3$) δ1.23 (d, J=6.8 Hz, 6H), 1.80 (s, 3H), 2.17 (s, 3H), 3.12 (hept, J=6.8 Hz, 1H), 3.35 (s, 2H), 4.32 (s, 1H), 4.57 (s, 1H), 4.60 (s with fine coupling, 1H), 4.82 (s with fine coupling, 1H), 6.58 (s, 1H) ppm.

IR (KBr) 3552, 3418, 2972 cm$^{-1}$.

Mass (m/z, %) 220 (M$^+$, 11), 205 (14), 163 (3), 91 (3).

EXAMPLE 63

13.2 g (59.8 mmol) of Compound No. 69 synthesized in Example 62 was dissolved in 100 ml of dichloromethane. To this solution, 1.184 ml (14.9 mmol) of boron trifluoride etherate was added and the mixture was stirred in a stream of argon for 2 hours and 45 minutes. The reaction mixture was then poured into a saturated aqueous solution of sodium hydrogencarbonate, and extracted with ethyl acetate. The extract layer was washed with water and then with a saturated aqueous solution of sodium chloride, dried over anhydrous magnesium sulfate, and concentrated, whereby a crude 2,3-dihydro-5-hydroxy-6-(2-propyl)-2,2,4-tetramethylbenzo[b]furan (Compound No. 71) was obtained as a yellow oil in a yield of 12.3 g.

The thus obtained product was used in the next reaction without purification.

$^1$H NMR (300 MHz, CDCl$_3$) δ1.22 (d, J=6.9 Hz, 6H), 1.46 (s, 6H), 2.13 (s, 3H), 2.92 (s, 2H), 3.13 (hept, J=6.9 Hz, 1H), 4.21 (s, 1H), 6.48 (s, 1H) ppm.

EXAMPLE 64

4.32 g of the mixture of Compound No. 69 and Compound No. 70 with a mixing ratio of 1:5 synthesized in Example 62 was dissolved in 30 ml of dichloromethane. To this solution, 0.603 ml (4.9 mmol) of boron trifluoride etherate was added and the mixture was stirred in a stream of argon at 0° C. for 1 hour and 45 minutes. The reaction mixture was then poured into a saturated aqueous solution of sodium hydrogencarbonate, and extracted with ethyl acetate. The extract layer was washed with water and then with a saturated aqueous solution of sodium chloride, and concentrated.

The concentrated product was placed on a silica gel column and eluted with a mixed solvent of ethyl acetate, diethyl ether and hexane (2:1:12), whereby a mixture of 2,3-dihydro-5-hydroxy-4-(2-propyl)-2,2,6-tetramethylbenzo[b]furan (Compound No. 72) and Compound No. 71 with a mixing ratio of 6:1 was obtained as a yellow oil in a yield of 3.52 g.

$^1$H NMR (300 MHz, CDCl$_3$) δ1.22 (d, J=6.9 Hz, 0.8H), 1.30 (d, J=7.2 Hz, 5.2H), 1.44 (s, 5.2H), 1.46 (s, 0.8H), 2.13 (s, 0.4H), 2.18 (s, 2.6H), 2.92 (s, 0.3H), 3.01 (s, 1.7H), 3.13 (hept, J=6.9 Hz, 0.1H), 3.19 (hept, J=7.2 Hz, 1H), 4.14 (s, 0.9H), 4.21 (s, 0.1H), 6.38 (s, 0.9H), 6.48 (s, 0.1H) ppm.

EXAMPLE 65

12.3 g of Compound No. 71 synthesized in Example 63 was dissolved in a mixed solvent consisting of 40 ml of DMF and 120 ml of DME. To this solution, 7.98 ml (67.1 mmol) of benzyl bromide and 23.1 g (168 mmol) of potassium carbonate were added. The mixture was refluxed in an atmosphere of argon for 6 hours.

The reaction mixture was poured into water and extracted with hexane. The extract layer was washed with water and then with a saturated aqueous solution of sodium chloride, dried over anhydrous magnesium sulfate, and concentrated.

The concentrated product was crystallized from ethyl acetate and filtered off, whereby 5-benzyloxy-2,3-dihydro-6-(2-propyl)-2,2,4-trimethylbenzo[b]furan (Compound No. 73) was obtained as crystals in a yield of 10.8 g.

The mother liquor was concentrated and crystallized from ethyl acetate, whereby Compound No. 73 was further obtained as crystals in a yield of 1.40 g.

Compound No. 73 is in the form of colorless crystals, with a melting point of 91.0°-92.0° C. when recrystallized from hexane and diethyl ether.

$^1$H NMR (300 MHz, CDCl$_3$) δ1.19 (d, J=6.9 Hz, 6H), 1.48 (s, 6H), 2.19 (s, 3H), 2.97 (s, 2H), 3.33 (hept, J=6.9 Hz, 1H), 4.75 (s, 2H), 6.51 (s, 1H), 7.30~7.53 (s, 5H) ppm.

IR (KBr) 2968, 1604 cm$^{-1}$.

Mass (m/z, %) 310 (M$^+$, 2), 219 (30), 163 (2), 91 (11).

EXAMPLE 66

3.42 g of the mixture of Compound No. 72 and Compound No. 71 with a mixing ratio of 6:1 synthesized in Example 64 was dissolved in a mixed solvent consisting of 10 ml of DMF and 30 ml of DME. To this solution, 2.22 ml (18.6 mmol) of benzyl bromide and 6.42 g (46.5 mmol) of potassium carbonate were added. The mixture was refluxed in an atmosphere of argon for 5 hours.

The reaction mixture was poured into water and extracted with hexane. The extract layer was washed with water and then with a saturated aqueous solution of sodium chloride, dried over anhydrous magnesium sulfate, and concentrated.

The concentrated product was placed on a silica gel column and eluted with a mixed solvent of ethyl acetate and hexane (1:6), whereby a mixture of 5-benzyloxy-2,3-dihydro-4-(2-propyl)-2,2,6-trimethylbenzo[b]furan (Compound No. 74) and Compound No. 73 with a mixing ratio of 6:1 was obtained in a yield of 4.65 g.

Compound No. 74 is in the form of colorless crystals, with a melting point of 85.0°-86.0° C. when recrystallized from ethanol and water.

$^1$H NMR (300 MHz, CDCl$_3$) δ1.24 (d, J=7.2 Hz, 6H), 1.46 (s, 6H), 2.28 (s, 3H), 3.07 (s, 2H), 3.52 (hept, J=7.2 Hz, 1H), 4.73 (s, 2H), 6.45 (s, 1H), 7.30~7.51 (m, 5H) ppm.

IR (KBr) 2976 cm$^{-1}$.

Mass (m/z, %) 310 (M$^+$, 2), 219 (32), 163 (1), 91 (10).

EXAMPLE 67

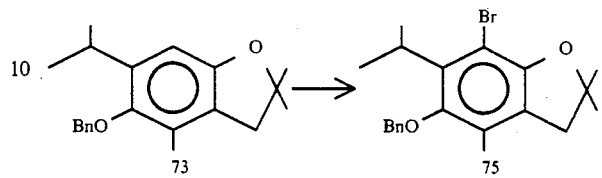

12.1 g of Compound No. 73 synthesized in Example 65 was dissolved in a mixed solvent consisting of 53 ml of THF and 6 ml of water. To this solution, 7.33 g (41.2 mmol) of N-bromosuccinimide were added, and the mixture was stirred in an atmosphere of argon for 1 hour.

The reaction mixture was poured into a saturated aqueous solution of sodium thiosulfate and extracted with hexane. The extract layer was washed with water and then with a saturated aqueous solution of sodium chloride, dried over anhydrous magnesium sulfate, and concentrated.

The concentrated product was crystallized from diethyl ether and hexane and filtered off, whereby 5-benzyloxy-7-bromo-2,3-dihydro-6-(2-propyl)-2,2,4-trimethylbenzo[b]furan (Compound No. 75) was obtained in a yield of 13.5 g (89.2%).

The mother liquor was concentrated and placed on a silica gel column and eluted with a mixed solvent of ethyl acetate and hexane (1:10), whereby Compound No. 75 was further obtained in a yield of 306 mg (2.0%).

Compound No. 75 is in the form of colorless columns, with a melting point of 156.0°-156.5° C. when recrystallized from diethyl ether and hexane.

$^1$H NMR (300 MHz, CDCl$_3$) δ1.42 (d, J=7.2 Hz, 6H), 1.53 (s, 6H), 2.14 (s, 3H), 3.01 (s, 2H), 3.73 (hept, J=7.2 Hz, 1H), 4.74 (s, 2H), 7.30~7.53 (m, 5H) ppm.

IR (KBr) 2960, 1603 cm$^{-1}$.

Mass (m/z, %) 390 (M$^+$, 1), 388 (M$^+$, 1), 299 (10), 297 (11), 218 (10), 91 (11).

EXAMPLE 68

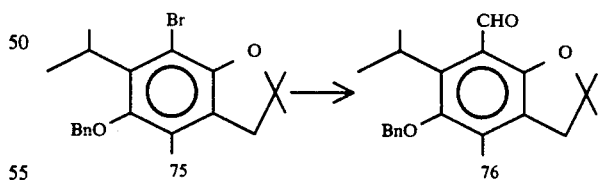

1.93 g (79.4 mmol) of magnesium (flakes) was added to 20 ml of anhydrous THF in an atmosphere of argon and the mixture was stirred at room temperature to prepare a solution. 0.6 ml (8.04 mmol) of ethyl bromide was added dropwise to this solution, whereby magnesium ethyl bromide was prepared.

To this magnesium ethyl bromide solution, 24.9 g (63.6 mmol) of Compound No. 75 synthesized in Example 67 in total was added, one tenth of the amount ten times, over a period of 30 minutes, while adding 80 ml of anhydrous THF dropwise from a dropping funnel. The reaction mixture was stirred for 50 minutes and then cooled to 0° C., and 11.8 ml (95.6 mmol) of N-methylformanilide was added thereto. After the reaction mixture was stirred for 20 minutes, the reaction mixture was then stirred at room temperature for 1 hour.

The reaction mixture was poured into 1N hydrochloric acid and extracted with ethyl acetate. The extract layer was washed with a saturated aqueous solution of sodium chloride, dried over anhydrous magnesium sulfate, and concentrated.

The concentrated product was crystallized from a mixed solvent of ethyl acetate and hexane, and filtered off, whereby 5-benzyloxy-2,3-dihydro-7-formyl-6-(2-propyl)-2,2,4-trimethylbenzo[b]furan (Compound No. 76) was obtained in a yield of 13.5 g (62.7%).

The mother liquor was concentrated and placed on a silica gel column and eluted with a mixed solvent of hexane and dichloromethane (1:1), whereby Compound No. 76 was further obtained in a yield of 7.41 g (34.5%).

Compound No. 76 is in the form of colorless crystals, with a melting point of 107.0°–108.5° C. when recrystallized from ethyl acetate.

$^1$H NMR (300 MHz, CDCl$_3$) δ1.39 (d, J=7.2 Hz, 6H), 1.53 (s, 6H), 2.23 (s, 3H), 2.90 (s, 2H), 3.99 (hept, J=7.2 Hz, 1H), 4.75 (s, 2H), 7.32~7.52 (m, 5H), 10.46 (s, 1H) ppm.

IR (KBr) 2960, 1685 cm$^{-1}$.

Mass (m/z, %) 338 (M$^+$, 1), 247 (25), 229 (4), 219 (2), 91 (12).

EXAMPLE 69

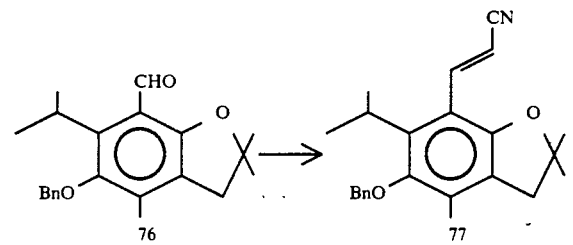

584 mg (14.6 mmol) of a 60% sodium hydride was suspended in 30 ml of anhydrous THF to prepare a suspension. To this suspension, 2.36 ml (14.6 mmol) of diethylcyanomethyl phosphonate was added in a stream of argon. To this mixture, a THF solution of 4.05 g (12.0 mmol) of Compound No. 76 synthesized in Example 68, which was dissolved in 10 ml of anhydrous THF was added dropwise, and the mixture was stirred for 5 minutes.

The reaction mixture was poured into 1N hydrochloric acid and extracted with ethyl acetate. The extract layer was washed with water and a saturated aqueous solution of sodium chloride, dried over anhydrous magnesium sulfate, and concentrated.

The concentrated product was crystallized from a mixed solvent of diethyl ether and hexane, and filtered off, whereby 3-[5-benzyloxy-2,3-dihydro-6-(2-propyl)-2,2,4-trimethylbenzo[b]furan-7-yl]-2-propenonitrile (Compound No. 77) was obtained in a yield of 3.48 g (80.4%).

The mother liquor was concentrated and placed on a silica gel column and eluted with a mixed solvent of ethyl acetate and hexane (1:4), whereby Compound No. 77 was further obtained in a yield of 365 mg (8.4%).

Compound No. 77 is in the form of colorless columns, with a melting point of 155.5°–156.5° C. when recrystallized from ethyl acetate.

$^1$H NMR (300 MHz, CDCl$_3$) δ1.37 (d, J=7.4 Hz, 6H), 1.51 (s, 6H), 2.20 (s, 3H), 2.91 (s, 2H), 3.80 (hept, J=7.4 Hz, 1H), 4.70 (s, 2H), 6.42 (d, J=16.5 Hz, 1H), 7.30~7.50 (m, 5H), 7.73 (d, J=16.5 Hz, 1H) ppm.

IR (KBr) 2974, 2216, 1605 cm$^{-1}$.

Mass (m/z, %) 361 (M$^+$, 2), 270 (26), 219 (6), 91 (10).

EXAMPLE 70

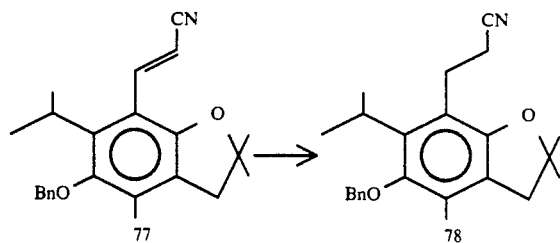

8.77 g (24.3 mmol) of Compound No. 77 synthesized in Example 69 was dissolved in a mixed solvent of 35 ml of methanol and 45 ml of THF. To this solution, 1.77 g (72.9 mmol) of magnesium (flakes) and 45 mg (0.177 mmol) of iodine were successively added in a stream of argon, and the mixture was stirred for 2 hours and 30 minutes.

The reaction mixture was poured into 1N hydrochloric acid and extracted with ethyl acetate. The extract layer was washed with water, a saturated aqueous solution of sodium hydrogencarbonate, and a saturated aqueous solution of sodium chloride, dried over anhydrous magnesium sulfate, and concentrated.

The concentrated product was crystallized from hexane, and filtered off, whereby 3-[5-benzyloxy-2,3-dihydro-6-(2-propyl)-2,2,4-trimethylbenzo[b]furan-7-yl]propanenitrile (Compound No. 78) was obtained in a yield of 7.73 g (87.6%).

The mother liquor was concentrated and placed on a silica gel column and eluted with a mixed solvent of dichloromethane and hexane (1:1), whereby Compound No. 78 was further obtained in a yield of 284 mg (3.2%).

Compound No. 78 is in the form of colorless, with a melting point of 114.5°–115.0° C. when recrystallized from hexane and diethyl ether.

$^1$H NMR (300 MHz, CDCl$_3$) δ1.35 (d, J=7.3 Hz, 6H), 1.47 (s, 6H), 2.17 (s, 3H), 2.61 (t, J=8.0 Hz, 2H), 2.91 (s, 2H), 3.04 (t, J=8.0 Hz, 2H), 3.45~3.65 (m, 1H), 4.73 (s, 2H), 7.30~7.52 (m, 5H) ppm.

IR (KBr) 2980, 2242, 1598 cm$^{-1}$.

Mass (m/z, %) 363 (M$^+$, 1), 272 (29), 231 (4), 189 (1), 91 (9).

EXAMPLE 71

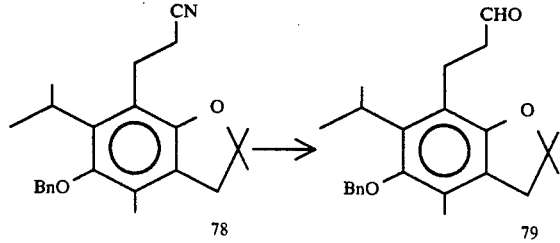

8.01 g (22.1 mmol) of Compound No. 78 synthesized in Example 70 was dissolved in 50 ml of anhydrous toluene. To this solution, 13.2 ml (23.2 mmol) of diisobutyl aluminum hydride (25% hexane solution) was added in a stream of argon at −78° C., and the mixture was stirred for 30 minutes.

With addition of methanol to this reaction mixture, the temperature of the reaction mixture was raised to room temperature.

The reaction mixture was then poured into 1N hydrochloric acid and extracted with ethyl acetate. The extract layer was washed with water, a saturated aqueous solution of sodium chloride, dried over anhydrous magnesium sulfate, and concentrated.

The concentrated product was crystallized from hexane, and filtered off, whereby 3-[5-benzyloxy-2,3-dihydro-6-(2-propyl)-2,2,4-trimethylbenzo[b]furan-7-yl]propanal (Compound No. 79) was obtained in a yield of 4.20 g (51.9%).

The mother liquor was concentrated and placed on a silica gel column and eluted with a mixed solvent of ethyl acetate and hexane (1:6), whereby Compound No. 79 was further obtained in a yield of 3.11 g (38.4%).

Compound No. 79 is in the form of colorless crystals, with a melting point of 88.0°–89.0° C. when recrystallized from hexane.

$^1$H NMR (300 MHz, CDCl$_3$) δ1.34 (d, J=7.3 Hz, 6H), 1.45 (s, 6H), 2.17 (s, 3H), 2.69 (t, J=7.8 Hz, 2H), 2.90 (s, 2H), 2.97 (t, J=7.8 Hz, 2H), 3.40~3.62 (m, 1H), 4.74 (s, 2H), 7.30~7.52 (m, 5H), 9.86 (s, 1H) ppm.

IR (KBr) 2970, 1722 cm$^{-1}$.

Mass (m/z, %) 366 (M$^+$, 5), 275 (100), 231 (44), 91 (60).

EXAMPLE 72

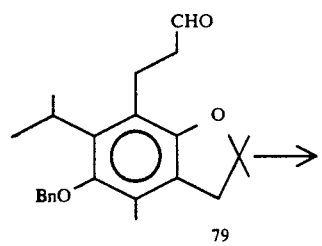

79

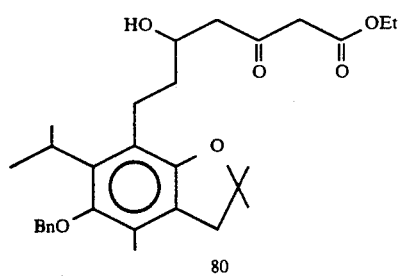

80

840 mg (23.8 mmol) of a 60% sodium hydride was suspended in 30 ml of anhydrous THF to prepare a suspension. To this suspension, 2.67 ml (21.0 mmol) of ethyl acetoacetate was added in a stream of argon at 0° C. The mixture was stirred for 30 minutes. To this mixture, 13.4 ml (23.8 mmol) of butyl lithium (15% hexane solution) was added, and the mixture was stirred for 35 minutes. The reaction mixture was cooled to −78° C., and a THF solution of 7.31 g (20.0 mmol) of Compound No. 79 synthesized in Example 71, which was dissolved in 25 ml of anhydrous THF was added, and the reaction mixture was stirred for 1 hour.

The reaction mixture was poured into 1N hydrochloric acid and extracted with ethyl acetate. The extract layer was washed with water and a saturated aqueous solution of sodium chloride, dried over anhydrous magnesium sulfate, and concentrated.

The concentrated product was placed on a silica gel column and eluted with a mixed solvent of ethyl acetate and hexane (1:3). The eluted product was then concentrated and placed on a silica gel column once again and eluted with dichloromethane, whereby ethyl 7-[5-benzyloxy-2,3-dihydro-6-(2-propyl)-2,2,4-trimethylbenzo[b]furan-7-yl]-5-hydroxy-3-oxoheptanoate (Compound No. 80) was obtained as a yellow oil in a yield of 7.26 g (73.2%).

$^1$H NMR (300 MHz, CDCl$_3$) δ1.27 (t, J=7.1 Hz, 3H), 1.34 (d, J=7.2 Hz, 6H), 1.47 (s with fine coupling, 6H), 1.60~1.78 (m, 2H), 2.16 (s, 3H), 2.55~2.80 (m, 4H), 2.92 (s, 2H), 3.20~3.50 (m, 1H), 3.50 (s, 2H), 3.95~4.08 (m, 1H), 4.18 (q, J=7.1 Hz, 2H), 4.80 (s, 2H), 7.30~7.55 (m, 5H) ppm.

IR (liquid film) 3516, 2976, 2936, 1746, 1723 cm$^{-1}$.

Mass (m/z, %) 496 (M$^+$, 2), 405 (17), 275 (58), 231 (50), 91 (75).

EXAMPLE 73

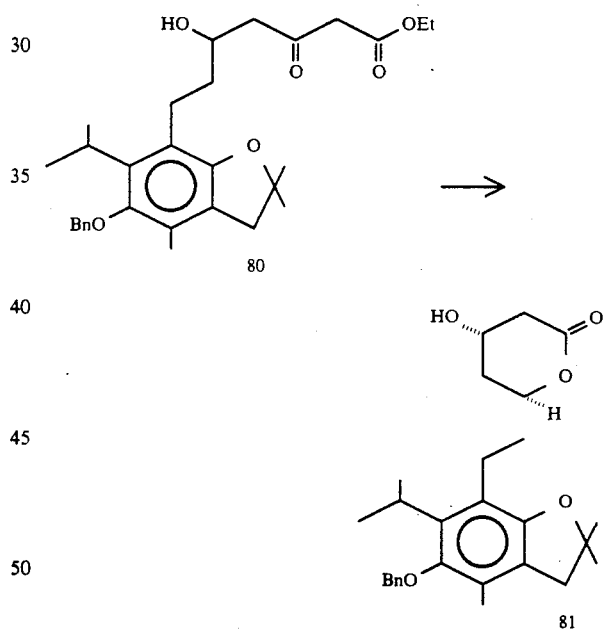

73 mg (0.720 mmol) of pivalic acid was added to 17.3 ml (17.3 mmol) of triethylborane (1.0M THF solution) in an atmosphere of argon at room temperature, and the mixture was stirred for 1 hour and 20 minutes, whereby a solution was obtained. To this solution, a THF solution of 7.16 g (14.4 mmol) of Compound No. 80 synthesized in Example 72, which was dissolved in 50 ml of anhydrous THF was added, and the mixture was stirred for 1 hour. The mixture was then cooled to −78° C. To this mixture, 22.5 ml of methanol was added. 10 minutes later, 408 mg (10.8 mmol) of sodium borohydride was added, and the mixture was stirred for 1 hour.

To this mixture, 38.9 ml of a 5N aqueous solution of sodium hydroxide was added, and the temperature of the reaction mixture was raised to 0° C., and 30 g of a 30% aqueous solution of hydrogen peroxide was added. With the temperature of the reaction mixture raised to room temperature, the reaction mixture was stirred for 2 hours.

The reaction mixture was then poured into 1N hydrochloric acid and extracted with ethyl acetate. The extract layer was successively washed with a saturated aqueous solution of sodium thiosulfate, water and a saturated aqueous solution of sodium chloride, dried over anhydrous magnesium sulfate, and concentrated.

The concentrated product was dissolved in 30 ml of toluene and refluxed for 3 hours and 30 minutes. After the solvent was distilled away from the reaction mixture, the concentrated product was placed on a silica gel column and eluted with a mixed solvent of ethyl acetate and hexane (2:1), whereby trans-($\pm$)-6-[5-benzyloxy-2,3-dihydro-6-(2-propyl)-2,2,4-trimethylbenzo[b]furan-7-yl]ethyl-4-hydroxytetrahydropyran-2-one (Compound No. 81) was obtained in a yield of 4.51 g (69.3%).

Compound No. 81 is in the form of colorless crystals, with a melting point of 134.5°–135.0° C. when recrystallized from ethyl acetate and hexane.

$^1$H NMR (300 MHz, CDCl$_3$) $\delta$1.36 (d, J=7.2 Hz, 3H), 1.36 (d, J=7.2 Hz, 3H), 1.45 (s, 3H), 1.45 (s, 3H), 1.73~2.10 (m, 5H), 2.16 (s, 3H), 2.63 (ddd, J=17.5, 4.1 and 1,4 Hz, 1H), 2.78 (dd, J=17.5 and 6.1 Hz, 1H), 2.65~2.90 (m, 2H), 2.90 (s, 2H), 3.40~3.60 (m, 1H), 4.37~4.46 (m, 1H), 4.76 (s, 2H), 4.70~4.85 (m, 1H), 7.30~7.55 (m, 5H) ppm.

IR (KBr) 3552, 2936, 2876, 1716 cm$^{-1}$.

Mass (m/z, %) 452 (M$^+$, 5), 361 (100), 343 (18), 301 (7), 231 (64), 189 (30), 91 (98), 43 (28).

EXAMPLE 74

74.8 g (420 mmol) of 2,6-di(2-propyl)phenol (Compound No. 82) was dissolved in 200 ml of DMF. To this solution, 13.7 g (42.0 mmol) of salcomine was added, and the mixture was stirred at 0° C. for 8 hours. The reaction mixture was further stirred at room temperature overnight, and poured into water and extracted with hexane. The extract was filtered through a celite filter. The hexane layer was washed with a saturated aqueous solution of sodium chloride, dried over anhydrous magnesium sulfate, and concentrated, whereby 2,6-di(2-propyl)-p-benzoquinone (Compound No. 83) was obtained as a red oil in a yield of 67.8 g (84.1%).

$^1$H NMR (300 MHz, CDCl$_3$) $\delta$1.12 (s, 6H), 1.14 (s, 6H), 3.07 (hept, J=6.9 Hz, 2H), 6.48 (s, 2H) ppm.

IR (liquid film) 2972, 1660, 1614 cm$^{-1}$.

Mass (m/z, %) 192 (M$^+$, 6), 164 (3), 149 (14), 121 (5).

EXAMPLE 75

67.6 g of Compound No. 83 synthesized in Example 74 was dissolved in a mixed solvent of 200 ml of dichloromethane and 100 ml of methanol. To this solution, 3.36 g (8.89 mmol) of sodium borohydride was added in a stream of argon at 0° C., and the reaction mixture was stirred for 1 hour. The reaction mixture was then stirred at room temperature overnight. To this reaction mixture, a small amount of acetone was added to terminate the reaction.

The reaction mixture was poured into 1N hydrochloric acid and extracted with ethyl acetate. The extract layer was washed with water and then with a saturated aqueous solution of sodium chloride, dried over anhydrous magnesium sulfate, and concentrated, whereby 2,6-di(2-propyl)hydroquinone (Compound No. 84) was obtained in a yield of 48.6 g (71.1%).

Compound No. 84 is in the form of colorless crystals, with a melting point of 102.0°–104.0° C. when recrystallized from ethyl acetate.

$^1$H NMR (300 MHz, CDCl$_3$) $\delta$1.22 (s, 6H), 1.25 (s, 6H), 3.14 (hept, J=6.9 Hz, 2H), 4.40 (s, 1H), 4.59 (s, 1H), 6.55 (s, 2H) ppm.

IR (KBr) 3328, 2972 cm$^{-1}$.

Mass (m/z, %) 194 (M$^+$, 14), 179 (22), 151 (1), 137 (2), 91 (2).

EXAMPLE 76

44.6 g (232 mmol) of Compound No. 84 synthesized in Example 75 was dissolved in 87.6 ml of acetic anhydride, and the solution was refluxed in a stream of argon for 2 hours and 20 minutes.

The reaction mixture was diluted with a mixed solvent of ethyl acetate and hexane (3:1). The reaction mixture, with addition of water thereto, was allowed to stand at room temperature overnight. An organic layer of the reaction mixture was successively washed with water, a saturated aqueous solution of sodium hydrogencarbonate and a saturated aqueous solution of sodium chloride, dried over anhydrous magnesium sulfate, and concentrated.

The concentrated product was crystallized from hexane, whereby 1,4-diacetoxy-2,6-di(2-propyl)benzene (Compound No. 85) was obtained in a yield of 47.3 g (73.2%).

Compound No. 85 is in the form of colorless crystals, with a melting point of 73.5°–75.0° C. when recrystallized from hexane.

$^1$H NMR (300 MHz, CDCl$_3$) $\delta$1.17 (s, 6H), 1.20 (s, 6H), 2.29 (s, 3H), 2.35 (s, 3H), 2.89 (hept, J=6.9 Hz, 2H), 6.86 (s, 2H) ppm.

IR (KBr) 2976, 1764 cm$^{-1}$.

Mass (m/z, %) 278 (M$^+$, 1), 236 (4), 194 (30), 179 (6), 151 (1), 91 (2).

EXAMPLE 77

42.1 g (151 mmol) of Compound No. 85 synthesized in Example 76 was dissolved in 100 ml of methanol. To this solution, 11.5 g (83.3 mmol) of potassium carbonate was added, and the mixture was stirred in an atmosphere of argon at 0° C. for 20 minutes. To this reaction mixture, 1.15 g (8.33 mmol) of potassium carbonate was further added, and the mixture was stirred for 30 minutes.

The reaction mixture was poured into water and extracted with ethyl acetate. The extract layer was washed with a saturated aqueous solution of sodium chloride, dried over anhydrous magnesium sulfate, and concentrated, whereby 4-acetoxy-3,5-di(2-propyl)phenol (Compound No. 86) was obtained in a yield of 33.7 g (94.4%).

Compound No. 86 is in the form of colorless crystals, with a melting point of 141.0°–141.5° C. when recrystallized from hexane.

$^1$H NMR (300 MHz, CDCl$_3$) $\delta$1.16 (s, 6H), 1.18 (s, 6H), 2.33 (s, 3H), 2.85 (hept, J=6.9 Hz, 2H), 4.85 (s, 1H), 6.60 (s, 2H) ppm.

IR (KBr) 3296, 2976, 1716 cm$^{-1}$.

Mass (m/z, %) 236 (M$^+$, 3), 194 (27), 179 (15), 151 (1), 91 (2).

EXAMPLE 78

31.7 g (134 mmol) of Compound No. 86 synthesized in Example 77 was dissolved in a mixed solvent consisting of 25 ml of DMF and 75 ml of DME. To this solution, 15.9 ml (161 mmol) of methallyl chloride and 55.6 g (403 mmol) of potassium carbonate were added. The reaction mixture was refluxed in an atmosphere of argon for 10 hours. The reaction mixture was poured into water and extracted with hexane. The extract layer was washed with a saturated aqueous solution of sodium chloride, dried over magnesium sulfate, and concentrated, whereby a crude 1-acetoxy-2,6-di(2-propyl)-4-(2-methyl-2-propenyloxy)benzene (Compound No. 87) was obtained as a yellow oil in a yield of 39.0 g. Compound No. 87 was used in the next reaction without purification.

$^1$H NMR (300 MHz, CDCl$_3$) δ1.17 (s, 6H), 1.20 (s, 6H), 1.85 (s, 3H), 2.33 (s, 3H), 2.87 (hept, J=6.9 Hz, 2H), 4.40 (s, 2H), 5.00 (s, 1H) 5.11 (s, 1H), 6.70 (s, 2H) ppm.

IR (liquid film) 2972, 1766 cm$^{-1}$.

Mass (m/z, %) 290 (M$^+$, 3), 248 (15), 193 (21), 149 (1), 91 (1).

EXAMPLE 79

38.0 g (131 mmol) of Compound No. 87 synthesized in Example 78 was dissolved in 150 ml of N,N-diethylaniline, and the solution was refluxed in an atmosphere of argon at 200°-210° C. for 9 hours. Most of the N,N-diethylaniline was distilled away from the reaction mixture under reduced pressure. The residue was dissolved in hexane and washed with 1N hydrochloric acid, water and a saturated aqueous solution of sodium chloride, dried over magnesium sulfate, and concentrated. The concentrated product was crystallized from diethyl ether and hexane, whereby 4-acetoxy-3,5-di(2-propyl)-2-(2-methyl-2-propenyloxy)phenol (Compound No. 88) was obtained in a yield of 24.0 g (63.2%).

Compound No. 88 is in the form of colorless columns, with a melting point of 140.0°-142.0° C. when recrystallized from diethyl ether and hexane.

$^1$H NMR (300 MHz, CDCl$_3$) δ1.05~1.40 (m, 12H), 1.84 (s, 3H), 2.33 (s, 3H), 2.74 (hept, J=6.9 Hz, 1H), 3.15 (hept, J=7.2 Hz, 1H), 3.37 (s, 2H), 4.57 (s, 1H), 4.82 (s, 1H), 4.86 (s, 1H), 6.67 (s, 1H) ppm.

IR (KBr) 3468, 2972, 1740 cm$^{-1}$.

Mass (m/z, %) 290 (M$^+$, 2), 248 (26), 233 (6), 205 (1), 163 (2), 91 (1), 43 (10).

EXAMPLE 80

10.0 g (34.5 mmol) of Compound No. 88 synthesized in Example 79 was dissolved in a mixed solvent consisting of 30 ml of DMF and 90 ml of DME. To this solution, 14.3 g (104 mmol) of potassium carbonate and 5.01 g (41.4 mmol) of allyl bromide were added, and the mixture was refluxed in an argon atmosphere for 2 hours.

The reaction mixture was poured into water and extracted with ethyl acetate. The extract layer was washed with a saturated aqueous solution of sodium chloride, dried over magnesium sulfate, and concentrated.

The concentrated product was placed on a silica gel column and eluted with a mixed solvent of ethyl acetate and hexane (1:10), whereby 1-acetoxy-2,6-di(2-propyl)-3-(2-methyl-2-propenyl)-4-(2-propenyloxy)benzene (Compound No. 89) was obtained as a light yellow oil in a yield of 11.3 g (99.4%).

$^1$H NMR (300 MHz, CDCl$_3$) δ1.05~1.38 (m, 12H), 1.80 (s, 3H), 2.33 (s, 3H), 2.76 (hept, J=6.8 Hz, 1H), 3.15 (hept, J=7.2 Hz, 1H), 3.23~3.50 (m, 2H), 4.35 (s, 1H), 4.49 (broad s, 2H), 4.71 (s with fine coupling, 1H), 5.23 (ddd, J=10.7, 1.7 and 1.7 Hz, 1H), 5.39 (ddd, J=17.2, 1.7 and 1.7 Hz, 1H), 6.02 (ddt, J=17.2, 10.7 and 5.0 Hz, 1H), 6.67 (s, 1H) ppm.

IR (liquid film) 2972, 1764 cm$^{-1}$.

Mass (m/z, %) 330 (M$^+$, 3), 288 (11), 247 (9), 193 (1), 163 (6), 91 (2), 43 (13).

EXAMPLE 81

2.67 g of Compound No. 89 synthesized in Example 80 was dissolved in 10 ml of N,N-diethylaniline. This solution was refluxed in an atmosphere of argon at 210° for 16 hours. The reaction mixture was poured into 1N hydrochloric acid and extracted with a mixed solvent of ethyl acetate and hexane. The extract layer was washed with water, and then with a saturated aqueous solution of sodium chloride, dried over anhydrous magnesium sulfate, and concentrated. The concentrated product was placed on a silica gel column and eluted with a mixed solvent of ethyl acetate and hexane (1:10), whereby 4-acetoxy-3,5-di(2-propyl)-2-(2-methyl-2-propenyl)-6-(2-propenyl)phenol (Compound No. 90) was obtained as a yellow oil in a yield of 1.65 g (61.7%).

$^1$H NMR (300 MHz, CDCl$_3$) δ1.17 (d, J=7.2 Hz, 3H), 1.20 (d, J=7.2 Hz, 3H), 1.28 (d, J=7.2 Hz, 3H), 1.30 (d, J=7.2 Hz, 3H), 1.84 (s, 3H), 2.33 (s, 3H), 3.12 (hept, J=6.9 Hz, 2H), 3.41 (s, 2H), 3.52 (s with fine coupling, 2H), 4.52 (broad s, 1H), 4.85 (broad s, 1H), 5.01 (d with fine coupling, J=17.4 Hz, 1H), 5.07 (s, 1H), 5.09 (d with fine coupling, J=10.2 Hz, 1H), 5.99 (ddt, J=17.4, 10.2 and 5.4 Hz, 1H) ppm.

IR (liquid film) 3556, 2976, 1764 cm$^{-1}$.

Mass (m/z, %) 330 (M$^+$, 3), 288 (22), 273 (1), 203 (2), 161 (1), 91 (2), 43 (13).

EXAMPLE 82

1.60 g (4.85 mmol) of Compound No. 90 synthesized in Example 81 was dissolved in 10 ml of dichloromethane. To this solution, 0.916 ml (5.82 mmol) of boron trifluoride etherate was added and the mixture was stirred in a stream of argon for 3 hours. The reaction mixture was then poured into a saturated aqueous solution of sodium hydrogencarbonate and extracted with ethyl acetate. The extract layer was washed with water and then with a saturated aqueous solution of sodium chloride, dried over anhydrous magnesium sulfate, and concentrated. The concentrated product was placed on a silica gel column, and eluted with a mixed solvent of ethyl acetate and hexane (1:6), whereby 5-acetoxy-2,3-dihydro-2,2-dimethyl-4,6-di(2-propyl)-7-(2-propenyl)-benzo[b]furan (Compound No. 91) was obtained as a light yellow oil in a yield of 1.44 g (89.9%).

$^1$H NMR (300 MHz, CDCl$_3$) δ1.10~1.41 (m, 12H), 1.43 (s with fine coupling, 1H), 2.32 (s, 3H), 2.84 (hept, J=7.2 Hz, 1H), 3.08 (d, J=4.0 Hz, 2H), 3.16 (hept, J=7.2 Hz, 1H), 3.35 (dd, J=6.0 and 1.5 Hz, 2H), 4.86~5.00 (m, 2H), 5.91 (ddt, J=17.8, 9.3 and 6.0 Hz, 1H) ppm IR (liquid film) 2976, 1764 cm$^{-1}$.

Mass (m/z, %) 330 (M$^+$, 4), 288 (27), 273 (1), 91 (2), 43 (12).

EXAMPLE 83

8.07 g (24.5 mmol) of Compound No. 91 synthesized in Example 82 was dissolved in 70 ml of anhydrous toluene. To this solution, 27.8 ml (48.9 mmol) of diisobutyl aluminum hydride (25% hexane solution) was added in a stream of argon at −78° C., and the mixture was stirred for 1 hour and 20 minutes.

With addition of a small amount of methanol to the reaction mixture, the reaction mixture was poured into 1N hydrochloric acid and extracted with ethyl acetate. The extract layer was washed with water and a saturated solution of sodium chloride, dried over anhydrous magnesium sulfate, and concentrated.

The concentrated product was crystallized from hexane, whereby 2,3-dihydro-2,2-dimethyl-4,6-di(2-propyl)-5-hydroxy-7-(2-propenyl)benzo[b]furan (Compound No. 92) was obtained in a yield of 6.59 g (93.4%).

Compound No. 92 is in the form of colorless crystals, with a melting point of 60.5°-62.0° C. when recrystallized from hexane.

$^1$H NMR (300 MHz, CDCl$_3$) δ1.29 (d, J=7.2 Hz, 6H), 1.35 (d, J=7.2 Hz, 6H), 1.41 (s, 6H), 3.01 (s, 2H), 3.15 (hept, J=7.2 Hz, 1H), 3.24 (hept, J=7.2 Hz, 1H), 3.33 (d with fine coupling, J=6.0 Hz, 2H), 4.92~5.00 (m, 2H), 5.90 (ddt, J=17.8, 9.5 and 6.0 Hz, 1H) ppm.

IR (KBr) 3640, 3616, 2972 cm$^{-1}$.

Mass (m/z, %) 288 (M$^+$, 26), 273 (2), 189 (2), 128 (1), 91 (2), 41 (4).

EXAMPLE 84

4.59 g (15.8 mmol) of Compound No. 92 synthesized in Example 83 was dissolved in a mixed solvent consisting of 10 ml of DMF and 30 ml of DME. To this solution, 3.25 g (19.0 mmol) of benzyl bromide and 6.54 g (47.4 mmol) of potassium carbonate were added, and the mixture was refluxed in an argon atmosphere for 6 hours.

The reaction mixture was poured into water and extracted with ethyl acetate. The extract layer was washed with a saturated solution of sodium chloride, dried over anhydrous magnesium sulfate, and concentrated.

The concentrated product was placed on a silica gel column and eluted with a mixed solvent of ethyl acetate and hexane (1:20), whereby 5-benzyloxy-2,3-dihydro-2,2-dimethyl-4,6-di(2-propyl)-7-(2-propenyl)benzo[b]furan (Compound No. 93) was obtained in a yield of 5.10 g (85.3%).

Compound No. 93 is in the form of colorless crystals, with a melting point of 78.0°-79.0° C. when recrystallized from diethyl ether and hexane.

$^1$H NMR (300 MHz, CDCl$_3$) δ1.25 (d, J=7.1 Hz, 6H), 1.34 (d, J=7.3 Hz, 6H), 3.09 (s, 2H), 3.43 (d with fine coupling, J=5.9 Hz, 2H), 3.52 (hept, J=7.2 Hz, 2H), 4.71 (s, 2H), 4.93~5.10 (m, 2H), 5.98 (ddt, J=17.9, 9.5 and 5.9 Hz, 1H) ppm.

IR (KBr) 2964 cm$^{-1}$.

Mass (m/z, %) 378 (M$^+$, 1), 287 (29), 246 (2), 91 (9), 41 (3).

EXAMPLE 85

2.17 g (8.9 mmol) of 9-BBN dimer was suspended in 20 ml of anhydrous THF. To this suspension, a THF solution of 4.49 g (11.9 mmol) of Compound No. 93 synthesized in Example 84, which was dissolved in 10 ml of anhydrous THF, was added. The reaction mixture was stirred for 1 hour and 20 minutes. To this reaction mixture, 1.44 ml of ethanol, 11.9 ml of a 2N aqueous solution of sodium hydroxide, and 8 ml of a 30% aqueous solution of hydrogen peroxide were successively added. The reaction mixture was stirred overnight and poured into 1N hydrochloric acid. The reaction mixture was extracted with ethyl acetate. The extract layer was washed with water, a saturated aqueous solution of sodium thiosulfate, a saturated aqueous solution of sodium chloride, dried over anhydrous magnesium sulfate, and concentrated.

The concentrated product was placed on a silica gel column and eluted with a mixed solvent of ethyl acetate and hexane (1:3), whereby 3-[5-benzyloxy-2,3-dihydro-2,2-dimethyl-4,6-di(2-propyl)benzo[b]furan-7-yl]propanol (Compound No. 94) was obtained in a yield of 4.13 g (87.6%).

Compound No. 94 is in the form of colorless crystals, with a melting point of 126.5°-127.57° C. when recrystallized from diethyl ether.

$^1$H NMR (300 MHz, CDCl$_3$) δ1.25 (d, J=7.2 Hz, 6H), 1.35 (d, J=7.2 Hz, 6H), 1.47 (s, 6H), 1.73~1.86 (m, 2H), 2.74 (t, J=7.1 Hz, 2H), 3.11 (s, 2H), 3.40~3.67 (m, 4H), 4.74 (s, 2H), 7.30~7.51 (m, 5H) ppm.

IR (KBr) 3560, 2968 cm$^{-1}$.

Mass (m/z, %) 396 (M$^+$, 1), 305 (6), 263 (9), 262 (8), 221 (4), 193 (1), 91 (9), 41 (3).

EXAMPLE 86

1.86 g (4.70 mmol) of Compound No. 94 synthesized in Example 85 was dissolved in a mixed solvent consisting of 30 ml of dimethyl sulfoxide (DMSO) and 20 ml of anhydrous THF. To this solution, 3.28 ml (23.5 mmol) of triethylamine and 2.99 g (18.8 mmol) of sulfur trioxide pyridine complex were successively added, and the mixture was stirred in an atmosphere of argon at room temperature for 1 hour and 30 minutes.

The reaction mixture was poured into 1N hydrochloric acid and extracted with ethyl acetate. The extract layer was washed with water and a saturated aqueous solution of sodium chloride, dried over anhydrous magnesium sulfate, and concentrated.

The concentrated product was placed on a silica gel column and eluted with a mixed solvent of ethyl acetate and hexane (1:10), whereby 3-[5-benzyloxy-2,3-dihydro-2,2-dimethyl-4,6-di(2-propyl)benzo[b]furan-7-yl]propanal (Compound No. 95) was obtained in a yield of 1.17 g (62.9%).

Compound No. 95 is in the form of colorless crystals, with a melting point of 120.0°-121.5° C. when recrystallized from ethyl acetate and hexane.

$^1$H NMR (300 MHz, CDCl$_3$) δ1.25 (d, J=7.2 Hz, 6H), 1.35 (d, J=7.3 Hz, 6H), 1.45 (s, 6H), 2.72 (t, J=7.6 Hz, 2H), 2.94~3.01 (m, 2H), 3.08 (s, 2H), 3.46~3.68 (m, 2H), 4.69 (s, 2H), 7.32~7.52 (m, 5H), 9.87 (s with fine coupling, 1H) ppm.

IR (KBr) 2976, 1724 cm$^{-1}$.

Mass (m/z, %) 394 (M$^+$, 1), 303 (21), 259 (5), 217 (2), 91 (10).

EXAMPLE 87

375 mg (9.38 mmol) of a 60% sodium hydride was suspended in 20 ml of anhydrous THF in a stream of argon. To this suspension, 1.22 g (9.38 mmol) of ethyl acetoacetate was added. The mixture was then stirred for 35 minutes, followed by the addition of 6.0 ml (9.38 mmol) of a 15% hexane solution of butyl lithium thereto. The reaction mixture was stirred for 40 minutes.

The reaction mixture was then cooled to −78° C. A THF solution of 2.46 g (6.25 mmol) of Compound No. 95 synthesized in Example 86, which was dissolved in 10 ml of anhydrous THF, was added to the reaction mixture, and the reaction mixture was stirred for 50 minutes.

A saturated aqueous solution of ammonium chloride was added to the reaction mixture. After the elevation of the temperature of the mixture to room temperature, the mixture was extracted with ethyl acetate. The extract layer was washed with water and a saturated aqueous solution of sodium chloride, dried over anhydrous magnesium sulfate, and concentrated.

The concentrated product was placed on a silica gel column and eluted with a mixed solvent of ethyl acetate and hexane (1:3), whereby ethyl 7-[5-benzyloxy-2,3-dihydro-2,2-dimethyl-4,6-di(2-propyl)benzo[b]furan-7-yl]-5-hydroxy-3-oxoheptanoate (Compound No. 96) was obtained as a light yellow oil in a yield of 2.70 g (83.3%).

$^1$H NMR (300 MHz, CDCl$_3$) δ1.21~1.30 (m, 9H), 1.35 (dd, J=7.3 and 2.9 Hz, 6H), 1.46 (s, 6H), 1.63~1.77 (m, 2H), 2.55~2.79 (m, 4H), 3.10 (s, 2H), 3.42~3.58 (m, 2H), 3.52 (s, 2H), 4.00~4.11 (m, 1H), 4.19 (q, J=7.1 Hz, 2H), 4.73 (s, 2H), 7.31~7.53 (m, 5H) ppm.

IR (liquid film) 3528, 2980, 2880, 1744 cm$^{-1}$.

Mass (m/z, %) 524 (M$^+$, 2), 433 (20), 391 (20), 387 (15), 303 (40), 259 (29), 91 (100).

EXAMPLE 88

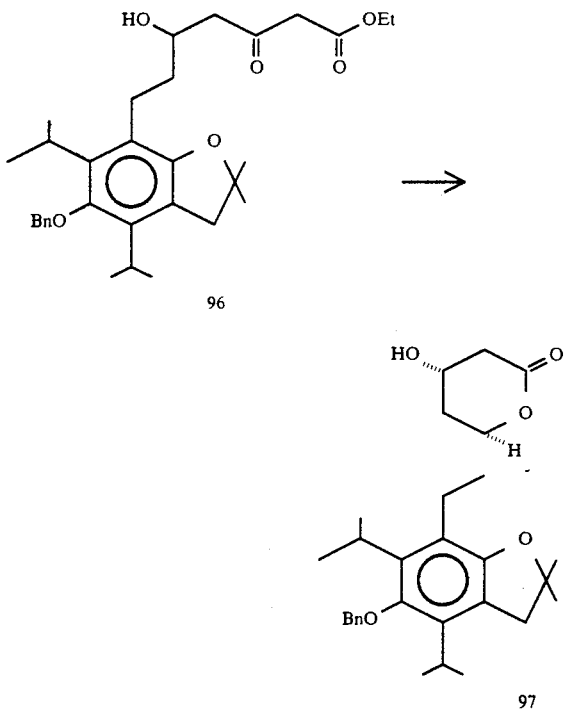

5.84 ml (5.84 mmol) of triethylborane (1.0M THF solution) was added to 30 mg (0.292 mmol) of pivalic acid in a stream of argon at room temperature. The mixture was stirred for 1 hour and 15 minutes to obtain a solution. To this solution was added dropwise a THF solution of 2.55 g (4.87 mmol) of Compound No. 96 synthesized in Example 87, which was dissolved in 50 ml of anhydrous THF. 50 minutes later, the reaction mixture was cooled to −78° C., and 7.59 ml of methanol was added to the reaction mixture. 10 minutes later, 192 mg (5.08 mmol) of sodium borohydride was then added thereto. Thus the reaction mixture was stirred for 1 hour. To this reaction mixture, 19.8 ml of a 5N aqueous solution of sodium hydroxide was added, and after the temperature of the reaction mixture was adjusted to 0° C., 19.8 ml of a 30% aqueous solution of hydrogen peroxide was added thereto, and the reaction mixture was stirred at room temperature for 3 hours.

The reaction mixture was poured into 1N hydrochloric acid and extracted with ethyl acetate. The extract layer was washed with a saturated aqueous solution of sodium thiosulfate, water and a saturated aqueous solution of sodium chloride, dried over anhydrous magnesium sulfate, and concentrated.

The concentrated product was dissolved in 10 ml of toluene. The solution was refluxed for 3 hours and 30 minutes. After the solvent was distilled away from the reaction mixture, the residue was placed on a silica gel column and eluted with a mixed solvent of ethyl acetate and hexane (2:1), whereby trans-(±)-6-[5-benzyloxy-2,3-dihydro-2,2-dimethyl-4,6-di(2-propyl)benzo[b]furan-7-yl]ethyl-4-hydroxytetrahydropyran-2-one (Compound No. 97) was obtained in a yield of 1.53 g (65.5%).

Compound No. 97 is in the form of colorless crystals, with a melting point of 155.0°–156.5° C. when recrystallized from diethyl ether.

$^1$H NMR (300 MHz, CDCl$_3$) δ1.24 (d, J=7.1 Hz, 6H), 1.36 (d, J=7.3 Hz, 3H), 1.37 (d, J=7.3 Hz, 3H), 1.43 (s, 3H), 1.45 (s, 3H), 1.79~2.10 (m, 5H), 2.64 (ddd, J=17.7, 4.0 and 1.5 Hz, 1H), 2.79 (dd, 17.7 and 5.1 Hz, 1H), 2.62~2.96 (m, 2H), 3.08 (s, 2H), 3.40~3.70 (m, 2H), 4.39~4.46 (m, 1H), 4.70 (s, 2H), 4.70~4.86 (m, 1H), 7.30~7.50 (m, 5H) ppm IR (KBr) 3560, 2980, 2932, 1718 cm$^{-1}$.

Mass (m/z, %) 480 (M$^+$, 4), 389 (100), 259 (44), 217 (18), 91 (99), 43 (26).

EXAMPLE 89

5.00 g (304 mmol) of 2-(t-butyl)-6-methylphenol (Compound No. 98) was dissolved in 7 ml of DMF. To this solution, 395 mg (1.22 mmol) of salcomine was added, and the mixture was stirred in an atmosphere of oxygen at room temperature overnight. The reaction mixture was poured into 1N hydrochloric acid and extracted with hexane. The extract layer was washed with water and a saturated aqueous solution of sodium chloride, dried over anhydrous magnesium sulfate, and concentrated.

The concentrated product was placed on a silica gel column and eluted with a mixed solvent of ethyl acetate and hexane (1:6), whereby 2-(t-butyl)-6-methyl-p-benzoquinone (Compound No. 99) was obtained as a red oil in a yield of 2.79 g (51.6%). In this reaction, Compound No. 98 was recovered in a yield of 1.34 g (26.9%).

$^1$H NMR (300 MHz, CDCl$_3$) δ1.29 (s, 9H), 2.05 (s with fine coupling, 1H), 6.54 (s, 2H) ppm.

IR (liquid film) 2968, 1660, 1638 cm$^{-1}$.

Mass (m/z, %) 178 (M$^+$, 5), 163 (4), 135 (5), 107 (3), 91 (3).

EXAMPLE 90

26.0 g (157 mmol) of Compound No. 99 synthesized in Example 89 was dissolved in 50 ml of dichloromethane. To this solution, 5.92 g (157 mmol) of sodium borohydride was added. To this mixture, several drops of methanol were gradually added, and the reaction mixture was stirred for 2 hours.

To the reaction mixture, 500 mg (13.2 mmol) of sodium borohydride was further added, and the temperature of the reaction mixture was raised to room temperature. After the reaction mixture was stirred for 30 minutes, a small amount of acetone was added to the reaction mixture. The reaction mixture was then poured into a saturated aqueous solution of ammonium chloride and extracted with ethyl acetate. The extract layer was washed with a saturated aqueous solution of sodium chloride, dried over anhydrous magnesium sulfate, and concentrated.

The concentrated product was placed on a silica gel column and eluted with a mixed solvent of ethyl acetate and hexane (1:10), whereby 2-(t-butyl)-6-methylhydroquinone (Compound No. 100) was obtained in a yield of 23.2 g (88.1%).

Compound No. 100 is in the form of colorless crystals, with a melting point of 58.0°–58.5° C. when recrystallized from a mixed solvent of ethyl acetate and hexane.

$^1$H NMR (300 MHz, CDCl$_3$) δ1.39 (s, 9H), 2.20 (s, 3H), 4.31 (s, 1H), 4.36 (s, 1H), 6.50 (d, J=3.0 Hz, 1H), 6.65 (d, J=3.0 Hz, 1H) ppm.

IR (KBr) 3280 cm$^{-1}$.

Mass (m/z, %) 180 (M$^+$, 10), 165 (19), 137 (10), 91 (2), 43 (6).

EXAMPLE 91

10.0 g (55.5 mmol) of Compound No. 100 synthesized in Example 90 was dissolved in 50 ml of acetone. To this solution, 5.76 ml (58.3 mmol) of methallyl chloride and 22.9 g (167 mmol) of potassium carbonate were added. This reaction mixture was refluxed in an atmosphere of argon for 8 hours.

The reaction mixture was poured into diluted hydrochloric acid and extracted with ethyl acetate. The extract layer was washed with water and a saturated aqueous solution of sodium chloride, dried over anhydrous magnesium sulfate, and concentrated.

The concentrated product was placed on a silica gel column and eluted with a mixed solvent of ethyl acetate and hexane (1:10), whereby 2-(t-butyl)-6-methyl-4-(2-methyl-2-propenyloxy)phenol (Compound No. 101) was obtained as a light yellow oil in a yield of 5.91 g (45.5%). In this reaction, 3.83 g of Compound No. 100 was recovered.

$^1$H NMR (300 MHz, CDCl$_3$) δ1.40 (s, 9H), 1.83 (s, 3H), 2.23 (s, 3H), 4.36 (s, 2H), 4.38 (s, 1H), 4.97 (s with fine coupling, 1H), 5.08 (s with fine coupling, 1H), 6.58 (d, J=3.0 Hz, 1H), 6.77 (d, J=3.0 Hz, 1H) ppm.

IR (liquid film) 3592, 2964 cm$^{-1}$.

Mass (m/z, %) 234 (M$^+$, 10), 179 (18), 163 (5), 91 (3), 55 (6).

EXAMPLE 92

5.19 g (25.2 mmol) of Compound No. 101 synthesized in Example 91 was dissolved in a mixed solvent of 7.53 ml of acetic anhydride and 10 ml of pyridine. This solution was refluxed in an atmosphere of argon for 4 hours.

The reaction mixture was poured into 1N hydrochloric acid and extracted with a mixed solvent of ethyl acetate and hexane. The extract layer was washed with water, a saturated aqueous solution of sodium hydrogencarbonate and a saturated aqueous solution of sodium chloride, dried over anhydrous magnesium sulfate, and concentrated.

The concentrated product was placed on a silica gel column and eluted with a mixed solvent of ethyl acetate and hexane (1:10), whereby 1-acetoxy-2-(t-butyl)-6-methyl-4-(2-methyl-2-propenyloxy)benzene (Compound No. 102) was obtained in a yield of 5.68 g (81.7%).

Compound No. 102 is in the form of colorless crystals, with a melting point of 34.0°–35.0° C. when recrystallized from ethanol and water.

$^1$H NMR (300 MHz, CDCl$_3$) δ1.32 (s, 9H), 1.83 (s, 3H), 2.09 (s, 3H), 2.32 (s, 3H), 4.38 (s, 2H), 4.98 (s, 1H), 5.09 (s, 1H), 6.63 (d, J=3.0 Hz, 1H), 6.82 (d, J=3.0 Hz, 1H) ppm.

IR (liquid film) 2972, 1766 cm$^{-1}$.

Mass (m/z, %) 276 (M$^+$, 2), 234 (13), 179 (17), 163 (3), 91 (1), 55 (9), 43 (13).

EXAMPLE 93

5.47 g (19.8 mmol) of Compound No. 102 synthesized in Example 92 was dissolved in 20 ml of N,N-diethylaniline and this solution was refluxed in an atmosphere of argon at 200° for 10 hours. Most of the N,N-diethylaniline was distilled away from the reaction mixture under reduced pressure, and the residue was poured into 1N hydrochloric acid and extracted with ethyl acetate. The extract layer was washed with water, and then with a saturated aqueous solution of sodium chloride, dried over anhydrous magnesium sulfate, and concentrated. The concentrated product was crystallized from hexane, whereby 4-acetoxy-5-(t-butyl)-3-methyl-2-(2-methyl-2-propenyl)phenol (Compound No. 103) was obtained in a yield of 4.50 g (82.3%).

Compound No. 103 is in the form of colorless crystals, with a melting point of 145.0°–146.0° C. when recrystallized from ethyl acetate and hexane.

$^1$H NMR (300 MHz, CDCl$_3$) δ1.31 (s, 9H), 1.80 (s, 3H), 1.98 (s, 3H), 2.33 (s, 3H), 3.33 (broad s, 2H), 4.60 (broad s, 1H), 4.82 (broad s, 1H), 4.84 (s, 1H), 6.74 (s, 1H) ppm.

IR (KBr) 3550, 2960, 1740 cm$^{-1}$.

Mass (m/z, %) 276 (M$^+$, 3), 234 (20), 219 (15), 163 (1), 91 (2), 43 (11).

EXAMPLE 94

4.30 g (15.6 mmol) of Compound No. 103 synthesized in Example 93 was dissolved in a mixed solvent consisting of 10 ml of DMF and 20 ml of DME. To this solution, 1.62 ml (18.7 mmol) of allyl bromide and 6.46 g (46.8 mmol) of potassium carbonate were added. The reaction mixture was refluxed in an atmosphere of argon for 3 hours, then poured into water and extracted with hexane. The extract layer was washed with a saturated aqueous solution of sodium chloride, dried over anhydrous magnesium sulfate, and concentrated.

The concentrated product was placed on a silica gel column and eluted with a mixed solvent of ethyl acetate and hexane (1:10), whereby 1-acetoxy-6-(t-butyl)-2-methyl-3-(2-methyl-2-propenyl)-4-(2-propenyloxy)benzene (Compound No. 104) was obtained as a colorless oil in a yield of 4.88 g (99.0%).

$^1$H NMR (300 MHz, CDCl$_3$) δ1.33 (s, 9H), 1.77 (s, 3H), 1.97 (s, 3H), 2.33 (s, 3H), 3.27 (broad d, J=16.2 Hz, 1H), 3.45 (broad d, J=16.2 Hz, 1H), 4.38 (broad s, 1H), 4.50 (broad s with fine coupling, 2H), 4.70 (broad s, 1H), 5.24 (ddd, J=10.5, 1.5 and 1.5 Hz, 1H), 5.39 (ddd, J=17.1, 1.8 and 1.5 Hz, 1H), 6.03 (ddd, J=17.1, 10.5 and 5.4 Hz, 1H), 6.78 (s, 1H) ppm.

IR (liquid film) 2972, 1766 cm$^{-1}$.

Mass (m/z, %) 316 (M$^+$, 3), 274 (10), 177 (3), 91 (1), 57 (12), 43 (13).

EXAMPLE 95

3.63 g (11.5 mmol) of Compound No. 104 synthesized in Example 94 was dissolved in 20 ml of N-methyl-2-pyrrolidone, and the solution was refluxed in an atmosphere of argon at 210° C. for 23 hours.

The reaction mixture was poured into a saturated aqueous solution of sodium chloride and extracted with ethyl acetate. The extract layer was dried over anhydrous magnesium sulfate, and concentrated.

The concentrated product was placed on a silica gel column and eluted with a mixed solvent of ethyl acetate and hexane (1:6), whereby a crude product of 4-acetoxy-3-(t-butyl)-5-methyl-6-(2-methyl-2-propenyl)-2-(2-propenyl)phenol (Compound No. 105) was obtained in a yield of 4.88 g (99.0%).

Compound No. 105 is in the form of colorless crystals, with a melting point of 127.0°–128.0° C. when recrystallized from diethyl ether and hexane.

$^1$H NMR (300 MHz, CDCl$_3$) δ1.45 (s, 9H), 1.79 (s, 3H), 1.97 (s, 3H), 2.29 (s, 3H), 3.29 (broad d, J=16.5 Hz, 1H), 3.41 (broad d, J=16.5 Hz, 1H), 3.65 (d with fine coupling, J=18.0 Hz, 1H), 3.76 (d with fine coupling, J=18.0 Hz, 1H), 4.46 (s with fine coupling, 1H), 4.77 (s with fine coupling, 1H), 5.10 (ddd, J=17.4, 1.8 and 1.8 Hz, 1H), 5.18 (s, 1H), 5.22 (ddd, J=10.2, 1.8 and 1.8 Hz, 1H), 6.07 (ddt, J=17.4, 10.2 and 5.1 Hz, 1H) ppm.

IR (KBr) 3528, 2976, 1740 cm$^{-1}$.

Mass (m/z, %) 316 (M$^+$, 3), 274 (19), 259 (3), 175 (1), 91.

EXAMPLE 96

260 mg (0.823 mmol) of Compound No. 105 synthesized in Example 95 was dissolved in 3 ml of dichloromethane. To this solution, 0.025 ml (0.206 mmol) of boron trifluoride etherate was added at 0° C. and the mixture was stirred in a stream of argon for 2 hours.

The reaction mixture was then poured into a saturated aqueous solution of sodium hydrogencarbonate, and extracted with ethyl acetate. The extract layer was washed with water and then with a saturated aqueous solution of sodium chloride, dried over anhydrous magnesium sulfate, and concentrated.

The concentrated product was placed on a silica gel column and eluted with a mixed solvent of ethyl acetate and hexane (1:10), whereby 5-acetoxy-6-(t-butyl)-2,3-dihydro-7-(2-propenyl)-2,2,4-trimethylbenzo[b]furan (Compound No. 106) was obtained as a colorless oil in a yield of 209 mg (80.4%).

$^1$H NMR (300 MHz, CDCl$_3$) δ1.44 (s, 9H), 1.92 (s, 3H), 2.28 (s, 3H), 2.91 (s with fine coupling, 2H), 3.58 (broad s, 2H), 4.91 (ddd, J=17.1, 1.8 and 1.8 Hz, 1H), 4.99 (ddd, J=10.2, 1.8 and 1.8 Hz, 1H), 5.97 (ddt, J=17.1, 10.2 and 5.4 Hz, 1H) ppm.

IR (liquid film) 2980, 1762 cm$^{-1}$.

Mass (m/z, %) 316 (M$^+$, 4), 274 (25), 259 (3), 23 (2), 217 (1), 161 (1), 91 (1), 43 (10).

EXAMPLE 97

187 mg (0.592 mmol) of Compound No. 106 synthesized in Example 96 was dissolved in 3 ml of anhydrous toluene in a stream of argon at −78° C. To this solution, 0.673 ml (1.18 mmol) of diisobutyl aluminum hydride (25% hexane solution) was added, and the mixture was stirred for 1 hour and 30 minutes.

To this reaction mixture, methanol was added, and the temperature of the reaction mixture was raised to room temperature. The reaction mixture was then poured into 1N hydrochloric acid and extracted with ethyl acetate.

The extract layer was washed with water and a saturated solution of sodium chloride, dried over anhydrous magnesium sulfate, and concentrated.

The concentrated product was placed on a silica-gel column and eluted with a mixed solvent of hexane and dichloromethane (2:1), whereby 6-(t-butyl)-2,3-dihydro-5-hydroxy-7-(2-propenyl)-2,2,4-trimethylbenzo[b]furan (Compound No. 107) was obtained as a yellow oil in a yield of 146 mg (90.0%).

$^1$H NMR (300 MHz, CDCl$_3$) δ1.41 (s, 6H), 1.54 (s, 9H), 2.09 (s, 3H), 2.92 (s, 2H), 3.63 (ddd, J=5.1, 1.8 and 1.8 Hz, 2H), 4.38 (s, 1H), 4.83 (ddd, J=17.4, 1.8 and 1.8 Hz, 1H), 4.98 (ddd, J=10.2, 1.8 and 1.8 Hz, 1H), 6.00 (ddt, J=17.4, 10.2 and 5.1 Hz, 1H) ppm.

IR (liquid film) 3600, 2980 cm$^{-1}$.

Mass (m/z, %) 274 (M$^+$, 10), 259 (2), 204 (2), 189 (1), 161 (1), 91 (2), 57 (3), 41 (6).

EXAMPLE 98

1.02 g (3.72 mmol) of Compound No. 107 synthesized in Example 97 was dissolved in a mixed solvent consisting of 2 ml of DMF and 6 ml of DME. To this solution, 0.532 ml (4.47 mmol) of benzyl bromide and 1.54 g (11.2 mmol) of potassium carbonate were added, and the mixture was refluxed in an atmosphere of argon for 4 hours.

The reaction mixture was poured into water and extracted with hexane. The extract layer was washed with a saturated aqueous solution of sodium chloride, dried over anhydrous magnesium sulfate, and concentrated.

The concentrated product was placed on a silica gel column and eluted with a mixed solvent of ethyl acetate and hexane (1:10), whereby 5-benzyloxy-6-(t-butyl)-2,3-dihydro-7-(2-propenyl)-2,2,4-trimethylbenzo[b]furan (Compound No. 108) was obtained as a light yellow oil in a yield of 1.19 g (87.8%).

$^1$H NMR (300 MHz, CDCl$_3$) δ1.44 (s, 6H), 1.52 (s, 9H), 2.14 (s, 3H), 2.90 (s, 2H), 3.60 (d, J=5.5 Hz, 2H), 4.69 (s, 2H), 4.93 (d with fine coupling, J=17.1 Hz, 1H), 5.00 (d with fine coupling, J=10.3 Hz, 1H), 6.00 (ddt, J=17.1, 10.3 and 5.5 Hz, 1H), 7.26~7.50 (m, 5H) ppm.

IR (liquid film) 2980 cm$^{-1}$.

Mass (m/z, %) 364 (M$^+$, 1), 273 (16), 232 (14), 159 (1), 91 (10), 41 (3).

EXAMPLE 99

583 mg (2.39 mmol) of 9-BBN dimer was suspended in 10 ml of anhydrous THF to prepare a suspension. To this suspension, a THF solution of 1.16 g (3.19 mmol) of Compound No. 108 synthesized in Example 98, which was dissolved in 2 ml of anhydrous THF, was added in a stream of argon at 0° C. The temperature of the reaction mixture was raised to room temperature, and the reaction mixture was stirred for 1 hour and 20 minutes. To this reaction mixture, 2.0 ml of ethanol and 6 ml of a 2N aqueous solution of sodium hydroxide were successively added. Furthermore, 1.7 ml of a 30% aqueous solution of hydrogen peroxide was added to the reaction mixture at 0° C., and the mixture was stirred overnight at room temperature and then poured into 1N hydrochloric acid. The reaction mixture was extracted with ethyl acetate. The extract layer was successively washed with water, a saturated aqueous solution of sodium thiosulfate and a saturated aqueous solution of sodium chloride, dried over anhydrous magnesium sulfate, and concentrated.

The concentrated product was placed on a silica gel column and eluted with a mixed solvent of ethyl acetate and hexane (1:3), whereby 3-[5-benzyloxy-6-(t-butyl)-2,3-dihydro-2,2,4-trimethylbenzo[b]furan-7-yl]propanol (Compound No. 109) was obtained in a yield of 1.02 g (83.3%).

Compound No. 109 is in the form of colorless crystals, with a melting point of 87.0°–88.0° C. when recrystallized from ethanol and water.

$^1$H NMR (300 MHz, CDCl$_3$) δ1.48 (s, 6H), 1.53 (s, 9H), 1.81~1.87 (m, 2H), 2.02~2.12 (m, 1H), 2.14 (s, 3H), 2.85~2.91 (m, 2H), 2.92 (s, 2H), 3.65~3.74 (m, 2H), 4.69 (s, 2H), 7.28~7.50 (m, 5H) ppm.

IR (KBr) 3340, 2936 cm$^{-1}$.

Mass (m/z, %) 382 (M+, 1), 291 (1), 235 (22), 207 (6), 91 (8), 57 (5).

EXAMPLE 100

414 mg (1.08 mmol) of Compound No. 109 synthesized in Example 99 was dissolved in a mixed solvent consisting of 10 ml of DMSO and 5 ml of THF. To this solution, 0.753 ml (5.40 mmol) of triethylamine and 688 mg (4.32 mmol) of sulfur trioxide pyridine complex were successively added in a stream of argon. The reaction mixture was stirred at room temperature for 1 hour and 30 minutes.

The reaction mixture was poured into 1N hydrochloric acid and extracted with ethyl acetate. The extract layer was successively washed with water and a saturated aqueous solution of sodium chloride, dried over magnesium sulfate, and concentrated.

The concentrated product was placed on a silica gel column and eluted with a mixed solvent of ethyl acetate and hexane (1:10), whereby 3-[5-benzyloxy-6-(t-butyl)-2,3-dihydro-2,2,4-trimethylbenzo[b]furan-7-yl]propanal (Compound No. 110) was obtained in a yield of 313 mg (76.3%).

Compound No. 110 is in the form of colorless crystals, with a melting point of 93.0°–94.0° C. when recrystallized from diethyl ether and hexane.

$^1$H NMR (300 MHz, CDCl$_3$) δ1.46 (s, 6H), 1.52 (s, 9H), 2.14 (s, 3H), 2.76~2.82 (m, 2H), 2.91 (s, 2H), 3.09~3.16 (m, 2H), 4.67 (s, 2H), 7.28~7.50 (m, 5H), 9.89 (s with fine coupling, 1H) ppm.

IR (KBr) 2932, 1722 cm$^{-1}$.

Mass (m/z, %) 380 (M+, 1), 289 (15), 245 (3), 232 (4), 205 (2), 189 (2), 161 (1), 91 (11), 41 (3).

EXAMPLE 101

0.127 ml (1.0 mmol) of ethyl acetoacetate was added to a suspension which was prepared by suspending 60 mg (1.5 mmol) of a 60% sodium hydride in 5 ml of anhydrous THF in a stream of argon at 0° C., and the resultant suspension was stirred for 30 minutes. 0.960 ml (1.5 mmol) of a 15% hexane solution of butyl lithium was added to the above suspension, and the mixture was stirred for 35 minutes and cooled to −78° C. To the above mixture, a THF solution of 380 mg (1.0 mmol) of Compound No. 110 synthesized in Example 100, which was dissolved in 2 ml of anhydrous THF was added, and the mixture was stirred for 1 hour and 40 minutes.

A saturated aqueous solution of ammonium chloride was added to the above reaction mixture. The temperature of the reaction mixture was raised to room temperature, and the reaction mixture was extracted with ethyl acetate. The extract layer was successively washed with water and a saturated aqueous solution of sodium chloride, dried over magnesium sulfate, and concentrated.

The concentrated product was placed on a silica gel column and eluted with a mixed solvent of ethyl acetate and hexane (1:3), whereby ethyl 7-[5-benzyloxy-6-(t-butyl)-2,3-dihydro-2,2,4-trimethylbenzo[b]furan-7-yl]-5-hydroxy-3-oxoheptanoate (Compound No. 111) was obtained as a colorless oil in a yield of 365 mg (71.6%).

$^1$H NMR (300 MHz, CDCl$_3$) δ1.28 (t, J=6.9 Hz, 3H), 1.46 (s, 6H), 1.53 (s, 9H), 1.70~1.86 (m, 2H), 2.13 (s, 3H), 2.73 (d, J=5.5 Hz, 2H), 2.74~2.90 (m, 1H), 2.91 (s, 2H), 2.94~3.08 (m, 1H), 3.15 (d, J=3.8 Hz, 1H), 3.52 (s, 2H), 4.20 (q, J=6.9 Hz, 2H), 4.68 (s, 2H), 7.28~7.50 (m, 5H) ppm.

IR (liquid film) 3520, 2932, 1744, 1718 cm$^{-1}$.

Mass (m/z, %) 510 (M+, 2), 401 (5), 363 (43), 289 (67), 233 (46), 91 (100).

EXAMPLE 102

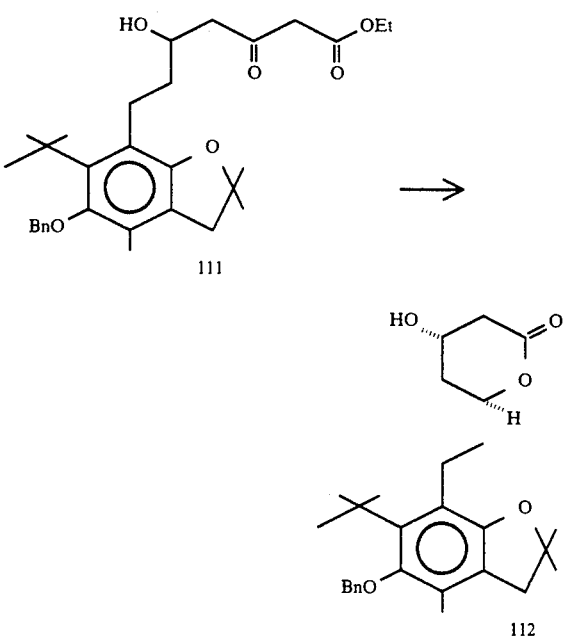

4 mg (0.038 mmol) of pivalic acid was added to 0.755 ml (0.755 mmol) of triethylborane (1.0M THF solution) in an atmosphere of argon at room temperature, and the mixture was stirred for 45 minutes, whereby a solution was obtained. To this solution, a THF solution of 350 mg (0.686 mmol) of Compound No. 111 synthesized in Example 101, which was dissolved in 4 ml of anhydrous THF was added dropwise, and the mixture was stirred for 45 minutes and cooled to −78° C. To this mixture, 1.1 ml of methanol was added. Then, 27 mg (0.714 mmol) of sodium borohydride was added. 40 minutes later, 27 mg (0.714 mmol) of sodium borohydride was further added and the mixture was stirred for 15 minutes.

To this mixture, 2.8 ml of a 5N aqueous solution of sodium hydroxide was added, and the temperature of the reaction mixture was raised to 0° C., and 2.8 ml of a 30% aqueous solution of hydrogen peroxide was added. With the temperature of the reaction mixture raised to room temperature, the reaction mixture was stirred overnight.

The reaction mixture was then poured into 1N hydrochloric acid and extracted with ethyl acetate. The extract layer was successively washed with water, a saturated aqueous solution of sodium thiosulfate, and a saturated aqueous solution of sodium chloride, dried over anhydrous magnesium sulfate, and concentrated.

The concentrated product was dissolved in 3 ml of toluene and refluxed for 3 hours. After the solvent was distilled away from the reaction mixture, the concentrated product was placed on a silica gel column and eluted with a mixed solvent of ethyl acetate and hexane (2:1), whereby trans-(±)-6-[5-benzyloxy-6-(t-butyl)-2,3-dihydro-2,2,4-trimethylbenzo[b]furan-7-yl]ethyl-4-hydroxytetrahydropyran-2-one (Compound No. 112) was obtained in a yield of 260 mg (81.3%).

Compound No. 112 is in the form of colorless needles, with a melting point of 182.0°–182.3° C. when recrystallized from ethyl acetate and hexane.

$^1$H NMR (300 MHz, CDCl$_3$) δ1.45 (s, 3H), 1.46 (s, 3H), 1.53 (s, 9H), 1.81~2.10 (m, 5H), 2.13 (s, 3H), 2.65 (ddd, J=17.6, 4.0 and 1.5 Hz, 1H), 2.80 (dd, J=17.6 and 5.0 Hz, 1H), 2.75~2.88 (m, 1H), 2.90 (s, 2H), 3.00~3.13 (m, 1H), 4.38~4.49 (m, 1H), 4.67 (s, 2H), 4.75~4.88 (m, 1H), 7.30~7.50 (m, 5H) ppm.

IR (KBr) 3552, 2968, 2936, 1716 cm$^{-1}$.

Mass (m/z, %) 466 (M$^+$, 4), 375 (100), 245 (25), 189 (20), 91 (85), 43 (29).

EXAMPLE 103

15.2 g (0.10 mmol) of 3-(t-butyl)phenol (Compound No. 113) was dissolved in 100 ml of anhydrous toluene and the mixture was stirred in an atmosphere of argon at 0° C. To this solution, 66.0 ml (0.103 mmol) of butyl lithium (15% hexane solution) was added, and the mixture solution was stirred for 30 minutes.

20.0 ml (0.200 mmol) of methallyl chloride was added to this mixture, and the mixture was refluxed for 6 hours. Thereafter, 10.0 ml (0.100 mmol) of methallyl chloride was further added to the mixture, and the mixture was refluxed for 3 hours and 30 minutes.

The reaction mixture was poured into 1N hydrochloric acid and extracted with hexane. The extract layer was washed with a saturated aqueous solution of sodium chloride, dried over anhydrous magnesium sulfate, and concentrated.

The concentrated product was placed on a silica gel column and successively eluted with hexane and a mixed solvent of hexane and ethyl acetate (50:1), whereby 5-(t-butyl)-2-(2-methyl-2-propenyl)phenol (Compound No. 114) was obtained as a colorless oil in a yield of 10.3 g (49.9%).

$^1$H NMR (300 MHz, CDCl$_3$) δ1.29 (s, 9H), 1.75 (s, 3H), 3.35 (s, 2H), 4.87 (s with fine coupling, 1H), 4.92 (s with fine coupling, 1H), 5.08 (s, 1H), 6.86 (d, J=1.9 Hz, 1H), 6.90 (dd, J=7.9 and 1.9 Hz, 1H), 7.01 (d, J=7.9 Hz, 1H) ppm.

IR (liquid film) 3480, 2968, 1650, 1624, 1580 cm$^{-1}$.

Mass (m/z, %) 204 (M$^+$, 42), 189 (100), 147 (11).

EXAMPLE 104

10.8 g (52.9 mmol) of Compound No. 114 synthesized in Example 103, 15.0 g (0.11 mol) of potassium carbonate and 7.00 ml (80.9 mmol) of allyl bromide were dissolved in a mixed solvent consisting of 20 ml of DMF and 40 ml of DME. This mixture was refluxed in an atmosphere of argon for 2 hours and 30 minutes.

The reaction mixture was poured into water and extracted with hexane. The extract layer was washed with a saturated aqueous solution of sodium chloride, dried over anhydrous magnesium sulfate, and concentrated.

The concentrated product was placed on a silica gel column and eluted with a mixed solvent of hexane and dichloromethane (10:1), whereby 5-(t-butyl)-2-(2-methyl-2-propenyl)-1-(2-propenyloxy)benzene (Compound No. 115) was obtained as a colorless oil in a yield of 10.8 g (84.3%).

$^1$H NMR (300 MHz, CDCl$_3$) δ1.30 (s, 9H), 1.73 (s, 3H), 3.33 (s, 2H), 4.55 (dt, J=5.0 and 1.6 Hz, 2H), 4.68 (broad s, 1H), 4.77 (broad s, 1H), 5.26 (ddd, J=10.5, 3.3 and 1.6 Hz, 1H), 5.43 (ddd, J=17.3, 3.3 and 1.6 Hz, 1H), 6.06 (ddt, J=17.3, 10.5 and 5.0 Hz, 1H), 6.88 (d, J=1.8 Hz, 1H), 6.92 (dd, J=7.8 and 1.8 Hz, 1H), 7.06 (d, J=7.8 Hz, 1H) ppm.

IR (liquid film) 3080, 2968, 1652, 1614, 1576 cm$^{-1}$.

Mass (m/z, %) 244 (M$^+$, 100), 229 (64), 163 (31), 147 (40), 57 (59).

EXAMPLE 105

10.2 g (42.2 mmol) of Compound No. 115 synthesized in Example 104 was dissolved in 50 ml of N,N-diethylaniline. This mixture was stirred at 210° C. in an atmosphere of argon for 11 hours and 20 minutes.

The reaction mixture was poured into 1N hydrochloric acid and extracted with hexane. The extract layer was successively washed with 1N hydrochloric acid three times and a saturated aqueous solution of sodium chloride three times, dried over anhydrous magnesium sulfate, and concentrated.

The concentrated product was placed on a silica gel column and eluted with a mixed solvent of hexane and dichloromethane (10:1), whereby 3-(t-butyl)-6-(2-methyl-2-propenyl)-2-(2-propenyl)phenol (Compound No. 116) was obtained as a colorless oil in a yield of 6.85 g (67.0%).

$^1$H NMR (300 MHz, CDCl$_3$) δ1.39 (s, 9H), 1.73 (s, 3H), 3.34 (s, 2H), 3.71 (dt, J=5.3 and 1.9 Hz, 2H), 4.78 (broad s, 1H), 4.87 (broad s, 1H), 5.02 (ddd, J=17.3, 3.7 and 1.9 Hz, 1H), 5.14 (ddd, J=10.2, 13.7 and 1.9 Hz, 1H), 5.27 (s, 1H), 6.04 (ddt, J=17.3, 10.2 and 5.3 Hz, 1H), 6.94 (s, 2H) ppm.

IR (liquid film) 3560, 2972, 1642, 1614, 1570 cm$^{-1}$.

Mass (m/z, %) 244 (M$^+$, 100), 229 (92), 187 (29), 173 (18), 159 (22), 145 (22).

EXAMPLE 106

9.00 g (34.6 mmol) of Compound No. 116 synthesized in Example 105 and 2.00 g (6.15 mmol) of salcomine were dissolved in 80 ml of DMF. This mixture was stirred in an atmosphere of oxygen for 5 days at a temperature in the range of 0° C. to room temperature.

Water and hexane was added to the reaction mixture, and the mixture was stirred for several ten minutes, and filtered through a celite filter. The water layer was separated from the filtrate, and the resultant organic layer was washed with a saturated aqueous solution of sodium chloride, dried over anhydrous magnesium sulfate, and concentrated.

The concentrated product was placed on a silica gel column and eluted with a mixed solvent of hexane and dichloromethane (4:1), whereby 2-(t-butyl)-5-(2-methyl-2-propenyl)-3-(2-propenyl)-p-benzoquinone (Compound No. 117) was obtained as a yellow oil in a yield of 3.198 g (33.3%).

$^1$H NMR (300 MHz, CDCl$_3$) δ1.41 (S, 9H), 1.72 (s, 3H), 3.09 (s, 2H), 3.55 (dt, J=5.6 and 1.8 Hz, 2H), 4.75 (broad s, 1H), 4.91 (broad s, 1H), 4.96 (d with fine coupling, J=17.3 Hz, 1H), 5.07 (d with fine coupling, J=10.3 Hz, 1H), 5.85 (ddt, J=17.3, 10.3 and 5.6 Hz, 1H), 6.45 (s, 1H) ppm.

IR (liquid film) 2972, 1652, 1574 cm$^{-1}$.

Mass (m/z, %) 258 (M$^+$, 100), 243 (39), 215 (44), 202 (50), 187 (31), 173 (22).

EXAMPLE 107

8.42 g (32.6 mmol) of Compound No. 117 synthesized in Example 106 was dissolved in a mixed solvent consisting of 50 ml of dichloromethane and 20 ml of methanol. This solution was stirred in an argon atmosphere at 0° C. To this solution, 369 mg (10.5 mmol) of sodium bron hydride was added, and the mixture solution was stirred for 2 hours and 20 minutes.

With addition of 90 mg (2.38 mmol) of sodium borohydride to the above mixture solution, the mixture was further stirred for 1 hour.

The reaction mixture was poured into 1N hydrochloric acid and extracted with ethyl acetate. The extract layer was washed with a saturated aqueous solution of sodium chloride, dried over anhydrous magnesium sulfate, and concentrated.

The concentrated product was placed on a silica gel column and successively eluted with a mixed solvent of hexane and dichloromethane (4:1) and a mixed solvent of hexane and dichloromethane (3:1), whereby 2-(t-butyl)-5-(2-methyl-2-propenyl)-3-(2-propenyl))hydroquinone (Compound No. 118) was obtained as a light red-yellow oil in a yield of 7.34 g (86.5%).

$^1$H NMR (300 MHz, CDCl$_3$) $\delta$1.54 (s, 9H), 1.73 (s, 3H), 3.26 (s, 2H), 3.73 (dt, J=4.9 and 2.0 Hz, 2H), 4.43 (broad s, 1H), 4.78 (s with fine coupling, 1H), 4.86 (s, 1H), 4.87 (s with fine coupling, 1H), 4.94 (ddd, J=17.3, 3.9 and 2.0 Hz, 1H), 5.14 (ddd, J=10.3, 3.9 and 2.0 Hz, 1H), 6.08 (ddt, J=17.3, 10.3 and 4.9 Hz, 1H), 6.38 (s, 1H) ppm.

IR (liquid film) 3548, 2956, 1638, 1616 cm$^{-1}$.

Mass (m/z, %) 260 (M$^+$, 100), 245 (68), 203 (18), 190 (15), 189 (16), 175 (16), 161 (19).

EXAMPLE 108

5.34 g (20.6 mmol) of Compound No. 118 synthesized in Example 107 was dissolved in 30 ml of 1,2-dichloroethane. This solution was stirred. To this solution, 0.52 ml (4.08 mmol) of boron trifluoride etherate was added, and the mixture solution was stirred at 0° C. in an atmosphere of argon for 1 hour and 20 minutes.

The reaction mixture was poured into water and extracted with ethyl acetate. The extract layer was washed with a saturated aqueous solution of sodium chloride, dried over anhydrous magnesium sulfate, and concentrated.

The concentrated product was crystallized from a mixed solvent of hexane and ethyl acetate, whereby 6-(t-butyl)-2,3-dihydro-2,2-dimethyl-5-hydroxy-7-(2-propenyl)benzo[b]furan (Compound No. 119) was obtained as crude crystals in a yield of 1.15 g (21.4%).

The thus obtained product was used in the next reaction.

$^1$H NMR (300 MHz, CDCl$_3$) $\delta$1.40 (s, 6H), 1.52 (s, 9H), 2.91 (s, 2H), 3.64 (dt, J=5.2 and 1.9 Hz, 2H), 4.40 (s, 1H), 4.82 (ddd, J=17.2, 3.8 and 1.9 Hz, 1H), 4.99 (ddd, J=10.3, 3.8 and 1.9 Hz, 1H), 5.99 (ddt, J=17.2, 10.3 and 5.2 Hz, 1H), 6.42 (s, 1H) ppm.

EXAMPLE 109

1.15 g (4.41 mmol) of Compound No. 119 synthesized in Example 108 was dissolved in a mixed solvent consisting of 4 ml of DMF and 8 ml of DME. To this solution, 1.83 g (13.2 mmol) of potassium carbonate and 0.63 ml (5.30 mmol) of benzyl bromide were added and the mixture was refluxed in an atmosphere of argon for 5 hours. To this reaction mixture, 0.30 ml (2.52 mmol) of benzyl bromide was added, and the mixture was further refluxed for 2 hours.

The reaction mixture was poured into water and extracted with hexane. The extract layer was successively washed with 1N hydrochloric acid and a saturated aqueous solution of sodium chloride three times, dried over anhydrous magnesium sulfate, and concentrated.

The concentrated product was placed on a silica gel column and successively eluted with a mixed solvent of hexane and dichloromethane (10:1) and a mixed solvent of hexane and dichloromethane (4:1), whereby 5-benzyloxy-6-(t-butyl)-2,3-dihydro-2,2-dimethyl-7-(2-propenyl)benzo[b]furan (Compound No. 120) was obtained in a yield of 1.44 g (93.6%).

Compound No. 120 is in the form of colorless scaly crystals, with a melting point of 73.0°–74.0° C. when recrystallized from hexane.

$^1$H NMR (300 MHz, CDCl$_3$) $\delta$1.41 (s, 6H), 1.50 (s, 9H), 2.95 (s, 2H), 3.67 (dt, J=5.2 and 1.9 Hz, 2H), 4.84 (ddd, J=17.2, 3.9 and 1.9 Hz, 1H), 4.95~5.05 (m, 3H), 6.00 (ddt, J=17.2, 10.3 and 5.2 Hz, 1H), 6.75 (s, 1H), 7.27~7.50 (m, 5H), ppm IR (KBr) 2980, 2920, 1642, 1614, 1596 cm$^{-1}$.

Mass (m/z, %) 350 (M$^+$, 25), 259 (53), 218 (100), 91 (66).

EXAMPLE 110

1.40 g (4.00 mmol) of Compound No. 120 synthesized in Example 109 was dissolved in 20 ml of anhydrous THF and the solution was stirred at 0° C. in an atmosphere of argon. To this solution, 722 mg (2.96 mmol) of 9-BBN dimer was added and the mixture was further stirred at room temperature for 1 hour. With the temperature of the reaction solution cooled to 0° C., 3.0 ml of ethanol, 5.0 ml of a 2N aqueous solution of sodium hydroxide and 4.0 g (35.3 mmol) of a 30% aqueous solution of hydrogen peroxide were successively added to the reaction solution, and the mixture was stirred for 1 hour.

The reaction mixture was poured into 1N hydrochloric acid and extracted with ethyl acetate. The extract layer was successively washed with 1N hydrochloric acid, a saturated aqueous solution of sodium thiosulfate and a saturated aqueous solution of sodium chloride three times, dried over anhydrous magnesium sulfate, and concentrated.

The concentrated product was crystallized from hexane and filtered off, whereby 3-[5-benzyloxy-6-(t-butyl)-2,3-dihydro-2,2-dimethylbenzo[b]furan-7-yl]propanol (Compound No. 121) was obtained in a yield of 1.07 g (72.6%).

The mother liquor was concentrated and placed on a silica gel column and eluted with a mixed solvent of hexane and ethyl acetate (4:1), whereby Compound No. 121 was further obtained in a yield of 325 mg (22.1%).

Compound No. 121 is in the form of colorless crystals, with a melting point of 96.0°–97.0° C. when recrystallized from hexane.

$^1$H NMR (300 MHz, CDCl$_3$) $\delta$1.46 (s, 6H), 1.53 (s, 9H), 1.76~1.88 (m, 2H), 2.98 (s with fine coupling, 2H), 3.01 (t, J=7.1 Hz, 2H), 3.57 (t, J=5.6 Hz, 2H), 5.01 (s, 2H), 6.73 (s, 1H), 7.28~7.48 (m, 5H) ppm.

IR (KBr) 3588, 2944, 1614, 1596 cm$^{-1}$.

Mass (m/z, %) 368 (M$^+$, 19), 221 (100), 193 (26), 91 (33), 57 (34).

EXAMPLE 111

1.35 g (3.67 mmol) of Compound No. 121 synthesized in Example 110 was dissolved in 15 ml of dimethyl sulfoxide. This solution was stirred in an atmosphere of argon at room temperature. To this solution, 1.80 ml (12.9 mmol) of trimethylamine, 7.5 ml of anhydrous THF, and 1.80 g (11.3 mmol) of sulfur trioxide pyridine complex were successively added in an atmosphere of argon. The reaction mixture was stirred for 25 minutes.

The reaction mixture was poured into dilute hydrochloric acid and extracted with hexane. The extract layer was washed with a saturated aqueous solution of sodium chloride twice, dried over magnesium sulfate, and concentrated.

The concentrated product was placed on a silica gel column and eluted with a mixed solvent of hexane and ethyl acetate (10:1), whereby 3-[5-benzyloxy-6-(t-butyl)-2,3-dihydro-2,2-dimethylbenzo[b]furan-7-yl]propanal (Compound No. 122) was obtained in a yield of 1.09 g (81.2%).

Compound No. 122 is in the form of colorless columns, with a melting point of 75.0°-75.5° C. when recrystallized from hexane.

$^1$H NMR (CDCl$_3$, 400 MHz) δ1.42 (s, 6H), 1.50 (s, 9H), 2.66~2.75 (m, 2H), 2.94 (s with fine coupling, 2H), 3.15~3.24 (m, 2H), 4.98 (s, 2H), 6.73 (s, 1H), 7.28~7.48 (m, 5H), 9.84 (t, J=1.6 Hz, 1H) ppm.

IR (KBr) 2916, 1726, 1616, 1596 cm$^{-1}$.

Mass (m/z, %) 366 (M$^+$, 40), 275 (100), 231 (76), 189 (20), 91 (75), 28 (36).

EXAMPLE 112

0.42 ml (3.30 mmol) of ethyl acetoacetate was added to a suspension which was prepared by suspending 134 mg (3.35 mmol) of 60% sodium hydride in 7.5 ml of anhydrous THF in a stream of argon at 0° C., and the resultant suspension was stirred for 15 minutes. 2.1 ml (3.28 mmol) of a 15% hexane solution of butyl lithium was added to the above suspension, and the mixture was stirred for 20 minutes and cooled to −78° C. To the above mixture, a THF solution of 1.00 g (2.73 mmol) of Compound No. 122 synthesized in Example 111, which was dissolved in 7.5 ml of anhydrous THF was added, and the reaction mixture was stirred for 1 hour.

After the completion of the reaction, the reaction mixture was poured into 1N hydrochloric acid and extracted with ethyl acetate. The extract layer was washed with a saturated aqueous solution of sodium chloride three times, dried over magnesium sulfate, and concentrated.

The concentrated product was placed on a silica gel column and eluted with a mixed solvent of hexane and ethyl acetate (4:1), whereby ethyl 7-[5-benzyloxy-6-(t-butyl)-2,3-dihydro-2,2-dimethylbenzo[b]furan-7-yl]-3-oxo-5-hydroxyheptanoate (Compound No. 123) was obtained in a yield of 986 mg (72.8%).

Compound No. 123 is in the form of colorless crystals, with a melting point of 79.0°-80.0° C. when recrystallized from ethyl acetate and hexane.

$^1$H NMR (CDCl$_3$, 300 MHz) δ1.27 (t, J=7.1 Hz, 3H), 1.44 (s, 3H), 1.45 (s, 3H), 1.52 (s, 9H), 1.64~1.78 (m, 2H), 2.63 (dd, J=16.4 and 3.8 Hz, 1H), 2.73 (dd, J=16.4 and 8.5 Hz, 1H), 2.83~3.20 (m, 2H), 2.97 (s, 2H), 3.39 (d, J=3.7 Hz, 1H), 3.50 (s, 2H), 3.96~4.09 (m, 1H), 4.19 (q, J=7.1 Hz, 2H), 5.01 (s, 2H), 6.72 (s, 1H), 7.28~7.48 (m, 5H) ppm.

IR (KBr) 3520, 2980, 2944, 1752, 1714 cm$^{-1}$.

Mass (m/z, %) 496 (M$^+$, 13), 366 (11), 349 (23), 275 (28), 231 (64), 219 (57), 201 (30), 91 (100), 43 (57), 28 (53).

EXAMPLE 113

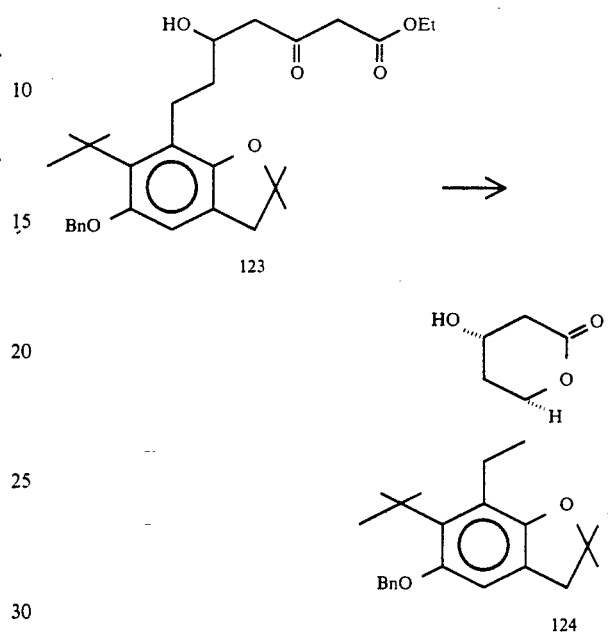

20 mg (0.20 mmol) of pivalic acid was added to 2.50 ml (2.50 mmol) of triethylborane (1.0M THF solution) in an atmosphere of argon at room temperature, and the mixture was stirred for 1 hour and 15 minutes, whereby a solution was obtained. To this solution, a THF solution of 950 mg (1.92 mmol) of Compound No. 123 synthesized in Example 112, which was dissolved in 9 ml of anhydrous THF was added, and the mixture was stirred for 1 hour and 15 minutes and cooled to −78° C. To this mixture, 3.0 ml of methanol and 87 mg (2.30 mmol) of sodium borohydride were successively added, and the mixture was stirred for 30 minutes.

To this mixture, 3.0 ml of a 5N aqueous solution of sodium hydroxide and 4.5 g (39.7 mmol) of a 30% aqueous solution of hydrogen peroxide were added, and the reaction mixture was ice-cooled. To the above reaction mixture, 3.0 ml of a 5N aqueous solution of sodium hydroxide was further added and the mixture was stirred for 30 minutes.

The reaction mixture was then poured into 1N hydrochloric acid and extracted with ethyl acetate. The extract layer was successively washed with 1N hydrochloric acid, a saturated aqueous solution of sodium thiosulfate, and a saturated aqueous solution of sodium chloride, dried over anhydrous magnesium sulfate, and concentrated.

The concentrated product was dissolved in 15 ml of anhydrous toluene and refluxed for 7 hours. After the completion of the reaction, the reaction mixture was concentrated, and placed on a silica gel column and eluted with a mixed solvent of dichloromethane and ethyl acetate (10:1), whereby trans-(±)-6-[5-benzyloxy-6-(t-butyl)-2,3-dihydro-2,2-dimethylbenzo[b]furan-7-yl]ethyl-4-hydroxytetrahydropyran-2-one (Compound No. 124) was obtained in a yield of 689 mg (79.6%).

Compound No. 124 is in the form of colorless columns, with a melting point of 172.5°–174.0° C. when recrystallized from ethyl acetate.

$^1$H NMR (300 MHz, CDCl$_3$) δ1.42 (s, 3H), 1.43 (s, 3H), 1.52 (s, 9H), 1.77~2.11 (m, 4H), 2.63 (ddd, J=17.5, 4.0 and 1.4 Hz, 1H), 2.78 (dd, J=17.5 and 5.1 Hz, 1H), 2.90 (ddd, J=13.5, 11.2 and 5.1 Hz, 1H), 2.94 (s, 2H), 3.12 (ddd, J=13.5, 11.4 and 5.1 Hz, 1H), 4.37~4.46 (m, 1H), 4.71~4.84 (m, 1H), 4.99 (s, 2H), 6.72 (s, 1H), 7.24~7.44 (m, 5H) ppm IR (KBr) 3484, 2940, 1716, 1614, 1596 cm$^{-1}$.

Mass (m/z, %) 452 (M$^+$, 38), 361 (85), 231 (66), 175 (20), 91 (00), 43 (22), 28 (70).

EXAMPLE 114

23.2 g (0.129 mol) of Compound No. 100 synthesized in Example 90, 27.0 g (0.195 mol) of potassium carbonate and 11.7 ml (0.137 mol) of allyl bromide were dissolved in 150 ml of acetone. This mixture was refluxed in an argon atmosphere for 7 hours.

The reaction mixture was poured into water and extracted with hexane. The extract layer was washed with a saturated aqueous solution of sodium chloride twice, dried over anhydrous magnesium sulfate, and concentrated.

The concentrated product was placed on a silica gel column and successively eluted with a mixed solvent of hexane and dichloromethane (1:1) and a mixed solvent of hexane and dichloromethane (2:3), whereby 2-(t-butyl)-4-(2-methyl-2-propenyloxy)-6-methylphenol (Compound No. 125) was obtained as a yellow oil in a yield of 14.3 g (50.4%).

$^1$H NMR (300 MHz, CDCl$_3$) δ1.40 (s, 9H), 2.22 (s, 3H), 4.40 (s, 2H), 4.46 (d with fine coupling, 5.4 Hz, 2H), 5.26 (d with fine coupling, J=9.6 Hz, 1H), 5.40 (d with fine coupling, J=17.2 Hz, 1H), 6.06 (ddt, J=17.2, 9.6 and 5.4 Hz, 1H), 6.57 (d, J=2.4 Hz, 1H), 6.77 (d, J=2.4 Hz, 1H) ppm.

IR (liquid film) 3596, 2964, 1652, 1604 cm$^{-1}$.

Mass (m/z, %) 220 (M$^+$, 92), 179 (100), 163 (33), 41 (53).

EXAMPLE 115

5.77 g (26.2 mmol) of Compound No. 125 synthesized in Example 114 and 5.0 ml (53.0 mmol) of acetic anhydride were added to 10 ml of pyridine. This mixture was refluxed in an atmosphere of argon for 4 hours and 30 minutes.

The reaction mixture was poured into water and extracted with hexane. The extract layer was successively washed with 1N hydrochloric acid, an aqueous solution of sodium hydrogencarbonate and a saturated aqueous solution of sodium chloride, dried over anhydrous magnesium sulfate, and concentrated.

The concentrated product was placed on a silica gel column and eluted with a mixed solvent of hexane and dichloromethane (1:1), whereby 1-acetoxy-2-(t-butyl)-6-methyl-4-(2-propenyloxy)benzene (Compound No. 126) was obtained as a colorless oil in a yield of 6.29 g (91.5%).

$^1$H NMR (300 MHz, CDCl$_3$) δ1.32 (s, 9H), 2.09 (s, 3H), 2.33 (s, 3H), 4.50 (dt, J=5.4 and 1.5 Hz, 2H), 5.28 (ddd, J=10.5, 3.0 and 1.5 Hz, 1H), 5.41 (ddd, J=17.1, 3.0 and 1.5 Hz, 1H), 6.06 (ddt, J=17.1, 10.5 and 5.4 Hz, 1H), 6.64 (d, J=2.7 Hz, 1H), 6.82 (d, J=2.7 Hz, 1H) ppm.

IR (liquid film) 2968, 1766, 1598 cm$^{-1}$.

Mass (m/z, %) 262 (M$^+$, 22), 220 (100), 179 (98), 163 (19), 43 (70), 41 (42).

EXAMPLE 116

4.35 g (16.6 mmol) of Compound No. 126 synthesized in Example 115 was dissolved in 35 ml of N,N-diethylaniline. This mixture was stirred at about 220° C. in an atmosphere of argon for 30 hours.

The reaction mixture was poured into 1N hydrochloric acid and extracted with ethyl acetate. The extract layer was successively washed with 1N hydrochloric acid and a saturated aqueous solution of sodium chloride three times, dried over anhydrous magnesium sulfate, and concentrated.

The concentrated product was placed on a silica gel column and eluted with a mixed solvent of hexane and ethyl acetate (40:1), whereby 4-acetoxy-5-(t-butyl)-3-methyl-2-(2-propenyl)phenol (Compound No. 127) was obtained in a yield of 2.39 g (54.9%).

Compound No. 127 is in the form of colorless scaly crystals, with a melting point of 104.5°–105.0° C. when recrystallized from hexane.

$^1$H NMR (300 MHz, CDCl$_3$) δ1.31 (s, 9H), 2.00 (s, 3H), 2.33 (s, 3H), 3.36~3.43 (m, 2H), 4.76 (s, 1H), 5.03 (ddd, J=17.1, 3.3 and 1.8 Hz, 1H), 5.07 (ddd, J=9.9, 3.3 and 1.8 Hz, 1H), 5.94 (ddt, J=17.1, 9.9 and 5.7 Hz, 1H), 6.72 (s, 1H) ppm.

IR (KBr) 3504, 3008, 2980, 2916, 1748, 1640, 1590 cm$^{-1}$.

Mass (m/z, %)
262 (M$^+$, 15), 220 (100), 205 (92), 43 (47).

EXAMPLE 117

2.29 g (8.74 mmol) of Compound No. 127 synthesized in Example 116 was dissolved in a mixed solvent consisting of 7 ml of DMF and 14 ml of DME. To this solution, 2.50 g (18.1 mmol) of potassium carbonate and 1.70 ml (17.2 mmol) of methallyl chloride were added, and the mixture was refluxed in an argon atmosphere for 7 hours.

The reaction mixture was poured into water and extracted with hexane. The extract layer was washed with a saturated aqueous solution of sodium chloride twice, dried over anhydrous magnesium sulfate, and concentrated.

The concentrated product was placed on a silica gel column and eluted with a mixed solvent of hexane and ethyl acetate (20:1), whereby 1-acetoxy-6-(t-butyl)-2-methyl-4-(2-methyl-2-propenyloxy)-3-(2-propenyl)benzene (Compound No. 128) was obtained as a colorless oil in a yield of 2.62 g (94.8%).

$^1$H NMR (300 MHz, CDCl$_3$) δ1.33 (s, 9H), 1.83 (s, 3H), 2.01 (s, 3H), 2.33 (s, 3H), 3.36 (dd, J=15.1 and 5.7 Hz, 1H), 3.51 (dd, J=15.1 and 5.7 Hz, 1H), 4.37 (d, J=12.0 Hz, 1H), 4.44 (d, J=12.0 Hz, 1H), 4.85~5.00 (m, 3H), 5.10 (s, 1H), 5.82~5.98 (m, 1H), 6.77 (s, 1H) ppm.

IR (liquid film) 2972, 1766, 1642 cm$^{-1}$.

Mass (m/z, %) 316 (M$^+$, 21), 274 (69), 219 (100), 163 (13), 57 (62), 55 (41), 43 (92).

EXAMPLE 118

5.69 g (18.0 mmol) of Compound No. 128 synthesized in Example 117 was dissolved in 30 ml of N-methyl-2-pyrrolidone. This mixture was refluxed in an atmosphere of argon for 9 hours and 20 minutes.

The reaction mixture was poured into 1N hydrochloric acid and extracted with hexane. The extract layer was washed with a saturated aqueous solution of sodium chloride, dried over anhydrous magnesium sulfate, and concentrated.

The concentrated product was placed on a silica gel column and eluted with a mixed solvent of hexane and ethyl acetate (50:1), whereby 5-acetoxy-2,3-dihydro-4-(t-butyl)-7-(2-propenyl)-2,2,6-trimethylbenzo[b]furan (Compound No. 129) was obtained in a yield of 3.45 g (60.6%).

Compound No. 129 is in the form of colorless columns, with a melting point of 65.5°~66.0° C. when recrystallized from hexane.

$^1$H NMR (300 MHz, CDCl$_3$) δ1.37 (s, 9H), 1.40 (s, 6H), 1.94 (s, 3H), 2.30 (s, 3H), 3.22 (s, 2H), 3.18~3.40 (m, 2H), 4.90~5.00 (m, 3H), 5.80~5.95 (m, 1H) ppm.
IR (KBr) 2980, 2932, 1764, 1642, 1566 cm$^{-1}$.
Mass (m/z, %) 316 (M$^+$, 12), 274 (57), 43 (100).

EXAMPLE 119

3.27 g (10.3 mmol) of Compound No. 129 synthesized in Example 118 was dissolved in 30 ml of anhydrous toluene and this solution was stirred in an atmosphere of argon at −78° C. To this solution, 12.5 ml (22.0 mmol) of diisobutyl aluminum hydride (25% hexane solution) was added, and the mixture solution was stirred for 30 minutes.

The reaction mixture was poured into 1N hydrochloric acid and extracted with ethyl acetate. The extract layer was washed with a saturated aqueous solution of sodium chloride twice, dried over anhydrous magnesium sulfate, and concentrated.

The concentrated product was placed on a silica gel column and eluted with a mixed solvent of hexane and dichloromethane (3:1), whereby 4-(t-butyl)-2,3-dihydro-5-hydroxy-7-(2-propenyl)-2,2,6-trimethylbenzo[b]furan (Compound No. 130) was obtained as a light red-yellow oil in a yield of 2.64 g (93.1%).

$^1$H NMR (300 MHz, CDCl$_3$) δ1.39 (s, 6H), 1.46 (s, 9H), 2.11 (s, 3H), 3.23 (s, 2H), 3.32 (dt, J=6.0 and 1.5 Hz, 1H), 4.30 (s, 1H), 4.91~5.01 (m, 2H), 5.88 (ddt, J=17.7, 9.5 and 6.2 Hz, 1H), ppm.
IR (KBr) 3600, 2976, 2928, 1642 cm$^{-1}$.
Mass (m/z, %) 274 (M$^+$, 100), 259 (30).

EXAMPLE 120

3.11 g (11.3 mmol) of Compound No. 130 synthesized in Example 119 was dissolved in a mixed solvent consisting of 10 ml of DMF and 20 ml of DME. To this solution, 3.09 g (22.4 mmol) of potassium carbonate and 1.50 ml (12.6 mmol) of benzyl bromide were added, and the mixture was refluxed in an atmosphere of argon for 3 hours and 30 minutes. To the above reaction mixture, 1.00 ml (8.4 mmol) of benzyl bromide was further added, and the mixture was refluxed for 3 hours and 30 minutes.

The reaction mixture was poured into water and extracted with ethyl acetate. The extract layer was washed with a saturated aqueous solution of sodium chloride twice, dried over anhydrous magnesium sulfate, and concentrated.

The concentrated product was placed on a silica gel column and eluted with a mixed solvent of hexane and ethyl acetate (100:1), whereby 5-benzyloxy-4-(t-butyl)-2,3-dihydro-7-(2-propenyl)-2,2,6-trimethylbenzo[b]furan (Compound No. 131) was obtained as a colorless oil in a yield of 2.20 g (53.2%).

$^1$H NMR (300 MHz, CDCl$_3$) δ1.42 (s, 6H), 1.46 (s, 9H), 2.21 (s, 3H), 3.23 (s, 2H), 3.32 (dt, J=6.1 and 1.7 Hz, 2H), 4.74 (s, 2H), 4.93~5.02 (m, 2H), 5.91 (ddt, J=17.7, 9.4 and 6.1 Hz, 1H), 7.27~7.52 (m, 5H) ppm
IR (liquid film) 2976, 2932, 1642 cm$^{-1}$.
Mass (m/z, %) 364 (M$^+$, 3), 273 (100), 232 (19), 91 (29).

EXAMPLE 121

1.08 g (4.43 mmol) of 9-BBN dimer was suspended in 10 ml of anhydrous THF to prepare a suspension. To this suspension, a THF solution of 2.15 g (5.90 mmol) of Compound No. 131 synthesized in Example 120, which was dissolved in 12 ml of anhydrous THF, was added in an atmosphere of argon at room temperature, and the mixture was stirred for 1 hour and 10 minutes. With the temperature of the reaction mixture cooled to 0° C., 3.5 ml of ethanol, 6.0 ml of a 2N aqueous solution of sodium hydroxide and 4.50 g (39.7 mmol) of a 30% aqueous solution of hydrogen peroxide were successively added to the above reaction mixture, and the mixture was stirred for 30 minutes.

The reaction mixture was poured into 1N hydrochloric acid and extracted with ethyl acetate. The extract layer was successively washed with a saturated aqueous solution of sodium chloride, a saturated aqueous solution of sodium thiosulfate and a saturated aqueous solution of sodium chloride, dried over anhydrous magnesium sulfate, and concentrated.

The concentrated product was placed on a silica gel column and eluted with a mixed solvent of hexane and ethyl acetate (4:1), whereby 3-[5-benzyloxy-4-(t-butyl)-2,3-dihydro-2,2,6-trimethylbenzo[b]furan-7-yl]propanol (Compound No. 132) was obtained in a yield of 2.13 g (94.4%).

$^1$H NMR (300 MHz, CDCl$_3$) δ1.45 (s, 6H), 1.46 (s, 9H), 1.72~1.82 (m, 2H), 2.23 (s, 3H), 2.71 (t, J=6.7 Hz, 2H), 2.85 (t, J=6.7 Hz, 1H), 3.25 (s, 2H), 3.48~3.58 (m, 2H), 4.74 (s, 2H), 7.28~7.52 (m, 5H) ppm.
IR (KBr) 3472, 2968 cm$^{-1}$.
Mass (m/z, %) 382 (M$^+$, 4), 291 (100), 235 (16), 91 (46).

EXAMPLE 122

2.00 g (5.24 mmol) of Compound No. 132 synthesized in Example 121 was dissolved in 20 ml of dimethyl sulfoxide. To this solution, 2.60 ml (18.7 mmol) of triethylamine, 10 ml of anhydrous THF, and 2.50 g (15.7 mmol) of sulfur trioxide pyridine complex were successively added in an atmosphere of argon at room temperature. The reaction mixture was stirred for 30 minutes.

The reaction mixture was poured into dilute hydrochloric acid and extracted with hexane. The extract layer was washed with a saturated aqueous solution of sodium chloride twice, dried over magnesium sulfate, and concentrated.

The concentrated product was crystallized from a mixed solvent of hexane and ethyl acetate, whereby 3-[5-benzyloxy-4-(t-butyl)-2,3-dihydro-2,2,6-trimethylbenzo[b]furan-7-yl]propanal (Compound No. 133) was obtained in a yield of 752 mg (37.8%).

The mother liquor was concentrated and placed on a silica gel column and eluted with a mixed solvent of hexane and ethyl acetate (10:1), whereby Compound No. 133 was further obtained in a yield of 757 mg (38.0%).

Compound No. 133 is in the form of colorless scaly crystals, with a melting point of 131.5°~132.5° C. when recrystallized from ethyl acetate and hexane.

¹H NMR (300 MHz, CDCl₃) δ1.41 (s, 6H), 1.45 (s, 9H), 2.23 (s, 3H), 2.60~2.68 (m, 2H), 2.85~2.93 (m, 2H), 3.21 (s, 2H), 4.74 (s, 2H), 7.28~7.52 (m, 5H), 9.83 (t, J=1.8 Hz, 1H) ppm.

IR (KBr) 2972, 1728, 1566 cm⁻¹.

Mass (m/z, %) 380 (M⁺, 3), 289 (100), 91 (30).

EXAMPLE 123

0.61 ml (4.79 mmol) of ethyl acetoacetate was added to a suspension which was prepared by suspending 190 mg (4.75 mmol) of 60% sodium hydride in 5 ml of anhydrous THF in a stream of argon at 0° C., and the resultant suspension was stirred for 20 minutes. 3.04 ml (4.75 mmol) of a 15% hexane solution of butyl lithium was added to the above suspension, and the mixture was stirred for 15 minutes and cooled to −78° C. To the above mixture, a THF solution of 1.39 g (3.67 mmol) of Compound No. 133 synthesized in Example 122, which was dissolved in 10 ml of anhydrous THF was added, and the mixture was stirred for 1 hour.

After the completion of the reaction, the reaction mixture was poured into 1N hydrochloric acid and extracted with ethyl acetate. The extract layer was washed with a saturated aqueous solution of sodium chloride three times, dried over magnesium sulfate, and concentrated.

The concentrated product was placed on a silica gel column and successively eluted with a mixed solvent of hexane and ethyl acetate (4:1) and a mixed solvent of hexane and ethyl acetate (3:1), whereby ethyl 7-[5-benzyloxy-4-(t-butyl)-2,3-dihydro-2,2,6-trimethylbenzo[b]furan-7-yl]-3-oxo-5-hydroxyheptanoate (Compound No. 134) was obtained as a colorless oil in a yield of 927 mg (49.5%).

¹H NMR (300 MHz, CDCl₃) δ1.26 (t, J=7.2 Hz, 3H), 1.44 (s, 3H), 1.44 (s, 3H), 1.46 (s, 9H), 1.56~1.74 (m, 2H), 2.22 (s, 3H), 2.52~2.84 (m, 4H), 3.24 (s, 2H), 3.51 (s, 2H), 3.63 (d, J=3.5 Hz, 1H), 3.83~4.00 (m, 1H), 4.18 (q, J=7.2 Hz, 2H), 4.75 (s, 2H), 7.28~7.52 (m, 5H) ppm.

IR (liquid film) 3524, 2976, 1748, 1718, 1650 cm⁻¹.

Mass (m/z, %) 510 (M⁺, trace), 419 (22), 329 (21), 289 (78), 189 (32), 91 (100), 57 (27), 43 (72), 31 (48).

EXAMPLE 124

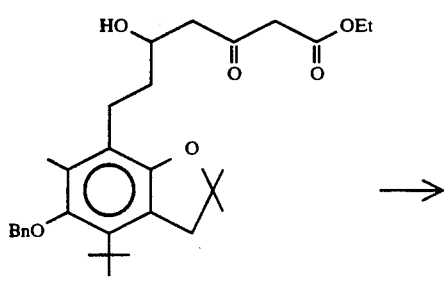

134

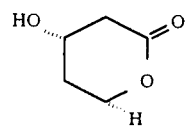

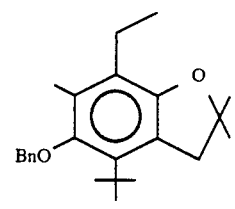

135

14 mg (0.14 mmol) of pivalic acid was added to 2.20 ml (2.20 mmol) of triethylborane (1.0M THF solution) under an argon atmosphere at room temperature, and the mixture was stirred for 1 hour and 15 minutes, whereby a solution was obtained. To this solution, a THF solution of 850 mg (1.67 mmol) of Compound No. 134 synthesized in Example 123, which was dissolved in 10 ml of anhydrous THF was added, and the mixture was stirred for 1 hour and cooled to −78° C. To this mixture, 2.5 ml of methanol and 80 mg (2.11 mmol) of sodium borohydride were successively added, and the mixture was stirred for 25 minutes.

To this mixture, 2.5 ml of a 5N aqueous solution of sodium hydroxide and 4.00 g (35.3 mmol) of a 30% aqueous solution of hydrogen peroxide were added, and the reaction mixture was ice-cooled. To the above reaction mixture, 2.0 ml of a 5N aqueous solution of sodium hydroxide was further added and the mixture was stirred for 1 hour.

The reaction mixture was then poured into 1N hydrochloric acid and extracted with ethyl acetate. The extract layer was successively washed with 1N hydrochloric acid, a saturated aqueous solution of sodium thiosulfate, and a saturated aqueous solution of sodium chloride, dried over anhydrous magnesium sulfate, and concentrated.

The concentrated product was dissolved in 10 ml of anhydrous toluene and refluxed for 3 hours and 45 minutes.

After the completion of the reaction, the reaction mixture was concentrated, and placed on a silica gel column and eluted with a mixed solvent of hexane and ethyl acetate (2:1), whereby trans-(±)-6-[5-benzyloxy-4-(t-butyl)-2,3-dihydro-2,2,6-trimethylbenzo[b]furan-7-yl]ethyl-4-hydroxytetrahydropyran-2-one (Compound No. 135) was obtained in a yield of 631 mg (81.2%).

Compound No. 135 is in the form of colorless crystals, with a melting point of 131.0°-131.5° C. when recrystallized from ether.

¹H NMR (300 MHz, CDCl₃) δ1.41 (, 3H), 1.42 (s, 3H), 1.45 (s, 9H), 1.75~2.10 (m, 4H), 2.25 (s, 3H), 2.62 (ddd, J=17.5, 4.0 and 1.4 Hz, 1H), 2.62~2.79 (m, 2H), 2.77 (dd, J=17.5 and 5.1 Hz, 1H), 3.21 (s, 2H), 4.35~4.45 (m, 1H), 4.66~4.78 (m, 1H), 4.74 (s, 2H), 7.28~7.52 (m, 5H) ppm.

IR (KBr) 3492, 2968, 1714, 1610 cm⁻¹.

Mass (m/z, %) 466 (M⁺, 3), 375 (100), 357 (13), 245 (19), 215 (14), 189 (44), 91 (83), 57 (29).

EXAMPLE 125

50.2 g (369 mmol) of 3-(2-propyl)phenol (Compound No. 136) was dissolved in a mixed solvent consisting of 30 ml of DMF and 90 ml of DME. To this solution, 40.1 ml (406 mmol) of methallyl chloride and 76.4 g (554 mmol) of potassium carbonate were added, and the mixture was refluxed in an atmosphere of argon for 4 hours. To this reaction mixture, 3.64 ml (40.6 mmol) of methallyl chloride was further added, and the mixture was refluxed for 5 hours.

The reaction mixture was poured into water and extracted with hexane. The extract layer was successively washed with water and a saturated aqueous solution of sodium chloride, dried over anhydrous magnesium sulfate, and concentrated.

The concentrated product was placed on a silica gel column and eluted with a mixed solvent of ethyl acetate and hexane (1:6), whereby 1-(2-methyl-2-propenyloxy)-3-(2-propyl)benzene (Compound No. 137) was obtained as a light yellow oil in a yield of 67.4 g (96.1%).

$^1$H NMR (300 MHz, CDCl$_3$) δ1.24 (d, J=6.9 Hz, 6H), 1.84 (s, 3H), 2.87 (hept, J=6.9 Hz, 1H), 4.42 (s, 2H), 4.98 (s, 1H), 5.10 (s, 1H), 6.70~6.76 (m, 1H), 6.80~6.85 (m, 2H), 7.20 (t, J=8.2 Hz, 1H) ppm.

IR (liquid film) 2968 cm$^{-1}$.

Mass (m/z, %) 190 (M$^+$, 10), 175 (7), 147 (8), 133 (3), 91 (5), 55 (16).

EXAMPLE 126

64.2 g (338 mmol) of Compound No. 137 synthesized in Example 125 was dissolved in 150 ml of N,N-diethylaniline. The mixture was stirred at 190° C. for 3 hours and at a temperature in the range of 200° to 210° C. for 22 hours, in an atmosphere of argon.

Most of N,N-diethylaniline was distilled away from the reaction mixture under reduced pressure, and the residue was poured into 1N hydrochloric acid and extracted with hexane. The extract layer was successively washed with water and a saturated aqueous solution of sodium chloride, dried over anhydrous magnesium sulfate, and concentrated.

The concentrated product was placed on a silica gel column and eluted with ethyl acetate, whereby a mixture of 2-(2-methyl-2-propenyl)-5-(2-propyl)phenol (Compound No. 138) and 2-(2-methyl-2-propenyl)-3-(2-propyl)phenol (Compound No. 139) with a mixing ratio of 6:4 was obtained as a red oil in a yield of 50.2 g.

$^1$H NMR (300 MHz, CDCl$_3$) δ1.20 (d, J=6.9 Hz, 2.4H), 1.22 (d, J=7.0 Hz, 3.6H), 1.74 (s, 1.8H), 1.83 (s, 1.2H), 2.84 (hept, J=7.0 Hz, 0.6H), 3.05 (hept, J=6.9 Hz, 0.4H), 3.34 (s, 1.2H), 3.41 (s, 0.8H), 4.57 (s, 0.4H), 4.83~4.88 (m, 1H), 4.91 (s, 0.6H), 4.94 (s, 0.4H), 5.11 (s, 0.6H), 6.68 (d with fine coupling, J=7.9 Hz, 0.4H), 6.71 (d, J=1.7 Hz, 0.6H), 6.74 (dd, J=7.7 Hz, 0.6H), 6.90 (d with fine coupling, J=7.9 Hz, 0.4H), 7.00 (d, J=7.7 Hz, 0.6H), 7.12 (dd, J=7.9 and 7.9 Hz, 0.4H) ppm.

EXAMPLE 127

50.2 g of the mixture of Compound No. 138 and Compound No. 139 with a mixing ratio of 6:4 synthesized in Example 126 was dissolved in a mixed solvent consisting of 25 ml of DMF and 75 ml of DME. To this solution, 25.6 ml (295 mmol) of allyl bromide and 50.9 g (369 mmol) of potassium carbonate were added, and the mixture was refluxed for 3 hours.

The reaction mixture was poured into water and extracted with hexane. The extract layer was washed with a saturated aqueous solution of sodium chloride, dried over anhydrous magnesium sulfate, and concentrated.

The concentrated product was placed on a silica gel column and eluted with a mixed solvent of ethyl acetate and hexane (1:20), whereby a mixture of 2-(2-methyl-2-propenyl)-1-(2-propenyloxy)-5-(2-propyl)benzene (Compound No. 140) and 2-(2-methyl-2-propenyl)-1-(2-propenyloxy)-3-(2-propyl)benzene (Compound No. 141) with a mixing ratio of 10:7 was obtained in a yield of 51.0 g.

$^1$H NMR (300 MHz, CDCl$_3$) δ1.18 (d, J=6.8 Hz, 2.5H), 1.23 (d, J=6.9 Hz, 3.5H), 1.72 (s, 1.8H), 1.80 (s, 1.2H), 2.86 (hept, J=6.9 Hz, 0.6H), 3.09 (hept, J=6.8 Hz, 0.4H), 3.33 (s, 1.2H), 3.44 (s, 0.8H), 4.31 (s, 0.4H), 4.50 (ddd, J=4.9, 1.7 and 1.7 Hz, 0.8H), 4.53 (ddd, J=5.0, 1.7 and 1.7 Hz, 1.2H), 4.67 (s, 0.6H), 4.69 (s, 0.4H), 4.77 (s, 0.6H), 5.23 (d with fine coupling, J=10.5 Hz, 0.4H), 5.25 (d with fine coupling, J=10.5 Hz, 0.6H), 5.39 (ddd, J=17.4, 1.7 and 1.7 Hz, 0.4H), 5.42 (ddd, J=17.3, 1.7 and 1.7 Hz, 0.6H), 5.88~6.07 (m, 1H), 6.70 (d, J=7.9 Hz, 0.4H), 6.72 (s, 0.6H), 6.77 (dd, J=7.7 and 1.6 Hz, 0.6H), 6.91 (d with fine coupling, J=7.9 Hz, 0.4H), 7.05 (d, J=7.7 Hz, 0.6H), 7.17 (dd, J=7.9 and 7.9 Hz, 0.4H) ppm.

EXAMPLE 128

50.3 g of the mixture of Compound No. 140 and Compound No. 141 with a mixing ratio of 10:7 synthesized in Example 127 was dissolved in 150 ml of N,N-diethylaniline. This mixture was stirred in an argon atmosphere at 220° C. for 10 hours.

Most of N,N-diethylaniline was distilled away from the reaction mixture under reduced pressure, and the residue was poured into 1N hydrochloric acid and extracted with a mixed solvent of hexane and ethyl acetate. The extract layer was successively washed with water and a saturated aqueous solution of sodium chloride, dried over anhydrous magnesium sulfate, and concentrated.

The concentrated product was placed on a silica gel column and eluted with a mixed solvent of ethyl acetate and hexane (1:10), whereby a mixture of 6-(2-methyl-2-propenyl)-2-(2-propenyl)-3-(2-propyl)phenol (Compound No. 142) and 2-(2-methyl-2-propenyl)-6-(2-propenyl)-3-(2-propyl)phenol (Compound No. 143) with a mixing ratio of 6:4 was obtained in a yield of 41.5 g.

$^1$H NMR (300 MHz, CDCl$_3$) δ1.19 (d, J=6.8 Hz, 2.4H), 1.20 (d, J=6.9 Hz, 3.6H), 1.73 (s, 1.8H), 1.82 (s, 1.2H), 3.08 (hept, J=6.8 Hz, 0.4H), 3.10 (hept, J=6.9 Hz, 0.6H), 3.35 (s, 1.2H), 3.38 (d, J=6.5 Hz, 0.8H), 3.41 (s, 0.8H), 3.47 (ddd, J=5.6, 1.8 and 1.7 Hz, 1.2H), 4.55 (s with fine coupling, 0.4H), 4.83 (s with fine coupling, 0.4H), 4.86 (s, 0.6H), 4.91 (s, 0.6H), 4.94 (ddd, J=17.0, 1.8 and 1.7 Hz, 0.6H), 5.02 (ddd, J=10.2, 1.8 and 1.7 Hz, 0.6H), 5.08~5.19 (m, 0.8H), 5.16 (s, 0.4H), 5.26 (s, 0.6H), 5.92~6.09 (m, 1H), 6.83 (d, J=7.9 Hz, 0.6H), 6.85 (d, J=8.0 Hz, 0.4H), 6.96 (d, J=7.9 Hz, 0.6H), 7.00 (d, J=8.0 Hz, 0.4H) ppm

EXAMPLE 129

41.0 g of the mixture of Compound No. 142 and Compound No. 143 with a mixing ratio of 6:4 synthesized in Example 128 was dissolved in 150 ml of DMF. With addition of 5.79 g (17.8 mmol) of salcomine to the above solution, the reaction mixture was stirred at 0° C. for 8 hours, and then, stirred at room temperature overnight, in an atmosphere of oxygen.

The reaction mixture was poured into water with addition thereto of hexane, and filtered through a celite filter. The hexane layer was successively washed with water and a saturated aqueous solution of sodium chloride, dried over anhydrous magnesium sulfate, and concentrated.

The concentrated product was placed on a silica gel column, eluted with a mixed solvent of hexane and dichloromethane (1:3), and then diluted with hexane. This reaction solution was successively washed with a 1N aqueous solution of sodium hydroxide, a saturated aqueous solution of ammonium chloride and a saturated aqueous solution of sodium chloride, dried over anhydrous magnesium sulfate, and concentrated, whereby a mixture of 5-(2-methyl-2-propenyl)-3-(2-propenyl)-2-(2-propyl)-p-benzoquinone (Compound No. 144) and 3-(2-methyl-2-propenyl)-5-(2-propenyl)-2-(2-propyl)-p-benzoquinone (Compound No. 145), and a mixture of Compound No. 142 and Compound No. 143 were obtained in a yield of 28.8 g.

8.68 g of a mixture which contained the mixture of Compound No. 144 and Compound No. 145 and the mixture of Compound No. 142 and Compound No. 143 with a mixing ratio of 2:1 was dissolved in 40 ml of a mixed solvent of dichloromethane and methanol (3:1). To this solution, 336 mg (8.89 mmol) of sodium borohydride was added in a stream of argon at 0° C. One hour later, acetone was added to the above reaction mixture and the mixture was stirred for a while.

The reaction mixture was poured into 1N hydrochloric acid and extracted with ethyl acetate. The extract layer was successively washed with water and a saturated aqueous solution of sodium chloride, dried over anhydrous magnesium sulfate, and concentrated.

The concentrated product was placed on a silica gel column and eluted with a mixed solvent of dichloromethane and hexane (1:1), whereby 4.87 g of the mixture of 5-(2-methyl-2-propenyl)-3-(2-propenyl)-2-(2-propyl)hydroquinone (Compound No. 146) and 3-(2-methyl-2-propenyl)-5-(2-propenyl)-2-(2-propyl)hydroquinone (Compound No. 147) with a mixing ratio of 6:1, and 566 mg of the mixture of Compound No. 146 and Compound No. 147 with a mixing ratio of 4:5 were obtained. Furthermore, the mixture of Compound No. 142 and Compound No. 143 with a mixing ratio of 7:6 was obtained in a yield of 2.15 g.

$^1$H NMR (300 MHz, CDCl$_3$) δ1.33 (d, J=7.1 Hz, 0.9H), 1.34 (d, J=7.1 Hz, 5.1H), 1.73 (s, 2.6H), 1.83 (s, 0.4H), 3.10~3.27 (m, 1H), 3.27 (s, 1.7H), 3.31 (d, J=6.5 Hz, 0.3H), 3.39 (s, 0.3H), 3.47 (ddd, J=5.5, 1.8 and 1.7 Hz, 1.7H), 4.31 (s, 0.9H), 4.32 (s, 0.1H), 4.50 (s, 0.1H), 4.67 (s, 0.1H), 4.82 (s, 0.9H), 4.85 (s, 1H), 4.91 (s, 0.9H), 4.91 (ddd, J=17.1, 1.8 and 1.7 Hz, 0.9H), 5.03 (ddd, J=10.1, 1.8 and 1.7 Hz, 0.9H), 5.09~5.13 (m, 0.1H), 5.13~5.18 (m, 0.1H), 5.90~6.05 (m, 1H), 6.38 (s, 0.9H), 6.41 (s, 0.1H) ppm.

EXAMPLE 130

11.3 g of the mixture of Compound No. 146 and Compound No. 147 with a mixing ratio of 4.2:1 synthesized in Example 129 was dissolved in 100 ml of dichloromethane. To this solution, 1.41 ml (11.5 mmol) of boron trifluoride etherate was added, and the mixture solution was stirred in a stream of argon at 0° C. for 1 hour, and at room temperature for 2 hours.

The reaction mixture was poured into a saturated aqueous solution of sodium hydrogencarbonate and extracted with ethyl acetate. The extract layer was successively washed with water and a saturated aqueous solution of sodium chloride, dried over anhydrous magnesium sulfate, and concentrated.

The concentrated product was placed on a silica gel column and eluted with a mixed solvent of hexane and dichloromethane (1:1), whereby 2,3-dihydro-2,2-dimethyl-5-hydroxy-7-(2-propenyl)-6-(2-propyl)benzo[b]furan (Compound No. 148) was obtained in a yield of 8.11 g (88.3%) from Compound No. 146, and 2,3-dihydro-2,2-dimethyl-5-hydroxy-7-(2-propenyl)-4-(2-propyl)benzo[b]furan (Compound No. 149) was obtained in a yield of 1.46 g (67.1%) from Compound No. 147.

Compound No. 148

$^1$H NMR (300 MHz, CDCl$_3$) δ1.33 (d, J=7.2 Hz, 6H), 1.42 (s, 6H), 2.92 (s, 2H), 3.17 (hept, J=7.2 Hz, 1H), 3.35 (d with fine coupling, J=5.9 Hz, 2H), 4.21 (s, 1H), 4.88~5.02 (m, 2H), 5.92 (ddt, J=17.0, 10.2 and 5.9 Hz, 1H), 6.43 (s, 1H) ppm.
IR (KBr) 3424, 2986, 1641 cm$^{-1}$.
Mass (m/z, %) 246 (M$^+$, 100), 231 (20), 175 (10).

Compound No. 149

$^1$H NMR (300 MHz, CDCl$_3$) δ1.28 (d, J=7.1 Hz, 6H), 1.44 (s, 6H), 3.01 (s, 2H), 3.12 (hept, J=7.1 Hz, 1H), 3.22 (d, J=6.7 Hz, 2H), 4.23 (s, 1H), 5.00~5.12 (m, 2H), 5.95 (ddt, J=16.9, 10.1 and 6.7 Hz, 1H), 6.35 (s, 1H) ppm.

EXAMPLE 131

7.68 g (31.2 mmol) of Compound No. 148 synthesized in Example 130 was dissolved in a mixed solvent consisting of 10 ml of DMF and 30 ml of DME. To this solution, 4.45 ml (37.4 mmol) of benzyl bromide and 6.46 g (46.8 mmol) of potassium carbonate were added, and the mixture was refluxed in an atmosphere of argon for 3 hours and 45 minutes.

The reaction mixture was poured into water and extracted with hexane. The extract layer was successively washed with water and a saturated aqueous solution of sodium chloride, dried over anhydrous magnesium sulfate, and concentrated.

The concentrated product was placed on a silica gel column and eluted with a mixed solvent of ethyl acetate and hexane (1:6), whereby 5-benzyloxy-2,3-dihydro-2,2-dimethyl-7-(2-propenyl)-6-(2-propyl)benzo[b]furan (Compound No. 150) was obtained in a yield of 7.64 g (72.9%), and Compound No. 148 was obtained in a yield of 1.83 g (7.4%).

$^1$H NMR (300 MHz, CDCl$_3$) δ1.31 (d, J=7.0 Hz, 6H), 1.43 (s, 6H), 2.95 (s, 2H), 3.10~3.27 (m, 1H), 3.38 (d with fine coupling, J=5.9 Hz, 2H), 4.90~5.03 (m, 2H), 5.00 (s, 2H), 5.93 (ddt, J=16.8, 10.5 and 5.9 Hz, 1H), 6.68 (s, 1H), 7.27~7.50 (m, 5H) ppm.
IR (KBr) 2972, 2928, 1639 cm$^{-1}$.
Mass (m/z, %) 336 (M$^+$, 23), 245 (100), 204 (21), 91 (77), 65 (21).

EXAMPLE 132

3.97 g (16.3 mmol) of 9-BBN dimer was suspended in 40 ml of anhydrous THF at 0° C. in a stream of argon to prepare a suspension. To this suspension, a THF solution of 7.29 g (21.7 mmol) of Compound No. 150 synthesized in Example 131, which was dissolved in 10 ml of anhydrous THF, was added, and the mixture was stirred for 1 hour and 30 minutes. The temperature of the reaction mixture was raised to room temperature, and the reaction mixture was further stirred for 30 minutes. 2.54 ml (43.4 mmol) of ethanol was added to this reaction mixture at 0° C., and the mixture was stirred for 30 minutes. Thereafter, 21.7 mmol of a 2N aqueous solution of sodium hydroxide, and 9.83 g of a 30% aqueous solution of hydrogen peroxide were successively added to the reaction mixture, and the mixture was stirred for 20 minutes. After the temperature of the reaction mixture was raised to room temperature, the reaction mixture was further stirred for 30 minutes.

The reaction mixture was poured into 1N hydrochloric acid and extracted with ethyl acetate. The extract layer was successively washed with water, a saturated aqueous solution of sodium thiosulfate and a saturated aqueous solution of sodium chloride, dried over anhydrous magnesium sulfate, and concentrated.

The concentrated product was placed on a silica gel column and eluted with a mixed solvent of ethyl acetate and hexane (1:2), whereby 3-[5-benzyloxy-2,3-dihydro-2,2-dimethyl-6-(2-propyl)benzo[b]furan-7-yl]propanol (Compound No. 151) was obtained in a yield of 7.06 g (91.9%).

$^1$H NMR (300 MHz, CDCl$_3$) δ1.34 (d, J=7.0 Hz, 6H), 1.47 (s, 6H), 1.70~1.80 (m, 2H), 2.76 (t, J=6.6 Hz, 2H), 2.99 (s, 2H), 3.12~3.27 (m, 1H), 3.50 (t, J=5.7 Hz, 2H), 5.01 (s, 2H), 6.67 (s, 1H), 7.28~7.50 (m, 5H) ppm.

IR (KBr) 3408, 2964, 1600 cm$^{-1}$.

Mass (m/z, %) 354 (M$^+$, 16), 263 (20), 221 (47), 193 (18), 91 (100).

EXAMPLE 133

2.58 g (7.27 mmol) of Compound No. 151 synthesized in Example 132 was dissolved in a mixed solvent consisting of 30 ml of DMSO and 20 ml of THF. To this solution, 5.07 ml (36.4 mmol) of triethylamine and 4.63 g (29.1 mmol) of sulfur trioxide pyridine complex were successively added at room temperature in a stream of argon. The reaction mixture was stirred for 15 minutes.

The reaction mixture was poured into 1N hydrochloric acid and extracted with ethyl acetate. The extract layer was successively washed with water, a saturated aqueous solution of sodium hydrogencarbonate and a saturated aqueous solution of sodium chloride, dried over magnesium sulfate, and concentrated.

The concentrated product was placed on a silica gel column and eluted with a mixed solvent of ethyl acetate and hexane (1:6), whereby 3-[5-benzyloxy-2,3-dihydro-2,2-dimethyl-6-(2-propyl)benzo[b]furan-7-yl]propanal (Compound No. 152) was obtained in a yield of 2.07 g (81.0%).

$^1$H NMR (300 MHz, CDCl$_3$) δ1.34 (d, J=7.1 Hz, 6H), 1.42 (s, 6H), 2.60 (t with fine coupling, J=8.0 Hz, 2H), 2.95 (t, J=8.0 Hz, 2H), 2.95 (s, 2H), 4.99 (s, 2H), 6.68 (s, 1H), 7.27~7.48 (m, 5H), 9.82 (t, J=1.8 Hz, 1H) ppm.

IR (KBr) 2962, 1731 cm$^{-1}$.

Mass (m/z, %) 352 (M$^+$, 38), 261 (100), 219 (38), 217 (65), 91 (67).

EXAMPLE 134

2.15 ml (16.9 mmol) of ethyl acetoacetate was added to a suspension which was prepared by suspending 676 mg (16.9 mmol) of 60% sodium hydride in 50 ml of anhydrous THF in a stream of argon at 0° C., and the resultant suspension was stirred for 1 hour. 10.8 ml (16.9 mmol) of a 15% hexane solution of butyl lithium was added to the above suspension, and the mixture was stirred for 50 minutes and cooled to −78° C. To the above mixture, a THF solution of 5.26 g (14.9 mmol) of Compound No. 152 synthesized in Example 133, which was dissolved in 10 ml of anhydrous THF was added, and the mixture was stirred for 2 hours.

The reaction mixture was poured into 1N hydrochloric acid and extracted with ethyl acetate. The extract layer was successively washed with water and a saturated aqueous solution of sodium chloride, dried over magnesium sulfate, and concentrated.

The concentrated product was placed on a silica gel column and eluted with a mixed solvent of ethyl acetate and hexane (1:3), whereby ethyl 7-[5-benzyloxy-2,3-dihydro-2,2-dimethyl-6-(2-propyl)benzo[b]furan-7-yl]-3-oxo-5-hydroxyheptanoate (Compound No. 153) was obtained in a yield of 3.63 g (50.5%).

$^1$H NMR (300 MHz, CDCl$_3$) δ1.26 (t, J=7.1 Hz, 3H), 1.33 (t, J=7.0 Hz, 3H), 1.34 (d, J=7.0 Hz, 3H), 1.45 (s, 3H), 1.46 (s, 3H), 1.50~1.77 (m, 2H), 2.56 (dd, J=16.0 and 3.5 Hz, 1H), 2.64~2.86 (m, 4H), 2.98 (s, 2H), 3.08~3.26 (m, 1H), 3.50 (s, 2H), 3.86~3.98 (m, 1H), 4.17 (q, J=7.1 Hz, 2H), 5.01 (s, 2H), 6.66 (s, 1H), 7.23~7.50 (m, 5H) ppm.

IR (liquid film) 3528, 2974, 2936, 1747, 1719 cm$^{-1}$.

Mass (m/z, %) 482 (M$^+$, 29), 391 (15), 352 (17), 345 (23), 261 (57), 219 (56), 217 (53), 201 (36), 91 (100).

EXAMPLE 135

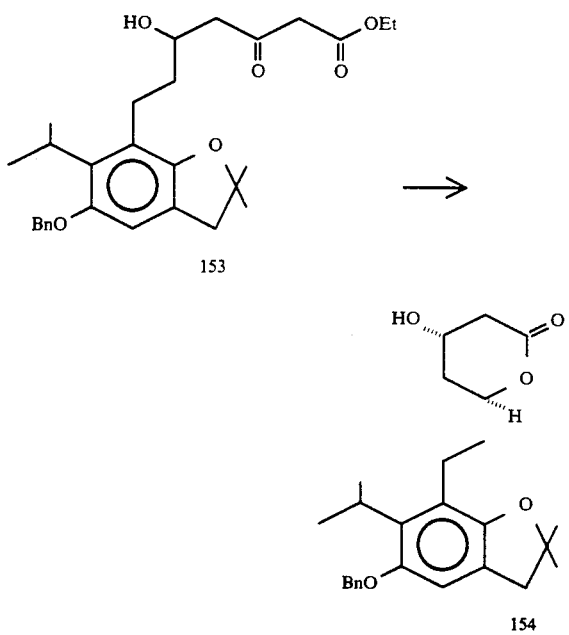

33 mg (0.322 mmol) of pivalic acid was added to 7.07 ml (7.07 mmol) of triethylborane (1.0M THF solution) in an atmosphere of argon at room temperature, and the mixture was stirred for 1 hour, whereby a solution was obtained. To this solution, a THF solution of 3.46 g (6.43 mmol) of Compound No. 153 synthesized in Example 134, which was dissolved in 5 ml of anhydrous THF was added dropwise. 80 minutes later, the mixture was cooled to −78° C. To this mixture, 10.0 ml of methanol and 182 mg (4.82 mmol) of sodium borohydride were successively added, and the mixture was stirred for 1 hour. Furthermore, 130 mg (3.44 mmol) of sodium borohydride was added to the reaction mixture, and the mixture was stirred for 2 hours.

After the temperature of the reaction mixture was raised to 0° C., 17.4 ml of a 5N aqueous solution of sodium hydroxide and 13.4 g of a 30% aqueous solution of hydrogen peroxide were successively added to the reaction mixture. The temperature of the reaction mixture was raised to room temperature, and the reaction mixture was stirred for 40 minutes.

The reaction mixture was poured into 1N hydrochloric acid and extracted with ethyl acetate. The extract layer was successively washed with a saturated aqueous solution of sodium thiosulfate, water and a saturated aqueous solution of sodium chloride, dried over anhydrous magnesium sulfate, and concentrated.

The concentrated product was dissolved in 30 ml of anhydrous toluene and refluxed for 3 hours and 30 minutes. The solvent was distilled away from the reaction mixture, and the concentrated product was placed on a silica gel column and eluted with a mixed solvent of ethyl acetate and hexane (2:1), whereby trans-($\pm$)-6-[5-benzyloxy-2,3-dihydro-2,2-dimethyl-6-(2-propyl)benzo[b]furan-7-yl]ethyl-4-hydroxytetrahydropyran-2-one (Compound No. 154) was obtained in a yield of 1.78 g (63.0%).

$^1$H NMR (300 MHz, CDCl$_3$) $\delta$1.34 (d with fine coupling, J=7.0 Hz, 6H), 1.42 (s, 3H), 1.43 (s, 3H), 1.70~2.08 (m, 5H), 2.62 (ddd, J=17.5, 4.0 and 1.4 Hz, 1H), 2.78 (dd, J=17.5 and 5.0 Hz, 1H), 2.66~2.87 (m, 2H), 2.94 (s, 2H), 3.12~3.30 (m, 1H), 4.37~4.43 (m, 1H), 4.69~4.80 (m, 1H), 6.67 (s, 1H), 7.30~7.48 (m, 5H) ppm IR (KBr) 3474, 2964, 1710 cm$^{-1}$.

Mass (m/z, %) 438 (M$^+$, 57), 347 (83), 287 (23), 245 (35), 217 (72), 201 (26), 175 (28), 91 (100).

EXAMPLE 136

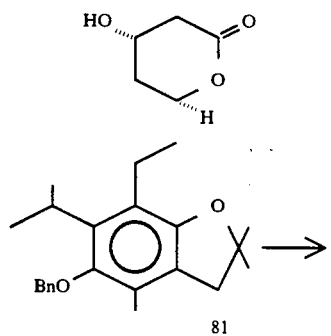

70 mg (0.155 mmol) of Compound No. 81 synthesized in Example 73 was dissolved in a mixed solvent consisting of 1.5 ml of ethyl acetate and 1.5 ml of methanol. With addition of 9 mg of 10% Pd/C to this solution, the solution was stirred at room temperature in an atmosphere of hydrogen for one day.

The reaction mixture, to which ethyl acetate was added, was filtered through a celite filter. The resultant filtrate was concentrated, placed on a silica gel column, and eluted with a mixed solvent of ethyl acetate and hexane (2:1), whereby trans-($\pm$)-6-[2,3-dihydro-5-hydroxy-6-(2-propyl)-2,2,4-trimethylbenzo[b]furan-7-yl]ethyl-4-hydroxytetrahydropyran-2-one (Compound No. 155) was obtained as a light yellow amorphous solid in a yield of 49 mg (87.3%).

$^1$H NMR (300 MHz, CDCl$_3$) $\delta$1.36(d, J=7.1 Hz, 3H), 1.37(d, J=7.1 Hz, 3H), 1.42(s, 3H), 1.43(s, 3H), 1.70~1.95(m, 4H), 1.97~2.08(m, 1H), 2.07(s, 3H), 2.62(ddd, J=17.4, 4.0 and 1.4 Hz, 1H), 2.77(dd, J=17.4 and 5.0 Hz, 1H), 2.65~2.81(m, 2H), 2.90(s, 2H), 3.10~3.32(m, 1H), 4.16(s, 1H), 4.36~4.46(m, 1H), 4.66~4.79(m, 1H) ppm.

IR (KBr) 3468, 2972, 2936, 1716 cm$^{-1}$.

Mass (m/z, %) 362 (M$^+$, 100), 232 (26), 217 (21), 189 (11), 43 (37).

EXAMPLE 137

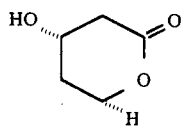

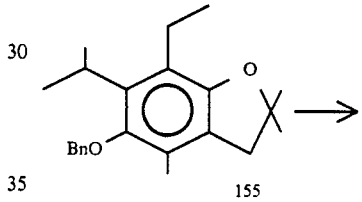

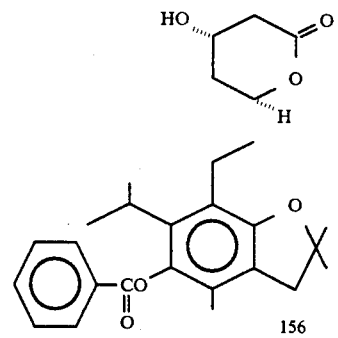

1.04 mg (2.88 mmol) of Compound No. 155 synthesized in Example 136 was dissolved in 5 ml of 1,2-dichloroethane. To this solution, 2.0 ml (14.3 mmol) of triethylamine and 1.06 g (5.95 mmol) of nicotinoyl chloride hydrochloride were added in an atmosphere of argon. The reaction mixture was stirred at a temperature in the range of $-25°$ to $-15°$ C. for 4 hours and 30 minutes. With addition of 200 mg (1.12 mmol) of nicotinoyl chloride hydrochloride to the reaction mixture, the mixture was stirred for 4 hours.

The reaction mixture was poured into dilute hydrochloric acid and extracted with ethyl acetate. The extract layer was washed with a saturated aqueous solution of sodium chloride twice, dried over magnesium sulfate, and concentrated.

The concentrated product was placed on a silica gel column and successively eluted with a mixed solvent of hexane and ethyl acetate (1:1) and a mixed solvent of

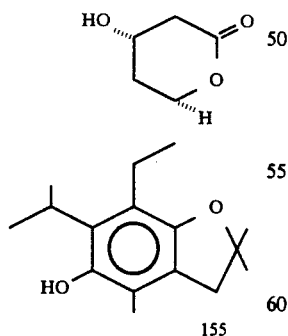

hexane and ethyl acetate (1:3), whereby trans-(±)-6-[2,3-dihydro-6-(2-propyl)-5-(pyridine-3-carboxy)-2,2,4-trimethylbenzo[b]furan-7-yl]ethyl-4-hydroxytetrahydropyran-2-one (Compound No. 156) was obtained in a yield of 850 mg (63.3%).

Compound No. 156 is in the form of colorless crystals, with a melting point of 185.5°-187.0° C. when recrystallized from diethyl ether and hexane.

$^1$H NMR (300 MHz, CDCl$_3$) δ1.12(d,J=7.0 Hz, 3H), 1.36(d,J=7.0 Hz, 3H), 1.46(s with fine coupling,3H), 1.48(s with fine coupling,3H), 1.70~2.07(m, 5H), 1.94(s,3H), 2.62(dd with fine coupling,J=17.5 and 3.9 Hz, 1H), 2.78(dd, J=17.5 and 5.2 Hz, 1H), 2.65~3.01(m, 2H), 2.94(s with fine coupling, 2H), 3.15~3.30(m, 1H), 4.37~4.45(m, 1H), 4.68~4.80(m, 1H), 7.50(dd,J=7.8 and 4.9 Hz, 1H), 8.48(ddd,J=7.8, 1.9 and 1.6 Hz, 1H), 8.88(dd,J=4.9 and 1.6 Hz, 1H), 9.43(s with fine coupling, 1H) ppm.

IR (KBr) 3264, 2976, 2934, 1748, 1595 cm$^{-1}$.

Mass (m/z, %) 467(M$^+$, 65), 449(7), 361(22), 231(40), 189(18), 106(100), 78(55), 43(27).

EXAMPLE 138

4.45 g (14.4 mmol) of the mixture of Compound No. 74 and Compound No. 73 with a mixing ratio of 6:1 synthesized in Example 66 was dissolved in a mixed solvent consisting of 28 ml of THF and 4 ml of water. To this solution, 2.82 g (15.8 mmol) of N-bromosuccinimide was added, and the reaction mixture was stirred at 0° C. in an atmosphere of argon for 30 minutes.

The reaction mixture was poured into a saturated aqueous solution of sodium thiosulfate and extracted with ethyl acetate. The extract layer was successively washed with a saturated aqueous solution of sodium thiosulfate twice, water, and a saturated aqueous solution of sodium chloride, dried over magnesium sulfate, and concentrated.

The concentrated product was placed on a silica gel column and eluted with a mixed solvent of ethyl acetate and hexane (1:6), whereby a mixture of 5-benzyloxy-7-bromo-2,3-dihydro-4-(2-propyl)-2,2,6-trimethylbenzo[b]furan (Compound No. 157) and Compound No. 75 with a mixing ratio of 6:1 was obtained in a yield of 4.99 g. The reaction product was recrystallized from diethyl ether and hexane, so that crystals of Compound No. 157 were obtained in a yield of 3.39 g.

Compound No. 157 is in the form of colorless columns, with a melting point of 96.0°-97.0° C. when recrystallized from diethyl ether and hexane.

$^1$H NMR (300 MHz, CDCl$_3$) δ1.23(d,J=7.3 Hz,6H), 1.52(s,6H), 2.37(s,3H), 3.17(s,2H), 3.49(hept,J=7.3 Hz,1H), 4.71(s,2H), 7.31~7.52(m,5H) ppm.

IR (KBr) 2976, 2962, 1601 cm$^{-1}$.

Mass (m/z, %) 390(M$^+$,1), 388(M$^+$,1), 299(12), 297(13), 218(8), 175(1), 91(10).

EXAMPLE 139

1.03 g (42.4 mmol) of magnesium (flakes) was added to 20 ml of anhydrous THF to prepare a solution. 0.67 ml (8.90 mmol) of ethyl bromide was added to the above solution at 0° C. in a stream of argon, whereby magnesium ethyl bromide was prepared.

To this magnesium ethyl bromide solution, 3.30 g (8.48 mmol) of Compound No. 157 synthesized in Example 138 was added, and the reaction mixture was refluxed for 20 minutes.

The above reaction mixture was added dropwise to a THF solution of 1.57 ml (12.7 mmol) of N-methylformanilide, which was dissolved in 10 ml of anhydrous THF, at −78° C. in a stream of argon. 10 minutes later, the temperature of the reaction mixture was raised to 0° C., and then, one hour later, the temperature thereof was raised to room temperature, and the reaction mixture was stirred overnight.

The reaction mixture was poured into 1N hydrochloric acid and extracted with ethyl acetate. The extract layer was successively washed with water, a saturated aqueous solution of sodium hydrogencarbonate, water and a saturated aqueous solution of sodium chloride, dried over anhydrous magnesium sulfate, and concentrated.

The concentrated product was crystallized from ethyl acetate and filtered off, whereby 5-benzyloxy-2,3-dihydro-7-formyl-4-(2-propyl)-2,2,6-trimethylbenzo[b]furan (Compound No. 158) was obtained in a yield of 1.50 g (52.3%).

The mother liquor was concentrated, placed on a silica gel column and eluted with a mixed solvent of ethyl acetate and hexane (1:6), whereby Compound No. 158 was further obtained in a yield of 945 mg (33.0%).

Compound No. 158 is in the form of colorless crystals, with a melting point of 93.0°-94.5° C. when recrystallized from ethyl acetate.

$^1$H NMR (300 MHz, CDCl$_3$) δ1.25(d,J=7.2 Hz,6H), 1.52(s,6H), 2.57(s,3H), 3.08(s,2H), 3.55(hept,J=7.2 Hz,1H), 4.70(s,2H), 7.30~7.50(m,5H), 10.38(s,1H) ppm.

IR (KBr) 2980, 1688, 1602 cm$^{-1}$.

Mass (m/z, %) 338(M$^+$,5), 247(100), 91(29).

EXAMPLE 140

335 mg (8.38 mmol) of a 60% sodium hydride was suspended in 10 ml of anhydrous THF at 0° C. in a stream of argon to prepare a suspension. To this suspension, 1.36 ml (8.38 mmol) of diethylcyanomethylphosphonate was added. To this mixture, a THF solution of 2.36 g (6.98 mmol) of Compound No. 158 synthesized in Example 139, which was dissolved in 10 ml of anhydrous THF was added dropwise, and the mixture was stirred for 10 minutes.

The reaction mixture was poured into 1N hydrochloric acid and extracted with ethyl acetate. The extract layer was successively washed with water and a saturated aqueous solution of sodium chloride, dried over anhydrous magnesium sulfate, and concentrated.

The concentrated product was crystallized from hexane and filtered off, whereby 3-[5-benzyloxy-2,3-dihydro-4-(2-propyl)-2,2,6-trimethylbenzo[b]furan-7-yl]-2-propenonitrile (Compound No. 159) was obtained in a yield of 2.06 g (81.8%).

Compound No. 159 is in the form of colorless crystals, with a melting point of 130.5°-131.0° C. when recrystallized from hexane.

$^1$H NMR (300 MHz, CDCl$_3$) δ1.24(d,J=7.2 Hz,6H), 1.50(s,6H), 2.35(s,3H), 3.07(s,2H), 3.53(hept,J=7.2 Hz,1H), 4.68(s,2H), 6.47(d,J=16.5 Hz,1H), 7.32~7.50(m,5H), 7.49(d,J=16.5 Hz,1H) ppm.

IR (liquid film) 2976, 2208 cm$^{-1}$.

Mass (m/z, %) 361(M$^+$,2), 270(31), 214(1), 91(11).

EXAMPLE 141

1.76 g (4.88 mmol) of Compound No. 159 synthesized in Example 140 was dissolved in a mixed solvent of 10 ml of methanol and 10 ml of THF. To this solution, 479 mg (19.7 mmol) of magnesium (flakes) and iodine (as a catalyst) were successively added at room temperature in a stream of argon, and the mixture was stirred for 2 hours.

The reaction mixture was poured into 1N hydrochloric acid and extracted with ethyl acetate. The extract layer was successively washed with water, a saturated aqueous solution of sodium hydrogencarbonate and a saturated aqueous solution of sodium chloride, dried over anhydrous magnesium sulfate, and concentrated.

The concentrated product was crystallized from ethyl acetate and hexane and filtered off, whereby 3-[5-benzyloxy-2,3-dihydro-4-(2-propyl)-2,2,6-trimethylbenzo[b]furan-7-yl]propanonitrile (Compound No. 160) was obtained in a yield of 1.63 g (92.1%).

Compound No. 160 is in the form of colorless silk-like crystals, with a melting point of 158.0°–159.0° C. when recrystallized from ethyl acetate and hexane.

¹H NMR (300 MHz, CDCl₃) δ1.23(d,J=7.2 Hz,6H), 1.46(s,6H), 2.28(s,3H), 2.57(t,J=7.6 Hz,2H), 2.93(t,J=7.6 Hz,2H), 3.08(s,2H), 3.51(hept,J=7.2 Hz,1H), 4.69(s,2H), 7.30~7.51(m,5H) ppm.

IR (KBr) 2980, 2248 cm⁻¹.

Mass (m/z, %) 363(M⁺,1), 272(31), 189(3), 91(10).

EXAMPLE 142

1.63 g (4.50 mmol) of Compoud No. 160 synthesized in Example 141 was suspended in 20 ml of anhydrous toluene. To this suspension, 2.69 ml (4.73 mmol) of diisobutyl aluminum hydride (25% hexane solution) was added in a stream of argon at −78° C., and the mixture was stirred for 1 hour.

With addition of methanol to this reaction mixture, the reaction mixture was poured into 1N hydrochloric acid and extracted with ethyl acetate. The extract layer was successively washed with water and a saturated aqueous solution of sodium chloride, dried over anhydrous magnesium sulfate, and concentrated.

The concentrated product was placed on a silica gel column and eluted with a mixed solvent of ethyl acetate and hexane (1:3), whereby a crude product of 3-[5-benzyloxy-2,3-dihydro-4-(2-propyl)-2,2,6-trimethylbenzo[b]furan-7-yl]propanal (Compound No. 161) was obtained in a yield of 1.30 g.

Compound No. 160 is in the form of colorless crystals, with a melting point of 127.0°–127.5° C. when recrystallized from ethyl acetate and hexane.

¹H NMR (300 MHz, CDCl₃) δ1.23(d,J=7.1 Hz,6H), 1.44(s,6H), 2.24(s,3H), 2.63(t with fine coupling,J=7.6 Hz,2H), 2.89(t,J=7.6 Hz,2H), 3.07(s,2H), 3.50(hept,J=7.1 Hz,1H), 4.69(s,1H), 7.30~7.50(m,5H), 9.83(s with fine coupling,1H) ppm.

IR (KBr) 2976, 1726 cm⁻¹.

Mass (m/z, %) 366(M⁺,1), 275(26), 233(3), 233(3), 189(1), 91(10).

EXAMPLE 143

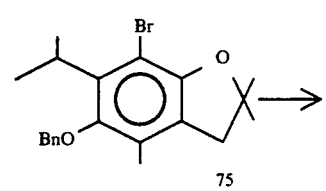

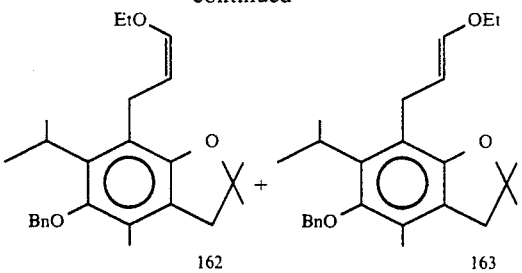

97 mg (4.0 mmol) of magnesium (flakes) was suspended in 4 ml of anhydrous THF to prepare a suspension. 0.01 ml (0.13 mmol) of ethyl bromide was added to the above suspension at room temperature in a stream of argon, whereby magnesium ethyl bromide was prepared.

To this magnesium ethyl bromide solution, 389 mg (1.0 mmol) of Compound No. 75 synthesized in Example 67 was gradually added, and the reaction mixture was stirred at room temperature for 30 minutes.

To the above reaction mixture, 0.18 ml (1.2 mmol) of acrolein diethyl acetal and 12 mg (0.01 mmol) of tetrakis(triphenylphosphine) palladium were added, and the mixture was refluxed for 2 hours and 30 minutes.

The reaction mixture was stirred for a while with addition thereto of a saturated aqueous solution of ammonium chloride and extracted with ethyl acetate. The extract layer was successively washed with a saturated aqueous solution of ammonium chloride, water and a saturated aqueous solution of sodium chloride, dried over anhydrous magnesium sulfate, and concentrated.

The concentrated product was placed on a silica gel column and eluted with a mixed solvent of dichloromethane and hexane (1:1), whereby a mixture of 5-benzyloxy-2,3-dihydro-7-[(3-ethoxy-2-(Z)-propene)-1-yl]-6-(2-propyl)-2,2,4-trimethylbenzo[b]furan (Compound No. 162) and 5-benzyloxy-2,3-dihydro-7-[(3-ethoxy-2-(E)-propene)-1-yl]-6-(2-propyl)-2,2,4-trimethylbenzo[b]furan (Compound No. 163) with a mixing ratio of 2:9 was obtained in a yield of 287 mg (72.8%).

Compound No. 163 is in the form of colorless crystals, with a melting point of 62.5°–63.5° C. when recrystallized from ethyl acetate.

¹H NMR (300 MHz, CDCl₃) δ1.22(t,J=7.0 Hz,3H), 1.35(d,J=7.2 Hz,6H), 1.46(s,6H), 2.16(s,3H), 2.90(s,2H), 3.25(d,J=6.8 Hz,2H), 3.40~3.58(m,1H), 3.67(q,J=7.0 Hz,2H), 4.76(s,2H), 4.92(dt,J=12.6 and 6.8 Hz,1H), 6.26(d,J=12.6 Hz,1H), 7.30~7.55(m,5H) ppm.

IR (KBr) 2978, 2926, 1651 cm⁻¹.

Mass (m/z, %) 394(M⁺,13), 303(100), 275(14), 231(46), 91(14).

Compound No. 162 is in the form of colorless crystals, with a melting point of 63.0°~64.5° C. when recrystallized from ethyl acetate.

¹H NMR (300 MHz, CDCl₃) δ1.28(t,J=7.1 Hz,3H), 1.37(d,J=7.2 Hz,6H), 1.46(s,6H), 2.16(s,3H), 2.91(s,2H), 3.44(dd,J=6.8 and 1.7 Hz,2H), 3.48~3.61(m,1H), 3.82(q,J=7.1 Hz,2H), 4.47(dd,J=6.8 and 6.3 Hz,1H), 4.77(s,2H), 5.91(dt,J=6.3 and 1.7 Hz,1H), 7.30~7.55(m,5H) ppm.

IR (KBr) 2976, 2932, 2876, 1666 cm⁻¹.

Mass (m/z, %) 394(M⁺,12), 303(100), 231(38), 91(20).

EXAMPLE 144

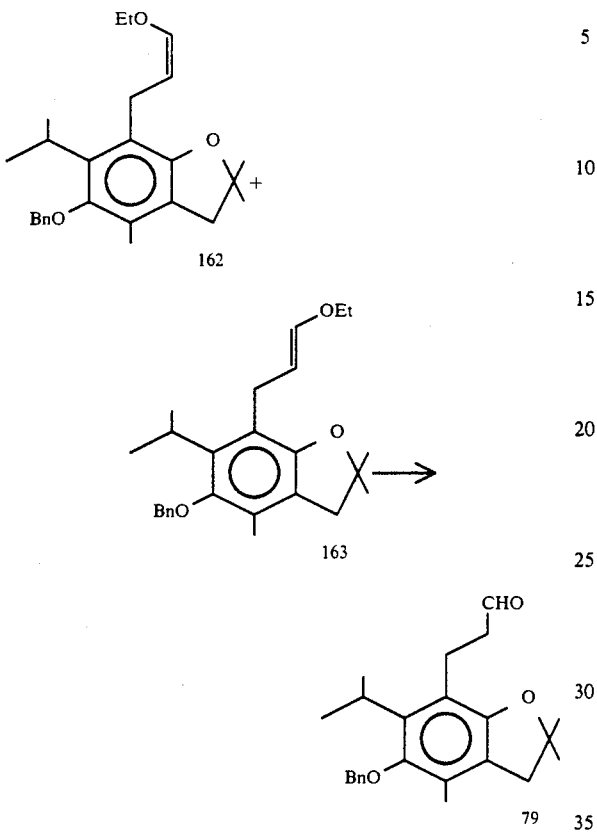

83 mg of the mixture of Compound No. 162 and Compound No. 163 with a mixing ratio of 10:11 synthesized in Example 143 was dissolved in 7 ml of THF. 1.5 ml of 1N sulfuric acid was added to this solution, and the mixture was stirred overnight at room temperature in an atmosphere of argon. To this reaction mixture, 2 ml of 1N sulfuric acid was further added, and the mixture was stirred for one day.

The reaction mixture was poured into water and extracted with ethyl acetate. The extract layer was successively washed with water, a saturated aqueous solution of sodium hydrogencarbonate and a saturated aqueous solution of sodium chloride, dried over anhydrous magnesium sulfate, and concentrated.

The concentrated product was placed on a silica gel column and eluted with a mixed solvent of dichloromethane and hexane (1:1), whereby Compound No. 79 was obtained as a colorless oil in a yield of 65 mg (84.2%).

Compound No. 79 is in the form of colorless crystals, with melting point of 88.0°–89.0° C. when recrystallized from hexane.

$^1$H NMR (300 MHz, CDCl$_3$) δ1.34(d,J=7.3 Hz,6H), 1.45(s,6H), 2.17(s,3H), 2.69(t,J=7.8 Hz,2H), 2.90(s,2H), 2.97(t,J=7.8 Hz,2H), 3.40~3.62(m,1H), 4.74(s,2H), 7.30~7.52(m,5H), 9.86(s,1H) ppm.

IR (KBr) 2970, 1722 cm$^{-1}$.

Mass (m/z, %) 366(M$^+$,5), 275(100), 231(44), 91(60).

EXAMPLE 145

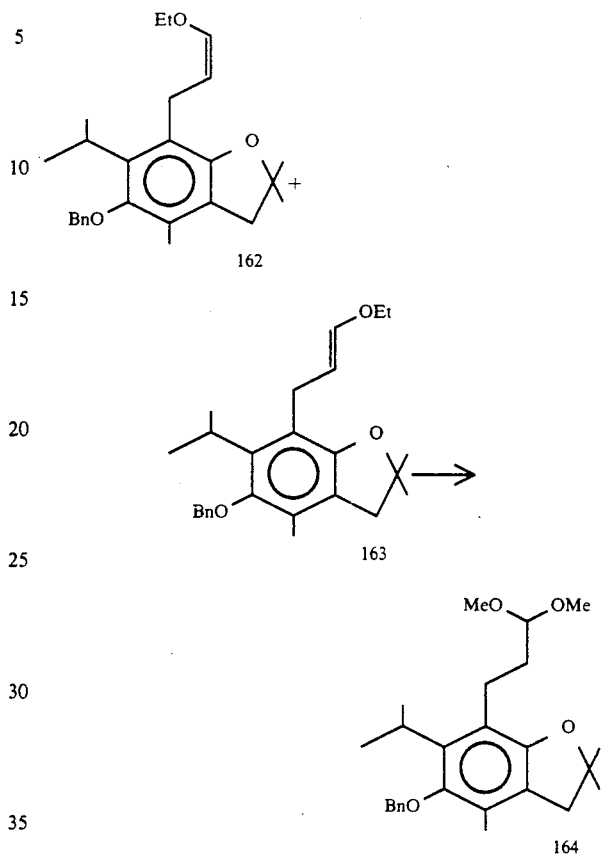

4.10 g of a crude product of the mixture of Compound No. 163 and Compound No. 162 synthesized in Example 143 was dissolved in a mixed solvent of 30 ml of methanol and 2 ml of 1N sulfuric acid. This reaction mixture was stirred in an argon atmosphere at room temperature for 3 hours.

The reaction mixture was poured into water and extracted with ethyl acetate. The extract layer was successively washed with a saturated aqueous solution of sodium hydrogencarbonate and a saturated aqueous solution of sodium chloride, dried over anhydrous magnesium sulfate, and concentrated.

The concentrated product was placed on a silica gel column and eluted with dichloromethane, whereby 3-[5-benzyloxy-2,3-dihydro-6-(2-propenyl)-2,2,4-trimethylbenzo[b]furan-7-yl]-1,1-dimethoxypropane (Compound No. 164) was obtained in a yield of 3.27 g.

Compound No. 164 is in the form of colorless crystals, with a melting point of 66.2°–67.8° C. when recrystallized from diethyl ether.

$^1$H NMR (300 MHz, CDCl$_3$) δ1.36(d,J=7.2 Hz,6H), 1.45(s,6H), 1.80~1.90(m,2H), 2.16(s,3H), 2.61~2.70(m,2H), 2.90(s,2H), 3.37(s,6H), 4.78(t,J=5.7 Hz,1H), 4.76(s,2H), 7.30~7.52(m,5H) ppm.

IR (KBr) 2976, 2832 cm$^{-1}$.

Mass (m/z, %) 412(M$^+$,17), 321(100), 289(76), 231(57), 91(17).

Test 1

Measurement of Inhibiting Effect on HMG Co-A Reductase

The inhibiting effect on HMG Co-A Reductase of representative examples of the 4-hydroxytetrahydropyran-2-one derivatives prepared in the above-discussed examples was measured in accordance with the method described in Journal of Biological Chemistry (J. Biol. Chem.) Vol. 234, page 2835 (1959) in order to investigate the inhibiting activity of each derivative in terms of the inhibiting ratio of the biosynthesis of cholesterol. The results are shown in the following Table 1:

TABLE 1

Inhibiting Ratio of Biosynthesis of Cholesterol[a]

| Example (Compound No.) | Inhibiting Activity[b] |
|---|---|
| 11 (13) | 50 |
| 12 (14) | 11 |
| 29 (31) | 90 |
| 31 (33) | 21 |
| 43 (45) | 39 |
| 44 (46) | 28 |
| 48 (50) | 12 |
| 50 (52) | 18 |
| 73 (81) | 427 |
| 102 (112) | 190 |
| 113 (124) | 300 |
| 135 (154) | 250 |
| 137 (156) | 180 |
| Compactin (ML-236B) | 100 |

[a] 0.1 μM samples were employed
[b] Relative value when the value of compactin is 100. The inhibiting ratio of compactin was in the range of 82% to 86%.

Test 2

Measurement of Reduction in Cholesterol Value

By use of model rats with triton-induced hyperlipemia, prepared in accordance with a method by Endo et al. (Endo, A., Thujita, K., Kuroda, M., and Tanzwas, K., Biochem. Biophys. Acta, 575, 266 (1979), the effect of the reduction in total serum cholesterol was investigated, using the value of compactin (ML-236B) as a reference. The results are shown in Table 2:

TABLE 2

| Example (Compound No.) | Reduction of Cholesterol Value |
|---|---|
| 11 (13) | 50 |
| 29 (31) | 100 |
| 43 (45) | 121 |
| 44 (46) | 37 |
| 73 (81) | 200 |
| 113 (124) | 70 |
| 135 (154) | 120 |
| 137 (156) | 220 |
| Compactin (ML-236B) | 100 |

Test 3

Measurement of Anti-Oxidation Function

The anti-oxidation function of some examples of the 4-hydroxytetrahydropyran-2-one derivatives prepared in the above-discussed examples was measured as a reference of the inhibition function of the automatic ABARTS reproduction of the rat brain homogenate in accordance with the method described in Nippon Yakuri-shi 87, 427–434 (1986) by K. Shintomi et al.

The anti-oxidation function of the tested samples was as follows when vitamin E was employed as a reference:

TABLE 3

| Example (Compound No.) | Anti-oxidation Function |
|---|---|
| 12 (14) | 106 |
| 48 (50) | 106 |
| 44 (46) | 106 |
| 50 (52) | 19 |
| Vitamin E | 100 |

What is claimed is:

1. A 4-hydroxytetrahydropyran-2-one derivative with general formula (I):

(I)

wherein $R_1$ represents hydrogen or a 2-tetrahydropyranyl group; $R_2$ and $R_3$ each represent hydrogen or an alkyl group having 1 to 6 carbon atoms, $R_4$ represents hydrogen, an alkyl group having 1 to 6 carbon atoms, an alkenyl group having 2 to 6 carbon atoms, an aryl group selected from the group consisting of phenyl, pyridyl, naphthyl, thienyl, furyl and imidazolyl, an aralkyl group selected from the group consisting of benzyl, pyridylmethyl, naphthylmethyl, thiophenylmethyl, furylmethyl and imidazolylmethyl, an acyl group selected from the group consisting of acetyl, propionyl, butyryl, valeryl and hexanoyl, an aroyl group selected from the group consisting of benzoyl, toluoyl, naphthoyl, pyridinecarbonyl and furoyl, or a substituted sulfonyl group selected from the group consisting of methanesulfonyl, benzenesulfonyl and toluenesulfonyl; A represents —$CH_2CH_2$— or —CH=CH—; and n is an integer of 1 or 2.

2. The 4-hydroxytetrahydropyran-2-one derivative as claimed in claim 1, wherein $R_1$ is hydrogen.

3. The 4-hydroxytetrahydropyran-2-one derivative as claimed in claim 1, wherein $R_1$ is a 2-tetrahydropyranyl group.

4. The 4-hydroxytetrahydropyran-2-one derivative as claimed in claim 1, wherein $R_2$ is hydrogen.

5. The 4-hydroxytetrahydropyran-2-one derivative as claimed in claim 1, wherein $R_2$ is an alkyl group having 1 to 6 carbon atoms.

6. The 4-hydroxytetrahydropyran-2-one derivative as claimed in claim 1, wherein $R_3$ is hydrogen.

7. The 4-hydroxytetrahydropyran-2-one derivative as claimed in claim 1, wherein $R_3$ is an alkyl group having 1 to 6 carbon atoms.

8. The 4-hydroxytetrahydropyran-2-one derivative as claimed in claim 1, wherein $R_2$ is hydrogen, and $R_3$ is hydrogen or an alkyl group having 1 to 6 carbon atoms.

9. The 4-hydroxytetrahydropyran-2-one derivative as claimed in claim 1, wherein $R_2$ is an alkyl group having 1 to 6 carbon atoms, and $R_3$ is hydrogen or an alkyl group having 1 to 6 carbon atoms.

10. The 4-hydroxytetrahydropyran-2-one derivative as claimed in claim 1, wherein $R_4$ is hydrogen.

11. The 4-hydroxytetrahydropyran-2-one derivative as claimed in claim 1, wherein $R_4$ is an alkyl group having 1 to 6 carbon atoms.

12. The 4-hydroxytetrahydropyran-2-one derivative as claimed in claim 1, wherein $R_4$ is an alkenyl group having 2 to 6 carbon atoms.

13. The 4-hydroxytetrahydropyran-2-one derivative as claimed in claim 1, wherein $R_4$ is an aryl group.

14. The 4-hydroxytetrahydropyran-2-one derivative as claimed in claim 1, wherein $R_4$ is an aralkyl group.

15. The 4-hydroxytetrahydropyran-2-one derivative as claimed in claim 1, wherein $R_4$ is an acyl group.

16. The 4-hydroxytetrahydropyran-2-one derivative as claimed in claim 1, wherein $R_4$ is an aroyl group.

17. The 4-hydroxytetrahydropyran-2-one derivative as claimed in claim 1, wherein $R_4$ is a substituted sulfonyl group.

18. The 4-hydroxytetrahydropyran-2-one derivative as claimed in claim 1, wherein A is —$CH_2CH_2$—.

19. The 4-hydroxytetrahydropyran-2-one derivative as claimed in claim 1, wherein A is —CH=CH—.

20. The 4-hydroxytetrahydropyran-2-one derivative as claimed in claim 1, wherein n is 1.

21. The 4-hydroxytetrahydropyran-2-one derivative as claimed in claim 1, wherein n is 2.

22. The 4-hydroxytetrahydropyran-2-one derivative as claimed in claim 13, wherein said aryl group represented by $R_4$ is selected from the group consisting of a phenyl group, a pyridyl group, a naphthyl group, a thienyl group, a furyl group, and an imidazolyl group.

23. The 4-hydroxytetrahydropyran-2-one derivative as claimed in claim 14, wherein said aralkyl group represented by $R_4$ is selected from the group consisting of a benzyl group, a pyridylmethyl group, a naphthylmethyl group, a thiophenylmethyl group, a furylmethyl group, and an imidazolylmethyl group.

24. The 4-hydroxytetrahydropyran-2-one derivative as claimed in claim 15, wherein said acyl group represented by $R_4$ is selected from the group consisting of an acetyl group, a propionyl group, a butyryl group, a valeryl group, and a hexanoyl group.

25. The 4-hydroxytetrahydropyran-2-one derivative as claimed in claim 16, wherein said aroyl group represented by $R_4$ is selected from the group consisting of a benzoyl group, a toluoyl group, a naphthoyl group, a pyridine-carbonyl group, and a furoyl group.

26. The 4-hydroxytetrahydropyran-2-one derivative as claimed in claim 17, wherein said substituted sulfonyl group represented by $R_4$ is selected from the group consisting of a methanesulfonyl group, a benzenesulfonyl group, and a toluenesulfonyl group.

27. The 4-hydroxytetrahydropyran-2-one derivative as claimed in claim 1, wherein $R_1$ is hydrogen; $R_2$ is an alkyl group having 1 to 6 carbon atoms; $R_3$ is hydrogen or an alkyl group having 1 to 6 carbon atoms; $R_4$ is a benzyl group, or a pyridine-carbonyl group; A is —$CH_2CH_2$—; and n is 1.

28. The 4-hydroxytetrahydropyran-2-one derivative as claimed in claim 1, which is selected from the group consisting of:

trans-(±)-6-[2,3-dihydro-5-(pyridine-3-carboxy)-2,3,4,6-tetramethylbenzo[b]furan-7-yl]ethyl-4-hydroxytetrahydropyran-2-one, trans-(±)-6-[(6-benzyloxy-2,2,5,7-tetramethyl)chroman-8-yl]-4-hydroxytetrahydropyran-2-one, trans-(±)-6-[5-benzyloxy-2,3-dihydro-6-(2-propyl)-2,2,4-trimethylbenzo[b]furan-7-yl]ethyl-4-hydroxytetrahydropyran-2-one, trans-(±)-6-[5-benzyloxy-6-(t-butyl)-2,3-dihydro-2,2,4-trimethylbenzo[b]furan-7-yl]ethyl-4-hydroxytetrahydropyran-2-one, trans-(±)-6-[5-benzyloxy-6-(t-butyl)-2,3-dihydro-2,2-dimethylbenzo[b]furan-7-yl]ethyl-4-hydroxytetrahydropyran-2-one, trans-(±)-6-[5-benzyloxy-2,3-dihydro-2,2-dimethyl-6-(2-propyl)benzo[b]furan-7-yl]ethyl-4-hydroxytetrahydropyran-2-one, and trans-(±)-6-[2,3-dihydro-6-(2-propyl)-5-(pyridine-3-carboxy)-2,2,4-trimethylbenzo[b]furan-7-yl]ethyl-4-hydroxytetrahydropyran-2-one.

* * * * *

UNITED STATES PATENT AND TRADEMARK OFFICE
CERTIFICATE OF CORRECTION

PATENT NO. : 5,149,834

DATED : September 22, 1992

INVENTOR(S) : Masakatsu MATUMOTO, et al.

It is certified that error appears in the above-identified patent and that said Letters Patent is hereby corrected as shown below:

In the abstract, the formula

" " -- --

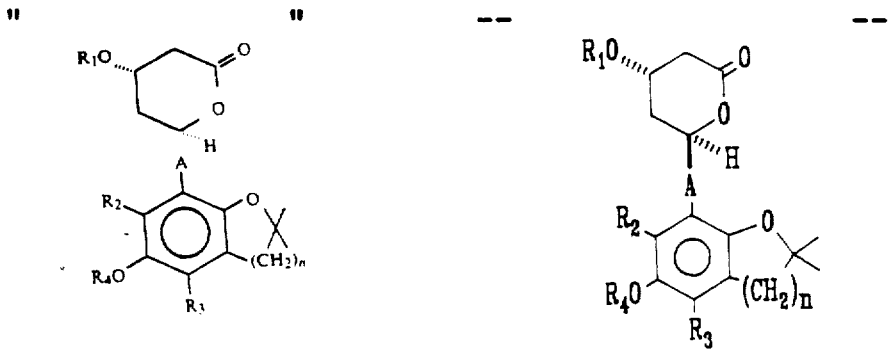

should appear line 8, delete "represent" and insert --represents--.

Column 2, the formula at lines 1-14

" " -- --

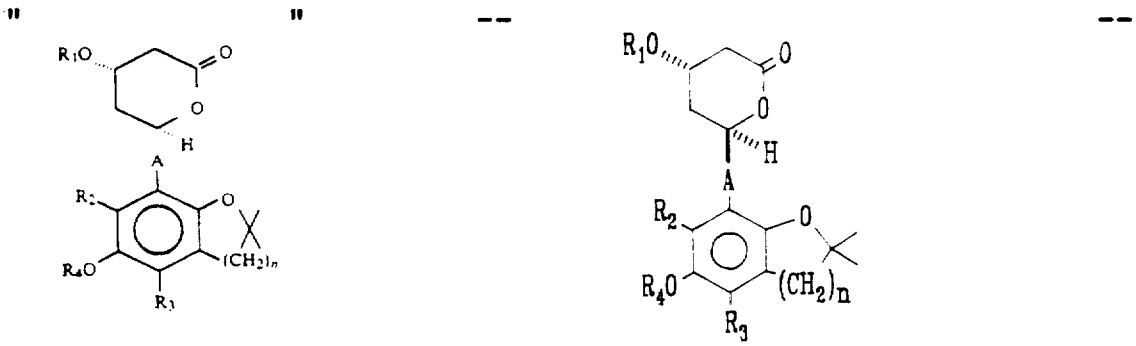

should appear

UNITED STATES PATENT AND TRADEMARK OFFICE
CERTIFICATE OF CORRECTION

PATENT NO. : 5,149,834

DATED : September 22, 1992

INVENTOR(S) : Masakatsu MATUMOTO, et al.

It is certified that error appears in the above-identified patent and that said Letters Patent is hereby corrected as shown below:

Column 4, the formula at lines 1-15

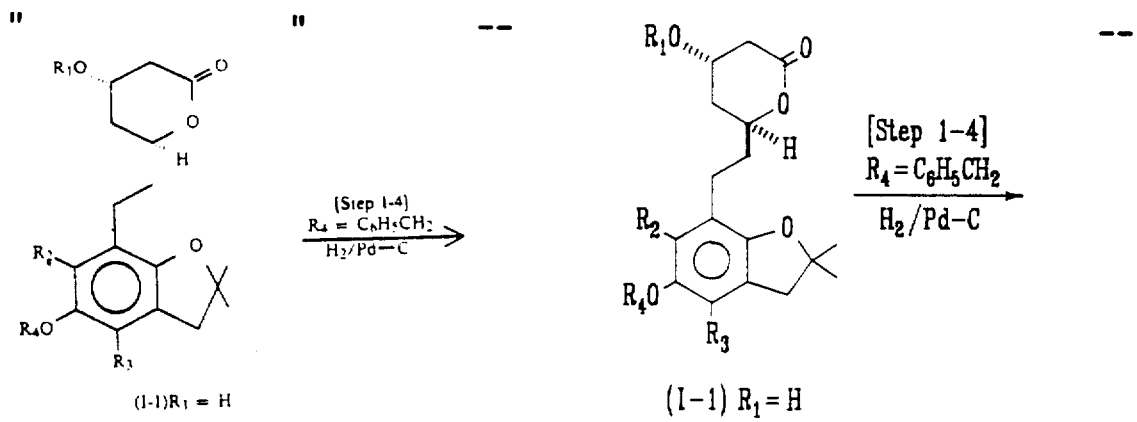

should appear the formula at lines 16-31

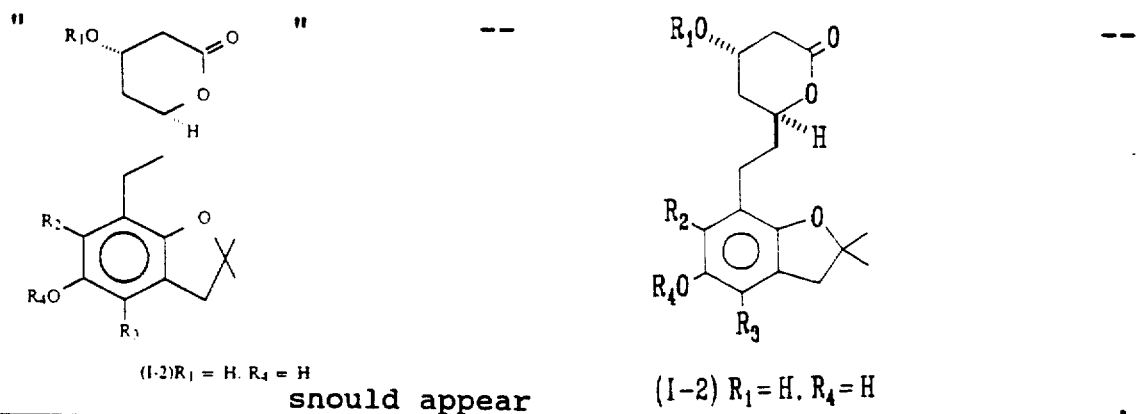

snould appear

UNITED STATES PATENT AND TRADEMARK OFFICE
CERTIFICATE OF CORRECTION

PATENT NO. : 5,149,834

DATED : September 22, 1992

INVENTOR(S) : Masakatsu MATUMOTO, et al.

It is certified that error appears in the above-identified patent and that said Letters Patent is hereby corrected as shown below:

Column 6, line 7, delete "1", line 34, delete "to" (first occurrence), the formula at lines 52-67

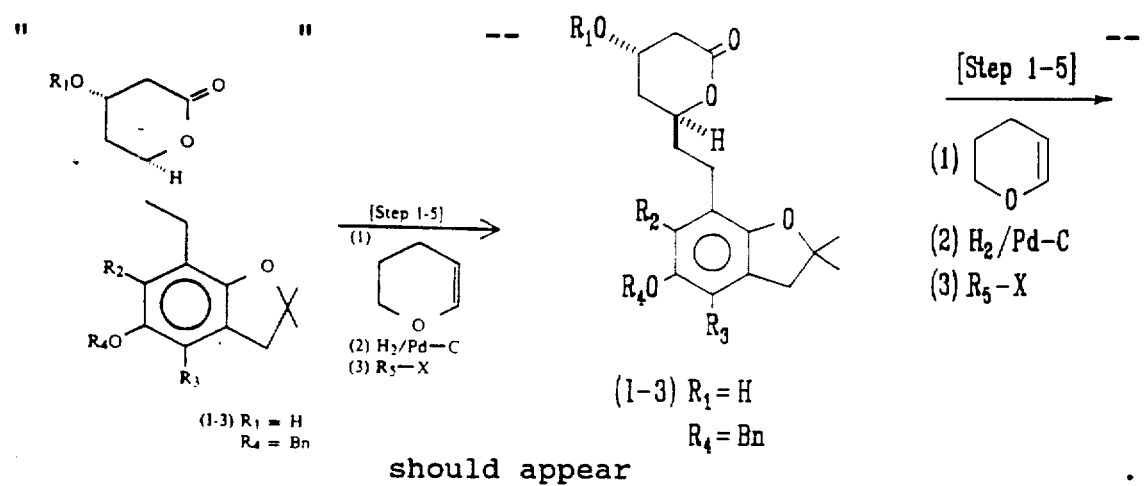

should appear

UNITED STATES PATENT AND TRADEMARK OFFICE
CERTIFICATE OF CORRECTION

PATENT NO. : 5,149,834

DATED : September 22, 1992

INVENTOR(S) : Masakatsu MATUMOTO, et al.

It is certified that error appears in the above-identified patent and that said Letters Patent is hereby corrected as shown below:

Column 7, the formula at lines 1-15

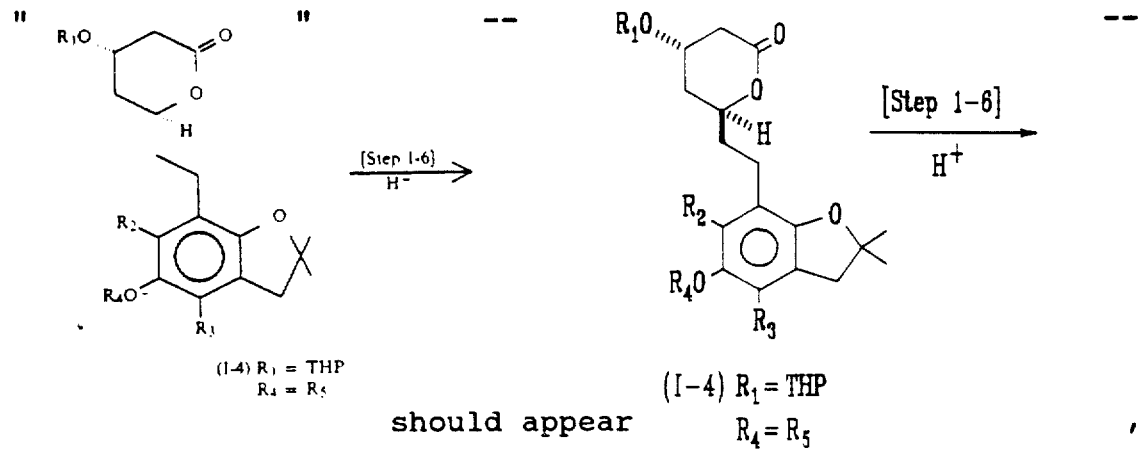

at lines 7 and 8,

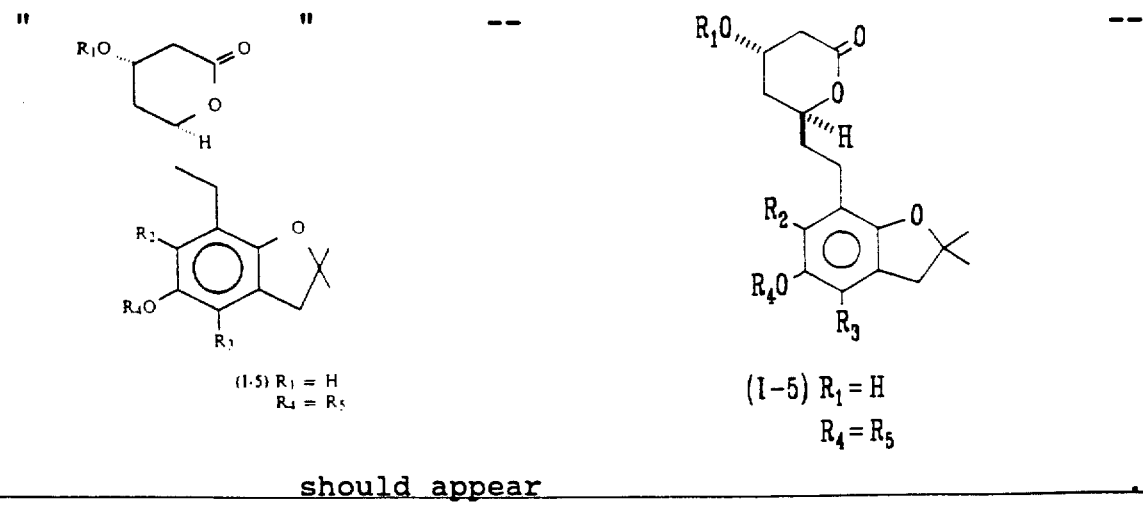

should appear

UNITED STATES PATENT AND TRADEMARK OFFICE
CERTIFICATE OF CORRECTION

PATENT NO. : 5,149,834

DATED : September 22, 1992

INVENTOR(S) : Masakatsu MATUMOTO, et al.

It is certified that error appears in the above-identified patent and that said Letters Patent is hereby corrected as shown below:

Column 8, line 55, delete "inhibitin" and insert -- inhibition --.

Column 9, formula (I-a)

"  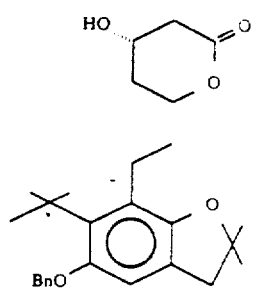  "   --  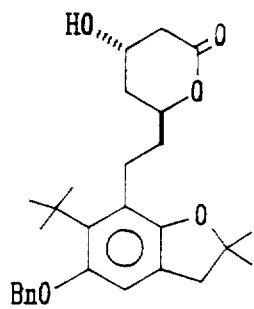  -- should appear formula (I-b)

"  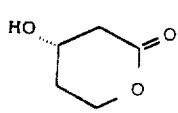  "   --  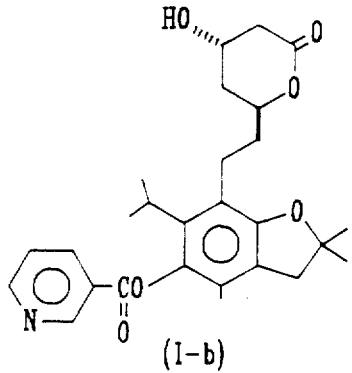  --

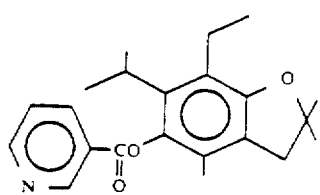

should appear

UNITED STATES PATENT AND TRADEMARK OFFICE
CERTIFICATE OF CORRECTION

PATENT NO. : 5,149,834                              Page 6 of 13

DATED : September 22, 1992

INVENTOR(S) : Masakatsu MATUMOTO, et al.

It is certified that error appears in the above-identified patent and that said Letters Patent is hereby corrected as shown below:

formula (I-c)

" 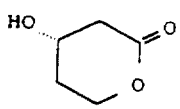 "    -- 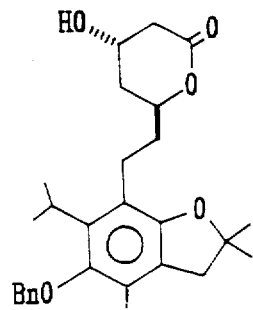 --

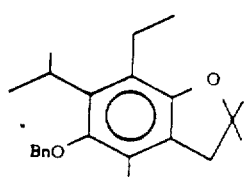

should appear formula (I-d)

" 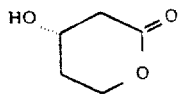 "    -- 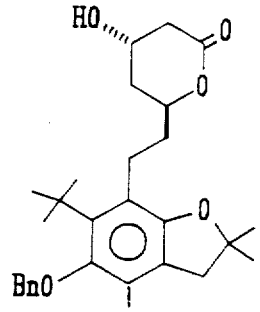 --

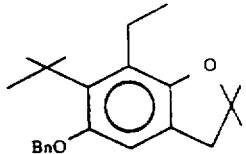

should appear

UNITED STATES PATENT AND TRADEMARK OFFICE
CERTIFICATE OF CORRECTION

PATENT NO. : 5,149,834
DATED : September 22, 1992
INVENTOR(S) : Masakatsu MATUMOTO, et al.

It is certified that error appears in the above-identified patent and that said Letters Patent is hereby corrected as shown below:

formula (I-e)

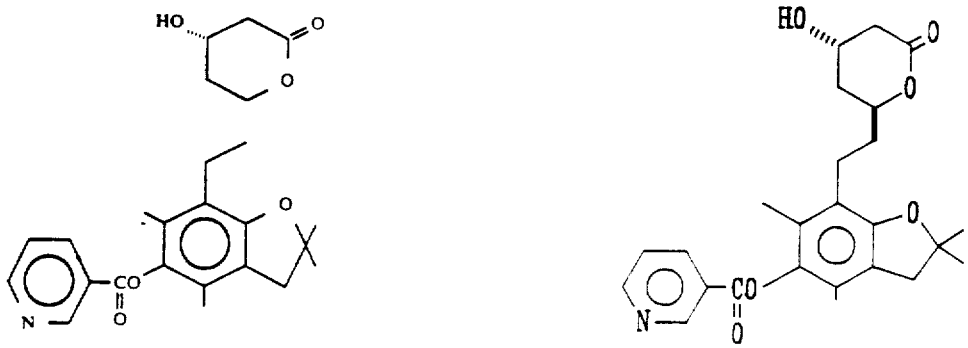

should appear

Column 15, line 63, delete "the".

Column 19, line 34, delete "chlorosuccinimde" and insert --chlorosuccinimide--, line 46, delete "A" and insert --An--.

Column 20, line 59, delete "caynoethyl" and insert --cyanoethyl--.

Column 32, line 53, delete "furan-7-ethyl" and insert --furan-7-yl)ethyl--.

Column 43, line 26, delete "to" (first occurrence).

Column 66, line 48, insert --(-- before "pyridine".

UNITED STATES PATENT AND TRADEMARK OFFICE
CERTIFICATE OF CORRECTION

PATENT NO. : 5,149,834

DATED : September 22, 1992

INVENTOR(S) : Masakatsu MATUMOTO, et al.

It is certified that error appears in the above-identified patent and that said Letters Patent is hereby corrected as shown below:

Column 82, Example 73, formula 81,

"  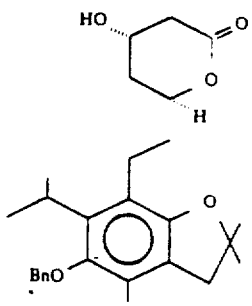  "  --  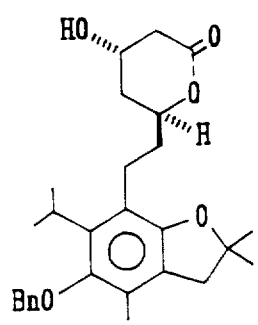  -- should appear

Column 89, Example 88, formula 97,

"  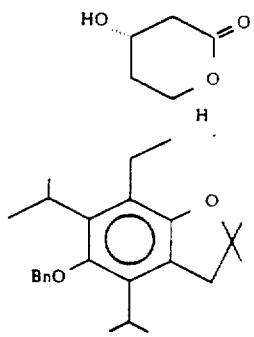  "  --  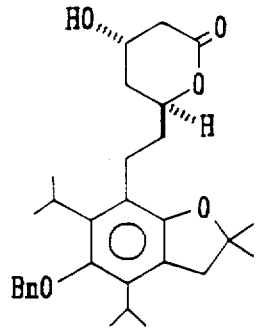  -- should appear

UNITED STATES PATENT AND TRADEMARK OFFICE
CERTIFICATE OF CORRECTION

PATENT NO. : 5,149,834  
DATED : September 22, 1992  
INVENTOR(S) : Masakatsu MATUMOTO, et al.

Page 9 of 13

It is certified that error appears in the above-identified patent and that said Letters Patent is hereby corrected as shown below:

Column 96, Example 102, formula 112,

"  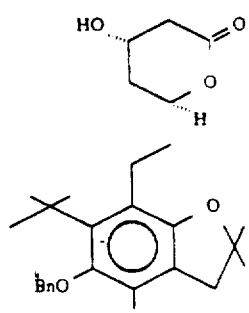  "  --  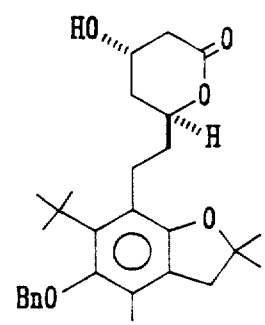  -- should appear

Column 102, Example 113, formula 124,

"  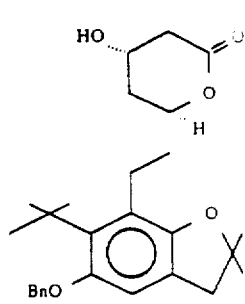  "  --  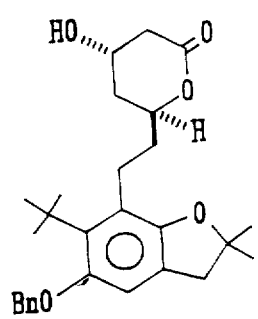  -- should appear

UNITED STATES PATENT AND TRADEMARK OFFICE
CERTIFICATE OF CORRECTION

PATENT NO. : 5,149,834

DATED : September 22, 1992

INVENTOR(S) : Masakatsu MATUMOTO, et al.

It is certified that error appears in the above-identified patent and that said Letters Patent is hereby corrected as shown below:

Column 108, Example 124, formula 135,

"  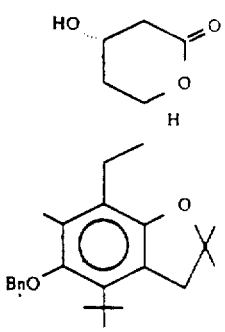  "   --  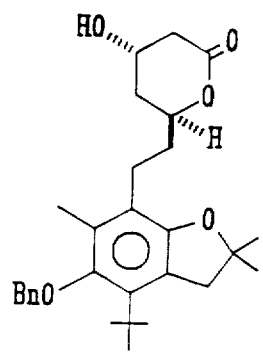  -- should appear

Column 114, Example 135, formula 154,

"  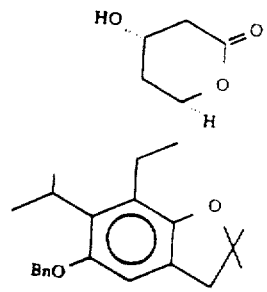  "   --  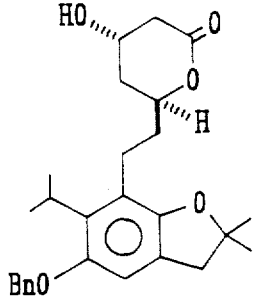  -- should appear

UNITED STATES PATENT AND TRADEMARK OFFICE
CERTIFICATE OF CORRECTION

PATENT NO. : 5,149,834

DATED : September 22, 1992

INVENTOR(S) : Masakatsu MATUMOTO, et al.

It is certified that error appears in the above-identified patent and that said Letters Patent is hereby corrected as shown below:

Column 115, Example 136, formula 81,

" " -- --

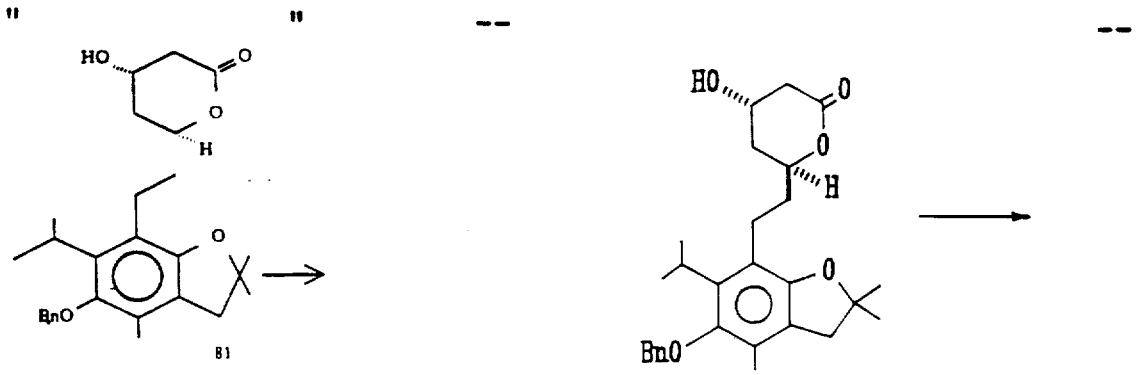

should appear formula 155,

" " -- --

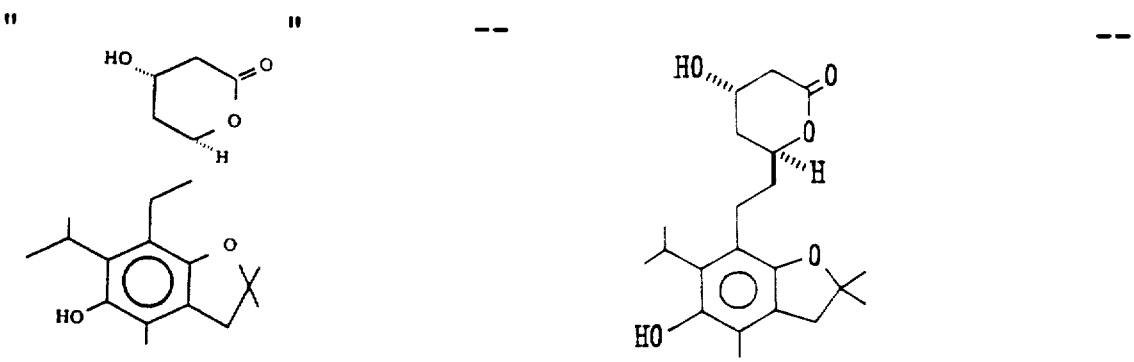

should appear

UNITED STATES PATENT AND TRADEMARK OFFICE
CERTIFICATE OF CORRECTION

PATENT NO. : 5,149,834

DATED : September 22, 1992

INVENTOR(S) : Masakatsu MATUMOTO, et al.

It is certified that error appears in the above-identified patent and that said Letters Patent is hereby corrected as shown below:

Column 116, Example 137, formula 155,

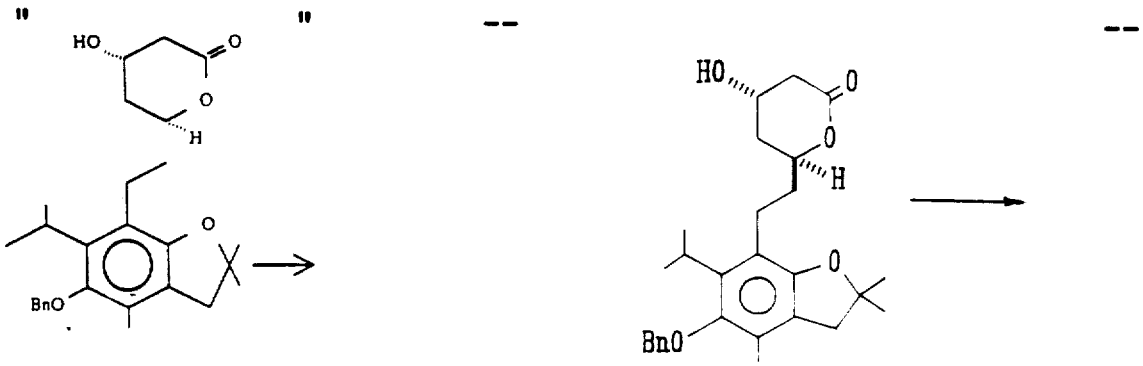

should appear formula 156,

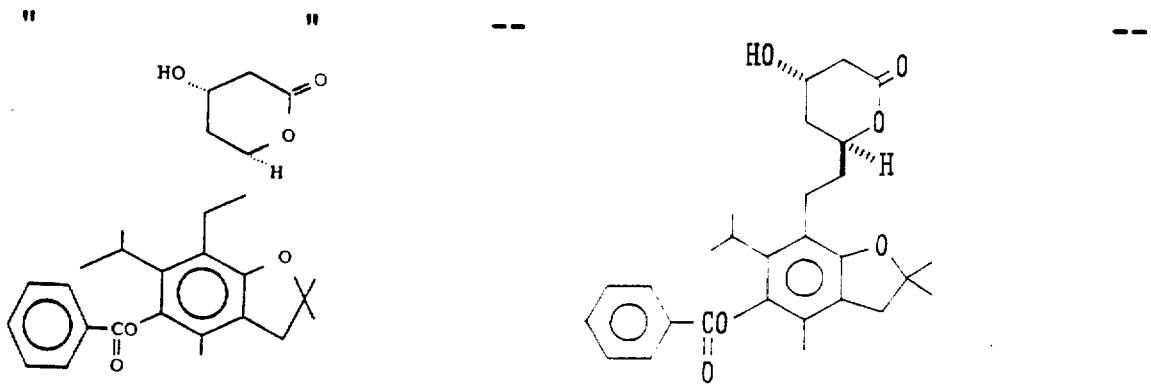

should appear

UNITED STATES PATENT AND TRADEMARK OFFICE
CERTIFICATE OF CORRECTION

PATENT NO. : 5,149,834

DATED : September 22, 1992

INVENTOR(S) : Masakatsu MATUMOTO, et al.

It is certified that error appears in the above-identified patent and that said Letters Patent is hereby corrected as shown below:

Column 124, formula (I),

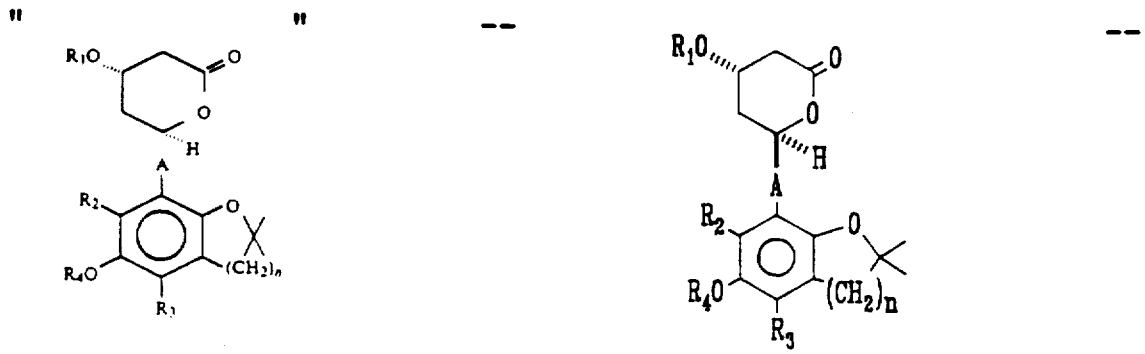

should appear

Signed and Sealed this

Twenty-second Day of March, 1994

Attest:

BRUCE LEHMAN

Attesting Officer     Commissioner of Patents and Trademarks

UNITED STATES PATENT AND TRADEMARK OFFICE
CERTIFICATE OF CORRECTION

PATENT NO. : 5,149,834

DATED : September 22, 1992

INVENTOR(S) : Masakatsu MATUMOTO et al

It is certified that error appears in the above-identified patent and that said Letters Patent is hereby corrected as shown below:

Column 4, line 56, after "$R_2$" insert --, $R_3$--.

line 11, delete "or solvents "

line 49, delete "formula (I)" and insert --formula (I-3)--.

Column 7, line 52, delete "pyridine" and insert --pyridinium--.

Column 8, line 7, delete "formula (I-3)" and insert --formula (I-4)--.

line 26-27, delete "pyridine" and insert --pyridinium--.

line 53, delete "Co A" and insert --CoA--.

line 59, insert --methyl group-- before "2-propyl".

UNITED STATES PATENT AND TRADEMARK OFFICE
CERTIFICATE OF CORRECTION

PATENT NO. : 5,149,834

DATED : September 22, 1992

INVENTOR(S) : Masakatsu MATUMOTO et al

It is certified that error appears in the above-identified patent and that said Letters Patent is hereby corrected as shown below:

Column 10, the formula at lines 10 - 19,

" 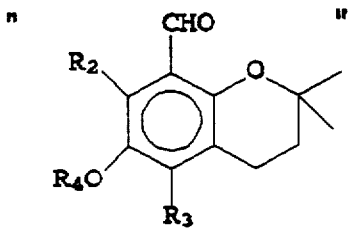 " should appear -- 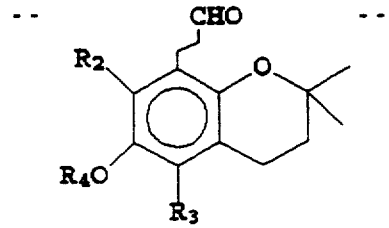 --

Column 10, the formula at lines 20 - 25,

" 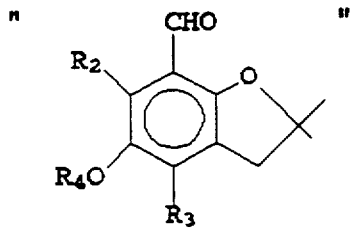 " should appear -- 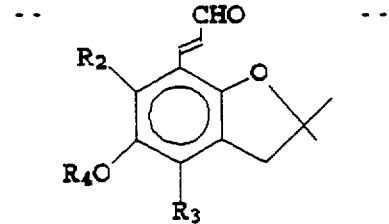 --

UNITED STATES PATENT AND TRADEMARK OFFICE
CERTIFICATE OF CORRECTION

PATENT NO. : 5,149,834
DATED : September 22, 1992
INVENTOR(S) : Masakatsu MATUMOTO et al It is certified that error appears in the above-identified patent and that said Letters Patent is hereby corrected as shown below:

Column 10, the formula at lines 30 - 35,

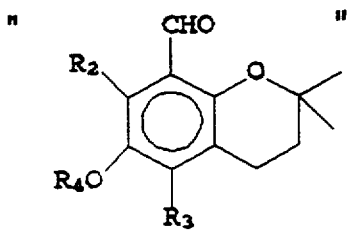   should appear   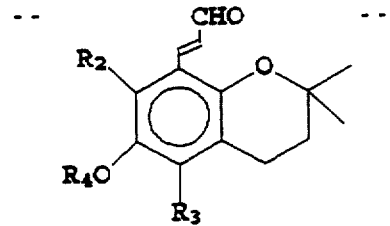

Column 11, line 23, delete "(I-d)" beside "formula (II-4)."

Column 12, line 27, delete "3,5-di-(2-propyl)-phenol" and insert --3,5-di(2-propyl)phenol--.

Column 13, line 44, delete "Step 1" and insert --Step 2-1--.

line 46, delete "Step 1" and insert --Step 2-1--.

Column 14, lines 60-61, connect "5-(2-methyl-" with "2-propenyl)-3-(2-propenyl)-2-(2-propyl)hydroquinone".

UNITED STATES PATENT AND TRADEMARK OFFICE
CERTIFICATE OF CORRECTION

PATENT NO. : 5,149,834

DATED : September 22, 1992

INVENTOR(S) : Masakatsu MATUMOTO et al

It is certified that error appears in the above-identified patent and that said Letters Patent is hereby corrected as shown below:

Column 15, lines 30-31, delete "2,3-dihydro-5-hydroxy-7-(2-propenyl)-6-(2-propyl)benzo[b]furan "

Column 16, line 67, delete "3-acetoxy" and insert --5-acetoxy--.

Column 18, lines 25-34, delete "(I-d)" beside "formula (IV-1A)."

Column 19, line 38, delete "(IV-9)" and insert --(IV-8)--.

Column 20, line 67, delete "formula (IV-A)" and insert --formula (IV-1A)--.

Column 21, lines 20-30, delete "(I-d)" beside "formula (IV-1A)."

line 62, delete "(IV-B)" and insert --(IV-13)--.

line 66, delete "pyridine p-toluene sulfonate" and insert --pyridinium p-toluene-sulfonate--.

UNITED STATES PATENT AND TRADEMARK OFFICE
CERTIFICATE OF CORRECTION

PATENT NO. : 5,149,834
DATED : September 22, 1992
INVENTOR(S) : Masakatsu MATUMOTO et al It is certified that error appears in the above-identified patent and that said Letters Patent is hereby corrected as shown below:

Column 22, line 27, delete "(IV-IV)" and insert
--(IV-14)--.

line 44, delete "(IV-13)" and insert --(II-1)--.

line 53, delete "(IV-14)" and insert --(II-5)--.

Column 22, the formula at lines 55-62,

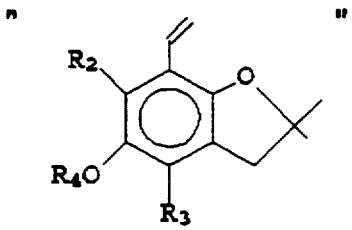   should appear   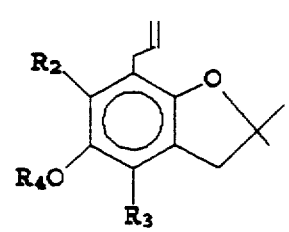

Signed and Sealed this

Fourteenth Day of May, 1996

Attest:

BRUCE LEHMAN

Attesting Officer     Commissioner of Patents and Trademarks